(12) United States Patent
Scanlon et al.

(10) Patent No.: US 12,357,480 B2
(45) Date of Patent: Jul. 15, 2025

(54) BIORESORBABLE, IMPLANTABLE DEVICE HAVING CONTROLLED DRUG DELIVERY

(71) Applicants: John James Scanlon, Wilmington, DE (US); Catherine Ann Scanlon, Wilmington, DE (US)

(72) Inventors: John James Scanlon, Wilmington, DE (US); Catherine Ann Scanlon, Wilmington, DE (US)

( * ) Notice: Subject to any disclaimer, the term of this patent is extended or adjusted under 35 U.S.C. 154(b) by 765 days.

(21) Appl. No.: 17/504,465

(22) Filed: Oct. 18, 2021

(65) Prior Publication Data

US 2022/0031482 A1 Feb. 3, 2022

Related U.S. Application Data

(62) Division of application No. 15/863,822, filed on Jan. 5, 2018, now Pat. No. 11,147,696.

(Continued)

(51) Int. Cl.
| | |
|---|---|
| *A61F 2/89* | (2013.01) |
| *A61F 2/915* | (2013.01) |
| *A61K 9/70* | (2006.01) |
| *A61K 31/436* | (2006.01) |
| *B29C 53/04* | (2006.01) |

(Continued)

(52) U.S. Cl.
CPC ............ *A61F 2/89* (2013.01); *A61F 2/915* (2013.01); *A61K 31/436* (2013.01); *B29C 53/04* (2013.01); *B29C 67/0014* (2013.01); *B29C 67/02* (2013.01); *B29C 69/001* (2013.01); *B29C 69/002* (2013.01); *A61F 2210/0004* (2013.01); *A61F 2240/001* (2013.01); *A61F 2250/0067* (2013.01); *B29K 2067/046* (2013.01); *B29K 2105/0035* (2013.01); *B29K 2995/006* (2013.01); *B29L 2031/7534* (2013.01)

(58) Field of Classification Search
CPC .................................................. A61F 2210/00
See application file for complete search history.

(56) References Cited

U.S. PATENT DOCUMENTS

| | | | | |
|---|---|---|---|---|
| 6,093,792 A | * | 7/2000 | Gross | C08G 63/64 528/196 |
| 8,206,635 B2 | * | 6/2012 | Ramzipoor | A61L 31/04 514/56 |

(Continued)

OTHER PUBLICATIONS

Kariduraganavar et al. Polymer Synthesis and Processing. Natural and Synthetic Biomedical Polymers. pp 1-31. 2014 (Year: 2014).*

*Primary Examiner* — Cachet I Proctor
(74) *Attorney, Agent, or Firm* — Squire Patton Boggs (US) LLP

(57) ABSTRACT

A bioresorbable, implantable device having controlled drug delivery is disclosed herein. The bioresorbable, implantable device is configured as a film, a roll, a tube, and a stent. The bioresorbable, implantable device is configured to release an active ingredient (the "drug") from the bioresorbable, implantable device when the bioresorbable, implantable device is implanted within a body. The bioresorbable, implantable device is configured to control the onset of the release of the drug, the sequence of drug delivery, and the duration of drug delivery by embedding the drug within at least one therapeutic layer positioned within bioresorbable, implantable device.

15 Claims, 19 Drawing Sheets

Related U.S. Application Data

(60) Provisional application No. 62/443,101, filed on Jan. 6, 2017.

(51) Int. Cl.
| | | |
|---|---|---|
| *B29C 67/00* | (2017.01) | |
| *B29C 67/02* | (2017.01) | |
| *B29C 69/00* | (2006.01) | |
| *B29K 67/00* | (2006.01) | |
| *B29K 105/00* | (2006.01) | |
| *B29L 31/00* | (2006.01) | |

(56) References Cited

U.S. PATENT DOCUMENTS

| | | | |
|---|---|---|---|
| 2003/0155558 A1* | 8/2003 | Yamazaki | B29C 41/32 |
| | | | 252/585 |
| 2008/0071346 A1* | 3/2008 | Brown | A61F 2/915 |
| | | | 623/1.15 |
| 2012/0094004 A1* | 4/2012 | Stopek | A61L 31/16 |
| | | | 427/2.1 |
| 2015/0306282 A1* | 10/2015 | Scanlon | A61L 31/18 |
| | | | 623/1.34 |

* cited by examiner

SECTION A-A

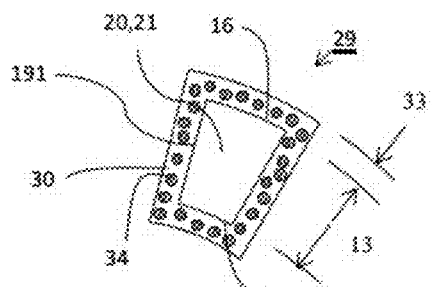
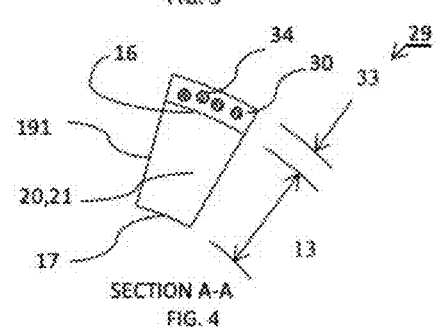
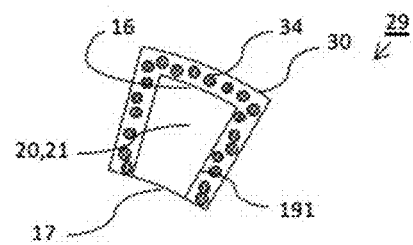
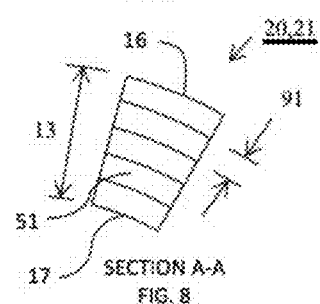
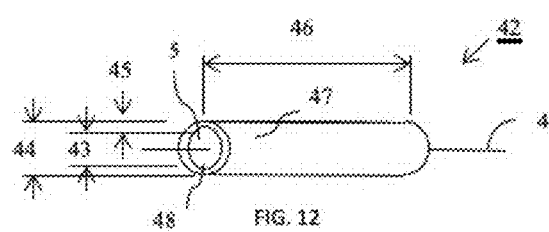
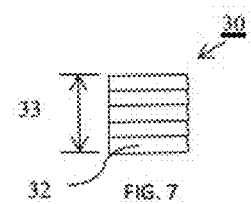
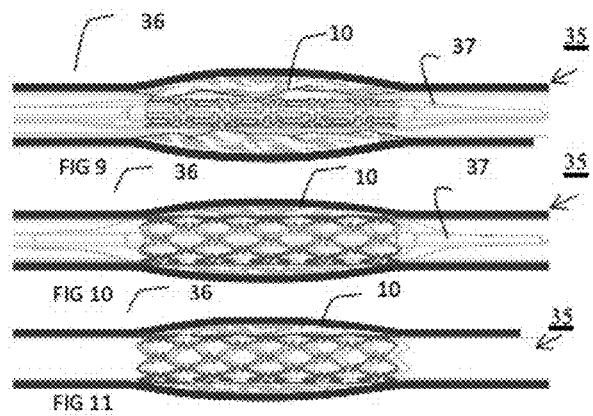
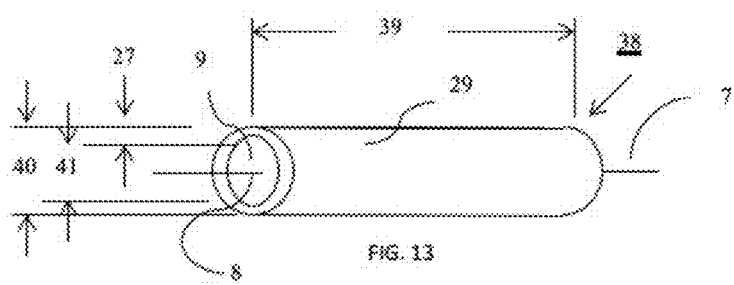
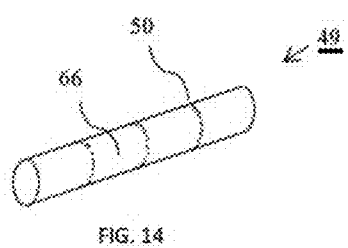

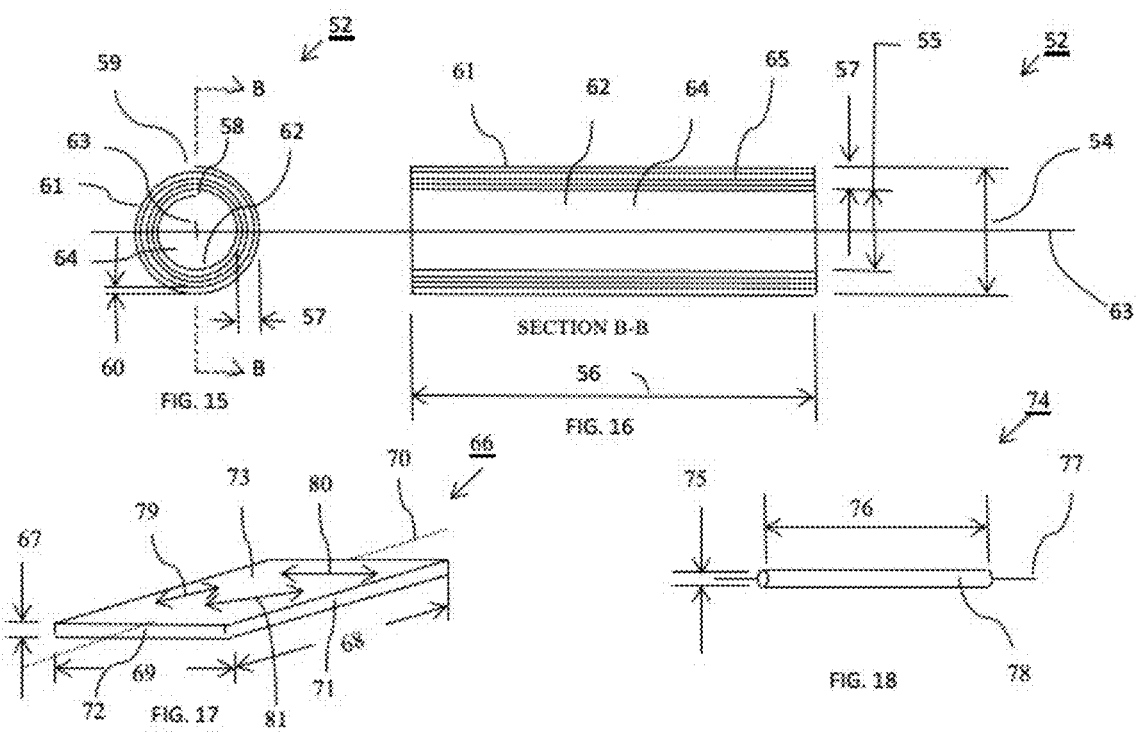
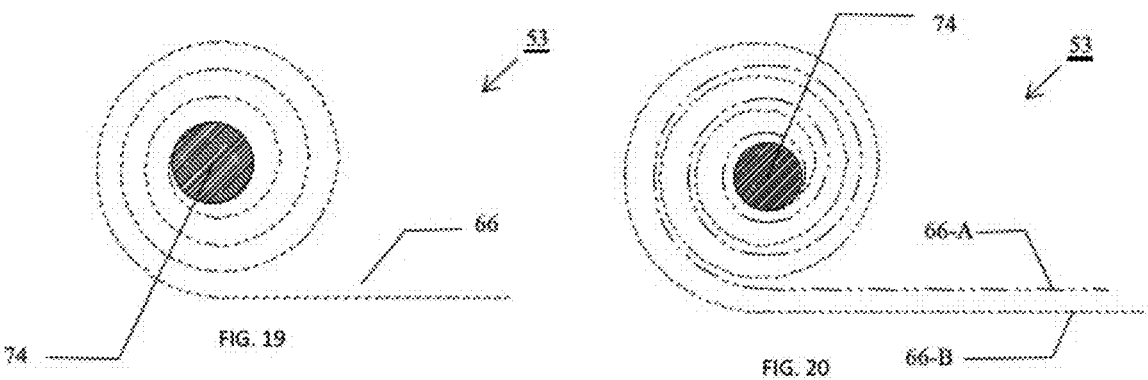
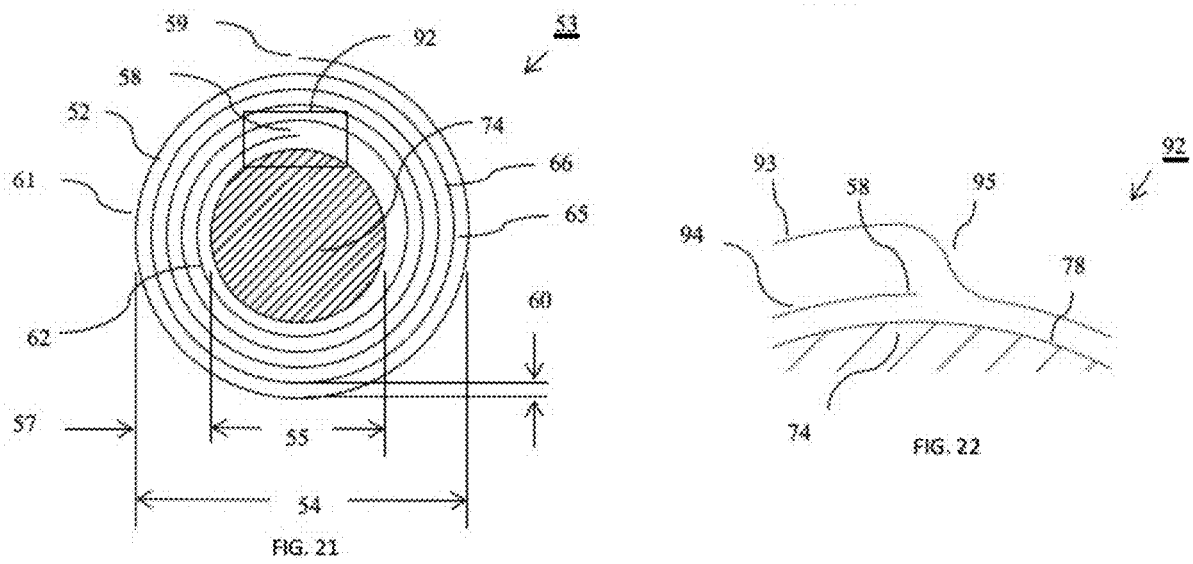

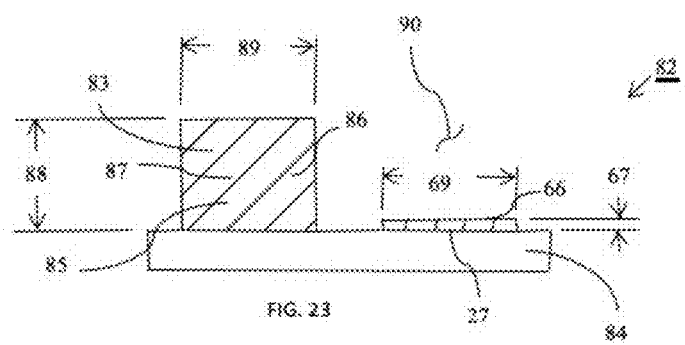
FIG. 23
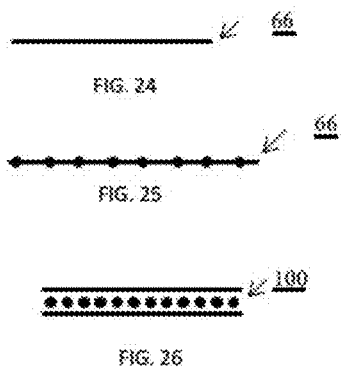
FIG. 24
FIG. 25
FIG. 26
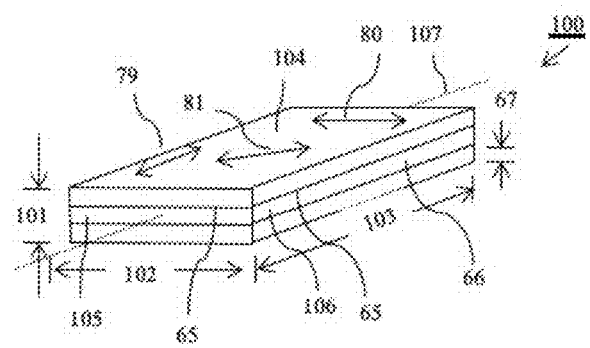
FIG. 27
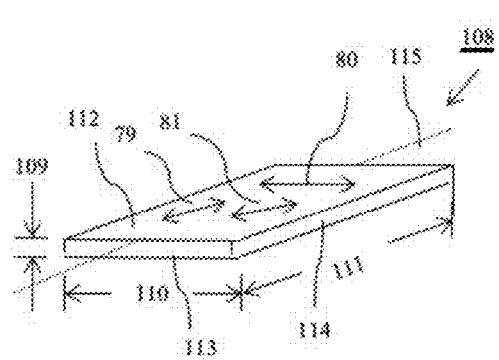
FIG. 28
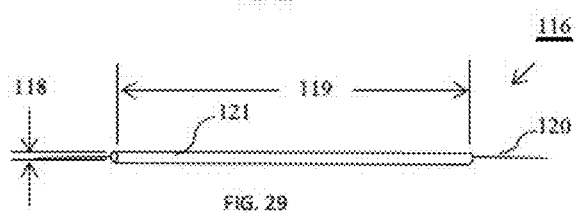
FIG. 29
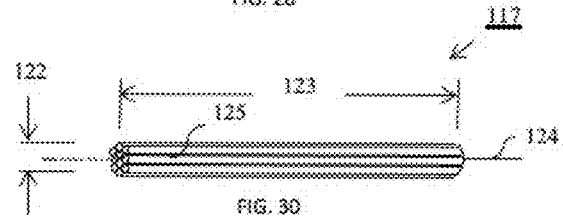
FIG. 30
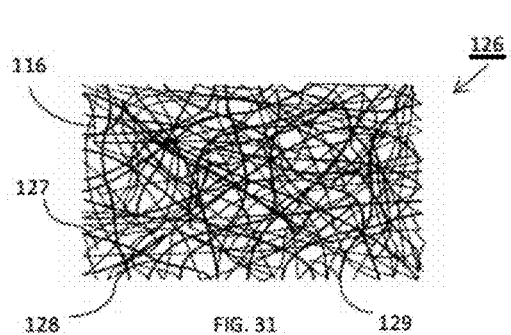
FIG. 31
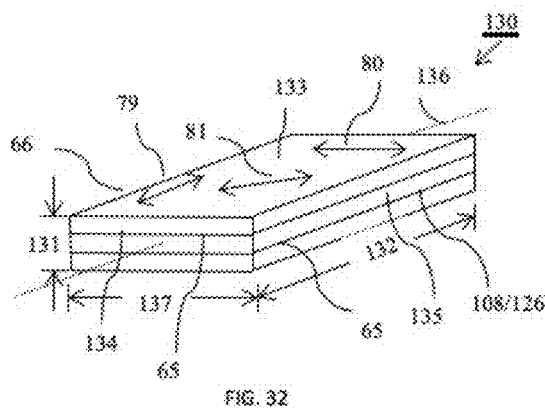
FIG. 32

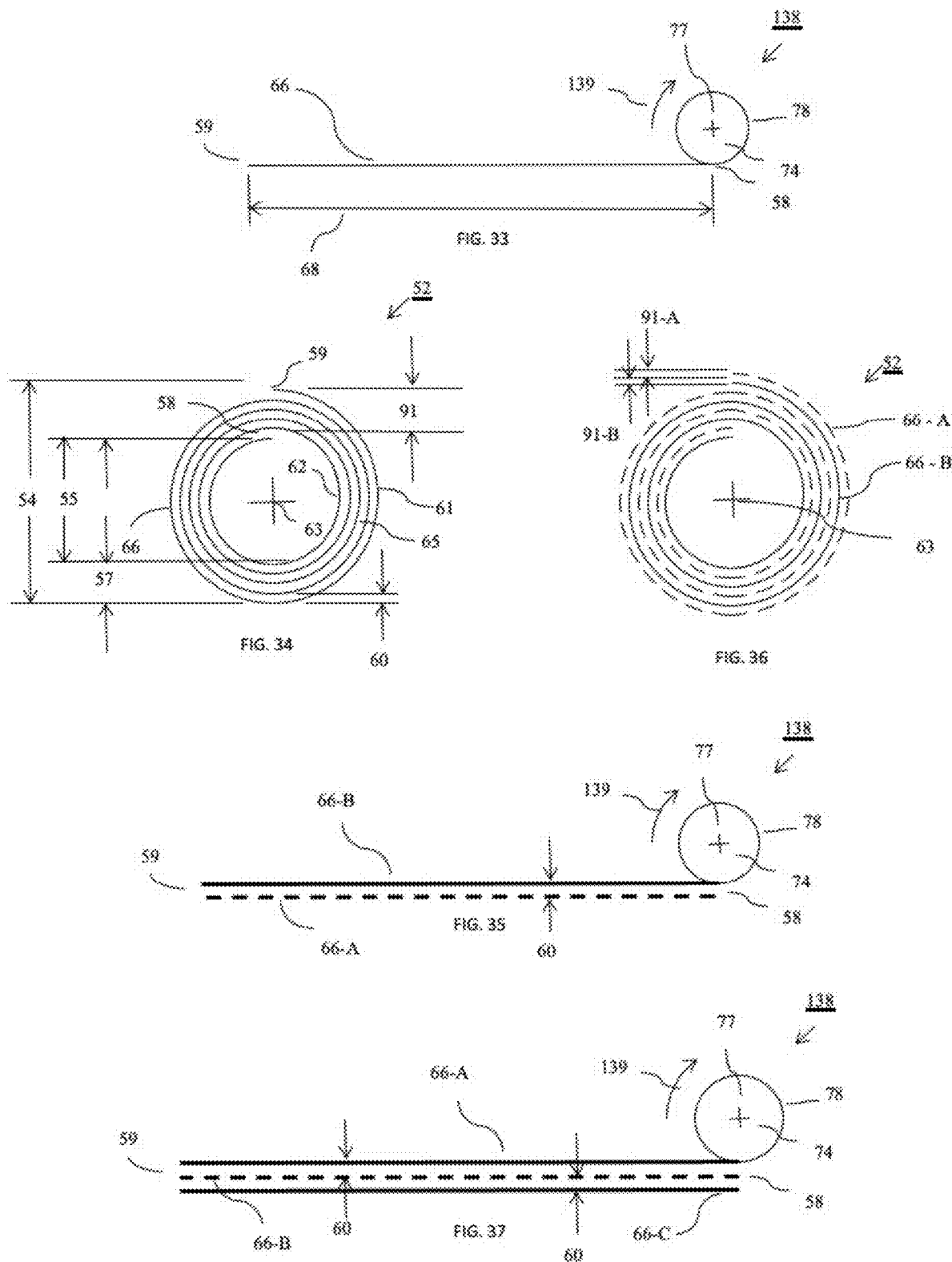

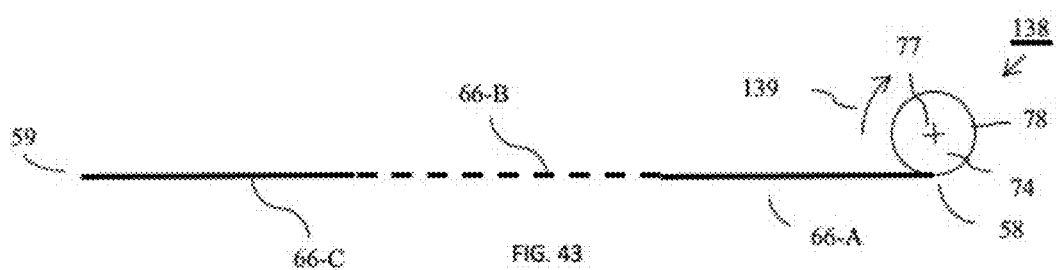
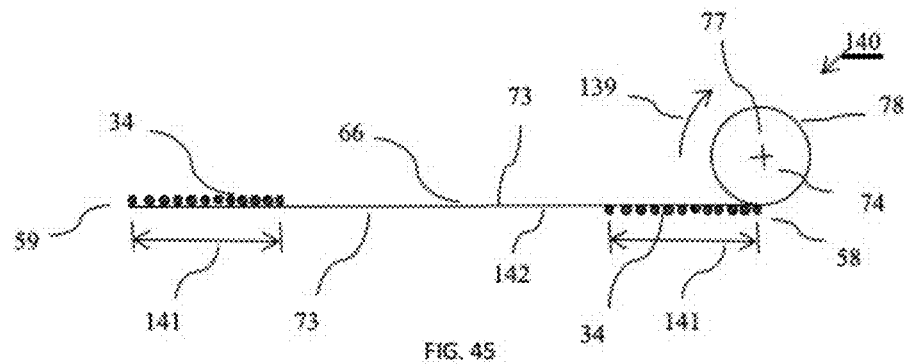
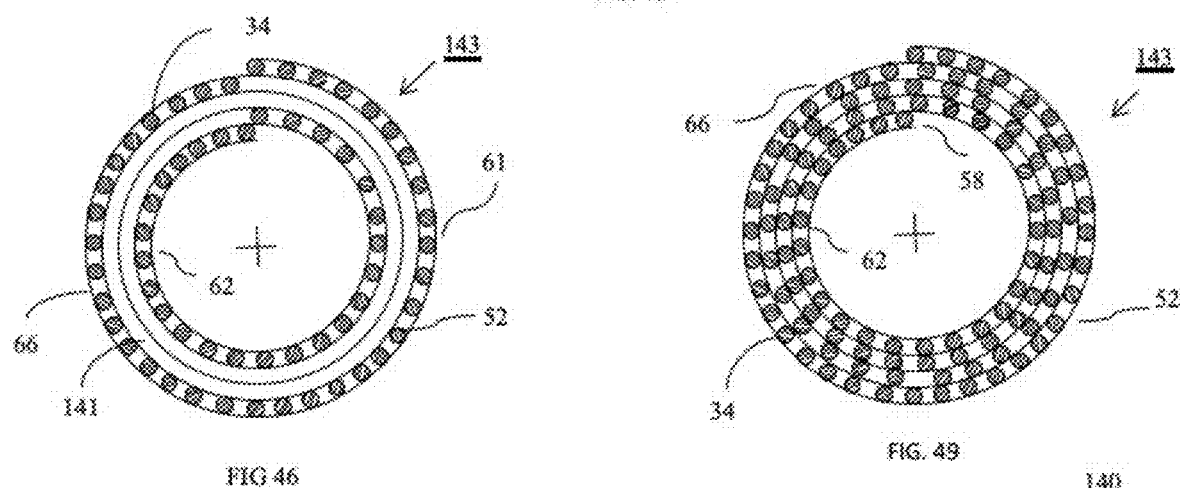

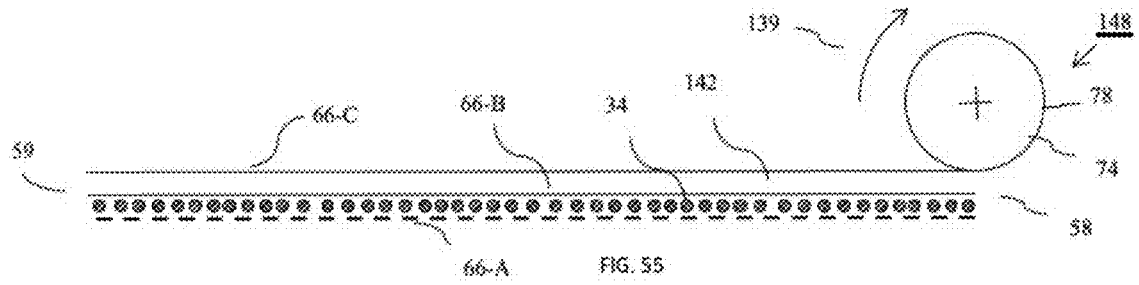
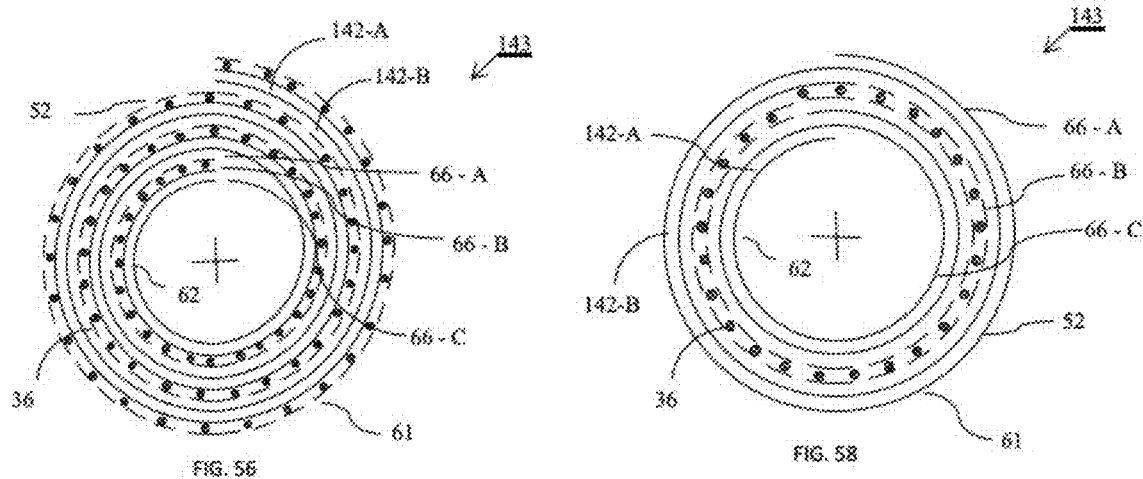
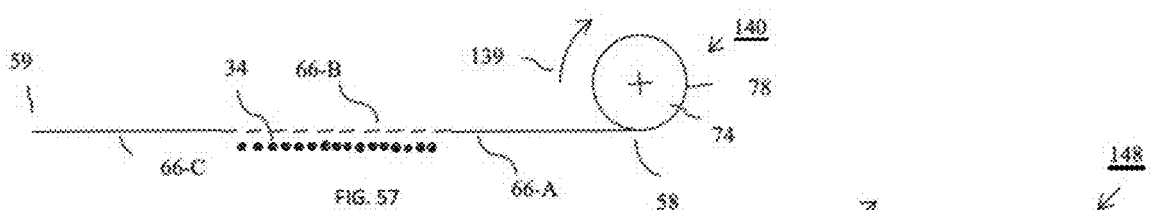
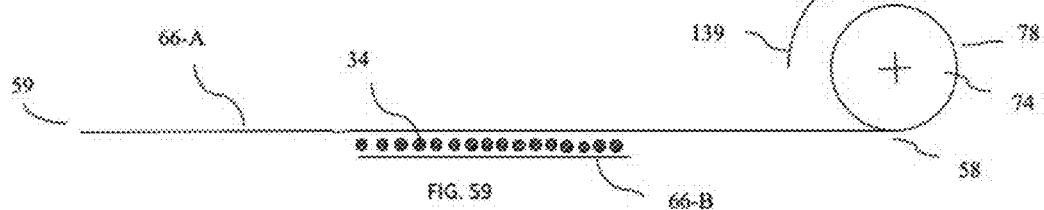
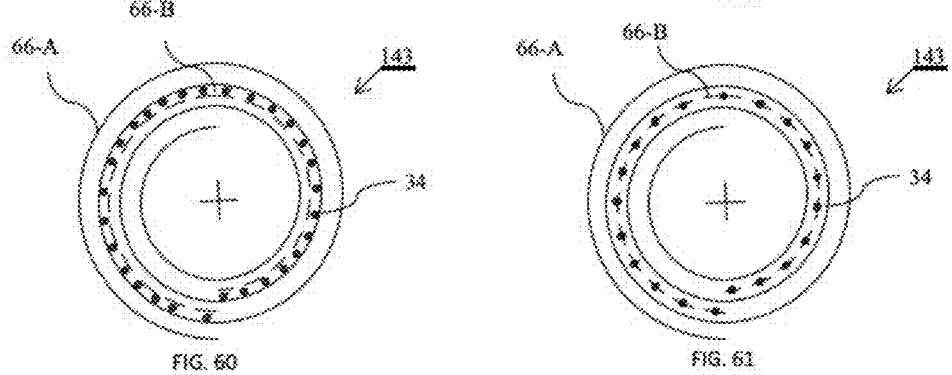

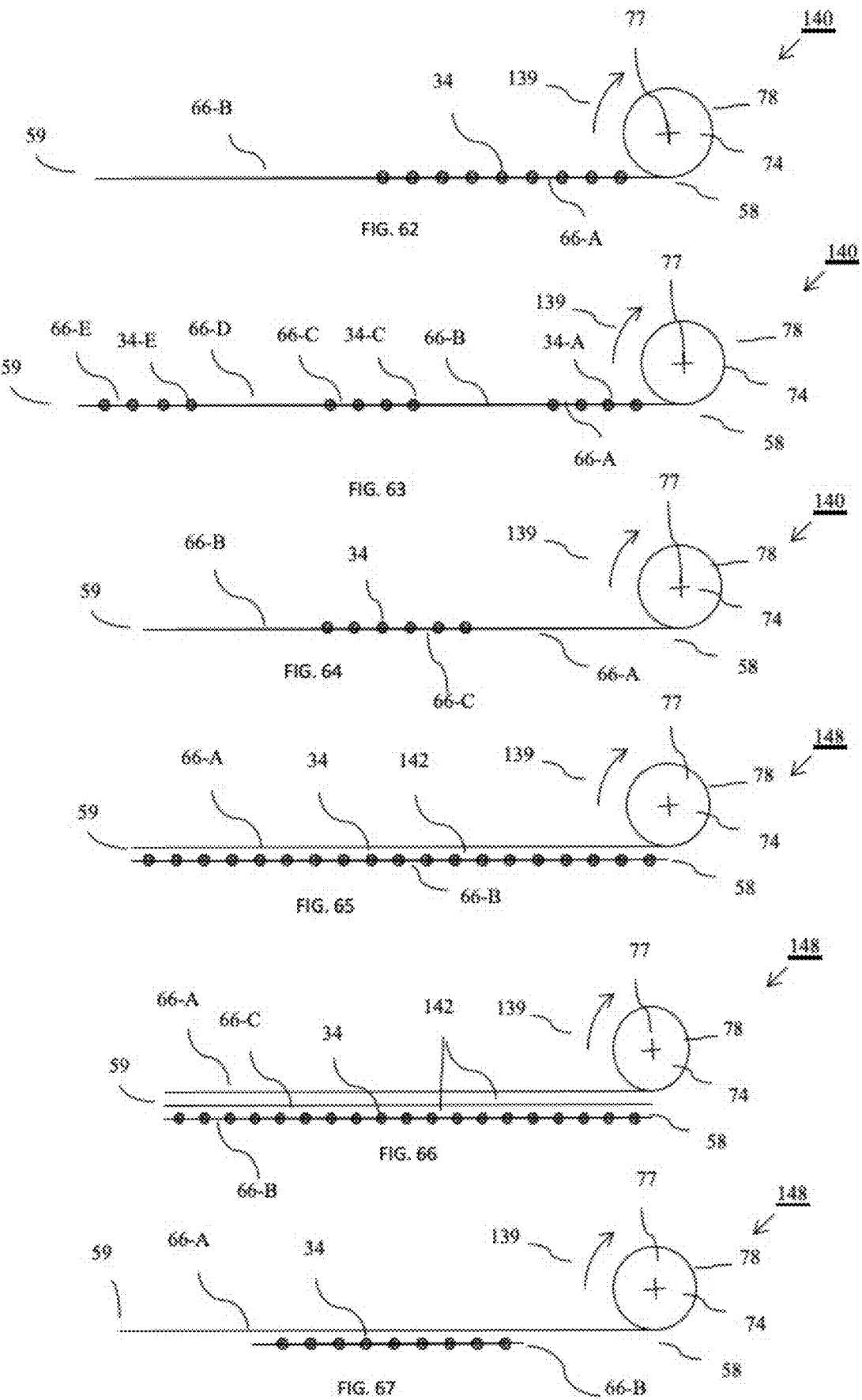

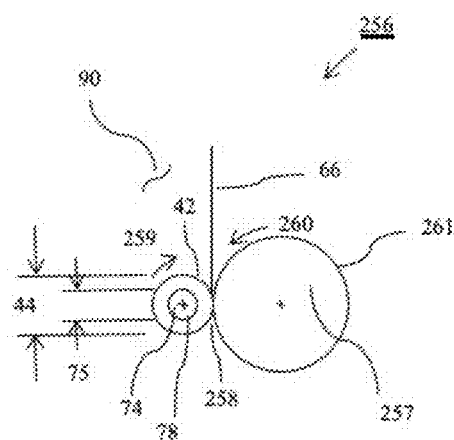
FIG. 68
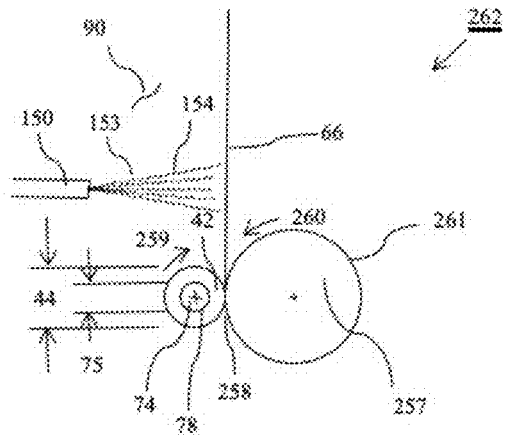
FIG. 69
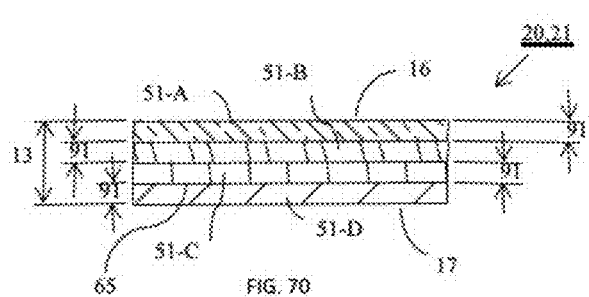
FIG. 70
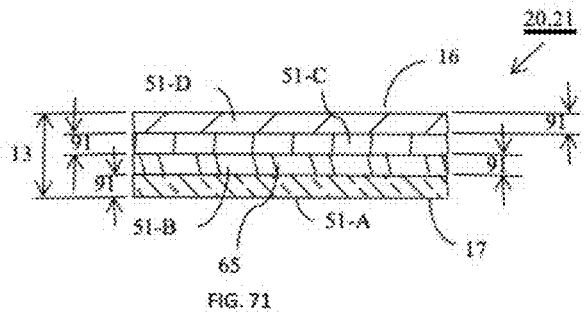
FIG. 71
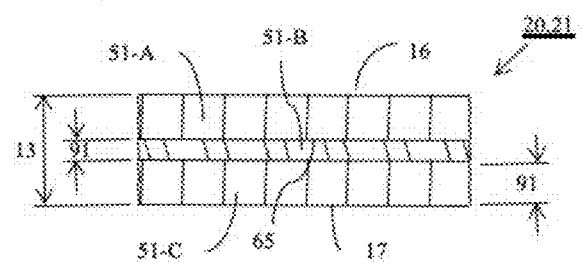
FIG. 72
FIG. 73
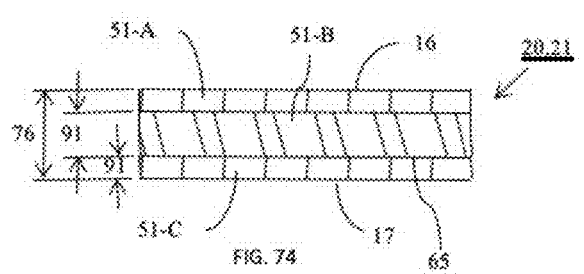
FIG. 74
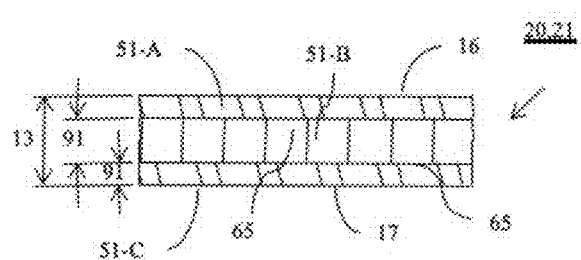
FIG. 75

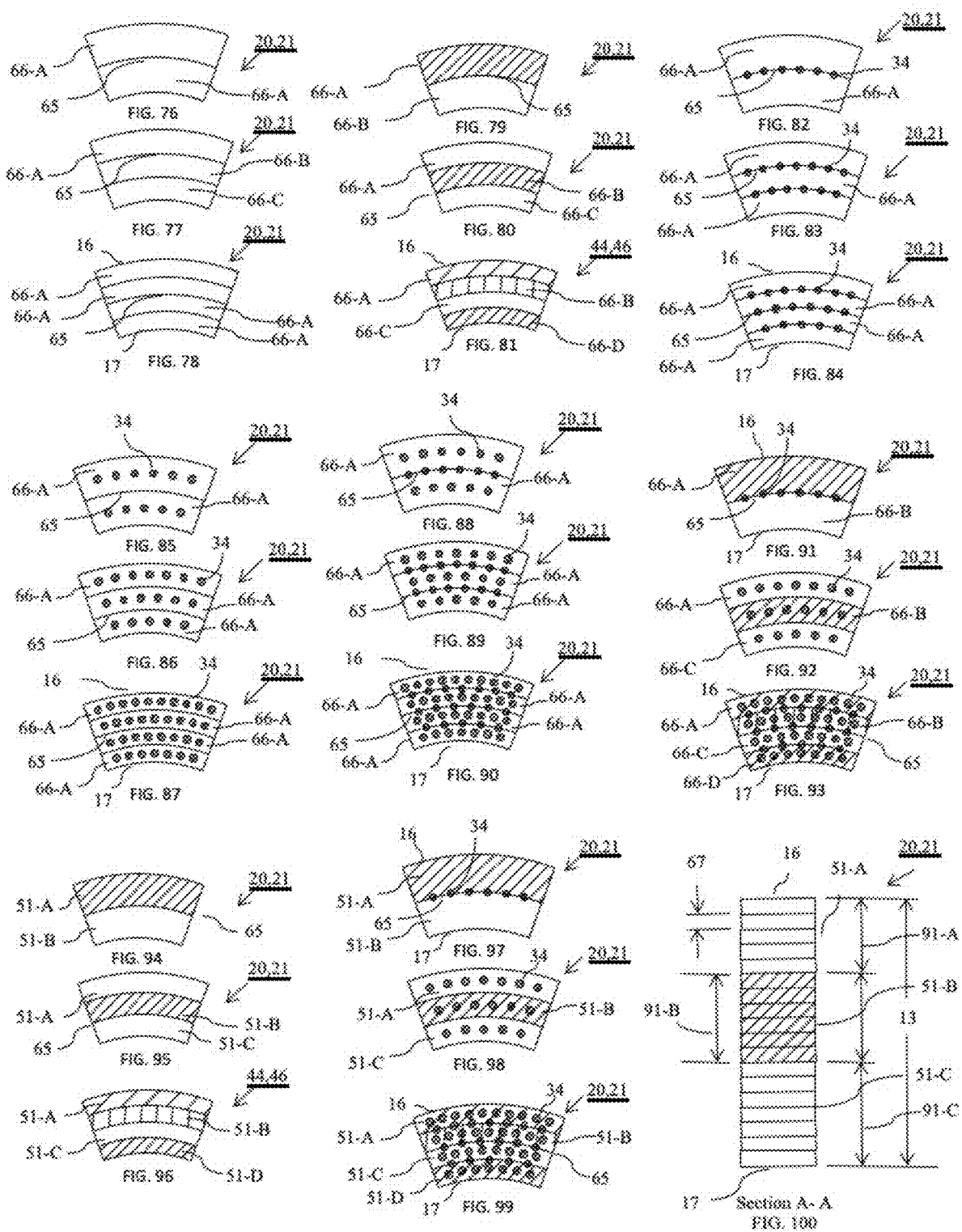

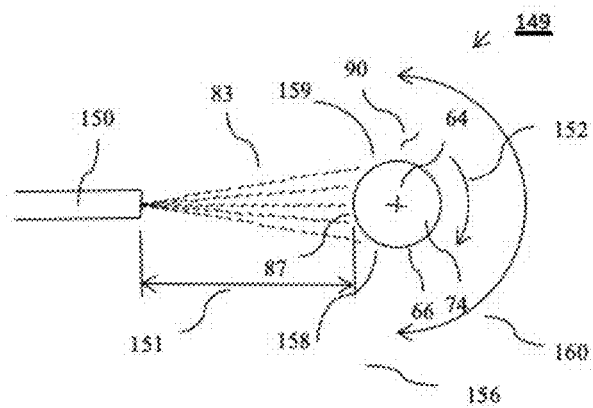
FIG. 101
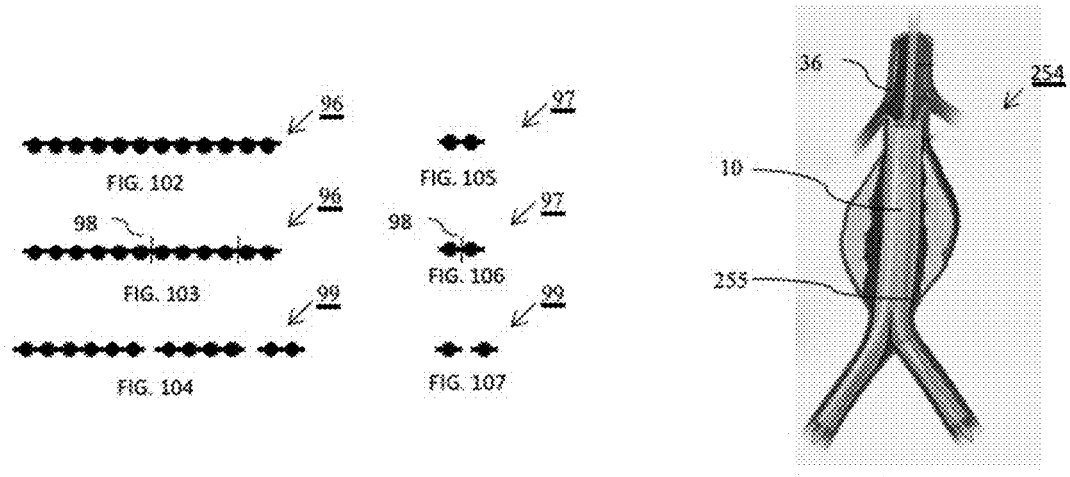
FIG. 102 FIG. 105
FIG. 103 FIG. 106
FIG. 104 FIG. 107
FIG. 108
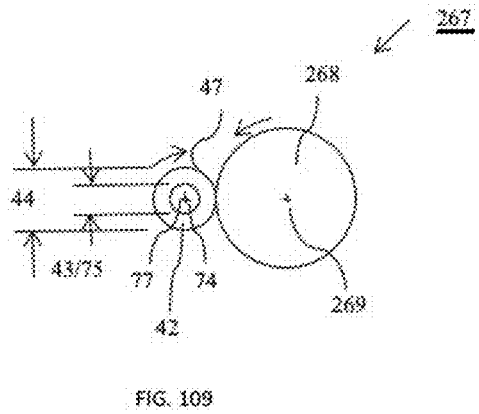
FIG. 109
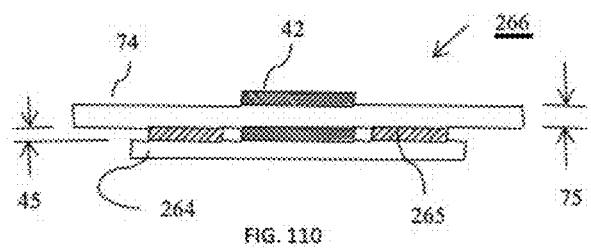
FIG. 110

EXAMPLE STENT MATERIAL 85 FORMULATIONS FOR USE IN PRODUCING THE FILM 66

| FORMULA NUMBER | STENT MATERIAL 85 | MOLAR RATIO (TOTAL = 100) | | | | | WEIGHT AVERAGE MOLECULAR WEIGHT (KG/MOL) | INHERENT VISCOSITY (dl/g) |
|---|---|---|---|---|---|---|---|---|
| | | L-lactide | DL-lactide | D-lactide | Glycolide | Caprolactone | | |
| F-1 | PL | 100 | | | | | 55 to 3,000 | 0.7 to 11.0 |
| F-2 | PL | 100 | | | | | 55 to 298 | 0.7 to 2.2 |
| F-3 | PL | 100 | | | | | >298 to 621 | >2.2 to 3.6 |
| F-4 | PL | 100 | | | | | >621 to 1,014 | >3.6 to 5.0 |
| F-5 | PL | 100 | | | | | >1,014 to 2,044 | >5.0 to 8.0 |
| F-6 | PL | 100 | | | | | >2,044 to 3,000 | >8.0 to 11.5 |
| F-7 | PDL | | 100 | | | | 55 to 3,000 | 0.7 to 11.0 |
| F-8 | PDL | | 100 | | | | 55 to 298 | 0.7 to 2.2 |
| F-9 | PDL | | 100 | | | | >298 to 621 | >2.2 to 3.6 |
| F-10 | PDL | | 100 | | | | >621 to 1,014 | >3.6 to 5.0 |
| F-11 | PDL | | 100 | | | | >1,014 to 2,044 | >5.0 to 8.0 |
| F-12 | PDL | | 100 | | | | >2,044 to 3,000 | >8.0 to 11.5 |
| F-13 | PD | | | 100 | | | 100 to 2,000 | 1.0 to 7.5 |
| F-14 | PD | | | 100 | | | 55 to 298 | 0.7 to 2.2 |
| F-15 | PD | | | 100 | | | >298 to 621 | >2.2 to 3.6 |
| F-16 | PD | | | 100 | | | >621 to 1,014 | >3.6 to 5.0 |
| F-17 | PD | | | 100 | | | >1,014 to 2,044 | >5.0 to 8.0 |
| F-18 | PD | | | 100 | | | >2,044 to 3,000 | >8.0 to 11.5 |
| F-19 | PG | | | | 100 | | 55-3,000 | 0.7 to 11.0 |
| F-20 | PG | | | | 100 | | 55 to 298 | 0.7 to 2.2 |
| F-21 | PG | | | | 100 | | >298 to 621 | >2.2 to 3.6 |
| F-22 | PG | | | | 100 | | >621 to 1,014 | >3.6 to 5.0 |
| F-23 | PG | | | | 100 | | >1,014 to 2,044 | >5.0 to 8.0 |
| F-24 | PG | | | | 100 | | >2,044 to 3,000 | >8.0 to 11.5 |
| F-25 | PC | | | | | 100 | 55-3,000 | 0.7 to 11.0 |
| F-26 | PC | | | | | 100 | 55 to 298 | 0.7 to 2.2 |
| F-27 | PC | | | | | 100 | >298 to 621 | >2.2 to 3.6 |
| F-28 | PC | | | | | 100 | >621 to 1,014 | >3.6 to 5.0 |
| F-29 | PC | | | | | 100 | >1,014 to 2,044 | >5.0 to 8.0 |
| F-30 | PC | | | | | 100 | >2,044 to 3,000 | >8.0 to 11.5 |
| F-31 | PLDL | 90 to <100 | >0 to 10 | | | | 55-3,000 | 0.7 to 11.0 |
| F-32 | PLDL | 80 to <90 | >10 to 20 | | | | 55-3,000 | 0.7 to 11.0 |
| F-33 | PLDL | 70 to <80 | >20 to 30 | | | | 55-3,000 | 0.7 to 11.0 |
| F-34 | PLDL | 60 to <70 | >30 to 40 | | | | 55-3,000 | 0.7 to 11.0 |
| F-35 | PLDL | 50 to < 60 | >40 to 50 | | | | 55-3,000 | 0.7 to 11.0 |
| F-36 | PLDL | 40 to <50 | >50 to 60 | | | | 55-3,001 | 0.7 to 11.1 |
| F-37 | PLDL | 30 to <40 | >60 to 70 | | | | 55-3,002 | 0.7 to 11.2 |
| F-38 | PLDL | 20 to <30 | >70 to 80 | | | | 55-3,003 | 0.7 to 11.3 |
| F-39 | PLDL | 10 to <20 | >80 to 90 | | | | 55-3,004 | 0.7 to 11.4 |
| F-40 | PLDL | >0 to <10 | >90 to <100 | | | | 55-3,004 | 0.7 to 11.4 |
| F-41 | PLG | 90 to <100 | | | >0 to 10 | | 55-3,000 | 0.7 to 11.0 |
| F-42 | PLG | 80 to <90 | | | >10 to 20 | | 55-3,000 | 0.7 to 11.0 |
| F-43 | PLG | 70 to <80 | | | >20 to 30 | | 55-3,000 | 0.7 to 11.0 |
| F-44 | PLG | 60 to <70 | | | >30 to 40 | | 55-3,000 | 0.7 to 11.0 |
| F-45 | PLG | 50 to < 60 | | | >40 to 50 | | 55-3,000 | 0.7 to 11.0 |
| F-46 | PLG | 40 to <50 | | | >50 to 60 | | 55-3,001 | 0.7 to 11.1 |
| F-47 | PLG | 30 to <40 | | | >60 to 70 | | 55-3,002 | 0.7 to 11.2 |
| F-48 | PLG | 20 to <30 | | | >70 to 80 | | 55-3,003 | 0.7 to 11.3 |
| F-49 | PLG | 10 to <20 | | | >80 to 90 | | 55-3,004 | 0.7 to 11.4 |
| F-50 | PLG | >0 to <10 | | | >90 to <100 | | 55-3,004 | 0.7 to 11.4 |

FIG. 111

EXAMPLE MATERIAL FORMULATIONS FOR USE IN PRODUCING THE FILM 66 (CONTINUED)

| FORMULA NUMBER | STENT MATERIAL(S) 85 | MOLAR RATIO (TOTAL = 100) | | | | | WEIGHT AVERAGE MOLECULAR WEIGHT (KG/MOL) | INHERENT VISCOSITY (dl/g) |
|---|---|---|---|---|---|---|---|---|
| | | L-lactide | DL-lactide | D-lactide | Glycolide | Caprolactone | | |
| F-51 | PLC | 90 to <100 | | | | >0 to 10 | 70 to 1,000 | 0.7 to 4.7 |
| F-52 | PLC | 80 to <90 | | | | >10 to 20 | 70 to 1,000 | 0.7 to 4.7 |
| F-53 | PLC | 70 to <80 | | | | >20 to 30 | 70 to 1,000 | 0.7 to 4.7 |
| F-54 | PLC | 60 to <70 | | | | >30 to 40 | 70 to 1,000 | 0.7 to 4.7 |
| F-55 | PLC | 50 to < 60 | | | | >40 to 50 | 70 to 1,000 | 0.7 to 4.7 |
| F-56 | PLC | 40 to <50 | | | | >50 to 60 | 71 to 1,000 | 0.7 to 4.8 |
| F-57 | PLC | 30 to <40 | | | | >60 to 70 | 72 to 1,000 | 0.7 to 4.9 |
| F-58 | PLC | 20 to <30 | | | | >70 to 80 | 73 to 1,000 | 0.7 to 4.10 |
| F-59 | PLC | 10 to <20 | | | | >80 to 90 | 74 to 1,000 | 0.7 to 4.11 |
| F-60 | PLC | >0 to <10 | | | | >90 to <100 | 74 to 1,000 | 0.7 to 4.11 |
| F-61 | PLD | 90 to <100 | | >0 to 10 | | | 100 to 2,000 | 1.0 to 7.5 |
| F-62 | PLD | 80 to <90 | | >10 to 20 | | | 100 to 2,000 | 1.0 to 7.5 |
| F-63 | PLD | 70 to <80 | | >20 to 30 | | | 100 to 2,000 | 1.0 to 7.5 |
| F-64 | PLD | 60 to <70 | | >30 to 40 | | | 100 to 2,000 | 1.0 to 7.5 |
| F-65 | PLD | 50 to < 60 | | >40 to 50 | | | 100 to 2,000 | 1.0 to 7.5 |
| F-66 | PLD | 40 to <50 | | >50 to 60 | | | 100 to 2,000 | 1.0 to 7.5 |
| F-67 | PLD | 30 to <40 | | >60 to 70 | | | 100 to 2,000 | 1.0 to 7.5 |
| F-68 | PLD | 20 to <30 | | >70 to 80 | | | 100 to 2,000 | 1.0 to 7.5 |
| F-69 | PLD | 10 to <20 | | >80 to 90 | | | 100 to 2,000 | 1.0 to 7.5 |
| F-70 | PLD | >0 to <10 | | >90 to <100 | | | 100 to 2,000 | 1.0 to 7.5 |
| F-71 | PDLG | | 90 to <100 | | >0 to 10 | | 16 to 2,000 | 0.2 to 6.0 |
| F-72 | PDLG | | 80 to <90 | | >10 to 20 | | 16 to 2,000 | 0.2 to 6.0 |
| F-73 | PDLG | | 70 to <80 | | >20 to 30 | | 16 to 2,000 | 0.2 to 6.0 |
| F-74 | PDLG | | 60 to <70 | | >30 to 40 | | 16 to 2,000 | 0.2 to 6.0 |
| F-75 | PDLG | | 50 to < 60 | | >40 to 50 | | 16 to 2,000 | 0.2 to 6.0 |
| F-76 | PDLG | | 40 to <50 | | >50 to 60 | | 16 to 2,000 | 0.2 to 6.0 |
| F-77 | PDLG | | 30 to <40 | | >60 to 70 | | 16 to 2,000 | 0.2 to 6.0 |
| F-78 | PDLG | | 20 to <30 | | >70 to 80 | | 16 to 2,000 | 0.2 to 6.0 |
| F-79 | PDLG | | 10 to <20 | | >80 to 90 | | 16 to 2,000 | 0.2 to 6.0 |
| F-80 | PDLG | | >0 to <10 | | >90 to <100 | | 16 to 2,000 | 0.2 to 6.0 |

FIG. 111 Continued

EXAMPLE BLEND FORMULATIONS FOR USE IN PRODUCING FILM 66

| BLEND NUMBER | STENT MATERIAL(S) 85 | PART #1 Wt. % | PART #2 Wt.% |
|---|---|---|---|
| B-81 | Blend of F-6 and at least one of the F-2, 3, 4, 5 | 90 to <100 | >0 to 10 |
| B-82 | Blend of F-5 and at least one of the F-2, 3, 4, 6 | 90 to <100 | >0 to 10 |
| B-83 | Blend of F-4 and at least one of the F-2, 3, 5, 6 | 90 to <100 | >0 to 10 |
| B-84 | Blend of F-3 and at least one of the F-2, 4, 5, 6 | 90 to <100 | >0 to 10 |
| B-85 | Blend of F-2 and at least one of the F-3, 4, 5, 6 | 90 to <100 | >0 to 10 |
| B-86 | Blend of F-6 and at least one of the F-2, 3, 4, 5 | 80 to <90 | >10 to 20 |
| B-87 | Blend of F-5 and at least one of the F-2, 3, 4, 6 | 80 to <90 | >10 to 20 |
| B-88 | Blend of F-4 and at least one of the F-2, 3, 5, 6 | 80 to <90 | >10 to 20 |
| B-89 | Blend of F-3 and at least one of the F-2, 4, 5, 6 | 80 to <90 | >10 to 20 |
| B-90 | Blend of F-2 and at least one of the F-3, 4, 5,6 | 80 to <90 | >10 to 20 |
| B-91 | Blend of F-6 and at least one of the F-2, 3, 4, 5 | 70 to <80 | >20 to 30 |
| B-92 | Blend of F-5 and at least one of the F-2, 3, 4, 6 | 70 to <80 | >20 to 30 |
| B-93 | Blend of F-4 and at least one of the F-2, 3, 5, 6 | 70 to <80 | >20 to 30 |
| B-94 | Blend of F-3 and at least one of the F-2, 4, 5, 6 | 70 to <80 | >20 to 30 |
| B-95 | Blend of F-2 and at least one of the F-3, 4, 5,6 | 70 to <80 | >20 to 30 |

FIG. 112

EXAMPLE BLEND FORMULATIONS FOR USE IN PRODUCING FILM 66 (CONTINUED) 276

| BLEND NUMBER | STENT MATERIAL(S) 85 | PART #1 Wt. % | PART #2 Wt.% |
|---|---|---|---|
| B-96 | Blend of F-6 and at least one of the F-2, 3, 4, 5 | 60 to <70 | >30 to 40 |
| B-97 | Blend of F-5 and at least one of the F-2, 3, 4, 6 | 60 to <70 | >30 to 40 |
| B-98 | Blend of F-4 and at least one of the F-2, 3, 5, 6 | 60 to <70 | >30 to 40 |
| B-99 | Blend of F-3 and at least one of the F-2, 4, 5, 6 | 60 to <70 | >30 to 40 |
| B-100 | Blend of F-2 and at least one of the F-3, 4, 5,6 | 60 to <70 | >30 to 40 |
| B-101 | Blend of F-6 and at least one of the F-2, 3, 4, 5 | 50 to < 60 | >40 to 50 |
| B-102 | Blend of F-5 and at least one of the F-2, 3, 4, 6 | 50 to < 60 | >40 to 50 |
| B-103 | Blend of F-4 and at least one of the F-2, 3, 5, 6 | 50 to < 60 | >40 to 50 |
| B-104 | Blend of F-3 and at least one of the F-2, 4, 5, 6 | 50 to < 60 | >40 to 50 |
| B-105 | Blend of F-2 and at least one of the F-3, 4, 5,6 | 50 to < 60 | >40 to 50 |
| B-106 | Blend of F-6 and at least one of the F-2, 3, 4, 5 | 40 to <50 | >50 to 60 |
| B-107 | Blend of F-5 and at least one of the F-2, 3, 4, 6 | 40 to <50 | >50 to 60 |
| B-108 | Blend of F-4 and at least one of the F-2, 3, 5, 6 | 40 to <50 | >50 to 60 |
| B-109 | Blend of F-3 and at least one of the F-2, 4, 5, 6 | 40 to <50 | >50 to 60 |
| B-110 | Blend of F-2 and at least one of the F-3, 4, 5,6 | 40 to <50 | >50 to 60 |
| B-111 | Blend of F-6 and at least one of the F-2, 3, 4, 5 | 30 to <40 | >60 to 70 |
| B-112 | Blend of F-5 and at least one of the F-2, 3, 4, 6 | 30 to <40 | >60 to 70 |
| B-113 | Blend of F-4 and at least one of the F-2, 3, 5, 6 | 30 to <40 | >60 to 70 |
| B-114 | Blend of F-3 and at least one of the F-2, 4, 5, 6 | 30 to <40 | >60 to 70 |
| B-115 | Blend of F-2 and at least one of the F-3, 4, 5, 6 | 30 to <40 | >60 to 70 |
| B-116 | Blend of F-6 and at least one of the F-2, 3, 4, 5 | 20 to <30 | >70 to 80 |
| B-117 | Blend of F-5 and at least one of the F-2, 3, 4, 6 | 20 to <30 | >70 to 80 |
| B-118 | Blend of F-4 and at least one of the F-2, 3, 5, 6 | 20 to <30 | >70 to 80 |
| B-119 | Blend of F-3 and at least one of the F-2, 4, 5, 6 | 20 to <30 | >70 to 80 |
| B-120 | Blend of F-2 and at least one of the F-3, 4, 5,6 | 20 to <30 | >70 to 80 |
| B-121 | Blend of F-6 and at least one of the F-2, 3, 4, 5 | 10 to <20 | >80 to 90 |
| B-122 | Blend of F-5 and at least one of the F-2, 3, 4, 6 | 10 to <20 | >80 to 90 |
| B-123 | Blend of F-4 and at least one of the F-2, 3, 5, 6 | 10 to <20 | >80 to 90 |
| B-124 | Blend of F-3 and at least one of the F-2, 4, 5, 6 | 10 to <20 | >80 to 90 |
| B-125 | Blend of F-2 and at least one of the F-3, 4, 5,6 | 10 to <20 | >80 to 90 |
| B-126 | Blend of F-6 and at least one of the F-2, 3, 4, 5 | >0 to <10 | >90 to <100 |
| B-127 | Blend of F-5 and at least one of the F-2, 3, 4, 6 | >0 to <10 | >90 to <100 |
| B-128 | Blend of F-4 and at least one of the F-2, 3, 5, 6 | >0 to <10 | >90 to <100 |
| B-129 | Blend of F-3 and at least one of the F-2, 4, 5, 6 | >0 to <10 | >90 to <100 |
| B-130 | Blend of F-2 and at least one of the F-3, 4, 5, 6 | >0 to <10 | >90 to <100 |
| B-131 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 90 to <100 | >0 to 10 |
| B-132 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 80 to <90 | >10 to 20 |
| B-133 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 70 to <80 | >20 to 30 |
| B-134 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 60 to <70 | >30 to 40 |
| B-135 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 50 to < 60 | >40 to 50 |

FIG. 112 Continued

EXAMPLE BLEND FORMULATIONS FOR USE IN PRODUCING FILM 66 (CONTINUED) 276

| BLEND NUMBER | STENT MATERIAL(S) 85 | PART #1 Wt. % | PART #2 Wt.% |
|---|---|---|---|
| B-136 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 40 to <50 | >50 to 60 |
| B-137 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 30 to <40 | >60 to 70 |
| B-138 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 20 to <30 | >70 to 80 |
| B-139 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | 10 to <20 | >80 to 90 |
| B-140 | Blend comprising at least one of F-7, 8, 9, 10, 11, 12, 31, 32, 33, 34, 35, 36, 37, 38, 39, 40, 71, 72, 73, 74, 75, 76, 77, 78, 79, 80 and at least one of the F-1, 2, 3, 4, 5, 6 | >0 to <10 | >90 to <100 |
| B-141 | Blend comprising at least one of F-13, 14, 15, 16, 17, 18, 61, 62, 63, 64, 65, 66, 67, 68, 69, 70 and at least one of the F-1, 2, 3, 4, 5, 6 | 90 to <100 | >0 to 10 |
| B-142 | Blend comprising at least one of F-13, 14, 15, 16, 17, 18, 61, 62, 63, 64, 65, 66, 67, 68, 69, 70 and at least one of the F-1, 2, 3, 4, 5, 6 | 80 to <90 | >10 to 20 |
| B-143 | Blend comprising at least one of F-13, 14, 15, 16, 17, 18, 61, 62, 63, 64, 65, 66, 67, 68, 69, 70 and at least one of the F-1, 2, 3, 4, 5, 6 | 70 to <80 | >20 to 30 |
| B-144 | Blend comprising at least one of F-13, 14, 15, 16, 17, 18, 61, 62, 63, 64, 65, 66, 67, 68, 69, 70 and at least one of the F-1, 2, 3, 4, 5, 6 | 60 to <70 | >30 to 40 |
| B-145 | Blend comprising at least one of F-13, 14, 15, 16, 17, 18, 61, 62, 63, 64, 65, 66, 67, 68, 69, 70 and at least one of the F-1, 2, 3, 4, 5, 6 | 50 to < 60 | >40 to 50 |
| B-146 | Blend comprising at least one of F-13, 14, 15, 16, 17, 18, 61, 62, 63, 64, 65, 66, 67, 68, 69, 70 and at least one of the F-1, 2, 3, 4, 5, 6 | 40 to <50 | >50 to 60 |
| B-147 | Blend comprising at least one of F-13, 14, 15, 16, 17, 18, 61, 62, 63, 64, 65, 66, 67, 68, 69, 70 and at least one of the F-1, 2, 3, 4, 5, 6 | 30 to <40 | >60 to 70 |
| B-148 | Blend comprising at least one of F-13, 14, 15, 16, 17, 18, 61, 62, 63, 64, 65, 66, 67, 68, 69, 70 and at least one of the F-1, 2, 3, 4, 5, 6 | 20 to <30 | >70 to 80 |
| B-149 | Blend comprising at least one of F-13, 14, 15, 16, 17, 18, 61, 62, 63, 64, 65, 66, 67, 68, 69, 70 and at least one of the F-1, 2, 3, 4, 5, 6 | 10 to <20 | >80 to 90 |
| B-150 | Blend comprising at least one of F-13, 14, 15, 16, 17, 18, 61, 62, 63, 64, 65, 66, 67, 68, 69, 70 and at least one of the F-1, 2, 3, 4, 5, 6 | >0 to <10 | >90 to <100 |
| B-151 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 90 to <100 | >0 to 10 |
| B-152 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 80 to <90 | >10 to 20 |
| B-153 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 70 to <80 | >20 to 30 |
| B-154 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 60 to <70 | >30 to 40 |
| B-155 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 50 to < 60 | >40 to 50 |
| B-156 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 40 to <50 | >50 to 60 |
| B-157 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 30 to <40 | >60 to 70 |

FIG. 112 Continued

EXAMPLE BLEND FORMULATIONS FOR USE IN PRODUCING FILM 66 (CONTINUED) 276

| BLEND NUMBER | STENT MATERIAL(S) 85 | PART #1 Wt. % | PART #2 Wt.% |
|---|---|---|---|
| B-158 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 20 to <30 | >70 to 80 |
| B-159 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | 10 to <20 | >80 to 90 |
| B-160 | Blend comprising at least one of F-19, 20, 21, 22, 23, 24, 41, 42, 43, 44, 45, 46, 47, 48, 49, 50, 71, 72, 73, 74, 75, 76, 77, 78, 79, 80 and at least one of the F-1, 2, 3, 4, 5, 6 | >0 to <10 | >90 to <100 |
| B-161 | Blend comprising at least one of F-25, 26, 27, 28, 29, 30, 51, 52, 53, 54, 55, 56, 57, 58, 59, 60 and at least one of the F-1, 2, 3, 4, 5, 6 | 90 to <100 | >0 to 10 |
| B-162 | Blend comprising at least one of F-25, 26, 27, 28, 29, 30, 51, 52, 53, 54, 55, 56, 57, 58, 59, 60 and at least one of the F-1, 2, 3, 4, 5, 6 | 80 to <90 | >10 to 20 |
| B-163 | Blend comprising at least one of F-25, 26, 27, 28, 29, 30, 51, 52, 53, 54, 55, 56, 57, 58, 59, 60 and at least one of the F-1, 2, 3, 4, 5, 6 | 70 to <80 | >20 to 30 |
| B-164 | Blend comprising at least one of F-25, 26, 27, 28, 29, 30, 51, 52, 53, 54, 55, 56, 57, 58, 59, 60 and at least one of the F-1, 2, 3, 4, 5, 6 | 60 to <70 | >30 to 40 |
| B-165 | Blend comprising at least one of F-25, 26, 27, 28, 29, 30, 51, 52, 53, 54, 55, 56, 57, 58, 59, 60 and at least one of the F-1, 2, 3, 4, 5, 6 | 50 to < 60 | >40 to 50 |
| B-166 | Blend comprising at least one of F-25, 26, 27, 28, 29, 30, 51, 52, 53, 54, 55, 56, 57, 58, 59, 60 and at least one of the F-1, 2, 3, 4, 5, 6 | 40 to <50 | >50 to 60 |
| B-167 | Blend comprising at least one of F-25, 26, 27, 28, 29, 30, 51, 52, 53, 54, 55, 56, 57, 58, 59, 60 and at least one of the F-1, 2, 3, 4, 5, 6 | 30 to <40 | >60 to 70 |
| B-168 | Blend comprising at least one of F-25, 26, 27, 28, 29, 30, 51, 52, 53, 54, 55, 56, 57, 58, 59, 60 and at least one of the F-1, 2, 3, 4, 5, 6 | 20 to <30 | >70 to 80 |
| B-169 | Blend comprising at least one of F-25, 26, 27, 28, 29, 30, 51, 52, 53, 54, 55, 56, 57, 58, 59, 60 and at least one of the F-1, 2, 3, 4, 5, 6 | 10 to <20 | >80 to 90 |
| B-170 | Blend comprising at least one of F-25, 26, 27, 28, 29, 30, 51, 52, 53, 54, 55, 56, 57, 58, 59, 60 and at least one of the F-1, 2, 3, 4, 5, 6 | >0 to <10 | >90 to <100 |
| B-171 | Blend comprising at least one of F-7, 8, 9, 10, 11, 12 and at least one of F-19, 20, 21, 22, 23, 24 | 90 to <100 | >0 to 10 |
| B-172 | Blend comprising at least one of F-7, 8, 9, 10, 11, 12 and at least one of F-19, 20, 21, 22, 23, 24 | 80 to <90 | >10 to 20 |
| B-173 | Blend comprising at least one of F-7, 8, 9, 10, 11, 12 and at least one of F-19, 20, 21, 22, 23, 24 | 70 to <80 | >20 to 30 |
| B-174 | Blend comprising at least one of F-7, 8, 9, 10, 11, 12 and at least one of F-19, 20, 21, 22, 23, 24 | 60 to <70 | >30 to 40 |
| B-175 | Blend comprising at least one of F-7, 8, 9, 10, 11, 12 and at least one of F-19, 20, 21, 22, 23, 24 | 50 to < 60 | >40 to 50 |
| B-176 | Blend comprising at least one of F-7, 8, 9, 10, 11, 12 and at least one of F-19, 20, 21, 22, 23, 24 | 40 to <50 | >50 to 60 |
| B-177 | Blend comprising at least one of F-7, 8, 9, 10, 11, 12 and at least one of F-19, 20, 21, 22, 23, 24 | 30 to <40 | >60 to 70 |
| B-178 | Blend comprising at least one of F-7, 8, 9, 10, 11, 12 and at least one of F-19, 20, 21, 22, 23, 24 | 20 to <30 | >70 to 80 |
| B-179 | Blend comprising at least one of F-7, 8, 9, 10, 11, 12 and at least one of F-19, 20, 21, 22, 23, 24 | 10 to <20 | >80 to 90 |
| B-180 | Blend comprising at least one of F-7, 8, 9, 10, 11, 12 and at least one of F-19, 20, 21, 22, 23, 24 | >0 to <10 | >90 to <100 |

FIG. 112 Continued

TABLE OF LIQUID FILM 87 AND SOLID FILM 66 THICKNESSES WHEN USING SOLUTIONS 83 HAVING DIFFERENT STENT MATERIAL 85 CONCENTRATIONS

| Liquid Film Thickness (mm) 88 | Approximate Solid Film Thickness (mm) 67 | | | | | | | | | |
|---|---|---|---|---|---|---|---|---|---|---|
| Stent Material 85 Concentration In Solution 83 (vol. %) | 1% | 2% | 3% | 4% | 5% | 6% | 7% | 8% | 9% | 10% |
| 0.0254 | 0.0003 | 0.0005 | 0.0008 | 0.0010 | 0.0013 | 0.0015 | 0.0018 | 0.0020 | 0.0023 | 0.0025 |
| 0.0508 | 0.0005 | 0.0010 | 0.0015 | 0.0020 | 0.0025 | 0.0030 | 0.0036 | 0.0041 | 0.0046 | 0.0051 |
| 0.0762 | 0.0008 | 0.0015 | 0.0023 | 0.0030 | 0.0038 | 0.0046 | 0.0053 | 0.0061 | 0.0069 | 0.0076 |
| 0.1016 | 0.0010 | 0.0020 | 0.0030 | 0.0041 | 0.0051 | 0.0061 | 0.0071 | 0.0081 | 0.0091 | 0.0102 |
| 0.1270 | 0.0013 | 0.0025 | 0.0038 | 0.0051 | 0.0064 | 0.0076 | 0.0089 | 0.0102 | 0.0114 | 0.0127 |
| 0.1524 | 0.0015 | 0.0030 | 0.0046 | 0.0061 | 0.0076 | 0.0091 | 0.0107 | 0.0122 | 0.0137 | 0.0152 |
| 0.1778 | 0.0018 | 0.0036 | 0.0053 | 0.0071 | 0.0089 | 0.0107 | 0.0124 | 0.0142 | 0.0160 | 0.0178 |
| 0.2032 | 0.0020 | 0.0041 | 0.0061 | 0.0081 | 0.0102 | 0.0122 | 0.0142 | 0.0163 | 0.0183 | 0.0203 |
| 0.2286 | 0.0023 | 0.0046 | 0.0069 | 0.0091 | 0.0114 | 0.0137 | 0.0160 | 0.0183 | 0.0206 | 0.0229 |
| 0.2540 | 0.0025 | 0.0051 | 0.0076 | 0.0102 | 0.0127 | 0.0152 | 0.0178 | 0.0203 | 0.0229 | 0.0254 |
| 0.2794 | 0.0028 | 0.0056 | 0.0084 | 0.0112 | 0.0140 | 0.0168 | 0.0196 | 0.0224 | 0.0251 | 0.0279 |
| 0.3048 | 0.0030 | 0.0061 | 0.0091 | 0.0122 | 0.0152 | 0.0183 | 0.0213 | 0.0244 | 0.0274 | 0.0305 |
| 0.3302 | 0.0033 | 0.0066 | 0.0099 | 0.0132 | 0.0165 | 0.0198 | 0.0231 | 0.0264 | 0.0297 | 0.0330 |
| 0.3556 | 0.0036 | 0.0071 | 0.0107 | 0.0142 | 0.0178 | 0.0213 | 0.0249 | 0.0284 | 0.0320 | 0.0356 |
| 0.3810 | 0.0038 | 0.0076 | 0.0114 | 0.0152 | 0.0191 | 0.0229 | 0.0267 | 0.0305 | 0.0343 | 0.0381 |
| 0.4064 | 0.0041 | 0.0081 | 0.0122 | 0.0163 | 0.0203 | 0.0244 | 0.0284 | 0.0325 | 0.0366 | 0.0406 |
| 0.4318 | 0.0043 | 0.0086 | 0.0130 | 0.0173 | 0.0216 | 0.0259 | 0.0302 | 0.0345 | 0.0389 | 0.0432 |
| 0.4572 | 0.0046 | 0.0091 | 0.0137 | 0.0183 | 0.0229 | 0.0274 | 0.0320 | 0.0366 | 0.0411 | 0.0457 |
| 0.4826 | 0.0048 | 0.0097 | 0.0145 | 0.0193 | 0.0241 | 0.0290 | 0.0338 | 0.0386 | 0.0434 | 0.0483 |
| 0.5080 | 0.0051 | 0.0102 | 0.0152 | 0.0203 | 0.0254 | 0.0305 | 0.0356 | 0.0406 | 0.0457 | 0.0508 |

BIORESORBABLE, IMPLANTABLE DEVICE HAVING CONTROLLED DRUG DELIVERY

PRIORITY CLAIMS

This divisional application claims benefits of Regular patent application Ser. No. 15/863,822 filed Jan. 5, 2018, entitled "BIORESORBABLE SCAFFOLD HAVING SUSTAINED DRUG DELIVERY" and Provisional Patent Application Ser. No. 62/443,101 filed Jan. 6, 2017 entitled "ANISIOTROPIC BIORESORBABLE STENT FORMED FROM INTERCONNECTED LAYERS OF HIGH MOLECULAR WEIGHT ISOTROPIC FILM."

FIELD OF INVENTION

The present invention relates to drug-eluting medical devices.

BACKGROUND OF INVENTION

When we talk to medical doctors, we find that there is a need for a medical device that provides mechanical support and local drug delivery. Many surgical procedures include the treatment of an injury that requires mechanical support to temporarily stabilize the treated area during healing and drug delivery to control scar tissue formation. Our bioresorbable film, roll, tube, and stent can satisfy this unmet need.

One example of the need to provide mechanical support and drug delivery is found in the treatment of atherosclerosis. Atherosclerosis is presently treated with an angioplasty procedure that comprises the steps of inserting an uninflated balloon catheter into a constricted segment of an artery, expanding the balloon in a way that compresses the plaque buildup against the artery so that the artery's passageway is opened to restore blood flow, deflating the balloon catheter, and then withdrawing the balloon catheter from the treated segment (the "treatment site"). The angioplasty procedure imparts an injury on the artery that can form scar tissue (aka neointimal hyperplasia) that can reclose the artery as it heals from the injury. A stent is delivered to the newly opened artery segment in a reduced diameter and expanded in diameter to provide radial support to the artery until it heals. The stent can also deliver a drug that inhibits scar tissue formation (neointimal growth). Historically, stents are made of metal alloys. The problem with a metal stent is that patients that suffer from atherosclerosis generally do not change their lifestyle choices and many patients will require a future re-vascularization procedure. The permanent metal implant can interfere with the re-vascularization procedure. In contrast, a bioresorbable stent provides temporarily radial support and drug delivery until the artery is healed and then the bioresorbable stent dissolves and is eliminated from the treated artery segment.

The industry's first generation bioresorbable stents had thick struts that protruded too far into the passageway of the artery and therefore sometimes created a thrombotic condition. Additionally, the first generation bioresorbable stents were made of low molecular weight bioresorbable polymers that were brittle and could fracture when over-expanded by the balloon catheter during deployment within the treatment site. The low molecular weight bioresorbable polymer also had a problem of fast dismantling, which resulted in early strut discontinuities that reduces the stent's radial strength. Additionally, the industry's first generation bioresorbable stents were radiolucent except for small radiopaque markers located on the proximal and distal ends of the stent, which made it difficult for clinicians to determine if the bioresorbable stent was in apposition with the artery.

The prior art bioresorbable stents have a thin drug-polymer matrix coating adhered to the outer surface of the stent. The thin surface applied coating typically released the drug during the first 90 days post implantation. The rapidly released drug has little time to diffuse into the adjacent tissue because liquid body fluids wash at least one part of the released drug away from the treatment site. To compensate for drug losses into the bloodstream the prior stents had high drug dosages that have been shown to inhibit healing of the injury imparted on opened segment of the artery. Our innovative bioresorbable stent is superior because the drug is positioned in strategically located layers that can be located on the outside surface(s) and/or inside of the thickness of the bioresorbable stent. These drug layers control the drug delivery onset time and release rate of the drug so that the drug can more effectively diffuse into the local tissue without side effects. For example, in vascular applications the released drug can prevent scar tissue development without interfering endothelial cells covering the struts.

SUMMARY

The present invention is a bioresorbable, implantable medical device. The bioresorbable, implantable medical device comprises the configuration of a film, a roll, a tube and/or a stent (aka a "Scaffold"). The bioresorbable, implantable device provides a therapeutic treatment. For example, the bioresorbable, implantable device provides mechanical support and/or drug delivery. The bioresorbable, implantable device comprises a material that undergoes a resorption process, wherein the term "resorption" refers to the material losing its mass after the bioresorbable, implantable device is implanted in the body. In layman's terms the bioresorbable material can be thought of as a material that dissolves and disappears from the implantation site over time while the therapy is performed and/or after the therapy is completed.

A bioresorbable stent, which is sometimes referred to as a scaffold, is fundamentally bioresorbable material configured into a series of sinusoidal or zigzag shaped linear ring struts that are held together with connecting link struts (collectively hereinafter referred to as the "struts"). Although at first glance the external appearance of all stents may look similar, there are significant differences within the struts' wall thicknesses. The present invention is different because the stent struts comprise layers.

The present invention is a bioresorbable stent comprising at least one raw material comprising ultra-high weight average molecular weight (Mw) bioresorbable polymer(s). Including at least one ultra-high weight average molecular weight (Mw) bioresorbable polymer raw material within the stent is beneficial because it produces a stronger stent. Additionally, the ultra-high weight average molecular weight (Mw) bioresorbable polymer provides greater ductility than a lower weight average molecular weight (Mw) bioresorbable polymer. An ultra-high weight average molecular weight (Mw) bioresorbable polymer also degrades more slowly than a low molecular weight polymer, which means that it retains its strength longer. A stronger bioresorbable polymer enables the use of thinner struts, minimizes or eliminates vascular recoil during injury healing after deployment of the stent, and/or reduces the risk of strut fracture during stent crimping and deployment. The ultra-high weight average molecular weight (Mw) polymer makes excellent drug release barriers that are useful in producing the bioresorbable stent having controlled drug delivery. Controlling drug delivery may affect the timing of the drug release or the duration of drug delivery. Although the ultra-high weight average molecular weight (Mw) bioresorbable polymer more slowly degrades than a lower weight average molecular weight (Mw) bioresorbable polymer, the stent of the present invention has significantly less mass, which may reduce the resorption time (i.e., the time when the mass of the stent is no longer present in the treatment site). The ultra-high weight average molecular weight (Mw) bioresorbable polymer may also enable the use of bioresorbable stents in more applications such as in branched or bifurcated anatomical lumens.

The present invention of the bioresorbable stent comprises at least one layer of a therapeutic substance. The bioresorbable stent having controlled drug delivery is produced from a tube that is formed from at least one relatively long, thin film that is wrapped around the central axis of the tube multiple times in a roll configuration. The film is made by dissolving at least one bioresorbable polymer in at least one liquid solvent to form a liquid solution. Additionally, at least one active ingredient (the "drug") may be incorporated into the liquid solution. The liquid solution is poured on a release media to form a thin liquid film on the release media, which results in a thin solid film temporarily adhered to the release media when the solvent is removed from the liquid film. The solid film is removed from the release media by peeling the solid film off the release media and organizing the solid film into a roll configuration. Alternatively, the liquid film can be directly formed in the roll configuration on a shape forming device and the solvent removed from the liquid film to form the tube. The therapeutic substance is incorporated into the tube wall thickness by positioning the therapeutic substance within at least one part of the film wall thickness or on at least one part of the outer major surfaces of the film prior to organizing the film into the shape of the roll. The very thin film thicknesses that are organized in a roll configuration are interconnected to the adjacent film thicknesses, which bonds the adjacent film thicknesses and results in a rigid tube having a solid tube wall thickness. The tube is converted into the stent by cutting a strut pattern into the tube.

The stent may include one or more coating(s) positioned on the outside surface(s) of the stent or components within the stent. The coating(s) may include one or more active ingredient(s) that are delivered within the treatment site and function as a therapeutic drug during one part of or the entire the treatment time. The coating(s) may also control or delay the degradation, corrosion, solubility, or erosion rate of the material(s) comprising the stent. The coating(s) may also increase the bond strength between the matrix and the reinforcement(s). Moreover, the coating(s) may also provide radiopacity to the stent.

The stent is delivered to the treatment site on a catheter. So that the stent can be delivered to the treatment site within the anatomical lumen, the outer diameter of the stent is temporarily reduced so that it has a low crossing profile by crimping the stent on the catheter. After crimping the stent on the catheter, the assembly is packaged, and sterilized. After delivery of the stent to the treatment site, where the catheter expands the nominal diameter of the stent from its crimped size to its deployed size, the catheter is withdrawn, and the stent temporarily supports the anatomical lumen until the treatment is completed. Preferably the implanted bioresorbable stent delivers at least one active ingredient. The degradative by-products from the stent are absorbed and/or resorbed.

Our invention provides a stent addressing the need for a better bioresorbable stent having (1) a controlled delivery of at least one therapeutic substance during at least one part of the duration that the mass of the stent is present within the anatomical lumen; (2) increased radial strength during the treatment time; (3) thinner struts to increase luminal capacity during the treatment time; (4) narrower struts to minimize anatomical lumen wall contact surface area and blockage of side artery branches; (5) thinner and/or narrower struts to improve the capability of the endothelial cells that are positioned on the inner lining of the anatomical lumen to cover the apposed struts to lower the risk of late stent thrombosis during the treatment time; (6) reduced strut fracturing; (7) improved radiopacity; (8) more controlled resorption rate; and (9) substantially complete stent mass loss to un-cage the vessel after the treatment time to partially or fully restore vasomotion and/or enable the anatomical lumen to partially or fully restore the vessel's normal capability of auto-regulating blood flow.

Accordingly, it is one object of the present invention to provide a bioresorbable film that includes or excludes at least one active ingredient.

Another object of the present invention is to provide a bioresorbable roll that includes or excludes at least one active ingredient.

One more object of the present invention is to provide a bioresorbable tube that includes or excludes at least one active ingredient.

It is an additional object of the present invention to provide a bioresorbable stent that includes or excludes at least one active ingredient.

A major object of the present invention is to provide a bioresorbable stent having a thin strut that has sufficient radial strength to support an artery opened by angioplasty balloon.

Another object of the present invention is to provide a bioresorbable stent having improved ductility to prevent the fracturing of the stent under normal operational conditions found during the delivery and/or deployment.

An object of the present invention is to provide a bioresorbable stent comprising one or more ultra-high weight average molecular weight (Mw) polymer(s).

Another object of the present invention is to provide method of forming the stent wall thickness in layers that degrade and/or resorb at different time intervals.

An object of the present invention is to include a plurality of radio dense reinforcements that make a radiopaque stent so that the stent is visible and imagable during delivery and deployment.

Finally, it is the object of the present invention to form a stent of ultra-high weight average molecular weight (Mw) raw material bioresorbable polymer(s) that results in a stent comprising post-processed polymer(s) having a weight average molecular weight (Mw) that is greater than 130 kilodaltons (kDa), 130 kilograms per mole (kg/mol) or an Inherent Viscosity that is greater than 1.3 dl/g.

BRIEF DESCRIPTION OF DRAWINGS

FIG. 3-5 depict various embodiments of a coating containing active ingredient(s) adhered to a linear ring strut or a link strut in cross sectional view.

FIG. 6 and FIG. 7 depict a cross-sectional view of a portion of a coating.

FIG. 8 depicts the linear ring strut or the link strut comprising five layers.

FIG. 9, FIG. 10, and FIG. 11 depict side view illustrations of the stent being delivered and deployed within an anatomical lumen within the treatment site.

FIG. 12 depicts a perspective view of an un-oriented tube.

FIG. 13 depicts a perspective view of an oriented tube.

FIG. 14 depicts an un-oriented tube including seams.

FIG. 15 depicts an exploded end view of a roll and FIG. 16 depicts an exploded, cross-sectional side view taken through section B-B of FIG. 15 of an embodiment of the roll.

FIG. 17 depicts a solid film.

FIG. 18 depicts a shaft.

FIG. 19 and FIG. 20 depict wrapping at least one solid film around the shaft.

FIG. 21 depicts the roll on the shaft and

FIG. 22 depicts a portion of the roll wherein the Over-Film Thickness passes over the Under-Film Thickness.

FIG. 23 depicts a liquid film on the left and the solid film on the right after a liquid solution is deposited on a release media.

FIG. 24 depicts the solid film excluding the active ingredient(s),

FIG. 25 depicts the solid film including the active ingredients within the solid film thickness and FIG. 26 depicts two solid films having active ingredient(s) positioned between the two film thicknesses.

FIG. 27 depicts a laminate comprised of three (3) solid films.

FIG. 28 depicts a fibrous sheet and FIG. 29 depicts a fiber.

FIG. 30 depicts a multi-fiber comprised of ten (10) fibers.

FIG. 31 depicts an infused fibrous sheet.

FIG. 32 depicts a fiber reinforced laminate comprised of at least one (1) solid film and at least one (1) fibrous sheet.

FIG. 33 depicts a side view of an embodiment of the Indirect Roll Formation Process, which comprises wrapping the solid film around the shaft to form the roll.

FIG. 34 depicts an exploded end view of an embodiment of the roll comprising a solid film.

FIG. 35. depicts a exploded side view of an embodiment of the Indirect Roll Formation process, which comprises wrapping two completely superimposed solid films around the shaft to form the roll.

FIG. 36 depicts an exploded end view of an embodiment of the roll comprising two superimposed solid films.

FIG. 37. depicts an exploded side view of an embodiment of the Indirect Roll Formation process, which comprises wrapping three completely superimposed solid films around the shaft to form the roll.

FIG. 43 depicts a side view of an embodiment of the Indirect Roll Formation Process, which comprises wrapping three solid films that are positioned in series around the shaft to form the roll.

FIG. 45, FIG. 47, FIG. 48, FIG. 50, and FIG. 51 depict embodiments of a side view of the Indirect Roll Formation Process Including Active Ingredients, which comprises wrapping solid film(s) including active ingredient(s) that are positioned on the surface of the film around the shaft to form the roll.

FIG. 46 and FIG. 49 depict an embodiment of the Roll Including Active Ingredient(s), wherein the roll depicted in FIG. 34 includes the active ingredients between at least two film thicknesses.

FIG. 55 depicts an exploded side view of the Indirect Roll Formation Process Including Multiple Films, which comprises wrapping three solid films having active ingredient(s) positioned between at least two of the films around the shaft to form the roll.

FIG. 56 depicts an embodiment of the Roll Including Active Ingredient(s), wherein the roll depicted in FIG. 38 includes the active ingredients positioned between at least two film thicknesses.

FIG. 57 depicts an embodiment the Indirect Roll Formation Process Including Active Ingredient(s) comprising the shaft, three different solid films positioned in series and the active ingredient(s) positioned on at least part or all of the film major surface of the middle solid film wherein the solid film A is positioned near the Beginning Of The Roll, the solid film C is positioned near the End Of The Roll and the solid film B is positioned between the solid film A and the solid film B to produce the Roll Including Active Ingredient(s) depicted in FIG. 58 that is formed into the tube that is made into the stent.

FIG. 58 depicts an embodiment of the Roll Including Active Ingredient(s), wherein the roll depicted in FIG. 44 includes the active ingredients.

FIG. 59 depicts an embodiment the Indirect Roll Formation Process Including Multiple Films comprising the shaft, two partially superimposed solid films and active ingredient(s), wherein the first solid film A is longer than the second solid film B and the active ingredient(s) are located between the solid film A and the solid film B to produce the Roll Including Active Ingredient(s) depicted in FIG. 60 that is formed into the tube that is made into the stent 10.

FIG. 60 and FIG. 61 depict embodiments of the Roll Including Active Ingredient(s), wherein the roll depicted in FIG. 40 includes the active ingredients.

FIG. 62, FIG. 63, FIG. 64, FIG. 65, FIG. 66, and FIG. 67 depict exploded side views of the Indirect Roll Formation Process Including Active Ingredients, which comprise wrapping solid film(s) including active ingredient(s) that are positioned within the thickness of the film around the shaft to form the roll.

FIG. 68 depicts the Heated Un-Oriented Tube Former and FIG. 69 depicts the Solvent Un-Oriented Tube Former.

FIG. 70 thru FIG. 75 and FIG. 94 thru 100 depict embodiments multi-layer wall thicknesses.

FIG. 76 thru FIG. 93 depicts stent wall thicknesses comprising multiple film thicknesses.

FIG. 101 depicts a Direct Roll Formation Process.

FIG. 102 thru FIG. 107 depict high and low molecular weight stent material molecule chains being cleaved into lower molecular weight stent molecule chains.

FIG. 108 depicts the stent combined with a graft to form a stent-graft.

FIG. 109 and FIG. 110 depict embodiments of devices that convert a non-concentric tub into a concentric tube.

FIG. 111 depicts Example Material Formulations For Use in Producing The Film that is formed into the un-oriented tube, which is converted into the oriented tube and/or the stent.

FIG. 112 depict Example Blend Formulations For Use in Producing The Film that is formed into the un-oriented tube, which is converted into the oriented tube and/or the stent.

INCORPORATION BY REFERENCE

All publications and patent applications mentioned in this specification are hereby incorporated by reference.

DETAILED DESCRIPTION OF PREFERRED EMBODIMENTS

Overview

Figure 1:
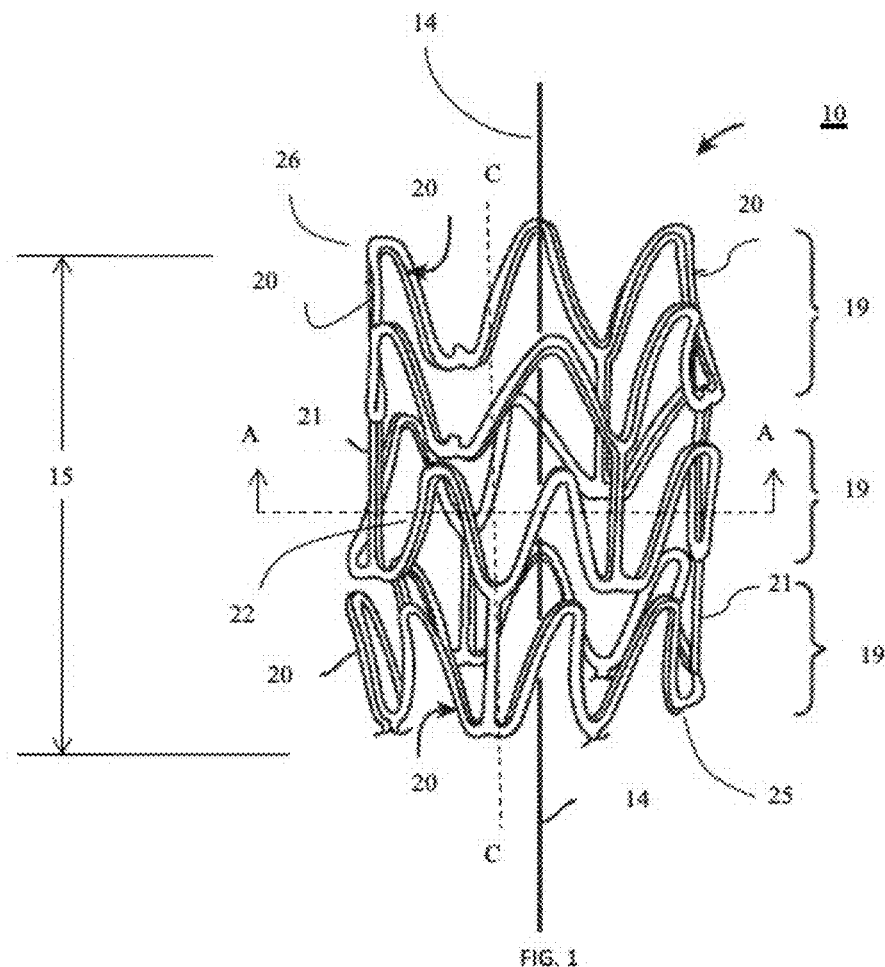
FIG. 1 depicts a perspective view of a portion of a stent.
Figure 2:
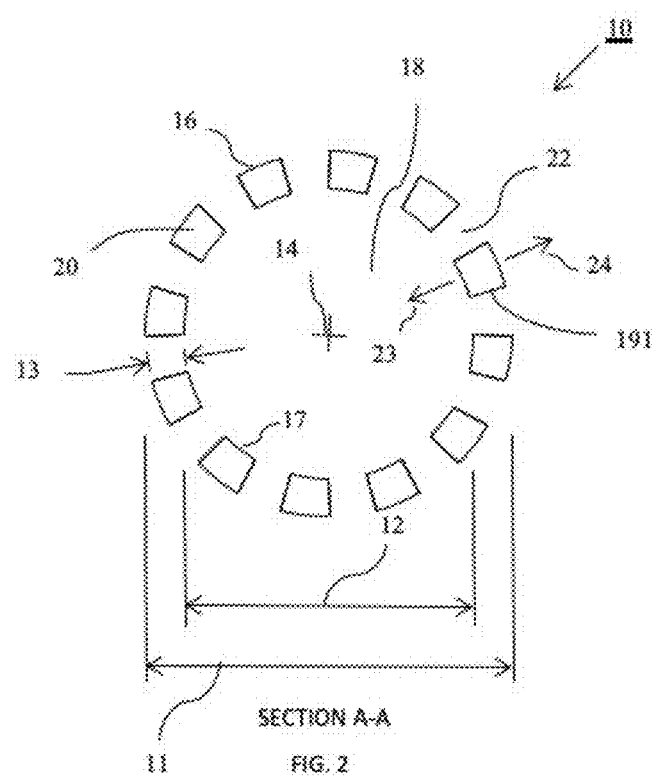
FIG. 2 depicts a cross-sectional view of a series of linear ring struts (excluding the link struts) taken through section A-A of FIG. 1.

The present invention relates to a stent 10. The bioresorbable stent 10 is sometimes referred to in the industry as a scaffold, but for simplicity and to be consistent with historical nomenclature, the scaffold is hereinafter referred to as the "stent 10". FIG. 1 depicts a perspective view of a portion of the stent 10 and FIG. 2 depicts a cross-sectional view of the stent 10 depicted in FIG. 1 through line A-A. The stent 10 is comprised of at least one stent material 85, a stent outer diameter 11, a stent inner diameter 12, a stent wall thickness 13, a stent central axis 14, a stent length 15, a stent outer surface 16, a stent inner surface 17, a stent central passageway 18, a plurality of rings 19, a plurality of linear ring struts 20, a plurality of link struts 21, a plurality of cells 22, a plurality of cutting surfaces 191, an inward direction 23, an outward direction 24, a proximal end 25, and a distal end 26. The rings 19 are arranged in series and interconnected by the link struts 21.

The stent 10 of the present invention may be of any dimensions that meet the requirements of the end-use applications and/or treatments. Without limitation, the stent's inner diameter 12 may be in the range of about 1.0 millimeter ("mm") to 30 mm and the length 15 may range from about 6 mm to 200 mm. In other embodiments, the stent's 10 inner diameter 12 may be equal to or less than 1 mm or equal to or greater than 30 mm to 45 mm and the stent's 10 length 15 may be equal to or less than 6 mm or equal to or greater than 200 mm to 800 mm. In the preferred embodiment the stent's wall thickness 13 may range from about 0.020 mm to 0.500 mm. In other embodiments, the stent's wall thickness 13 may be equal to or less than 0.020 mm or equal to or greater than 0.500 mm to 1.0 mm. The linear ring strut width 279 (depicted in FIG. 114) and the link strut width 280 (depicted in FIG. 114) may be in the range of about 0.030 to 0.400 mm. In other embodiments the linear ring strut width 279 and the link strut width 280 may be less than 0.030 mm or greater than 0.400 mm.

In the preferred embodiment, the stent 10 includes a stent-to-anatomical lumen coverage area ("STALCA") within the range of greater than 0.0% to about less than 99.0%, more preferably in the range of about 1.0% to 45.0%, and most preferably equal to or less than about 35.0% or whatever is experimentally determined to be the optimum STALCA for the end-use application determined by those skilled in the art. For example, the STALC may be less than 10%, less than 15%, less than 20%, less than 25%, less than 30%, less than 40% or less than 50%. In other embodiments, the stent 10 includes a STALCA equal to or greater than 90% to 100%. The STALCA equals the surface area of the stent's 40 abluminal surface 16 area divided by the surface area of the anatomical lumen 36 within the treatment site.

In the preferred embodiment, the stent 10 or implanted stent 10 has a radial strength within the range of greater than 0.0 millimeters mercury ("mm Hg") to about 1,800 mm Hg, more narrowly in the range of about 400 mm Hg to 1,800 mm Hg until the anatomical lumen 36 is self-supporting. In other embodiments, the stent 10 or implanted stent 10 has a radial strength equal to or above 1,800.0 mm Hg to 10,000 mm Hg. The required strength of the implanted stent 10 is dependent on the treatment as known by those skilled in the art of stenting.

FIG. 3 depicts a non-limiting example of a Coating On Strut 29. As depicted in FIG. 3, the wall thickness 13 of the stent 10 may include a coating 30. The coating 30 may be adhered to part or all the surfaces and/or components of the stent 10. For, example the coating 30 may be adhered to all the outer surfaces of the struts 20, 21 as depicted in FIG. 3, on the outer surface 16 of the struts 20, 21 as depicted in FIG. 4 or on the outer surface 16 and the two cutting edges 191 as depicted in FIG. 5. The coating 30 may be adhered to the inner surface 17 (not depicted). In an embodiment, the stent 10 is a "bare" stent 10, which means the stent 10 does not include the coating 30. As depicted in FIG. 6, which is a cross sectional I view of a non-limiting example of a portion of the coating 30, the coating 30 is comprised of a coating material 31 and a coating thickness 33. As depicted in FIG. 7, which is a cross-sectional view of a non-limiting example of a portion the coating 30, the coating 30 may be comprised of one or more coating layer(s) 32. The coating 30 depicted in FIG. 7 is comprised of five coating layers 32, but there may be any number of coating layers 32 within the coating thickness 33. The stent 10 and/or the coating 30 may include one or more therapeutic substances in the form of an active ingredient 34, wherein one or more active ingredient(s) 34 means that the active ingredient 34 has either one chemical composition ("one active ingredient") or multiple chemical compositions ("multiple active ingredients"). The active ingredient(s) 34 are depicted as black circles in the figures having the same size. The active ingredients(s) 34 may be other shapes and may be of different sizes in other embodiments. There may be spacing between the active ingredient(s) 34, wherein the spacing is the same or different. Although the figures depict only one row of the active ingredient(s) 34 there may be one or multiple rows of the active ingredient(s) 34. The adhered coating 30 may include an amorphous active ingredient 34 and the body of the stent 10 may include a crystalline active ingredient 34.

The stent 10 wall thickness 13 comprises at least one layer 51. In an embodiment, the stent 10 comprises multiple layers 51 as depicted in FIG. 8. Although, FIG. 8 depicts five layers 51, there can be up to two thousand layers 51 within the linear ring strut 20 and link strut 21 wall thicknesses 13.

As depicted in FIG. 9, FIG. 10, and FIG. 11 in an embodiment, the stent 10 is configured so that it may be deployed within an anatomical lumen 36 at a treatment site 35. The treatment site 35 is the portion of the anatomical lumen 36 wherein at least one part of the outer surface 16 of the linear ring struts 20 and the link struts 21 contact the anatomical lumen 36. In the preferred embodiment, the anatomical lumen 36 is a blood carrying tubular vessel or blood vessel. In other embodiments, the anatomical lumen 36 may be other living body parts. Without intent on limiting, the clinical need for the stent 10 is to help prop open the partially or fully clogged anatomical lumen 36 and decrease its chance of narrowing again, deliver therapeutic drugs that minimize or prevent restenosis and/or device thrombosis, and/or provide other treatments. The stent 10 is delivered and deployed within the anatomical lumen 36 at the treatment site 35 with a catheter 37. One or more content(s) 6 may flow from the proximal end 25 to the distal end 26 of the stent 10, or vice versa, after deployment of the stent 10.

The stent 10 is preferably comprises an un-oriented tube 42 (FIG. 12) or an oriented tube 38 (FIG. 13). FIG. 13 depicts the oriented tube 38. The oriented tube 38 is comprised of an oriented tube outer diameter 40, an oriented tube inner diameter 41, an oriented tube wall thickness 27, an oriented tube central axis 7, an oriented tube outer surface 29, an oriented tube inner surface 9, an oriented tube length 39 and an oriented tube central passageway 8. FIG. 12 depicts the un-oriented tube 42. The un-oriented tube 42 is comprised of an un-oriented tube inner diameter 43, an un-oriented tube outer diameter 44, an un-oriented tube wall thickness 45, an un-oriented tube length 46, an un-oriented tube outer surface 47, an un-oriented tube inner surface 48, an un-oriented tube central passageway 5 and an un-oriented tube central axis 4. FIG. 14 depicts an Un-oriented Tube Including Seam(s) 49. The stent 10 may comprise a tube including seam(s) 49. The Un-oriented Tube Including Seam(s) 49 is comprised of the solid film 66 and a seam 50. The seam(s) 50 may be oriented perpendicular to the central axis 4 or at any angle to the central axis 4. The seam 50 comprises overlapping and/or abutting film minor surfaces 71 that are interconnected.

Figures 113, 114, 115:
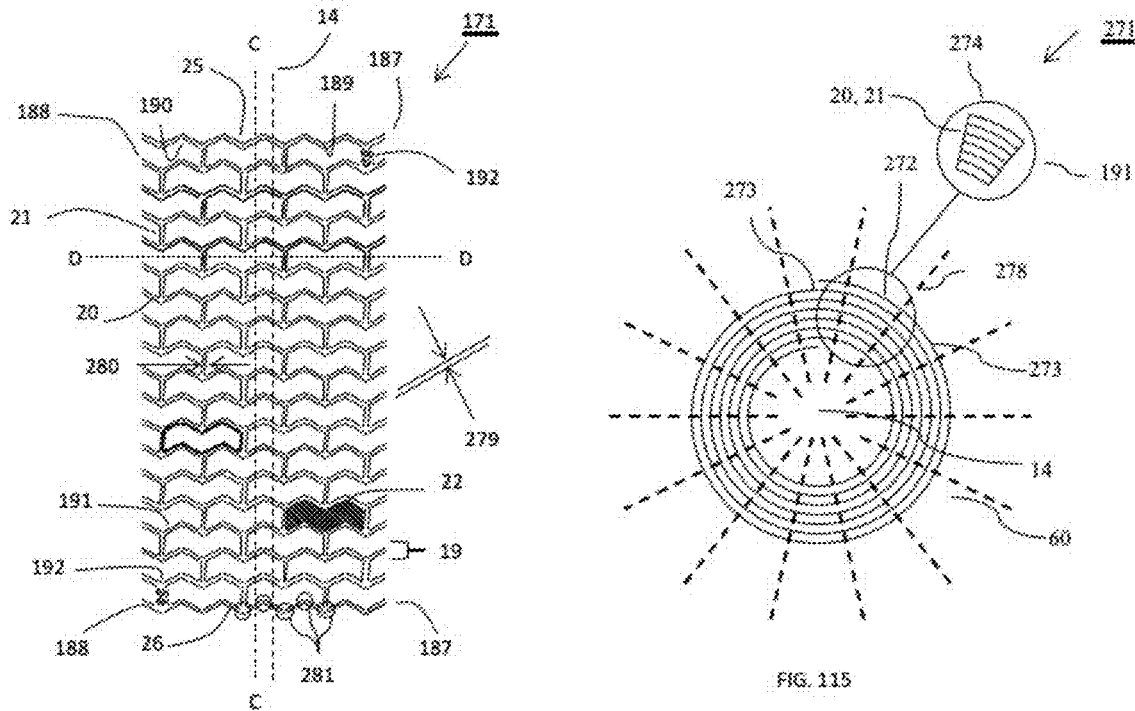
FIG. 113 depicts a Table of Liquid Film And Solid Film Thicknesses When Using Solutions Having Different Stent Material Concentrations that is formed into the solid film that is formed into the un-oriented tube, which is converted into the oriented tube and/or the stent.
FIG. 114 is a strut pattern.
FIG. 115 depicts an embodiment of an exploded un-oriented tube or an exploded oriented tube, wherein parts of the wall thicknesses are being removed to produce the stent.

In the preferred embodiment, the un-oriented tube 42 comprises a roll 52. The roll 52 comprises an arrangement of at least one solid film 66 in a spiral configuration as depicted in FIG. 15 and FIG. 16. As depicted in FIG. 15 and FIG. 16, the roll 52 comprises a roll outer diameter 54, a roll inner diameter 55, a roll length 56, a roll thickness 57, a beginning of roll 58, an end of roll 59, a distance between the film thicknesses 60, a roll outer surface 61, a roll inner surface 62, the roll passageway 64, and the roll central axis 63. The solid film 66 comprises a film thickness 67, a film length 68, a film width 69, a film central axis 70, a film long minor surface 71, a film short minor surface 72 and a film major surface 73 as depicted in FIG. 17. The roll 52 is formed on a cylindrical-shaped shaft 74 as depicted in FIG. 18. In another embodiment, the solid film 66 comprises at least one fiber 116. The shaft 74 comprises a shaft outer diameter 75, a shaft length 76, a shaft central axis 77, and shaft outer surface 78 as depicted in FIG. 17. In an embodiment, the shaft 74 may also include a tapered shaft length 76 to facilitate removal of the un-oriented tube 42 from the shaft 74. The film width 69 is generally what is needed to produce at least one stent 10. The film thickness 67 is preferably less than 0.025 mm. In other embodiments, the film thickness 67 can be as thin as 0.00005 mm. However, typically the film thickness 67 is in the range of what is depicted in FIG. 113. The film length 68 can be relatively long. For example, to produce the roll 52 depicted in FIG. 34 with a solid film 66 having the film thickness 67 equal to 0.0038 mm, the film length 68 is about 203 mm to produce an un-oriented tube 42 having a wall thickness 45 equal to 0.080 mm. In other embodiments, the film length 68 may be longer or shorter depending on the desired tube diameter, wall thickness and film thickness.

Wrapping at least one solid film 66 around the shaft outer surface 78 multiple times as depicted in FIG. 19 forms the roll 52. Alternatively, or additionally, wrapping multiple solid films 66 around the shaft 74 forms the roll 52 as depicted in FIG. 20. The film thicknesses 67 are interconnected at the bond 65, which is positioned between each of the adjacent film thicknesses 67 as depicted in FIG. 21, which depicts an exploded side view of the Roll On Shaft 53. FIG. 21 depicts four bonds 65. Depending on how many times the film(s) 66 are wrapped around the shaft 74, in other embodiments there may be more or less bonds 65 required to interconnect the film thicknesses 67. Interconnecting the multiple adjacent film thicknesses 67 converts the roll 52 into the solid un-oriented tube 42 wall thickness 45. In an embodiment, the bond 65 comprises a bond between each of the adjacent film thicknesses 67 that is held together by chemical bonds such as covalent bonds, ionic bonds, polar bonds, hydrogen bonds and/or by van der Wal forces. In an embodiment, at least one of the molecule chains within the first film thickness 67 partially migrates into the adjacent second film thickness 67 by crossing the bond 65 and/or at least one of the molecule chains within the second film thickness 67 partially migrates into the adjacent first film thickness 67 by crossing the bond 65, which interconnects the first and second film thicknesses 67. Heating both the film thicknesses 67 and/or swelling at least one of the film thicknesses 67 cause the molecules within the film thicknesses 67 to migrate across the bond 65 and when the heat and/or the solvent(s) 86 are removed from the film thicknesses 67 the two adjacent film thicknesses 67 are interconnected. When interconnecting each of the adjacent film thicknesses 67, pressure may be applied to the film thicknesses 67 when they are being heated and/or cooled to form the interconnection. Pressure may also be exerted on the bond 65 when the solid film(s) 66 shrink onto the shaft when heated and/or cooled. It should be appreciated that even though FIG. 19, FIG. 20, FIG. 33, FIG. 35, FIG. 37, FIG. 39, FIG. 41, FIG. 43, FIG. 45, FIG. 47, FIG. 48, FIG. 50, FIG. 51, FIG. 53, FIG. 55, FIG. 57, FIG. 59, FIG. 62, FIG. 63, FIG. 64, FIG. 65, FIG. 66 and FIG. 67 depict the solid films 66 being wrapped around the shaft 74 when the solid film(s)

66 are in the horizontal position that the solid films 66 may be wrapped around the shaft 74 when the solid film(s) 66 are in the vertical position or any position in between horizontal and vertical.

FIG. 21 depicts a Roll On The Shaft 53. As depicted in FIG. 21, wrapping at least one solid film 66 around the shaft 74 forms the roll 52. Alternatively, The Roll On Shaft 53 may comprise at least one film 66, a laminate 100, a fibrous sheet 108, an Infused Fibrous sheet 126, a Fiber reinforced Laminate 130, or any combinations thereof. After the roll 52 is converted into the un-oriented tube 42, the Beginning Of The Roll 58 is located closer to the inner surface 48 and the End Of The Roll 59 is located closer to the outer surface 47 of the roll 52 that is formed into the unoriented tube 42, which is converted into the oriented tube 38 and/or the stent 10. As depicted in FIG. 22, which is a portion 92 of the roll 52 depicted in FIG. 21, once each additional wrap crosses over the point where the previous wrap was completed an Over-Film Thickness 93 is formed on top of the Under-Film Thickness 94. Still referring to FIG. 22, when each wrap is completed the solid film 66 forms an abrupt transition 95 where the distance from the shaft 74 outer surface 78 is greater for the Over-Film Thickness 93 than the Under-Film Thickness 94. The solid film 66 forms an abrupt transition 95 because there is an immediate change in the diameter of the underlying surface when the solid film 66 being laid down rides over the film thickness 67 of the previously laid down solid film 66 or the Under-Film. Therefore, each film thickness 67 gets farther away from the shaft outer surface 78 as it is laid down on the previous film thickness 67. As previously mentioned, FIG. 21 depicts the film thicknesses 67 of the solid film 66 in an exploded view where there is the separation distance 60 between the Under-Film and the shaft 74 and the separation distance 60 between the Under-Film Thickness 94 and the Over-Film Thickness 93 to make it easier to visualize the spiral configuration of the solid film 66 within the roll 52. In the preferred embodiment, there is no separation distance 60 or very little separation distance 60 between the film thicknesses 67. In other embodiments of the roll 52, there may be some separation distance(s) 60.

FIG. 23 depicts a Deposited Solution 82. The solid film 66 is formed by depositing a liquid solution 83 on a release media 84 as depicted in FIG. 23. Provisional Patent Application Ser. No. 62/443,101 filed Jan. 6, 2017; entitled "ANISIOTROPIC BIORESORBABLE STENT FORMED FROM INTERCONNECTED LAYERS OF HIGH MOLECULAR WEIGHT ISOTROPIC FILM" provides additional information about producing solid films 66 and forming the solid films 66 into the stent 10, which is incorporated herein as a reference. The release media 84 may be, for example, comprised of polyethylene sheet or the like. The liquid solution 83 is comprised of at least one stent material 85 and at least one liquid solvent 86. The liquid solution 83 may be comprised of between greater than 0 wt. % to 35 wt. % stent material(s) 85 and the remainder of the liquid solution 83 that has a total wt. % of 100% is solvent(s) 86 and/or the active ingredient(s) 34. In other embodiments, the liquid solution 83 comprises equal to or greater than 35 wt. % stent material(s) 85 and the remainder is solvent(s) 86 and/or active ingredient(s) 34. In an embodiment the liquid solution 83 has a viscosity within the range of greater than $3.0 \times 10^{-4}$ Pa-S to 50.0 Pa-S, more narrowly less than 3 Pa-S, at approximately the time of placement of the liquid solution 83 on the release media 84. Depositing the liquid solution 83 on the release media 84 forms a liquid film 87 having a liquid film thickness 88 and a liquid film width 89. After deposition, the liquid solvent 86 is removed by, for example, evaporation or vaporization of the liquid solvents 86 within a gaseous medium 90 leaving the solid film 66, which is substantially comprised of the stent material 85, on the release media 84. The solid film 66 is comprised of the solid film thickness 67 and the solid film width 69. The solid film 66 is removed from the release media 84 by pealing the solid film 66 off the release media 84 to form the roll 52 that is formed into the un-oriented tube 42, which is converted into the oriented tube 38 and/or the stent 10. A device may be used to control static build up on the solid film 66. The solid film 66 formed on the release media 84 is generally amorphous having a crystallinity between 0% to 25%, more narrowly less than 15%. The solid film 66 of the present invention is unique because it shrinks when heated and/or cooled. It is believed that the solid film(s) 66 shrink when they are heated and/or cooled because the solid film(s) 66 are being converted from a more amorphous state to a more crystalline state during the thermal cycle, wherein the crystalline portions of the solid film(s) 66 fold and take up less space, which results in shrinkage.

The solid film 66 may include molecular orientation that is imparted on the solid film 66 when it is dry or swollen by stretching in the solid film 66 in a machine direction 79, a transverse direction 80 or a biaxial direction 81, which is a combination of machine direction and transverse direction prior to or during forming of the solid film 66 into the un-oriented tube 42 or the oriented tube 38, which are converted into the stent 10. A dry solid film 66 means that the solvent 86 is completely removed from the solid film 66, which results in the solid film 66 comprising only the stent material(s) 85 or all stent material(s) 85 and/or the active ingredient(s) 34 except for a small residual amount of the solvent(s) 86 equal to or less than 0.01 wt. % solvent(s) 86. The swollen solid film 66 means the solid film 66 comprises the stent material(s) 85 and/or the active ingredient(s) 34 and at least one part solvent(s) 86. It is believed that it is easier to obtain molecular orientation of the molecular chains within the stent material(s) 85 in the direction of strain in a swollen solid film 66 than a dry solid film 66 because the chains have fewer entanglements, which allow the chains to more easily slip by each other when the solid film 66 is strained. The swollen solid film 66 may be formed by not allowing the liquid film 78 to completely dry.

The swollen solid film 66, wherein the swollen solid film 66 has constituents equal a total of 100 wt. %, preferably comprises between equal to 0.01 wt. % to 65 wt. % solvent(s) 86 and the remainder of the swollen solid film 66 comprises the stent material(s) 85 and/or the active ingredient(s) 34. In other embodiments, the swollen solid film 66 comprises greater than 65 wt. % to 99 wt. % solvent(s) 86 and the remainder comprises the stent materials(s) 85 and/or the active ingredient(s) 34. A swollen solid film 66 that contains solvent(s) 86 are useful for interconnecting the film thicknesses 67 without heating the roll 52. The swollen solid film 66 interconnects with other swollen solid film(s) 66 and/or other dry solid film(s) 66 when they are adjacently positioned within the roll 52 and/or Roll Including Active Ingredient(s) 143. As the swollen film 66 dries some of the solvent(s) 86 within the swollen solid film 66 migrates into the adjacent solid film 66, which allows the molecules to bridge the bond 65 and form a solvent bond between the two film thicknesses 67 as the films dry to form the un-oriented tube 42 and/or the oriented tube 38. Alternatively, or additionally, the dry solid film 66 is converted into the swollen solid film 66 or the swollen solid film 66 is made more swollen by adding more solvent(s) 86 to the dry or swollen solid film 66.

In an embodiment, stretching the swollen, solid film 66 results in a Swollen Film Transverse Widening Ratio ("SFTWR") between greater than 0.0 to 10.0. In other embodiments the SFTWR is equal to or greater than 10.0. The SFTWR equals the swollen solid film's width 69 after widening divided by the swollen solid film's width 69 prior to widening. In an embodiment, stretching the swollen, solid film 66 results in a Swollen Film Axial Elongation Ratio ("SFAER") between greater than 0.0 to 10.0. In other embodiments, the SFAER is equal to or greater than 10.0. The SFAER equals the swollen solid film's length 68 after elongating divided by the swollen solid film's length 68 prior to elongating. The SFAER to SFTWR ratio equals the SFAER divided by the SFTWR. In an embodiment, the SFAER to SFTWR ratio is equal to 1.0 to 10.0. In other embodiments, the SFAER to SFTWR ratio is equal to or greater than 10.0 or equal to or less than 1.0.

In an embodiment, stretching the swollen, solid film 66 results in a Swollen Film Draw Down Thickness ("SFDDT") between 0.0 and 10.0. In other embodiments the SFDDT is equal to or greater than 10.0. The SFDDH equals the average film thickness 67 of the swollen solid film 66 before stretching divided by the average film thickness 67 of the swollen solid film 66 after stretching. In an embodiment, stretching the swollen, solid film 66 results in a Swollen Film Draw Down Width ("SFDDW") between 0.0 and 10.0. In other embodiments the SFDDW is equal to or greater than ten 10. The SFDDW equals the nominal width 69 of the swollen solid film 66 before stretching divided by width 69 of the swollen solid film 66 after stretching. Swollen solid film(s) 66 wrapped around the shaft 74 may interconnect with or without heating the solid film(s) 66 on the shaft 74. In an embodiment, solvent bonding interconnects the film thicknesses 67 of the swollen solid film(s) 66. In another embodiment, solvent bonding interconnects the substantially dry solid film(s) 66.

The solid film 66 may include the active ingredient(s) 34 or exclude the active ingredient(s) 34. The active ingredient(s) 34 may be positioned within the solid film 66 by incorporating the active ingredient(s) 34 into the liquid solution 83 prior to depositing the liquid solution 83 on the release media 84. The active ingredient(s) 34 are preferably incorporated into the liquid solution 83 within greater than 0 seconds to 60 minutes before depositing the liquid solution 83 including the active ingredient(s) 34 on the release media 84. In other embodiments, the active ingredient(s) 34 may be incorporated into the liquid solution 83 between at least one of the following timeframes before depositing the liquid solution 83 including the active ingredient(s) 34 on the release media 84: (1) greater than 0 seconds to 2 hours, (2) greater than 0 seconds to 3 hours, (3) greater than 0 seconds to 4 hours, (4) greater than 0 seconds to 5 hours, (5) greater than 0 seconds to 6 hours, (6) greater than 0 seconds to 7 hours, (7) greater than 0 seconds to 8 hours, (8) greater than 0 seconds to 24 hours, (9) greater than 0 seconds to 7 days, (10) greater than 0 seconds to 1 month, or (11) greater than 0 seconds to 1 year. In still another embodiment, the active ingredient(s) 34 may be incorporated into the liquid solution 83 between greater than 0 seconds to 10 years before depositing the liquid solution 83 including the active ingredient(s) 34 on the release media 84. Alternatively, or additionally, the active ingredient(s) 34 may be added to the solvent(s) 86 prior to adding the stent material(s) 85 when preparing the liquid solution 83.

In an embodiment, the solid film 66, the roll 52, the un-oriented tube 42 and/or the oriented tube 38 include at least one part or entirely crystalline or amorphous sirolimus, crystalline or amorphous everolimus, crystalline or amorphous biolimus, crystalline or amorphous corolimus, crystalline or amorphous ridaformolimus, crystalline or amorphous umirolimus, crystalline or amorphous myolimus, crystalline or amorphous novolimus, crystalline or amorphous zotarolimus, and other crystalline or amorphous macrolide immunosuppressant's or other crystalline or amorphous inhibitors of neointimal growth, wherein crystalline means the active ingredient 34 has a degree of crystallinity ranging from 50 to 100% and amorphous means an active ingredient 34 having a degree of crystallinity ranging from 0 to less than 50%.

FIG. 24 depicts the film 66 excluding the active ingredient(s) 34. In this embodiment, the film 66 may be formed into the roll 52 to provide strength to the wall thickness 13 of the stent 10. Alternatively, or additionally, the film 66 excluding the active ingredient(s) 34 may be used as a barrier layer 51 to control the timing of the release and/or the rate release of the active ingredient(s) 34, which may be referred to as a barrier layer 51 herein. FIG. 25 depicts the film 66 including the active ingredient(s) 34, which may be referred to as a therapeutic layer 51 within this specification. In this embodiment, the film 66 may be formed into the roll 52 to provide a therapeutic layer 51 that releases at least one or all the active ingredient(s) 34 during the treatment time. Additionally, the film 66 including the active ingredient(s) 34 may change the mechanical properties of the stent 10 by, for example, stiffening the stent 10 with a material that has a higher elastic modulus than the stent material(s) 85 comprising the remainder of the film 66. FIG. 26 depicts a laminate 100 comprising the active ingredient(s) 34 positioned between two active ingredient-free films 66. In this embodiment, the roll 52 comprising the laminate 66 provides strength to the thickness of the stent 10 and provides controlled delivery of the active ingredient(s) 34 when the stent 10 is implanted within the anatomical lumen 36.

Without intent on limiting, the stent 10, the solid film 66, the film thickness 67, the un-oriented tube 42, the oriented tube 38, the laminate 100, the fiber 116, the multi-fiber 117, the fibrous sheet 108, the infused fibrous sheet 126, the fiber-reinforced laminate 130, the reinforcement(s), the layer 51, the roll 52, the coating 30 or combinations thereof may include one or more active ingredient(s) 34 selected from the group of: anti-angiogenesis agents, 17-beta-estradiol, 23 peptide fragment known as single chain Fv fragment (scFv A5), 4-amino-2,2,6,6tetramethylpiperidine-1-oxyl (4-amino-TEMPO), 40-epi-(N1-tetrazolyl)-rapamycin (ABT-578), 40-epi-(N1-tetrazolyl)-rapamycin (zotarolimus, manufactured by Abbott Labs), 40-O-(2-ethoxy)ethyl-rapamycin (biolimus), 40-O-(2-hydroxy)ethyl-rapamycin (everolimus), 40-O-(2-hydroxy)ethylrapamycin (trade name everolimus from Novartis), 40-O-(3-hydroxy)propyl-rapamycin, 40-O-[2-(2-hydroxy)ethoxy]ethyl-rapamycin, 40-O-tetrazolerapamycin, 5-Fluorauracil (5-FU), nonsteroidal anti-inflammatory drugs (NSAID), abciximab, ABT 806, ABT-348, ABT-578 (Abbott Laboratories), acidic FGF, actinomcin D, actinomycin, actinomycin D or derivatives and analogs thereof, actinomycin D or derivatives and analogs thereof (manufactured by Sigma-Aldrich, or COSMEGEN available from Merck) (synonyms of actinomycin D include dactinomycin, actinomycin IV, actinomycin 11, actinomycin X1, and actinomycin C1), active agents, Adriamycin PFS (Doxorubicin Hydrochloride), Adriamycin RDF (Doxorubicin Hydrochloride), Adrucil™ (Fluorouracil), agents affecting extracellular matrix production and organization, agents delivered inside a polymeric particle, agents that bind to the FKBP12 binding protein, agents that bind to the mammalian target of rapamycin (mTOR) and thereby blocks the cell cycle mainly of the smooth muscle cell from the G1 to S phase, agents that block T-cell activation or proliferation, agents that block T-cell activation or proliferation, agents that decrease cytokine expression on the cell surface membrane and results in an inhibition of T-cell activation and lower smooth muscle cell selectivity, agents that fight cancer, agents that have ability to stabilize microtubules and thereby inhibit cell division in the G0/G1 and G2/M phases, agents that increase lipid transportation, agents that inhibit platelet aggregation, agents that inhibit smooth muscle cell proliferation, agents that inhibit the calcineurin receptor, agents that interfere with endogenous vasoactive mechanisms, agents that prevent angiogenesis in the tumor, agents that prevent or reduce blood clotting, agents that prevent or reduce local allergic reactions, agents that promote angiogenesis mechanism, agents that promote endothelialization, agents that promote re-endothelialization, agents that promote reendothelialization at a rate faster than the loss of mechanical properties of a stent, agents that promote hemostasis, agents that promote vasculogenesis mechanism, agents that reduce allergic reaction, agents that reduce neointimal hyperplasia, agents that reduce the size of tumors, agents that reduce vascular hyperplasia, agents that treat hepatocellular carcinoma (HCC), agents that treat hepatocellular carcinoma (HCC), agents that treat liver cancer, alclofenac, alclometasone dipropionate, algestone acetonide, all limus drugs such as macrolide antibiotics, all taxoids such as taxols, alpha amylase, alpha-interferon, amcinafal, amcinafide, amfenac sodium, amiprilose hydrochloride, an inhibitor of mammalian target of rapamycin (mTOR), anakinra, analgesics, anesthetic agents, angiopeptin, angiotensin converting enzyme inhibitors such as captopril (e.g., Capoten® and Capozide® from Bristol-Myers Squibb), anirolac, anitrazafen, anorexics, anti-angiogenesis drugs, anti-cancer agents, anti-coagulants, anti-EGFR antibodies, anti-infective substances, anti-inflammatory agents, anti-irritant agents, anti-migratory agents, anti-mitotic agents, anti-neoplastic agent, anti-proliferative agents, anti-sense nucleotides and transforming nucleic acids, anti-thrombotic agents, anti-TNF agents, anti-VEGF antibodies, antiallergic agents, antiarrhythmics, antibiotic agents, antibiotics, antibodies, antibodies of biological inflammatory signaling molecules, antibody CD-133, antibody CD-34, antibody vegf type 2 receptor, anticholinergics, anticoagulant agents, antifibrin agents, antihelmintics, antihistamines, antihypertensives, antimicrobials, antimitotic agents, antimitotics, antineoplastic agents, antineoplastics, antioxidant substances, antiplatelet agents, antiproliferative drugs, antipruritics, antipyretics, antispasmodics, antithrombin agents, antithrombotic agents, antiviral agents, Ap-17, apazone, argatroban, aspirin (acetylsalicylic acid), Avastin, Avastin™ (Bevacizumab), azathioprine, AZD 8055, bacteria, balsalazide disodium, bARKct inhibitors, batistimat, bendazac, benoxaprofen, benzalkonium heparin, benzydamine hydrochloride, benzydamine hydrochloride, beta-blockers, Bevacizumab, bioactive agents, Biolimus, Biolimus A9, biological inhibitors of pro-inflammatory signaling molecules, biologically active agents, bisphosphonates, Bleomycin, bromelains, broperamole, budesonide, buffering agents, calcium channel blockers, calcium channel blockers (e.g., nifedipine), Camptosar (Irinotecan hydrochloride), Camptosar™ (Irinotecan), Capecitabine (Xeloda™), Capecitabine (Xeloda™), Capox, Carboplatin, Carboplatin AUC 6, carprofen, Cetuximab, chaperone inhibitors, chemotherapeutic agents, ciclopofen, cilazapril, cilostazole, cintazone, Cisplatin, cliprofen, clobetasol, clobetasol propionate, clobetasone butyrate, clopidogrel, clopirac, cloticasone propionate, colchicine, collagen type 1, cormethasone acetate, compound(s) that are toxic to targeted cells, coronary vasodilators, corolimus, corticosteroids, cortodoxone, crystalline forms of drugs, cyclosporine, cytostatic substances, cytostatics, cytostatic drugs, dactolisib, D-phe-pro-argchloromethylketone (synthetic antithrombin), decongestants, deflazacort, deforolimus, desonide, desoximetasone, dexamethasone, dexamethasone derivatives, dexamethasone dipropionate, dextran, diagnostic agents, diclofenac potassium, diclofenac sodium, diflorasone diacetate, diflumidone sodium, diflunisal, difluprednate, diftalone, dimethyl sulfoxide, dipyridamole, diuretics, DNA (Deoxyribonucleic acid), docetaxel, docetaxel (e.g., Taxotere® from Aventis), Doxorubicin hydrochloride, doxorubicin hydrochloride (e.g., Adriamycin® from Pfizer), drocinonide, drugs, drugs that interfere with cells ability to reproduce, Ecto-nucleotidases, EDTA, EDTA (Ethylenediaminetetraacetic acid), Efudex™ (Fluorouracil), Eloxatin (Oxaliplatin), endothelial cell binding agents, endothelial progenitor cells (EPC), endrysone, enlimomab, enolicam sodium, EPC (epithelial cell) antibodies, epidermal growth factor inhibitors, epirizole, Epirubicin (Ellence™), Epo D, Epo (Erythropoietin, hematopoietin, hemopoietin), Erbitux (Cetuximab), estradiol, estrogen, etodolac, etofenamate, everolimus, C53H83NO14, everolimus (certican or RAD-001), 40-O-(2-hydroxyethyl) derivatives of sirolimus, dihydroxy-12-[(2R)-1-[(1S,3R,4R)-4-(2-hydroxyethoxy)-3-methoxycyclohexyl]-propan-2yl]-19,30-dimethoxy-15,17,21,23,29,35-hexamethyl-11,36-dioxa-4-aza-tricyclo[30.3.1.0 hexatriaconta-16,24,26,28-tetraene-2,3,10,14,20-pentone, felbinac, fenamole, fenbufen, fenclofenac, fenclorac, fendosal, feno fibrate, fenofibrate, fenpipalone, fentiazac, fibroblast growth factor (bFGF), fibroblast growth factor (bFGF), fibroblast growth factor (FGF) antagonists, fish oil (e.g., omega 3-fatty acid), FKBP-12 binding agents, FKBP-12 mediated mTOR inhibitors, flazalone, fluazacort, flufenamic acid, flumizole, flunisolide, flunisolide acetate, flunixin, flunixin meglumine, fluocortin butyl, fluorometholone acetate, fluorouracil, Fluorplex (Fluorouracil), fluquazone, flurbiprofen, fluretofen, fluticasone propionate, Folfiri, FolfiriBevacizumab, Folfiri-Cetuximab, Folfox, fondaparinux, forskolin, furaprofen, furobufen, Gefitinib (Iressa™), geldanamycin, Gemcitabine, genetic therapeutic agents, genetically engineered epithelial cells, genetically modified epithelial cells, genistein, glucocorticoids, glucocorticosteroids, glycoprotein IIb/IIIa platelet membrane receptor antagonist antibody, growth factors and delivery vectors including recombinant micro-organisms and liposomes, halcinonide, halobetasol propionate, halofuganone, halofuginone, halopredone acetate, heparinoids, hirudin, histamine antagonists, hormones, human apolioproteins (e.g., AI, AII, AIII, AIV, AV, etc.), hydrocortisone, hypnotics, hypothemycin, ibufenac, ibuprofen, ibuprofen aluminum, ibuprofen piconol, idraparinus, ilonidap, imatinib mesylate, imiquimod (as well as other imidazoquinoline immune response modifiers), immunoliposomes, immunosuppressive agents, immunosuppressives, indomethacin, indomethacin sodium, indoprofen, indoxole, intrazole, Irinotecan hydrochloride, isoflupredone acetate, isoxepac, isoxicam, lipophilic drugs, junction membrane protein vascular endothelial (VE)-cadherin, ketoprofen, leptomycin, leptomycin B, Leucovorin calcium, limus drugs, linifanib (ABT-869), liprostin, lisinopril (e.g., Prinivil® and Prinzide® from Merck), living cells, living tissue, lofemizole hydrochloride, lomoxicam, Lomustine (CCNU), loteprednol etabonate, lovastatin (a cholesterol-lowering drug that inhibits HMG-CoA reductas, brand name Mevacor® from Merck), low molecular weight heparins, macrolide antibiotics including FKBP-12 binding compounds, materials that influence pH in environment surrounding stent 10, materials that promote improvement in elasticity of anatomical lumen, materials that promote remodeling of anatomical lumen, materials that provide reparative effect on anatomical lumen, materials that slow down aging process of anatomical lumen, meclofenamate sodium, meclofenamic acid, meclorisone dibutyrate, medications, mefenamic acid, mesalamine, meseclazone, methotrexate, methylprednisolone suleptanate, midostaurin, mineralocorticoids, Mitomycin, mitomycin (e.g., Mutamycin® from Bristol-Myers Squibb), mitotic inhibitors, modified DNA, mometasone furoate, mometasone furoate monohydrate, monoclonal antibodies (e.g., those specific for platelet-derived growth factor (PDGF) receptors), morniflumate, mTOR inhibitors, muscle relaxants, myolimus, nabumetone, naproxen, naproxen sodium, naproxol, natural therapeutic agents, naturally derived or genetically engineered lipoproteins, nimazone, nitric oxide, nitric oxide donors, nitroprusside, non-genetic therapeutic agents, novolimus, nucleic acids, nucleotide metabolizing enzymes, olsalazine sodium, one or more different polymer structures that could be inert or have a structure that allows them to react with each other if activated, orgotein, orpanoxin, osteopontin, osteopontin, (Asp-Val-Asp-Val-Pro-Asp-Gly-Asp-Ser-Leu-Ala-Try-Gly), Oxalipatin, oxaprozin, oxyphenbutazone, p-para-a-agonists, paclitaxel, paclitaxel (e.g., TAXOL® available from Bristol-Myers Squibb), Panitumumab, paranyline hydrochloride, parasympatholytics, Pegylated liposomal doxorubicine, pentosan polysulfate sodium, peptides, perfenidone, peripheral and cerebral vasodilators, perm irolast potassium, peroxisome proliferator-activated receptor gammaligands (PPAR.gamma.), pharmaceutically active agents, pharmaceutically active agents having optimized morphology, pharmaceuticals, phenbutazone sodium glycerate, phosphodiesterase inhibitors, phospholamban inhibitors, pimecorlimus, pimecrolimus, pindolol, pirfenidone, piroxicam, piroxicam cinnamate, piroxicam olamine, pirprofen, platelet derived growth factor, Platinol (Cisplatin), Platinol-AQ (Cisplatin), polymeric particle delivered inside an injectable hydrogel, polypeptides, prednazate, prifelone, prodolic acid, progestin, prophylactic agents, proquazone, prostacyclin and prostacyclin analogues, prostaglandin inhibitors, protease inhibitors, proteasome inhibitors, protein-tyrosine kinase inhibitors, proteins, proxazoles, proxazole citrate, psychostimulants, radiation, rapamcin hydroxyesters (as disclosed in U.S. Pat. No. 5,362,718), rapamycin, rapamycin derivatives, recombinant hirudin, Regorafenib, resiquimod, Resten, Resten-NG, restenoic reducing agents, RGD mimetics, RGD peptide sequences, ridaformolimus, Ridogrel, rimexolone, romazarit, salcolex, salicylic acid, salnacedin, salsalate, sanguinarium chloride, SAR-943, seclazone, sedatives, Serca 2 gene/protein, sermetacin, serotonin blockers, sirolimus, sirolimus salicylate, $C_{51}H_{79}NO_{13}$, small molecule anti-angiogenesis drugs, sodium heparin, solvent soluble heparin, sorafenib, statins, stem cells, steroidal anti-inflammatory drugs, steroids, Stivarga (Regoranfenib), Stivarga (Regoranfenib), structural derivatives and functional analogues of everolimus, structural derivatives and functional analogues of rapamycin, substances or agents that attract and bind endothelial progenitor cells, sudoxicam, sulindac, super oxide dismutase mimetics, super oxide dismutase mimics, super oxide dismutases, suprofen, suramin, sympathomimetics, synthetic therapeutic materials, tacrolimus, tacrolimus (FK506), $C_{44}H_{69}NO_{12}$, talmetacin, talniflumate, talosalate, Taxol, TDMAC-heparin, tebufelone, temsirolimus, temsirolimus (CCI-779 or amorphous rapamycin 42-ester with 3-hydroxy-2-(hydroxymethyl)-2-methyl-propionic acid as disclosed in U.S. patent Ser. No. 10/930,487), tenidap, tenidap sodium, tenoxicam, tesicam, tesimide, tetrydamine, therapeutic agents, thioprotease inhibitors, thrombin inhibitors such as ANGIOMAX (from Biogen), tiopinac, tixocortol pivalate, tolmetin, tolmetin sodium, Topotecan, toxic compounds, tranquilizers, trapidil, Trastuzumab, triazolopyrimidine (a PDGF antagonist), triclonide, triflumidate, vapiprost, vascular cell growth inhibitors, vascular cell growth promoters, vascular endothelial growth factor, vascular endothelial growth factors (e.g., VEGF-2), vasodilating agents, vasodilators, Vectibix (Panitumumab), vinblastine, vincristine, Vinorelbine (Navelbine™), virus, Wellcovorin (Leucovorin Calcium), Xa inhibitor, xanthine derivatives, Xeloda (Capecitabine), Xelox, Zaltrap (Ziv-Afibercept), zidometacin, zomepirac sodium, zotarolimus, zotarolimus (reference U.S. Pat. Nos. 6,015,815 and 6,329,386), .gamma.-hiridun, their functional equivalents, analogs thereof, derivatives thereof, prodrugs thereof, co-drugs thereof, and any combination or combinations thereof.

Without intent on limiting, the stent 10, the solid film 66, the film thickness 67, the un-oriented tube 42, the oriented tube 38, the laminate 100, the fiber 116, the multi-fiber 117, the fibrous sheet 108, the infused fibrous sheet 126, the fiber-reinforced laminate 130, the reinforcement(s), the layer 51, the roll 52, the coating 30 or combinations thereof may include one or more active ingredient(s) 34 that are anti-cancer agents. The anti-cancer agents may be selected from the group of: Adrucil™ (Fluorouracil), Adriamycin PFS (Doxorubicin Hydrochloride), Adriamycin RDF (Doxorubicin Hydrochloride), Avastin™ (Bevacizumab), Bevacizumab, Bleomycin, Camptosar (Irinotecan Hydrochloride), Carboplatin, Carboplatin AUC 6, Capecitabine (Xeloda™), Capox, Camptosar™ (Irinotecan), Cetuximab, Cisplatin, Doxorubicin Hydrochloride, Docetaxel, Drugs that interfere with cells ability to reproduce, Efudex™ (Fluorouracil), Eloxatin (Oxaliplatin), Epirubicin (Ellence™), Erbitux (Cetuximab), Folfiri, FolfiriBevacizumab, Folfiri-Cetuximab, Folfox, Fluorplex (Fluorouracil), 5-Fluorauracil (5-FU), Fluorouracil, Gefitinib (Iressa™), Gemcitabine, Irinotecan Hydrochloride, Lomustine (CCNU), Leucovorin Calcium, Methotrexate, Mitomycin, Oxalipatin, Panitumumab, Paclitaxel (Taxol™), Pegylated liposomal doxorubicine, Platinol (Cisplatin), Platinol-AQ (Cisplatin), Radiation, Regorafenib, Stivarga (Regoranfenib), Topotecan, Trastuzumab, Vectibix (Panitumumab), Vinorelbine (Navelbine™), Wellcovorin (Leucovorin Calcium), Xeloda (Capecitabine), Xelox, Zaltrap (Ziv-Afibercept), chemical equivalents, analogs thereof, functional equivalents, combination, or combinations thereof.

Alternatively, or additionally, the stent 10, the roll 52, the unoriented tube 42, and/or the oriented tube 38 may at least partially or completely comprise a laminate 100. FIG. 27 depicts the laminate 100. The laminate 100 may be wrapped around the shaft 74 to form the roll 52 that is formed into the un-oriented tube 42, which is converted into the oriented tube 38 and/or the stent 10. The laminate comprises the solid film 66 superimposed with at least one other solid film 66 to form the laminate 100. In an embodiment, there may be at least one active ingredient 34 within the laminate 100. The laminate 100 is comprised of a laminate thickness 101, a laminate width 102, a laminate length 103, a laminate major surface 104, a laminate long minor surface 106, a laminate short minor surface 105, and a laminate lengthwise axis 107. The roll 52 or the Roll Including Active Ingredient(s) 143 may comprise superimposed solid films 66 that are interconnected or disconnected within the roll 52 or the Roll Including Active Ingredient(s) 143, the un-oriented tube 42, the oriented tube 38 and/or the stent 10. The bond 65 may interconnect the solid film(s) 66 within the laminate 100 before or after formation of the roll 52. Alternatively or additionally, laminate 100 may comprise the at least one swollen, solid film 66 between two dry, solid films 66, wherein the residual solvent 86 within the swollen solid film 66 creates a solvent weld between the dry solid films 66 that interconnects the films 66 as the solvent 86 evaporates or vaporizes during drying of the laminate 100 and/or the un-oriented tube 42. Moreover, the laminate 100 may include molecular chain orientation that is imparted on the laminate 100 when the solid film(s) 66 are dry or swollen by stretching in the laminate 100 in the machine direction 79, the transverse direction 80 or the biaxial direction 81 prior to or during formation of the roll 52 or the Roll Including Active Ingredient(s) 143 that is formed into the oriented tube 38 and/or the stent 10.

FIG. 28 depicts a fibrous sheet 108. Alternatively, or additionally, the stent 10 may include at least one fibrous sheet 108. The fibrous sheet 108 may be wrapped around the shaft 74 by itself or with at least one solid film 66 to form the roll 52 or the Roll Including Active Ingredient(s) 143 that is formed into the un-oriented tube 42, which is converted into the oriented tube 38 and/or the stent 10. The fibrous sheet 108 is comprised of a fibrous sheet thickness 109, a fibrous sheet width 110, a fibrous sheet length 111, a fibrous sheet major surface 112, a fibrous sheet long minor surface 114, a fibrous sheet short minor surface 113, and a fibrous sheet lengthwise axis 115. Moreover, the fibrous sheet 108 may include molecular chain orientation that is imparted on the fibrous sheet 108 when it is dry or swollen by stretching in the fibrous sheet 108 in the machine direction 79, the transverse direction 80 or the biaxial direction 81 prior to or during formation of the roll 52 or the Roll Including Active Ingredient(s) 143 that is formed into the oriented tube 38 and/or the stent 10.

The fibrous sheet 108 is comprised of at least one fiber 116 and/or at least one multi-fiber 117, which are depicted in FIG. 29 and FIG. 30, respectively. The fiber 116 is comprised of a fiber thickness 118, a fiber length 119, a fiber lengthwise axis 120 and a fiber outer surface 121. The multi-fiber 117 is comprised of a multi-fiber thickness 122, a multi-fiber length 123, a multi-fiber lengthwise axis 124 and a multi-fiber outer surface 125. The fibers 116 within the multi-fiber 117 may be twisted, knitted or braided. The fibrous sheet 108 may be converted into an Infused Fibrous Sheet 126. As depicted in FIG. 31, the Infused Fibrous Sheet 126 is comprised of at least one fiber 116 and/or multi-fiber 117, a plurality of void spaces 127 positioned between the fiber(s) 116 and/or the multi-fiber(s) 117, a plurality of nodes 128 positioned where the fiber(s) 116 and/or the multi-fiber (s) 117 intersect or cross over, and a matrix 129. The matrix 129, which is at least partially or completely comprised of the stent material(s) 85, partially or completely fills the void spaces 127, which are located between the fiber(s) 116 and/or multi-fiber(s) 117. In an embodiment, the fiber 116 and/or the multi-fiber 108 may include the active ingredient(s) 34. The matrix 129 may be positioned within the void spaces 127 by infusing the liquid solution 83 into the void spaces 127 one or more times and removing the liquid solvent(s) 86 from the matrix 129. For example, the liquid solution 83 may be poured onto the fibrous sheet 108 so that the void spaces 127 are at least partially filled with liquid solution 83. When the solvent(s) 86 within the liquid solution 83 are removed from the liquid solution 83, the stent material 85 remains within the void spaces 127 forming the matrix 129 between the fiber(s) 116 and/or multi-fibers 117. The surface 121, 125 modification may improve the process of infusing the fibrous sheet 108 by increasing the adhesion between the matrix 129 and the fiber 116 or multi-fiber 117 by improving the way the liquid solution 83 wets out the fibrous sheet 108. The surface 121, 125 modification may improve the ability of the liquid solution 83 to penetrate into the plurality of void spaces 127 positioned within the wall thickness 109 of the fibrous sheet 108. The liquid solution 83 used to infuse the fibrous sheet 108 comprises the at least one stent material 85 and at least one solvent 86 that does not dissolve the fiber(s) 116 and/or multi-fiber(s) 117 when the liquid solution 83 contacts the fiber(s) 116 and/or the multi-fibers 117. The matrix 129 and/or the void space 127 may include at least one active ingredient 34.

Imparting changes in the properties of the surface(s) 9, 16, 17, 29, 47, 48, 61, 62, 71, 72, 73, 78, 104, 105, 106, 121, 125, 191 using a high frequency corona discharge or air plasma techniques may modify at least one of the surfaces. In other embodiments, some or all the surface(s)s may be modified by imparting changes in the properties of the surface(s) using atmospheric plasma treatment, flame plasma, or chemical plasma. The modification technique may change the surface energy of at least one of the stent material(s) 85 within the stent 10 or the stent's 10 components. Modifications to some or all the surface(s) within the stent 10 or the stent's components, for example, may improve adhesion to the other solid film(s) 66, fiber(s) 116, multi-fiber(s) 117, layer(s) 51, laminate(s) 91, fibrous sheet(s) 102, infused fibrous sheet(s) 120, fiber-reinforced laminate(s) 130, coating(s) 30, or other materials. The surface modification(s) may also improve biocompatibility of the stent 10 after deployment of the stent 10 within the anatomical lumen 36.

At least one of the surface(s) may be modified with acid; sulfuric acid; potassium chlorate; hydrochloric acid; ultra-violet light; ozone; chromic acid; formalin-fixed paraffin-embedded (FFPE) modification; agents that generate oxygen in the form of hydroxyl; agents that produce hydroxyl, aldehyde, carboxyl, or other enhancing groups on the surface; agents that modify the carbon/oxygen ratio of the surface(s); agents that create at least one charged groups that are anions; agents that modify the surface with at least one cation; serum; protein; oxidizing agent; oxygen plasma; silanization; radiation or combinations thereof. Without intent on limiting, in other embodiments, the modification(s) include modifying the surface tension, surface energy, increasing or decreasing the surface charge density, charge, hydrophobicity, hydrophilicity, wettability, polylysine coating, agents that enhance cell or tissue culture growth, or any combinations thereof.

The fibrous sheet 108 and/or the infused fibrous sheet 126 may be incorporated into the laminate 100 to form a Fiber-reinforced Laminate 130 as depicted in FIG. 32. Alternatively, or additionally, the stent 10 includes the Fiber-reinforced laminate 130. The Fiber-reinforced Laminate 130 may be wrapped around the shaft 74 by itself or with at least one solid film 66 to form the roll 52 that is formed into the un-oriented tube 42, which is converted into the oriented tube 38 and/or the stent 10. The Fiber-reinforced Laminate 130 is comprised of a fiber-reinforced laminate height 131, a fiber-reinforced laminate width 137, a fiber-reinforced laminate length 132, a fiber-reinforced laminate major surface 133, a fiber-reinforced laminate long minor surface 135, a fiber-reinforced laminate short minor surface 134, and a fiber-reinforced laminate lengthwise axis 136. The superimposed solid film(s) 66, the fibrous sheet 108, and/or the infused fibrous sheet 126 that are within the Fiber-reinforced Laminate 130 may be interconnected or disconnected prior to forming the Fiber-reinforced Laminate 130 into the roll 52 and/or the Roll Including Active Ingredient(s) 143 that is formed into the un-oriented tube 42, which is converted into the oriented tube 38 and/or the stent 10. The knit line 65 may interconnect the solid film(s), 66, the fibrous sheet(s) 108 and/or the infused fibrous sheet 126 that are within the Fiber-Reinforced Laminate 130 before or after forming the solid film(s), 66, the fibrous sheet(s) 108 and/or the infused fibrous sheet 126 into the roll 52. Moreover, the Fiber-reinforced Laminate 130 may include molecular chain orientation that is imparted on the Fiber-reinforced Laminate 130 when it is dry or swollen by stretching in the Fiber-reinforced Laminate 130 in the machine direction 79, the transverse direction 80 or the biaxial direction 81 prior to or during formation of the roll 52 or the Roll Including the Active Ingredient(s) 143 that is formed into the oriented tube 38, which is converted into the stent 10.

FIG. 33 depicts an Indirect Roll Formation Process 138. The Indirect Roll Formation Process 138 forms the Roll 52. As depicted in FIG. 33, the Indirect Roll Formation Process 138 comprises the shaft 74, at least one solid film 66 and a Film Rotation Direction 139. As depicted in FIG. 19 and FIG. 33, the roll 52 is formed by positioning The Beginning Of The Roll 58 in contact with the Shaft Outer surface 78 and wrapping the solid film 66 around the shaft 74 in the Film Rotation Direction 139 until the entire length 68 of the solid film 66 encircles the shaft 74. The Film Rotation Direction 139 can be clockwise or counterclockwise. It is also possible to roll the cylindrical-shaped shaft 74 over the solid film(s) 66 to wrap the solid film(s) 66 around the shaft 74. The Indirect Roll Formation Process 138 forms the roll 52 depicted in FIG. 34. Although FIG. 34 depicts the solid film 66 wrapped around the shaft 74 five times, it is possible in other embodiments to wrap the solid film 66 around the shaft 74 between 2 to 2,000 times by increasing the length 68 of the solid film 66. The length 68 of the solid film 68 may range from about 3 mm to 8,000 cm. In other embodiments, the length 69 of the solid film 66 is longer or shorter. In other embodiments, the solid film 66 is wrapped around the shaft equal to or greater than 2,000 times. Once part or all of the length 68 of the solid film 66 is wrapped around the shaft 74, the End Of The Roll 59 or anywhere between the Beginning Of The Roll 58 and/or the End Of The Roll 59 may be secured to the Under-Film Thickness 94 to prevent the roll 52 from unwinding. Although the figures depict the Beginning Of The Roll 58 and the End Of The Roll 59 starting and ending at the same circumferential position on the roll 52 (e.g., at 90 degrees), in other embodiments the Beginning Of The Roll 58 and the End Of The Roll 59 may be positioned at different circumferential positions (anywhere from 0 to 360 degrees). For example, the Beginning Of The Roll 58 may be positioned at 270 degrees and the End Of The Roll 59 may be positioned at 90 degrees. The Indirect Roll Formation Processes 138 and the rolls 52 depicted in the figures are shown in exploded view to clearly illustrate the configuration of the solid film(s) 66 within the roll 52 that is formed into the unoriented tube 42, which is converted into the oriented tube 38 and/or the stent 10. It should be appreciated that the separation distance 60 ideally equals 0.000 mm or is substantially nonexistent in the actual roll 52 and that the Over-Film Thicknesses 93 lie directly on the Under-Film Thicknesses 94 without any space between the film thicknesses 67. Alternatively, or additionally, the Indirect Roll Formation Process 138 may form at least one of the laminate 100, the fibrous sheet 108, the infused fibrous sheet 126 and/or the Fiber-reinforced Laminate 130 into the roll 52.

Figure 39:
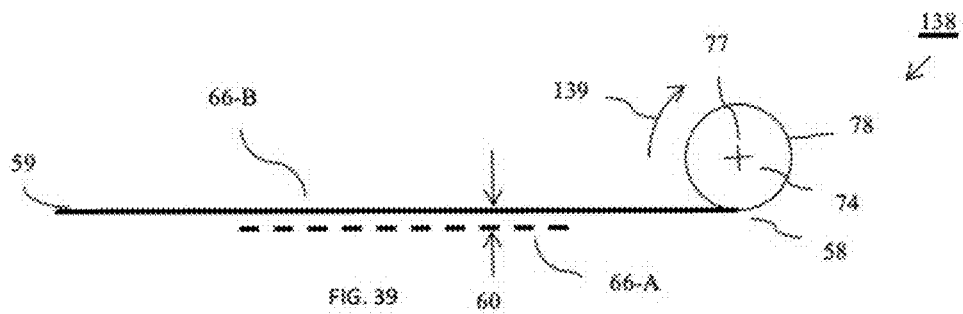
FIG. 39 depicts an exploded side view of an embodiment of the Indirect Roll Formation process, which comprises wrapping two partially superimposed solid films around the shaft to form the roll.

Alternatively, as depicted in FIG. 20 and FIG. 35, wrapping two partially or completely superimposed solid films 66 around the shaft 74 forms the roll 52 that is formed into the un-oriented tube 42, which is converted into the oriented tube 38 and/or the stent 10. FIG. 35 depicts the Indirect Roll Formation process 138, wherein the solid film 66-B is completely superimposed on solid film 66-A. FIG. 39 depicts the Indirect Roll Formation Process 138, wherein the solid film 66-B is partially superimposed on solid film 66-A. In an embodiment, the solid film 66-A and solid film 66-B, depicted in FIG. 20 and FIG. 35, may comprise the same stent material(s) 85. In other embodiments, the solid film 66-A and solid film 66-B, depicted in FIG. 20 and FIG. 35 may comprise different stent materials 85. In an embodiment, the solid film 66-A has the same film thickness 67 as solid film 66-B. In another embodiment, the solid film 66-A has the film thickness 67 greater than the solid film 66-B. In yet one more embodiment, the solid film 66-B has the film thickness 67 greater than the solid film 66-A. It should be appreciated that the film thicknesses 67 of all embodiments are within the film thickness 67 limitations provided within this specification, more narrowly within the specifications provided in FIG. 113. The Roll Formation Process 138 depicted in FIG. 35 produces the roll 52 depicted in FIG. 36. As depicted in FIG. 35, the roll 52 is formed by positioning The Beginning Of The Roll 58 in contact with the Shaft Outer surface 78 and wrapping the solid films 66 around the shaft 74 in the Film Rotation Direction 139 until the entire length 68 of the solid films 66 encircle the shaft 74. Since the roll 52 depicted in FIG. 36 includes two solid films 66, the films 66 may be wrapped around the shaft 74 between 2 to 1000 times to produce the roll 52 that is formed into the un-oriented tube 42, which is converted into the oriented tube 38 and/or the stent 10. In other embodiments, the roll 52 comprising two solid films 66 are wrapped around the shaft 74 equal to or greater than 1000 times. When the roll 52 comprises at least two solid films 66 comprising two different stent material(s) 85, two discrete layers 51 are formed within the un-oriented tube 42. The layers 51 are discrete because when the film thicknesses 67 within the roll 52 are interconnected during conversion of the roll 52 into the un-oriented tube 42 there is very little or no mixing of the stent material(s) 85 comprising the adjacent layers 51 at the bond 65, which results each layer 51 substantially retaining its unique composition after the interconnection is made. As depicted in FIG. 36, when looking at the roll 52 in exploded cross-sectional view, in an embodiment wherein the stent material(s) 85 comprising the solid film 66-A are different than the stent material(s) 85 comprising the solid film 66-B, a layer thickness 91 is formed within the roll 52, wherein the solid film 66-A forms a layer thickness 91-A and the solid film 66-B forms a layer thickness 99-B. In an embodiment wherein the stent material(s) 85 comprising the solid film 66-A and the solid film 66-B are the same, there is one layer 91 formed. One method of observing the discrete layers within the stent 10 wall thickness 13 is to examine the cross-section of the stent 10 wall thickness 13 with an optical microscope using cross-polarized light. DuPont Engineering Polymers Failure Analysis Using Microscopic Techniques authored by Edith Bohme provide techniques for examining the layers 51.

Although FIG. 36 shows superimposed solid film 66-A and solid film 66-B being wrapped around the shaft 74 three times, the superimposed solid film 66-A and solid film 66-B can be wrapped around the shaft 74 more than three times by increasing the length 68 of the solid film 66-A and the solid film 66-B. It should be appreciated, that the pattern of the solid film 66-B being positioned near the inner surface 62 of the roll 52 and the solid film 66-A positioned on the outer surface 61 of the roll 52 may be reversed so that solid film 66-A is on the inner surface 62 and solid film 66-B is on the outer surface 61. In the preferred embodiment, the pattern of two alternating films 66 that is depicted in FIG. 36 and its variants may be repeated within the roll thickness 57 between 1 to 1000 times. In other embodiments, the pattern of two alternating solid films 66 that are depicted in FIG. 36 and its variants may be repeated within the roll thickness 57 equal to or greater than 1000 times.

In another embodiment, as depicted in FIG. 37, wrapping three partially or fully superimposed solid films 66 around the shaft 74 forms the roll 52 that is formed into the un-oriented tube 42, which is converted into the oriented tube 38 and/or the stent 10. In an embodiment, all the solid films 66-A, solid film 66-B and solid film 66-C depicted in FIG. 37 comprise the same stent material(s) 85. In other embodiments, at least one or all of the solid film 66-A, solid film 66-B and solid film 66-C depicted in FIG. 37 may comprise different stent material(s) 85. When the solid film 66-A comprises a different stent material 85 than solid film 66-B and solid film 66-C, solid film 66-B comprises different stent material 85 than solid film 66-A and solid film 66-C and solid film 66-C comprises different stent material 85 than solid film 66-A and solid film 66-B, three different layers 51 are formed within the stent 10 wall thickness 13, which have a layer thickness 91-A, layer thickness 91-B and layer thickness 91-C. In an embodiment, two of the layers 51 comprise the same stent material 85 and one layer 51 comprises a different stent material 85, wherein the layer 51 comprising the different stent material 85 separates the two layers comprising the same stent material 85. In an embodiment, the solid film 66-A has the same film thickness 67 as solid film 66-B and solid film 66-C. In other embodiments, at least one of the solid films 66 within the embodiment depicted in FIG. 37 is larger than at least one or all the other solid film 66. It should be appreciated that the film thicknesses 67 of all embodiments are within the film thickness 67 limitations provided within this specification, more narrowly within the film thickness 67 limitations provided in FIG. 113.

Figure 38:
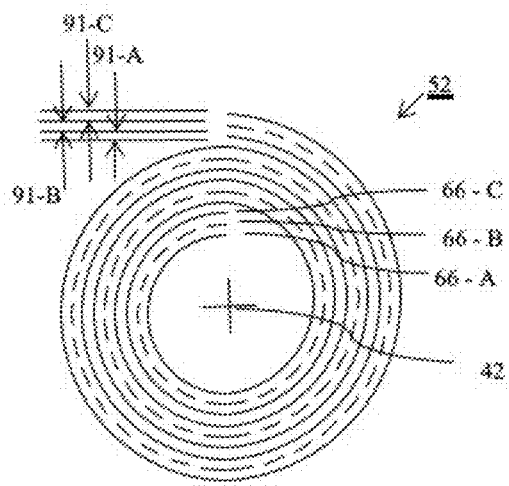
FIG. 38 depicts an exploded end view of an embodiment of the roll comprising three superimposed solid films.

The Roll Formation Process 138 depicted in FIG. 37 produces the roll 52 depicted in FIG. 38. As depicted in FIG. 37, the roll 52 is formed by positioning The Beginning Of The Roll 58, which comprises three solid films 66, in contact with the Shaft Outer surface 78 and wrapping the superimposed solid film 66-A, solid film 66-B and solid film 66-C around the shaft 74 in the Film Rotation Direction 139 until the entire length 68 of the solid films 66 encircle the shaft 74. The solid film 66-A may be connected to the solid film 66-B and solid film 66-A may be connected to solid line 66-C with the bond 65 prior to wrapping the solid films 66 around the shaft 74. In other embodiments, solid film 66-A, solid film 66-B and solid film 66-C may be disconnected prior to wrapping the solid films 66 around the shaft. Since the roll 52 depicted in FIG. 38 includes three solid films 66, the superimposed films 66 may be wrapped around the shaft 74 between 1 to 334 times to produce the roll 52, which is converted into the un-oriented tube 34. In other embodiments, the roll 52 comprising three solid films 66 are wrapped around the shaft 74 equal to or greater than 334 times. The pattern of three alternating films 66 that is depicted in FIG. 36 and its variants may be repeated within the roll thickness 57 between 1 to 334 times. In other embodiments, the pattern of two alternating films that is depicted in FIG. 36 and its variants may be repeated within the roll thickness 57 equal to or greater than 334 times. It should be appreciated that it is possible for the position of solid film 66-A, solid film 66-B and solid film 66-C to be positioned differently that what is shown in FIG. 37, wherein solid film 66-C is positioned on the bottom, solid film 66-B is positioned in the middle and solid film 66-A is positioned on the top of the stack of the superimposed films 66. For example, where the position of the solid film 66 within the stack of superimposed films 66 is (top, middle, bottom), each solid film 66 may alternatively have the position within the stack of the superimposed solid films 66 depicted in FIG. 37 in one of the following configurations: (66-A, 66-C, 66-B) or (66-B, 66-A, 66-C) or (66B, 66-C, 66-A) or (66-C, 66-B, 66-A) or (66-C, 66-A, 66-B).

Although FIG. 37 and FIG. 38 depict three completely superimposed solid film(s) 66, in other embodiments there may be more than three completely superimposed solid film(s) 66 wrapped around the shaft 74 to form the roll 52 that is formed into the un-oriented tube 42, which is converted into the oriented tube 38 and/or the stent 10. The maximum number of solid films 66 that may be incorporated into the roll 52 depends on the practical limit of the un-oriented tube wall thickness 45, the number of wraps of the solid films 66 around the shaft 74 and the film thickness 67 limitations provided within this specification, more narrowly the film thicknesses 67 provided in FIG. 113. When there are greater than three solid films 66 incorporated into the roll 52, each of the solid films 66 may comprise the same stent material(s) 85 or at least one or all of the solid film(s) 66 may comprise different stent material(s) 85. The solid film 66-A may be connected or disconnected to the solid film 66-B and the solid film 66-B may be connected or disconnected to solid film 66-C and so on with the bond 65 prior to wrapping the solid films 66 around the shaft 74. The pattern of greater than three alternating films 66 (not depicted) may be repeated within the roll thickness 57 equal to between 1 time to 1000 times divided by the number of the superimposed films 66. In other embodiments, the pattern of greater than three alternating solid films 66 may be repeated within the roll thickness 57 the number of times that is equal to or greater than 1000 times divided by the number of superimposed solid films 66. It is believed that between 2 to 500 separate solid films 66 may be at least partially or completely superimposed prior to wrapping the superimposed solid films 66 around the shaft 74 to form the roll 52 that forms the un-oriented, which is converted into the oriented tube 38 and/or the stent 10. In other embodiments, there may be equal to or greater than 500 separate solid films 66 at least partially or completely superimposed prior to wrapping the superimposed solid films 66 around the shaft 74 to form the roll 52.

Figure 40:
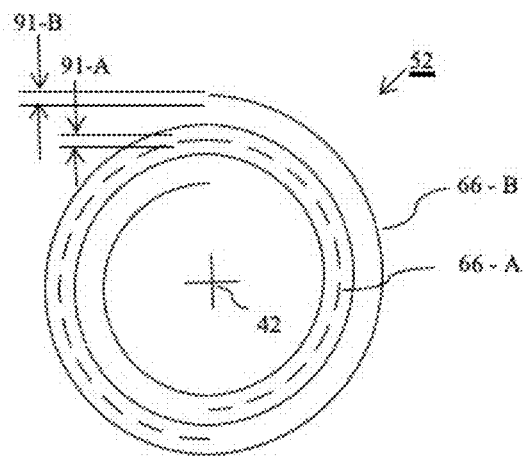
FIG. 40 depicts an exploded side view of an embodiment of the roll comprising two partially superimposed solid films.

In another embodiment, as depicted in FIG. 39, wrapping two partially superimposed solid films 66 around the shaft 74 forms the roll 52 that is formed into the un-oriented tube 42, which is converted into the oriented tube 38 and/or the stent 10. FIG. 39 depicts one long solid film 66-B that is partially superimposed one short solid film 66-A. The roll 52 is formed by positioning the Beginning Of The Roll 58 of solid film 66-B on the shaft outer surface 78, partially wrapping the solid film 66-B around the shaft 74 until solid film 66-A is near the shaft 74 and then wrapping the solid film 66-B and the solid film 66-A around the shaft 74 until the entire length 68 of the solid film 66-B and the solid film 66-A are wrapped around the shaft 74. The Indirect Roll Formation Process 138 depicted in FIG. 39 results in the roll 52 depicted in FIG. 40. It should be appreciated that the solid film 66-A may be positioned on top of the solid film 66-B. Moreover, the solid film 66-A may be positioned near the Beginning Of The Roll 58 instead of the middle of the roll and/or near the End Of The Roll 59 instead of the middle of the roll. In other embodiments, the solid film 66-A may be positioned on either the top and/or the bottom of the solid film 66-B. Furthermore, it should be appreciated that although FIG. 39 depicts that the film 66-A covers about 50% of the length 68 of the solid film 66-B that in other embodiments the solid film 66-A covers greater than or less than 50% of the length 68 of the solid film 66-A. The solid films 66 depicted in FIG. 39 and FIG. 40 may have the same film thickness 67 or different film thicknesses 67. For example, solid film 66A may be thicker than solid film 66-B or the opposite. The solid films 66-A and solid film 66-B, depicted in FIG. 39 and FIG. 40, may comprise the same stent material(s) 85 or comprise different stent materials 85. When solid film 66-A comprises a different stent material 85 than solid film 66-B, the layers 51 are formed, which have the layer thickness 91-A and layer thickness 91-B. Moreover, though FIG. 40 depicts in exploded cross sectional view that the solid film 66-B forms one complete wrap and solid film 66-B forms three complete wraps, in other embodiments solid film 66-B and/or solid film 66-A may form a greater or lesser amount of wraps than what is shown in the figures or at least one of the wraps may incompletely surround the circumference of the roll 52. Additionally, it should be appreciated that there may be greater than one long solid film 66 and greater than one short film 66 positioned within the roll 52 and that the long films 66 may be of the same or different lengths 68 and the short films 66 may be of the same or different lengths 68.

Figure 41:
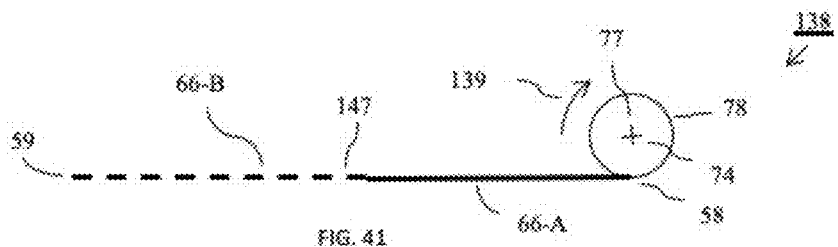
FIG. 41 depicts a side view of an embodiment of the Indirect Roll Formation process, which comprises wrapping two solid films that are positioned in series around the shaft to form the roll.
Figure 42:
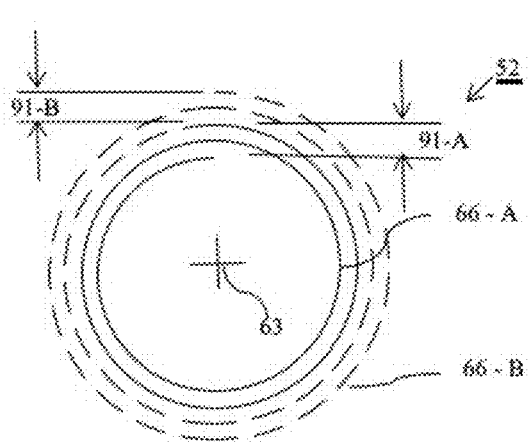
FIG. 42 depicts an exploded side view of an embodiment of the roll comprising two different films positioned in series.

In another embodiment of the Indirect Roll Formation Process 138, as depicted in FIG. 41, wrapping two different solid films 66 that are positioned in series around the shaft 74 forms the roll 52 that is formed into the un-oriented tube 42, which is converted into the oriented tube 38 and/or the stent 10. FIG. 41 depicts solid film 66-A being wrapped around the shaft 74 first and solid film 66-B being wrapped around the shaft 74 second. The Roll Formation Process 138 depicted in FIG. 41 produces the roll 52 depicted in FIG. 42. The solid film 66-A may be connected to the solid film 66-B with an optional splice 147 prior to wrapping the solid films 66 around the shaft 74, wherein the splice 147 that connects the two solid film(s) 66 may be abutting or overlapping. Alternatively, the solid films 66-A and 66-B may be disconnected prior to wrapping the solid films 66 around the shaft 74 so that each separate solid film 66 is individually wrapped around the shaft 74. The solid films 66 depicted in FIG. 41 and FIG. 42 may have the same film thickness 67 or different film thicknesses 67. For example, solid film 66-A may be thicker than solid film 66-B or the opposite. The solid films 66-A and solid film 66-B, depicted in FIG. 41 and FIG. 42, may comprise the same stent material(s) 85 or comprise different stent materials 85. When solid film 66-A comprises a different stent material 85 than solid film 66-B, the layers 51 are formed, which have the layer thickness 91-A and layer thickness 91-B. Although FIG. 42 depicts the solid film 66-A and solid film 66-B being wrapped around the shaft 74 two times, the solid film 66-A may be wrapped around the shaft 74 greater than or less than two times and solid film 66-B may be wrapped around the shaft 74 greater than or less than two times by increasing or decreasing the length 68 of the solid film 66-A and the solid film 66-B. Moreover, although FIG. 42 depicts that solid film 66-A and solid film 66-B are both are wrapped around the shaft 74 the same number of times, in other embodiments solid film 66-A may be wrapped around the shaft 74 greater or lesser times than solid film 66-B. It should be appreciated, that the pattern of the solid film 66-A being positioned near the inner surface 62 of the roll 52 and the solid film 66-B on the outer surface 61 may be reversed so that solid film 66-B is on the inner surface 62 and solid film 66-A is on the outer surface 61. It is also possible that the roll thickness 57 pattern shown in FIG. 42, wherein there are two film thicknesses 67 comprising solid film 66-A and two film thicknesses 67 comprising solid film 66-B, may be repeated multiple times until the roll thickness 57 reaches a dimension that is suitable for producing the unoriented tube 42. For example, and without intent on limiting, the roll thickness 57 may include the pattern starting from the roll inner surface 62 to the roll outer surface 61 comprising: (1) two film thicknesses 67 comprising solid film 66-A and two film thicknesses 67 comprising solid film 66-B; (2) two film thicknesses 67 comprising solid film 66-A and two film thicknesses 67 comprising solid film 66-B ("first repeat"); (2) two film thicknesses 67 comprising solid film 66-A and two film thicknesses 67 comprising solid film 66-B ("2nd repeat") and (4) so on until the desired roll thickness 57 is achieved, or the opposite. To repeat the pattern in the embodiment depicted in FIG. 43, one additional solid film 66-A and one additional solid film 66-B must be added to the roll depicted in FIG. 42 to produce the 1st repeat and one additional solid film 66-A and one additional solid film 66-B must be added to the roll depicted in FIG. 42 to produce the 2nd repeat. The pattern depicted in FIG. 41 and FIG. 42 may be repeated between 1 to 500 times. In other embodiments of the roll 52 configuration having two different solid films 66 positioned in series in a repeating pattern may be repeated equal to or greater than 500 times.

In yet one more embodiment of the Indirect Roll Formation Process 138, as depicted in FIG. 43, wrapping at least three different solid films 66 that are positioned in series around the shaft 74 forms the roll 52 that is formed into the un-oriented tube 42, which is converted into the oriented tube 38 and/or the stent 10. FIG. 43 depicts solid film 66-A being wrapped around the shaft 74 first, solid film 66-B being wrapped around the shaft 74 second and solid film 66-C being wrapped around the shaft 74 third. The Roll Formation Process 138 depicted in FIG. 43 produces the roll 52 depicted in FIG. 44. The solid film 66-A may be connected to the solid film 66-B and solid film 66-B may be connected to solid film 66-C with the optional splice 147 that interconnects the solid films 66 prior to wrapping the solid films 66 around the shaft 74, wherein the splice 147 may be the abutting or overlapping. Alternatively, the solid films 66-A, 66-B and 66-C may be disconnected prior to wrapping the solid films 66 around the shaft 74 so that each individual solid film 66 is wrapped around the shaft 74 sequentially. The solid films 66 depicted in FIG. 43 and FIG. 44 may have the same film thickness 67 or different film thicknesses 67 that are within the limitations provided within this specification, more narrowly within the specifications provided in FIG. 113. For example, solid film 66-A may be thicker than solid film 66-B and solid film 66-C, solid film 66-B may be thicker than solid film 66-A and solid film 66-C or solid film 66-C may be thicker than solid film 66-A and solid film 66-B. In other embodiments, there may be any combinations or permutations of film thicknesses 67 that are selected from the limitations provided within this specification, more narrowly the specifications provided in FIG. 113, that may be incorporated into the roll 52, wherein the film thicknesses 67 are selected from the group of: (1) F-A is thinnest, (2) F-A is second thinnest, (3) F-A is third thinnest, (4) F-A is thickest, (5) F-A is second thickest, (6) F-A is third thickest, (7) F-B is thinnest, (8) F-B is second thinnest, (9) F-B is third thinnest, (10) F-B is thickest, (11) F-B is second thickest, (12) F-B is third thickest, (13) F-C is thinnest, (14) F-C is second thinnest, (15) F-C is third thinnest, (16) F-C is thickest, (17) F-C is second thickest or (18) F-C is third thickest; wherein "F-A" refers to solid film 66-A, "F-B" refers to solid film 66-B and "F-C" refers to solid film 66-C.

Figure 44:
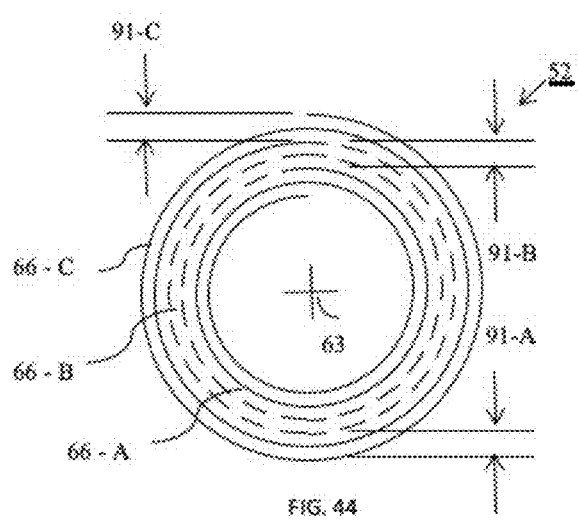
FIG. 44 depicts an exploded side view of an embodiment of the roll comprising three different films positioned in series.

In an embodiment, all the solid films 66-A, solid film 66-B and solid film 66-C depicted in FIG. 43 and FIG. 44 may comprise the same stent material(s) 85. In other embodiments, at least one or all the solid film 66-A, solid film 66-B and solid film 66-C depicted in FIG. 43 and FIG. 44 may comprise different stent material(s) 85. When the solid film 66-A comprises different stent material(s) 85 than solid film 66-B and solid film 66-C, solid film 66-B comprises different stent material(s) 85 than solid film 66-A and solid film 66-C and solid film 66-C comprises different stent material(s) 85 than solid film 66-A and solid film 66-B, the layers 51 form within the roll thickness 57, which have a layer thickness 91-A, layer thickness 91-B and layer thickness 91-C.

Although FIG. 44 depicts solid film 66-A, solid film 66-B and solid film 66-C being wrapped around the shaft 74 two times, the solid film 66-A may be wrapped around the shaft 74 greater than or less than two times, solid film 66-B may be wrapped around the shaft 74 greater than or less than two times and solid film 66-C may be wrapped around the shaft 74 greater than or less than two times by increasing or decreasing the length 68 of the solid film 66-A, the solid film 66-B and/or the solid film 66-C. Moreover, although FIG. 42 depicts that solid film 66-A, solid film 66-B and solid film 66-C are both are wrapped around the shaft 74 the same number of times, in other embodiments solid film 66-A may be wrapped around the shaft 74 greater or lesser times than solid film 66-B and/or solid film 66-C, solid film 66-B may be wrapped around the shaft 74 greater or lesser times than solid film 66-A and/or solid film 66-C and solid film 66-C may be wrapped around the shaft 74 greater or lesser times that solid film 66-A and/or solid film 66-B.

It should be appreciated that it is possible for the position of solid film 66-A, solid film 66-B and solid film 66-C to be positioned differently than what is shown in FIG. 43, wherein solid film 66-A is positioned near the Beginning Of The Roll 58, solid film 66-B is positioned in the middle of the roll and solid film 66-C is positioned near the End Of The Roll 59 of the solid films 66 arranged in series. For example, where the position of the solid film 66 within the series is formatted (near Beginning Of The Roll 58, middle of the roll, near End Of The Roll 59), each solid film 66 may have the position within the series depicted in FIG. 61 in one of the following configurations: (F-A, F-C, F-B) or (F-B, F-A, F-C) or (F-B, F-C, F-A) or (F-C, F-B, F-A) or (F-C, F-A, F-B); wherein "F-A" refers to solid film 66-A, "F-B" refers to solid film 66-B and "F-C" refers to solid film 66-C.

Although FIG. 41 and FIG. 42 depict three solid film(s) 66 in series, in other embodiments there may be more than three solid film(s) 66 wrapped around the shaft 74 in series to form the roll 52 that is formed into the un-oriented tube 42, which is converted into oriented tube 38 and/or the stent 10. The maximum number of films 66 that may be incorporated into the roll 52 depends on the practical limit of the un-oriented tube wall thickness 45 and/or the number of wraps of the films 66 around the shaft 74. When there are more than three solid films 66 incorporated into the roll 52 in series, each of the solid films 66 may comprise the same stent material(s) 85 or at least two of the film(s) 66 may comprise different stent material(s) 85. In an embodiment, there may be between 2 to 1000 solid films 66 wrapped around the shaft 74 in series when forming the roll 52. In other embodiments, there may be equal to or greater than 1000 solid films wrapped around the shaft 74 in series when forming the roll 52.

FIG. 45 depicts on embodiment of an Indirect Formation Process Including Active Ingredient(s) 140 from the side view. The Indirect Roll Formation Process Including Active Ingredients 140 forms the Roll Including Active Ingredient(s) 143 that is formed into the un-oriented tube 42, which is converted into the oriented tube 38 and/or the stent 10. As depicted in FIG. 45, the Roll Formation Process Including Active Ingredients 140 comprises the shaft 74, the solid film 66, the Film Rotation Direction 139, the active ingredient(s) 34, the Film Major surface 73, an Active Ingredient Storage Area 141 and an Active Ingredient-Free Area 142. In this example, the active ingredient(s) 34 are positioned at least partially on the major surfaces 73 of the solid film 66 within at least one Active Ingredient Storage Areas 141. The active ingredient(s) 34 may be applied to either one or both major outer surface(s) 73 of the solid film(s) 66 by spraying, brushing or rolling the active ingredient(s) 34 onto at least one of the major surfaces 73 of the solid film 66, wherein the active ingredient(s) 34 may be in a liquid, solid or solid and liquid form (a "mixture"). Alternatively, the active ingredient(s) 34 may be applied to the solid film 66 by chemical vapor deposition (e.g. electrostatic spray assisted vapor deposition, sherardizing, epitaxy), physical vapor deposition (cathodic arc deposition, electron beam physical vapor deposition, ion plating, ion beam assisted deposition, magnetron sputtering, pulsed laser deposition, sputter deposition, vacuum deposition, vacuum evaporation, evaporation deposition, pulsed electron deposition), and roll-to-roll coating processes (air knife coating, anilox coater, flexo coater, gap coating, gravure coating, immersion (dip coating), kiss coating, metering rod (Meyer bar) coating, reverse roll coating, forward roll coating, silk screen coater, rotary screen coater, extrusion coating, curtain coating, slide coating, slot die bead coating, tensioned-web slot die coating, inkjet printing, lithography, flexography). The active ingredient(s) 34 comprising solid particles or liquid droplets may include a charge that attracts the active ingredient(s) 34 or the vehicle carrying the active ingredient(s) 34 to the targeted Active Ingredient Storage Area 141. For example, the active ingredient(s) 34 in the form of the particle or droplet 154 may include a positive charge that propels the active ingredient(s) 34 toward the grounded solid film 66 or a grounded object positioned directly behind Active Ingredient Storage Area 141 on part or the entire major surface of the solid film 66 in a way that results in the active ingredient(s) 34 being positioned within the Active Ingredient Storage Area 141 prior to forming the Roll Including Active Ingredient(s) 143. The active ingredient(s) 34 may be un-dissolved, partially dissolved or completely dissolved in at least one solvent 86 when applied to part or the complete major outer surface(s) 73 of the solid film 66 in a way that when the solvent 86 is removed that the active ingredient(s) 34 are at least partially or completely adhered to or at least partially or completely imbedded in the solid film's 66 major outer surface(s) 73 within the Active Ingredient Storage Area(s) 141. Alternatively, or additionally, the active ingredient(s) 34 may be mixed with at least one solvent 86 and at least one stent material 85 to form a solution 83 or mixture that may be sprayed onto at least one of the major surfaces 73 of the solid film 66 within the Active Ingredient Storage Area 141 and the solution 83 is allowed to partially or completely dry, which results in the active ingredient(s) 34 being adhered to at least one of the major surfaces 73 of the solid film(s) 66.

Alternatively, or additionally, the active ingredient(s) 34 may be applied in a solid form. The solid particles of the active ingredient(s) 34 may be applied to the swollen film 66, wherein the swollen film 66 comprises the solid film 66 wherein the solvent(s) 86 have not been completely removed from the solid film 66. The particles comprising the active ingredient(s) 34 may be within the size range of greater than 0.000 to 0.010 mm, more narrowly between 0.000 to 0.005 mm. The swollen film 66 is softer than the completely solid film that contains 0 wt. % solvent(s) 86 to less than 0.5 wt. % solvent(s) 86 and if the solid particles of the active ingredient(s) 34 are, for example, sprayed or otherwise impacted on the outer major surface(s) 73 of the swollen film 66, the solid particles comprising the active ingredient(s) 34 at least partially penetrate the solid film thickness 67, which results in the solid active ingredient(s) 34 being adhered to the outer major surface(s) 73 of the solid film 66 or imbedded within the solid film 66 when the solvent(s) 86 are substantially completely removed from the solid film 66. Alternatively, or additionally, the solid particles comprising the active ingredient(s) 34 may also be applied to the softened film 66, wherein warming the solid film 66 produces the softened solid film 66. If the solid particles comprising the active ingredient(s) 34 are, for example, sprayed on at least one of the outer major surface(s) 73 of the warm, softened film 66 or otherwise impacted on the warm, softened film 66, the solid particles comprising the active ingredient(s) 34 at least partially penetrate the warm, softened solid film thickness 67, which results in the solid active ingredient(s) 34 being adhered to or embedded within the outer major surface(s) 73 of the solid film 66 when the warmed, softened solid film 66 is cooled. The solid film 66 may be heated up to about the melting temperature of at least one or all of the stent material(s) 85 within the solid film 66 to soften the solid film 66 to enable at least partial or complete penetration of the applied solid particles comprising the active ingredient(s) 34 to adhere to the outer major surface(s) 73 of the solid film 66 or remain embedded within the solid film 66 when the solid film 66 is cooled to a temperature below the glass transition temperature of at least one of the stent material(s) 85 comprising the solid film 66 or cooling the warmed solid film 66 to a normal room temperature.

The active ingredient(s) 34 or the active ingredient(s) 34 and at least one stent material 85 may be positioned within the roll 52, the un-oriented tube 42, the oriented tube 38 and/or the stent 10 in at least one of the following locations: (1) between all the film thicknesses 67 (refer to FIG. 49), (2) between at least one part of the film thicknesses 67 and not between one part of the film thicknesses 67 (refer to FIG. 46), (3) within all the film thicknesses 67 (refer to FIG. 25), (4) within at least one part of the film thicknesses 67 and not within at least one other part of the film thicknesses 67 (refer to FIG. 62, FIG. 63, FIG. 64), (5) within all of the film thicknesses 67 and between all of the film thicknesses 67 (refer to FIG. 88, FIG. 89, FIG. 90), (6) within at least one part of the film thicknesses 67 and between at least one part of the film thicknesses 67, (7) within all of the film thicknesses 67 and between at least one part of the film thicknesses 67 or (8) within at least one part of the film thicknesses 67 and between all of the film thicknesses 67. In an embodiment, positioning the active ingredient(s) 34 within two Active Ingredient Storage Areas 141 produces the Roll Including Active Ingredient(s) 143 depicted in FIG. 46. The Roll Including Active Ingredient(s) 143 is produced by positioning the Beginning Of The Roll 58 in contact with the shaft outer surface 78 and wrapping the solid film 66 around the cylindrical-shaped shaft 74 in the film rotation direction 139 until the entire length 68 of the solid film 66 encircles the shaft 74 in a way that positions the active ingredient(s) 34 between the film thicknesses 67 of the wrapped solid film 66 as depicted in FIG. 45. Another method of producing the Roll Including Active Ingredient(s) 143 depicted in FIG. 46 is to arrange the active ingredient(s) 34 on the solid film 66 as depicted in FIG. 47. The active ingredient(s) 34 may be included in any of the solid film 66, the roll 52, the coating 30 and the stent 10 configurations or combinations thereof depicted in the figures. Alternatively, at least one solid film 66 may not include the active ingredient(s) 34 (refer to FIG. 24).

In another embodiment of the Roll Including Active Ingredient(s) 143 there may be only one Active Ingredient Storage Area 141 near the Beginning Of The Roll 58, which results in the active ingredient(s) 34 being positioned only near the inner surface 62 of the roll 52 (not depicted). Conversely, there may be only one Active Ingredient Storage Area 141 near the End of the Roll 59, which results in the active ingredient(s) 34 being positioned only near the outer surface 61 of the roll 61 (not depicted). When there are active ingredient(s) 34 located near the inner surface 48 of the un-oriented tube 42 and the outer surface 47 of the un-oriented tube 42, the active ingredient(s) 34 positioned near the inner surface 48 may be the same or different than those positioned near the outer surface 47. For example, those positioned near the outer surface 47 may inhibit restenosis and those positioned near the inner surface 48 may promote endothelialization or inhibit thrombosis (e.g., antiplatelet), when the un-oriented tube 42 that is made from the Roll Including Active Ingredient(s) 143 is converted into the oriented tube 38 and/or the stent 10. In one more embodiment, the Indirect Roll Formation Process Including Active Ingredient(s) 140 comprises the solid film 66 having one Active Ingredient Storage Area 141 and the remainder of the solid film 66 is an Active Ingredient-free Area 142 as depicted in FIG. 48, wherein the Active Ingredient-free Area 142 is 2 near the End Of The Roll 59. The Indirect Roll Formation Process Including Active Ingredient(s) 140 depicted in FIG. 48 produces the Roll Including Active Ingredient(s) 143 depicted in FIG. 49. Alternatively, FIG. 48 may comprise one solid film 66-A including the active ingredient(s) 34 and one solid film 66-B excluding the active ingredient(s) 34, wherein solid film 66-A is wrapped first around the shaft 74 at least one time and the solid film 66-B is wrapped second around the shaft 74 at least one time to form the Roll Including Active Ingredient(s) 143, or the opposite.

Figure 50:
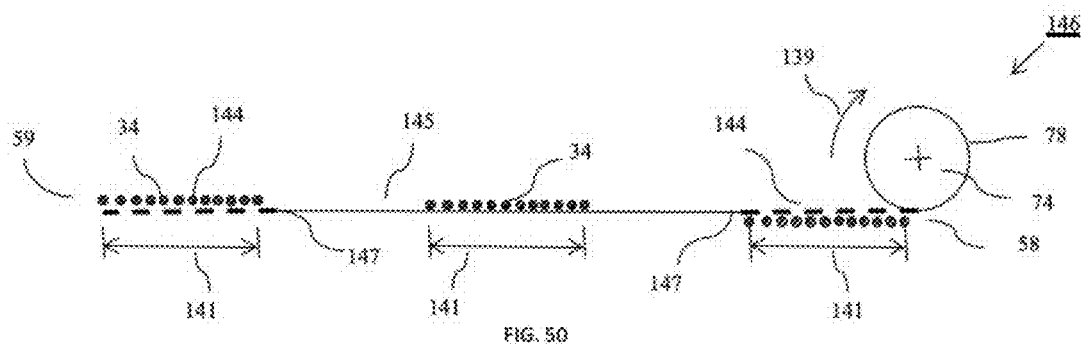
Figure 51:
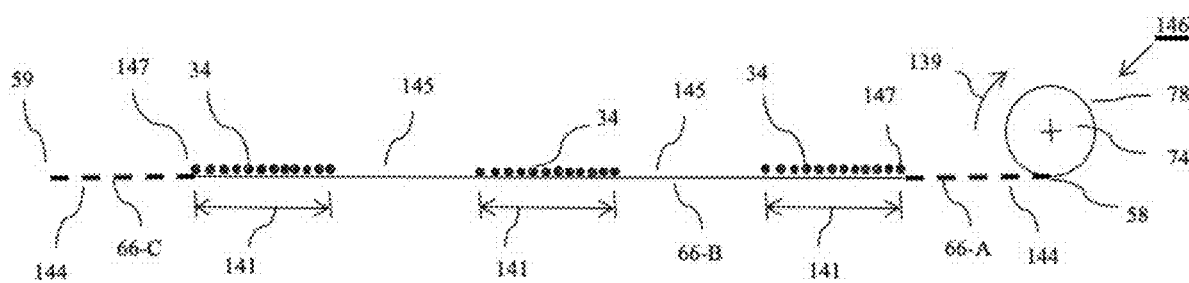
Figure 52:
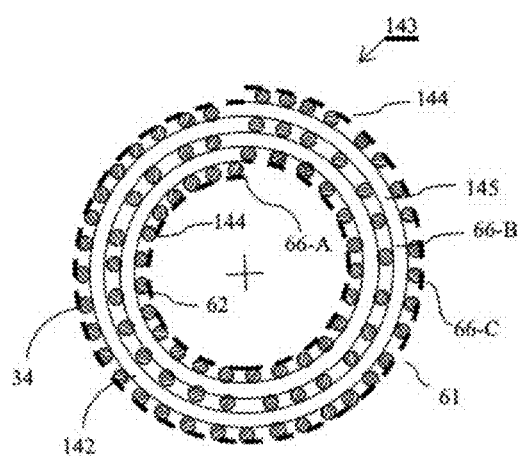
FIG. 52 depicts the Roll Including Active Ingredient(s), wherein the films positioned near the inner surface and the outer surface comprises a fast rate degrading and/or resorbing film and the film positioned in the middle of the roll wall thickness is a slow or medium rate degrading and/or resorbing film.

Referring to FIG. 50, the Indirect Roll Formation Process Including Fast Degrading Rate Films 146 comprises at least one Fast Degrading Rate Film 144 and at least one Slow Or Medium Degrading Rate Film 145. The Fast Degrading Rate Film 144 allows at least part or all of the active ingredient(s) 34 positioned near the Fast Degrading Rate Film 144 to be delivered by the stent 10 into the treatment site 35. In embodiments, the Fast Degrading Rate Film 144 allows at least part or all of the active ingredient(s) 34 to be delivered by the stent 10 into the treatment site 35 within greater than 0 to 7 days, within greater than 0 to 14 days, within greater than 0 to 21 days, greater than 0 to 28 days, within greater than 0 to 35 days, within greater than 0 to 42 days, within greater than 0 to 56 days, within greater than 0 to 63 days after the stent 10 is deployed within the anatomical lumen 36. The Slow Or Medium Degrading Rate Film 145 provides mechanical support to the stent 10 until the anatomical lumen 36 is self-supporting. In an embodiment, the Fast Degrading Rate Film 144 is depicted in FIG. 50 and FIG. 51 as a dashed line and the Slow Or Medium Degrading Rate Film 145 is depicted as a solid line for ease of illustration. The Fast Degrading Rate Film 144 may be positioned near the Beginning of the Roll 58 and/or the End of the Roll 59 and the Slow Or Medium Degrading Rate Film 145 may be positioned between the two Fast Degrading Rate Films 144. The Fast Degrading Rate Film 144 and the Slow Or Medium Degrading Rate Film may be connected with the optional abutting or overlapping splice 147 as depicted in FIG. 50. The Roll Including Active Ingredients(s) 143 is formed using The Roll Formation Process Including Fast Degrading Rate Film 146 by placing the Beginning Of The Roll 58 in contact with the shaft outer surface 78 and wrapping the interconnected solid films 66 around the shaft 74 in the film rotation direction 139 until the entire lengths 68 of the spliced solid films 66 encircle the shaft 74 as depicted in FIG. 50. Alternatively, the three separate solid films 66 may be individually wrapped around the shaft 74 by: (1) wrapping the first Fast Degrading Rate Film 144 including the active ingredient(s) 34 around the shaft 74 at least one time with the active ingredient(s) 34 facing away from the shaft 74; (2) wrapping the only Slow Or Medium Degrading Rate Film 145 including active ingredient(s) 34 around the shaft 74 at least one time with the active ingredient(s) 34 facing toward the shaft 74 on top of the previously wrapped Fast Degrading Rate Film 144 including the active ingredient(s) 34; and (3) wrapping the second Fast Degrading Rate Film 114 including the active ingredient(s) 34 around the shaft 74 at least one time with the active ingredient(s) 34 facing toward the shaft 74 on top of the previously wrapped Slow Or Medium Degrading Rate Film 144 including the active ingredient(s) 34. In yet more embodiment, as depicted in FIG. 51, the three separate solid films 66 may be individually wrapped around the shaft 74 by: (1) wrapping the first Fast Degrading Rate Film 144 excluding the active ingredient(s) 34 around the shaft 74; (2) wrapping the only Slow Or Medium Degrading Film 145 including active ingredient(s) 34 located in the three Active Ingredient Storage Areas 141 around the shaft 74 with the active ingredient(s) 34 facing toward the shaft 74 on top of the previously wrapped Fast Degrading Rate Film 144 excluding the active ingredient(s) 34; and (3) wrapping the second Fast Degrading Rate Film 114 excluding the active ingredient(s) 34 around the shaft 74 at least one time on top of the previously wrapped Slow or Medium Degrading Rate Film 144 including the active ingredient(s) 34. The methods depicted in FIG. 50 and FIG. 51 result in producing the Roll Including Active Ingredient(s) 143 depicted in FIG. 52. As depicted in FIG. 52, in an embodiment the Fast Degrading Rate Film 144, which is shown as a dashed line for ease of visualization, may be facing the anatomical lumen 36 near the outer surface 66 and near the contents 6 near the inner surface 61, when the Roll Including Active Ingredient(s) 143 is formed into the un-oriented tube 43, which is converted into oriented tube 38 and/or the stent 10. Additionally, the interior portion of the stent 10 wall thickness 13 may also include the active ingredient(s) 34 so that drug delivery occurs during at least part or the complete time that it takes for the Slow Or Medium Degrading Rate Film 144 to be resorbed.

FIG. 52 depicts an embodiment of the Roll Including Active Ingredient(s) 143, wherein the Fast Degrading Rate Film 144 located near the roll inner surface 62 comprises one wrap of the Fast Degrading Rate Film 144, the Slow Or Medium Degrading Rate Film 144 located in the middle of the roll thickness 57 comprises three wraps of the Slow Or Medium Degrading Rate Film 145 and the other Fast Degrading Rate Film 144 located near the roll outer surface 61 comprises one wrap of the Fast Degrading Rate Film 144. Additionally, FIG. 52 depicts that the Roll Including Active Ingredient(s) 143 includes: (1) one layer of the active ingredient(s) 34 positioned near the roll outer surface 61 that is positioned between one Fast Degrading Rate Film 144 thickness 67 (facing abluminal surface) and one Slow Degrading Rate Film 145 thickness 67 (facing luminal surface); (2) one layer the active ingredient(s) 34 that is positioned between two Slow Degrading Rate Film 144 thicknesses 67 (facing abluminal surface) and two Slow Degrading Rate Film 144 thicknesses 67 (facing luminal surface); and (3) one layer of the active ingredient(s) 34 positioned near the roll inner surface 62 that is positioned between one Fast Degrading Rate Film 144 thickness 67 (facing luminal surface) and one Slow Degrading Rate Film 145 thickness 67 (facing abluminal surface). It should be appreciated that there may be greater than or less than three layers of the active ingredient(s) 34 within the Roll Including Active Ingredient(s) 143; there may be greater than or less than two wraps of the Fast Degrading Rate Film 144 within the Roll Including Active Ingredients 143 and there may be greater than or less than three wraps of the Slow Or Medium Degrading Rate Film 145 within the Roll Including Active Ingredient(s) 143.

Figure 54:
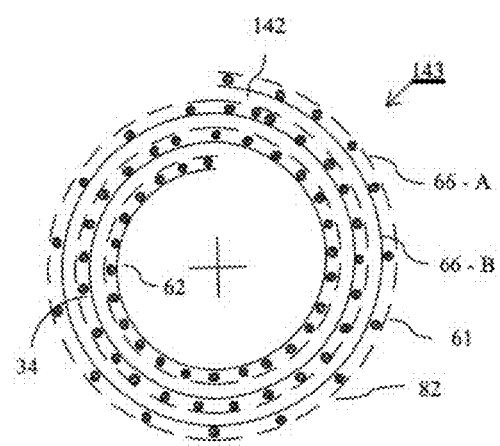
FIG. 54 depicts an embodiment of the Roll Including Active Ingredient(s), wherein the roll depicted in FIG. 36 includes active ingredients positioned between at least two of the film thicknesses.
Figure 53:
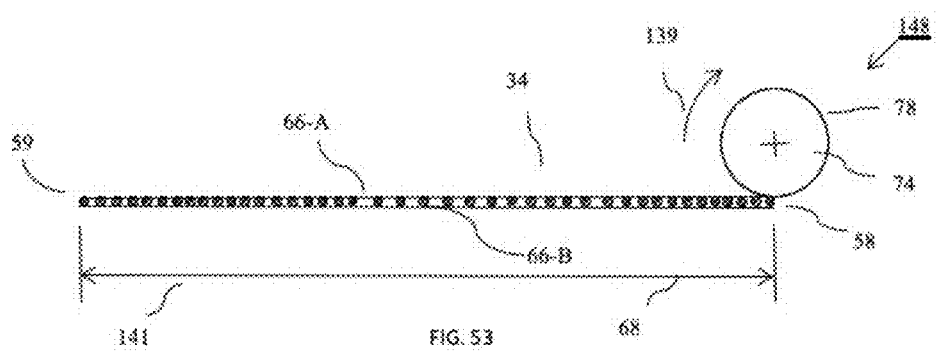
FIG. 53 depicts an exploded side view of the Indirect Roll Formation Process Including Multiple Films, which comprises wrapping two solid films having active ingredient(s) positioned between the films around the shaft to form the roll.

As depicted in FIG. 53, in an embodiment of the Indirect Roll Formation Process Including Multiple Films 148, the active ingredient(s) 34 are positioned between at least two of the solid films' 66 major surfaces 73 within at least one of the active ingredient Storage Area(s) 141. The Roll Including Active Ingredient(s) 143 is made by positioning the Beginning Of The Roll 58 in contact with the shaft outer surface 78 and wrapping the multiple solid films 66 around the shaft 74 in the film rotation direction 139 until the entire length 68 of the multiple solid films 66 encircle the shaft 74. The Indirect Roll Formation Process Including Multiple Films 148 depicted in FIG. 53 produces the Roll Including Active Ingredient(s) 143 as depicted in FIG. 54 that is formed into the un-oriented tube 38, which is converted into the oriented tube 38 and/or the stent 10. Alternatively, as depicted in FIG. 55, in another embodiment of the Indirect Roll Formation Process Including Multiple Films 148, there are three solid films 66 comprising the Indirect Roll Formation Process Including Multiple Films 148. FIG. 55 depicts the solid film 66-A as a dashed line on the bottom, the solid film 66-B in the middle as a solid line and solid film 66-C on the top as a solid line. There is a layer of the active ingredient(s) 34 located between the solid film 66-A and the solid film 66-B and an Active Ingredient-Free Area 142 located between solid film 66-B and solid film 66-C in FIG. 55. The Active Ingredient-Free Area 142 has no active ingredient(s) 34 located between the two solid films 66. In another embodiment, the active ingredient(s) 34 may be located between solid film 66-B and solid film 66-C and the Active Ingredient-Free Area 142 may be positioned between solid film 66-A and solid film 66-B. In yet one more embodiment, the active ingredient(s) 34 may be positioned between solid film 66-A and solid film 66-B and the active ingredient(s) may be positioned between solid film 66-B and solid film 66-C. The three superimposed solid films 66 including the active ingredient(s) 34 are wrapped around the shaft 74 to form the Roll Including Active Ingredient(s) 143 depicted in FIG. 56. Although FIG. 55 depicts three solid films 66 comprising the roll 52, one layer of the active ingredient(s) 34 between two of the solid films 66 and one Active Ingredient-Free Area 142, in other embodiments there may be greater than three solid films 66, greater than one layer of the active ingredient(s) 34 between greater than two of the solid films 66 and greater than one Active Ingredient-Free Area 142 within the Roll Including Active Ingredients 143. The solid film 66-A, the solid film 66-B and the solid film 66-C may comprise the same stent material(s) 85 or at least one or all or the solid films 66 may comprise different stent material(s) 85. The film thickness 67 within solid film 66-A, the film thickness 67 within solid film 66-B or the film thickness 67 within solid film 66-C may be the same or at least one or all the solid films 66 may comprise different thicknesses 67.

As depicted in FIG. 57, in an embodiment the Indirect Roll Formation Process Including Active Ingredient(s) 140 may comprise the shaft 74, three different solid films 66 positioned in series and active ingredient(s) 34 positioned on at least part or all of the film major surface 73 of the middle solid film 66-B. FIG. 57 depicts the solid film 66-A positioned near the Beginning Of The Roll 58, the solid film 66-C positioned near the End Of The Roll 59 and the solid film 66-B positioned between the solid film 66-A and the solid film 66-B. The Indirect Roll Formation Process Including Active Ingredient(s) 140 depicted in FIG. 57 produces the Roll Including Active Ingredient(s) 143 depicted in FIG. 58 that is formed into the unoriented tube 42, which is converted into the oriented tube 38 and/or the stent 10. The Roll Including Active Ingredient(s) 143 depicted in FIG. 58 is formed by wrapping the solid film 66-A around the shaft 74 first, wrapping the solid film 66-B including the active ingredient(s) 34 around the shaft 74 second and wrapping the solid film 66-C around the shaft 74 third. As depicted in FIG. 58, the Indirect Roll Formation Process Including Active Ingredient(s) 140 results in the Roll Including Active Ingredient(s) 143 comprising two Active Ingredient-Free Areas 142 located near the inner surface of the roll 62, one Active Ingredient Storage Area 141 located near the middle of the roll thickness 57 and two Active Ingredient-Free Areas 142 located near the outer surface of the roll 61. In other embodiments, there may be greater than or less than two Active Ingredient-Free Zones 142 located near the roll inner surface 62 and/or roll outer surface 61 and greater than or less than one Active Ingredient Storage Areas 141 located near the middle of the roll thickness 57.

As depicted in FIG. 59, in an embodiment the Indirect Roll Formation Process Including Multiple Films 148 may comprise the shaft 74, two partially superimposed solid films 66 and active ingredient(s) 34, wherein the first solid film 66-A is longer than the second solid film 66-B and the active ingredient(s) 34 are located between the solid film 66-A and the solid film 66-B. The Indirect Roll Formation Process Including Multiple Films 148 depicted in FIG. 59 produces the Roll Including Active Ingredient(s) 143 depicted in FIG. 60 that is formed into the un-oriented tube 42, which is converted into the oriented tube 38 and/or the stent 10. Positioning the solid film 66-A against the shaft 74 and wrapping solid film 66-A and the solid film 66-B that includes the active ingredient(s) around the shaft 74 until the entire length 69 of the solid film 66-A encircles the shaft 74 produces the Roll Including Active Ingredient (s) 143 depicted in FIG. 60. Alternatively, or additionally, the active ingredient(s) 34 may be positioned within the solid film 66-B, which results in forming the Roll Including Active Ingredients 143 depicted in FIG. 61 that is formed into the un-oriented tube 42, which is converted into the oriented tube 38 and/or the stent 10. Although FIG. 60 and FIG. 61 depict wrapping the solid film 66-A around the shaft 74 one time prior to wrapping the solid film 66-B around the shaft 74 and wrapping the solid film 66-B around the shaft 74 one time after wrapping the solid film 66-A around the shaft 74 and wrapping the solid film 66-A around the shaft 74 one additional time after wrapping the solid film 66-B around the shaft 74, in other embodiments the solid film 66-A may be wrapped around the shaft 74 greater than one time prior to wrapping the solid film 66-B around the shaft 74, the solid film 66-B may be wrapped around the shaft 74 greater than one time and the solid film 66-A may be wrapped around the shaft 74 greater than one time after wrapping the solid film 66-B around the shaft 74. Additionally, even though FIG. 60 and FIG. 61 show that the solid film 66-A is wrapped around the shaft 74 the same number of times prior to wrapping the solid film 66-B around the shaft 74 as after wrapping the solid film 66-B around the shaft 74, in other embodiments the solid film 66-A may be wrapped around the shaft 74 additional times prior to wrapping the solid film 66-B around the shaft 74 than after wrapping the solid film 66-B around the shaft 74, or the opposite. Furthermore, in other embodiments, the solid film 66-B may be wrapped around the shaft 74 greater than one time when forming the Roll Including active ingredient 143. The length 68 of the solid film 66-B may cover between 0.2% to 98% of the length 68 of the solid film 66-A. In other embodiments, the length of solid film 66-B may cover equal to or less than 0.2% of the length of the solid film 66-A or equal to or greater than 98% of the length of the solid film 66-A. Although the Roll Formation Process Including Multiple Films 148 depicted in FIG. 59 shows that the active ingredient(s) 34 are positioned so that the Roll Including Active Ingredient(s) 143 will have the active ingredient(s) 34 positioned around about one circumference of the roll 52, in other embodiments the active ingredient(s) 34 may be positioned around greater than or less than one circumference of the roll 52. While the Roll Including Active Ingredient(s) 143 depicted in FIG. 60 and FIG. 61 show that the active ingredient(s) 34 are positioned approximately in the middle of the roll thickness 57, in other embodiments the active ingredient(s) 34 may be located: (1) near the roll inner surface 62, (2) the roll outer surface 61, (3) the middle of the roll thickness 57 and the roll inner surface 62, (4) the middle of the roll thickness 57 and the roll outer surface 61, (5) the roll inner surface 62 and the roll outer surface 61 or (6) the roll inner surface 61 and the middle of the roll 57 and the roll outer surface 62.

The Rolls Including Active Ingredient(s) 143 depicted in FIG. 60 and FIG. 61 may be adapted by superimposing at least one additional solid film 66 in the Indirect Roll Formation Process Including Multiple Films 148 depicted in FIG. 59. For example, the additional solid film 66-C, solid film 66-D, solid film 66-E and so on may be incorporated into the Indirect Roll Formation Process Including Multiple Films 148. The additional solid film(s) 66 may be partially or completely superimposed on and/or under the solid film 66-A and/or solid film 66-B to form a multilayer unoriented tube 42 including active ingredient(s) 34 instead of a bilayer un-oriented tube 42 including active ingredient(s) 34. In an embodiment the additional active ingredient(s) 34 may be located: (1) between at least one of the additional solid film(s) 66 and the solid film 66-A and/or solid film 66-B, (2) between at least two additional solid film(s), (3) within at least one of the additional solid film(s) 66, (4) between at least one of the additional solid film(s) 66 and the solid film 66-A or solid film 66-B and within at least one of the additional solid film(s) 66 and/or (5) between at least two additional solid film(s) 66 and within at least one of the additional solid film(s) 66. The solid film 66-A, solid film 66-B and the additional solid film(s) 66 depicted in FIG. 59, FIG. 60 and FIG. 61 may be comprised of the same stent material(s) 85. Alternatively, at least one or all the solid film 66-A, solid film 66-B and the additional solid film(s) 66 depicted in FIG. 59, FIG. 60 and FIG. 61 may be comprised of different stent material(s) 85. The solid film 66-A, solid film 66-B and the additional solid film(s) 66 depicted in FIG. 59, FIG. 60 and FIG. 61 may have the same film thickness 67. Alternatively, at least one or all the solid film 66-A, solid film 66-B and the additional solid film(s) 66 depicted in FIG. 59, FIG. 60 and FIG. 61 may have different film thicknesses 67.

Notwithstanding that the Rolls Including Active Ingredient(s) 143 depicted in FIG. 46, FIG. 49, FIG. 52, FIG. 54, FIG. 56, FIG. 58 and FIG. 60 and the variants thereof depict the active ingredient(s) 34 positioned between at least two film thicknesses 67, in other embodiments the active ingredient(s) 34 may be positioned within at least one or all the solid film(s) 66 or all the film thicknesses 67. FIG. 62 through FIG. 67 depict examples of the Roll Formation Process Including Active Ingredient(s) 140, wherein the active ingredient(s) 34 are at least partially or completely positioned within the film thickness 67 prior to forming the Roll Including Active Ingredient(s) 143. The active ingredient(s) 34 may be incorporated into the solid film thickness 67 by mixing the active ingredient(s) 34 in the solution 83 used to form the liquid film 87 and the solid film 66 depicted in FIG. 23. In an embodiment the active ingredient(s) 34 are completely dissolved in the solution 83 so that the dissolved active ingredient(s) 34 are substantially evenly dispersed within the stent material(s) 85 comprising the solid film 66. In another embodiment the active ingredient(s) 34 completely un-dissolved in the solution 83 so that the solid particles comprising the active ingredient(s) 34 are randomly or uniformly dispersed within the stent material(s) 85 comprising the solid film 66. In another embodiment the active ingredient(s) 34 are partially dissolved within the solution 83 so that the randomly or uniformly dispersed solid active ingredient(s) 34 particles are separated by a relative uniform mixture of the dissolved active ingredient(s) 34 and the stent material(s) 85. Though FIG. 62 through FIG. 67 depict the active ingredient(s) 34 in circular shape, in other embodiments the active ingredient(s) 34 may be other shapes. Moreover, even though the figures depict the active ingredient(s) 34 having the same size, in other embodiment(s) 34 the size of the active ingredient(s) 34 within the solid film 34 may vary from particle to particle. The number of sizes of the particles comprising the active ingredient(s) 34 is virtually unlimited within the boundary specifications provided herein. It should be appreciated that although the figures show the active ingredient(s) 34 protruding from the film major surfaces 73, that in other embodiments the active ingredient(s) 34 are completely encapsulated within the solid film(s) 66 or that at least part of the active ingredient(s) 34 protrude outside the film major surface(s) 73 and at least part of the active ingredient(s) 34 are encapsulated within the solid film 66.

FIG. 62 depicts and embodiment of the Indirect Roll Formation Process Including Active Ingredient(s) 140, wherein the active ingredient(s) 34 are located at least partially or completely within the solid film 66 near the Beginning Of The Roll 58, which results in the active ingredient(s) 34 being positioned near the inner surface 48 of the un-oriented tube 42 that is converted into the oriented tube 38 and/or the stent 10. Alternatively, in another embodiment the active ingredient(s) 34 may be located at least partially or completely within the film thickness 67 near the End Of The Roll 59, which results in the active ingredient(s) 34 being positioned near the outer surface 47 of the un-oriented tube 42 (not depicted). The Indirect Roll Formation Process Including Active Ingredient(s) 140 depicted in FIG. 62 may comprise two separate or connected solid films 66. The Roll Including Active Ingredients 143 may be produced by wrapping the solid film 66-A, which includes the active ingredient(s) 34, around the shaft 74 first and then wrapping the solid film 66-B, which excludes the active ingredient(s) 34 around the shaft 74 second, or the opposite. The solid film 66-A and/or the solid film 66-B may be wrapped around the shaft 74 once or multiple times. In an embodiment, the solid film 66-A may be wrapped around the shaft 74 the same number of times as solid film 66-B. In other embodiments, the solid film 66-A is wrapped around the shaft 74 more times than solid film 66-B or the solid film 66-B is wrapped around the shaft 74 more times than solid film 66-A. In yet one more embodiment, the active ingredient(s) 34 may be incorporated into solid film 66-A and solid film 66-B, so that every wrap around the shaft 74 comprises a solid film 66 comprising a mixture of the active ingredient(s) 34 and the stent material(s) 85. The solid film 66-A and the solid film 66-B may comprise the same stent material(s) 85. In other embodiments, the solid film 66-A and solid film 66-B may comprise different stent material(s) 85. The solid film 66-A and the solid film 66-B may comprise the same film thickness 67. In other embodiments, the solid film 66-A and solid film 66-B may comprise different film thicknesses 67. For example, solid film 66-A may be thicker than solid film 66-B or the opposite.

FIG. 63 depicts an embodiment of the Indirect Roll Formation Process 140, wherein the active ingredient(s) 34 are located within the solid film 66 near the Beginning Of The Roll 58, the End Of The Roll 59 and in the middle, which results in the active ingredient(s) 34 being positioned near the inner surface 48 of the un-oriented tube 42, outer surface 47 of the un-oriented tube 42 and in the middle of the un-oriented tube wall thickness 45. The Indirect Roll Formation Process Including Active Ingredient(s) 140 depicted in FIG. 63 comprises five separate or connected solid films 66. The Roll Including Active Ingredients 143 that is formed into the un-oriented tube 42, which is converted into the oriented tube 38 and/or the stent 10, may be produced by wrapping the solid film 66-A, which includes the active ingredient(s) 34, around the shaft 74 first, then wrapping the solid film 66-B, which excludes the active ingredient(s) 34 around the shaft 74 second, wrapping the solid film 66-C, which includes the active ingredient(s) 34, around the shaft 74 third, wrapping the solid film 66-D, which excludes the active ingredient(s) 34 around the shaft 74 fourth and wrapping the solid film 66-E, which includes the active ingredient(s) 34 around the shaft 74 fifth. The solid film 66-A, solid film 66-B, solid film 66-C, solid film 66-D and solid film 66-E may be wrapped around the shaft 74 once or multiple times. The solid film 66-A, solid film 66-B, solid film 66-C, solid film 66-D and solid film 66-E may be wrapped around the shaft 74 the same number of times or at least one or all the solid films 66 may be wrapped around the shaft 74 a different number of times. For example, the solid film 66-B and solid film 66-D may be wrapped around the shaft 74 more times than solid film 66-A, solid film 66-C and solid film 66-E, or the opposite. It is possible that solid film 66-E be wrapped around the shaft 74 more than solid film 66-C and solid film 66-C be wrapped around the shaft 74 more that solid film 66-A so that the dosage active ingredient(s) 34-E is greater than the dosage of active ingredient(s) 34-C and the dosage of active ingredient(s) 34-C is greater than the dosage of active ingredient(s) 34-A, or the opposite. It is also possible that the solid film 66-C is wrapped around the shaft 74 more times than solid film 66-E and/or solid film 66-A so that the dosage of active ingredient(s) 34-C is greater than the dosage of active ingredient(s) 34-E and/or active ingredient(s) 34-A. Alternatively, or additionally, the quantity (or "dosage") of the active ingredient(s) 34 in each wrap of the solid film 66 may be the same or different within each wrap or within each Active Ingredient Storage Area 141. For example, the dosage of active ingredient(s) 34-A, active ingredient(s) 34-C and active ingredient(s) 34-E may be the same or different, wherein: (1) the dosage of active ingredient(s) 34-A is greater than active ingredient(s) 34-C and the dosage of active ingredient(s) 34-C is greater than active ingredient(s) 34-E; (2) the dosage of active ingredient(s) 34-E is greater than active ingredient(s) 34-C and the dosage of active ingredient(s) 34-C is greater than active ingredient(s) 34-A; (3) the dosage of active ingredient(s) 34-A is greater than active ingredient(s) 34-E and the dosage of active ingredient(s) 34-A is greater than active ingredient(s) 34-C; (4) the dosage of active ingredient(s) 34-E is greater than active ingredient(s) 34-A and the dosage of active ingredient(s) 34-A is greater than active ingredient(s) 34-C; (5) the dosage of active ingredient(s) 34-C is greater than active ingredient(s) 34-A and the dosage of active ingredient(s) 34-A is greater than active ingredient(s) 34-E; and (6) the dosage of active ingredient(s) 34-C is greater than active ingredient(s) 34-E and the dosage of active ingredient(s) 34-E is greater than active ingredient(s) 34-A. The solid film 66-A, solid film 66-B, solid film 66-C, solid film 66-D and solid film 66-E may comprise the same stent material(s) 85 or at least one of the solid films 66 may comprise different stent material(s) 85. The solid film 66-A, solid film 66-B, solid film 66-C, solid film 66-D and solid film 66-E may comprise the same film thickness 67 or at least one or all the solid films 66 may comprise a different film thickness 67. The solid film 66-A, solid film 66-B, solid film 66-C, solid film 66-D and solid film 66-E may comprise the same film length 68 or at least one of the solid films 66 may comprise a different film length 68. The Film Formation Process Including Active Ingredient(s) 140 depicted in FIG. 63 may be adapted so that there are greater than three Active Ingredient Storage Areas 141 and two Active Ingredient-Free Areas 142. For example, two active ingredient-Free Areas 142 may be added to the Indirect Roll Formation Process 138 depicted in FIG. 63 so that there is one active ingredient-Free Area 142 located near the Beginning Of The Roll 58 and one active ingredient-Free Area 142 located near the End of the Roll 59 so that the first and last wrap of the solid film(s) 66 around the shaft 74 do not include the active ingredient(s) 34. In yet one more example, there may be four or more active ingredient Storage Areas 141 and three or more active ingredient-Free Areas 142 incorporated into the Roll Formation Process 138 depicted in FIG. 63 so that the pattern of two active ingredient Storage Areas 141 separated by one active ingredient-Free Area 142 is repeated within the roll thickness 57 until the desired un-oriented tube 42 wall thickness 45 is achieved.

FIG. 64 depicts one more embodiment of Indirect Roll Formation Process Including Active Ingredient(s) 140, wherein the active ingredient(s) 34 are located within the film thickness 67 and the Active Ingredient Storage Area 141 is located in the middle of the roll thickness 57 of the film length 68. The Indirect Roll Formation Process Including Active Ingredient(s) 140 depicted in FIG. 64 comprises three solid films: (1) solid film 66-A, which is positioned near the Beginning of the Roll 58; (2) solid film 66-B, which is positioned near the End of the Roll 59 and (3) solid film 66-C, which is positioned between solid film 66-A and solid film 66-B. First wrapping solid film 66-A around the shaft 74, then wrapping solid film 66C around the shaft 74 and finally wrapping solid film 66-B around the shaft 74 forms the Roll Including Active Ingredients 143 that is formed into the un-oriented tube 74, which is converted into the oriented tube 38 and/or the stent 10. The solid film 66-A may be connected or disconnected to solid film 66-C and the solid film 66-C may connected to the solid film 66-B prior to forming the Roll Including Active Ingredients 143. Solid film 66-A, solid film 66-B and solid film 66-C may comprise the same stent material(s) 85. Alternatively, the at least one of the solid films 66-A, 66-B or 66-C may comprise at least one different stent material 85 than at least one of the other solid films 66. The length 68 of the solid film 66-A, the solid film 66-B and the solid film 66-C may be the same or at least one or all the solid films 66 may have a different length 68. For example, solid film 66-A may be greater in length 68 than solid film 66-B and solid film 66-B may be greater in length 68 than solid film 66-C; solid film 66-B may be greater in length 68 than solid film 66-C and solid film 66-C may be greater in length 68 than solid film 66-A; solid film 66-C may be greater in length 68 than solid film 66-A and solid film 66-A may be greater in length 68 than solid film 66-B; solid film 66-B may be greater in length 68 than solid film 66-A and solid film 66-A may be greater in length 68 than solid film 66-C; solid film 66-B and solid film 66-A may be greater in length 68 than solid film 66-C; solid film 66-C may be greater in length 68 that solid film 66-A and solid film B and solid film 66-A; solid film 66-A may be greater in length 68 than solid film 66-B and solid film 66-C; and solid film 66-B may be greater in length 68 than solid film 66-A and solid film 66-C. Notwithstanding that FIG. 64 depicts that solid film 66-A, solid film 66-C and solid film 66-B have the same film thickness 67, in other embodiments at least one of the solid films 66 may have a different film thickness 67 than at least one of the other solid films 66.

FIG. 65 depicts one more embodiment of the Indirect Roll Formation Process Including Multiple Films 148, wherein there is one solid film 66-A superimposed on another solid film 66-B, wherein the solid film 66-B has the active ingredient(s) 34 located within the film thickness 67 and solid film 66-A does not include any active ingredient(s) 34. Wrapping the two superimposed solid films 66 around the shaft 74 forms the Roll Including Active Ingredient(s) 143 that is formed into the un-oriented tube 42, which is converted into the oriented tube 38 and/or the stent 10. Although, FIG. 65 depicts the solid film 66-B including the active ingredient(s) 34 within the film thickness 67 and sold film 66-A excluding the active ingredient(s) within the film thickness 67, in other embodiments the solid film 66-A may include the active ingredient(s) 34 within the film thickness 67 and the solid film 66-B may exclude the active ingredient(s) 34, both solid film 66-A and solid film 66-B may exclude the active ingredient(s) 34 within the film thicknesses 67 or both solid film 66-A and solid film 66-B may include the active ingredient(s) 34 within the film thicknesses 67. The solid film 66-A and solid film 66-B depicted in FIG. 65 may comprise the same stent material(s) 85. Alternatively, the solid film 66-A depicted in FIG. 65 may comprise different stent material(s) 85 than solid film 66-B depicted in FIG. 65. In an embodiment the solid film 66-A and solid film 66-B depicted in FIG. 65 may comprise the same film thicknesses 67. Alternatively, the solid film 66-A depicted in FIG. 65 may be thicker than the solid film 66-B depicted in FIG. 65, or the opposite.

The Indirect Roll Formation Process Including Multiple Films 148 depicted in FIG. 65 may be adapted by superimposing at least one additional solid film 66-C on solid film 66-B prior to wrapping the solid films 66 around the shaft 74 as depicted in FIG. 66. The Indirect Roll Formation Process Including Multiple Films 148 may be adapted even further by including the active ingredient(s) 34 within the solid film 66-A and/or the solid film 66-C. In addition to the configuration depicted in FIG. 66, the Indirect Roll Formation Process Including Multiple Films 148 may be configured so that the active ingredient(s) 34 are located in one of the following configurations: (1) the solid film 66-A includes the active ingredient(s) 34 and the solid film 66-B and the solid film 66-C do not include the active ingredient(s) 34; (2) the solid film 66-C includes the active ingredient(s) 34 and the solid film 66-A and the solid film 66-B do not include the active ingredient(s) 34; (3) the solid film 66-A and the solid film 66-B include the active ingredient(s) 34 and the solid film 66-C does not include the active ingredient(s) 34; (4) the solid film 66-A and the solid film 66-C include the active ingredient(s) 34 and the solid film 66-B does not include the active ingredient(s) 34; and (4) the solid film 66-B and the solid film 66-C include the active ingredient(s) 34 and the solid film 66-A does not include the active ingredient(s) 34. As depicted in FIG. 66, there may be an Active Ingredient-Free Area 142 between the solid film 66-A and the solid film 66-C and between the solid film 66-C and the solid film 66-B. In other embodiments, there may be at least one Active Ingredient Storage Area 141 (not depicted) located between the solid film 66-A and the solid film 66-C and/or between the solid film 66-C and the solid film 66-B. The solid film 66-A, the solid film 66-B and the solid film 66-C depicted in FIG. 66 may be comprised of the same stent material(s) 85. In other embodiments of the Roll Formation Process Including Multiple Films 148, the solid film 66-A comprises different stent material(s) 85 than the solid film 66-B and the solid film 66-C; the solid film 66-B comprises different stent material(s) 85 than the solid film 66-A and the solid film 66-C or the solid film 66-C comprises different stent material(s) 85 than the solid film 66-A and the solid film 66-C. Additionally, in yet more embodiments the Roll Formation Process Including Multiple Films 148 may comprise at least one of the following configurations: (1) the solid film 66-A and solid film 66-B may comprise the same stent material(s) 85 and solid film 66-C may comprise different stent material(s) 85; (2) the solid film 66-A and solid film 66-C may comprise the same stent material(s) 85 and solid film 66-B may comprise different stent material(s) 85; (3) the solid film 66-B and solid film 66-C may comprise the same stent material(s) 85 and solid film 66-A may comprise different stent material(s) 85; and (4) the solid film 66-C and solid film 66-A may comprise the same stent material(s) 85 and solid film 66-B may comprise different stent material(s) 85. The solid film 66-A, the solid film 66-B and the solid film 66-C depicted in FIG. 66 may have the same thickness 67. In other embodiments, the solid film 66-A may have a different thickness 67 than solid film 66-B and solid film 66-C; the solid film 66-B may have a different thickness 67 than the solid film 66-A and the solid film 66-C and the solid film 66-C may have a different thickness 67 than solid film 66-A and solid film 66-C. Additionally, in yet more embodiments, the Roll Formation Process 138 may have at least one of the following configurations: (1) the solid film 66-A and solid film 66-B may have the same thickness 67 and the solid film 66-C may have a different thickness 67; (2) the solid film 66-A and the solid film 66-C may have the same thickness 67 and solid film 66-B may have a different thickness 67; (3) the solid film 66-B and solid film 66-C may have the same thickness 67 and solid film 66-A may have a different thickness 67; and (4) the solid film 66-C and the solid film 66-A may have the same thickness 67 and the solid film 66-B may have a different thickness 67. Although FIG. 66 depicts three solid films 66 within the Indirect Roll Formation Process Including Multiple Films 148, in other embodiments, there may be greater than three solid films 66. Therefore, the Roll Formation Process 138 depicted in FIG. 38 may be adapted to include solid film 66-A, solid film 66-B, solid film 66-C, solid film 66-D, solid film 66-E, solid film 66-F and so on, wherein at least one solid film 66 includes the active ingredient(s) 34 within the film thickness 67. It should be appreciated that wrapping the superimposed films 66 around the shaft 74 creates a repeating pattern in the roll thickness 57, wherein the pattern is the configuration depicted in FIG. 66 comprising film 66-A thickness 67, film 66-C thickness 67 and film 66-B thickness 67.

FIG. 67 depicts one more embodiment of the Indirect Roll Formation Process Including Multiple Films 148, wherein there is one longer, solid film 66-A superimposed on another shorter solid film 66-B and the solid film 66-B has the active ingredient(s) 34 located within the film thickness 67 and solid film 66-A does not include any active ingredient(s) 34. The Roll Formation Process Including Multiple Films 148 depicted in FIG. 67 forms the Roll Including Active Ingredients(s) 143 by wrapping the two solid films 66 around the shaft 74. The resultant Roll Including Active Ingredient(s) 143 is configured so that the active ingredient(s) 34 are positioned within the middle of the thickness 57 of the roll 53. In other embodiments, the film 66-A includes the active ingredient(s) 34 and the film 66-B excludes the active ingredient(s) 34. In still other embodiments, both solid film 66-A and solid film 66-B include active ingredient(s) 34 within the film thicknesses 67 or both solid film 66-A and solid film 66-B exclude the active ingredient(s) 34 within the film thicknesses 67. The solid film 66-A and solid film 66-B depicted in FIG. 67 may comprise the same stent material(s) 85. Alternatively, the solid film 66-A depicted in FIG. 67 may comprise different stent material(s) 85 than solid film 66-B depicted in FIG. 67. In an embodiment the solid film 66-A and solid film 66B depicted in FIG. 67 may comprise the same film thicknesses 67. Alternatively, the solid film 66-A depicted in FIG. 67 may be thicker than the solid film 66-B depicted in FIG. 67, or the opposite.

Although it is not depicted in the figures, there is another embodiment wherein the active ingredient(s) 34 are positioned between at least two or all the film thicknesses 67 and within at least one or all the film thicknesses 67. Positioning the active ingredient(s) 34 between the film thicknesses 67 and within the film thicknesses 67 enables greater control over the release of the active ingredient(s) 34 during the duration of the treatment. For example, as each film thickness 67 or each layer 51 erodes additional active ingredient(s) 34 may be released into the treatment site 35 surrounding the implanted stent 10 in a layer-by-layer or film thickness-by-film thickness sequence. In an embodiment, at least one or all the active ingredient(s) 34 stored within the film thicknesses 67 may be more amorphous and at least one or all the active ingredient(s) 34 stored between the film thicknesses 67 may be more crystalline, which provides two different mechanisms of drug delivery: (1) the more soluble lower crystallinity active ingredient(s) 34 have a faster therapeutic effect but have a tendency to be washed away from the treatment site 35 thereby providing short term therapy and (2) the less soluble higher crystallinity active ingredient(s) 34 have a slower therapeutic effect but have a tendency to be retained within the treatment site 35 thereby providing longer term therapy. The two drug delivery mechanisms provide a controlled release of the active ingredient(s) 34 for a time that the mass of the stent 10 remains within the anatomical lumen 36. In other embodiments, at least one or all the less amorphous active ingredient(s) 34 are stored between at least two of the film thicknesses 67 and at least one or all the more crystalline active ingredient(s) 34 are stored within at least one of the film thicknesses 67. In still other embodiments, at least one or all the less amorphous active ingredient(s) 34 are stored between at least two of the film thicknesses 67 and within at least one of the film thicknesses 67 or at least one or all the more crystalline active ingredient(s) 34 are stored within at least one of the film thicknesses 67 and between at least two of the film thicknesses 67.

In an embodiment, at least one or all the active ingredient(s) 34 stored within the film thicknesses 67 may have a lower weight average molecular weight and at least one or all the active ingredient(s) 34 stored between the film thicknesses 67 may have a higher weight average molecular weight which provides two different mechanisms of drug delivery: (1) the more soluble lower weight average molecular weight active ingredient(s) 34 have a faster therapeutic effect (2) the less soluble higher weight average molecular weight active ingredient(s) 34 have a slower therapeutic. The two drug delivery mechanisms provide a controlled release of the active ingredient(s) 34. In other embodiments, at least one or all the lower weight average molecular weight active ingredient(s) 34 are stored between at least two of the film thicknesses 67 and at least one or all the higher weight average molecular weight active ingredient(s) 34 are stored within at least one of the film thicknesses 67. In still other embodiments, at least one or all the lower weight average molecular weight active ingredient(s) 34 are stored between at least two of the film thicknesses 67 and within at least one of the film thicknesses 67 or at least one or all the higher weight average molecular weight active ingredient(s) 34 are stored within at least one of the film thicknesses 67 and between at least two of the film thicknesses 67.

In an embodiment, the low weight average molecular weight active ingredient(s) 34 (molecular weight between greater than 0 to 600,000 g/mol) may have a low crystallinity or a high crystallinity. In an embodiment, the high weight average molecular weight active ingredient(s) 34 (molecular weight between 600,000 to 2,000,000 g/mol) may have a low crystallinity or a high crystallinity.

FIG. 68 depicts a Heated Tube Former 256. The Heated Tube Former 256 minimally includes a pinch roller 257 and the shaft 74. FIG. 68 depicts a method of producing the un-oriented tube 42, wherein at least one solid, film 66 is fed between the cylindrical-shaped shaft 74 and the cylindrical-shaped pinch roller 257. The solid film(s) 66 being fed into the Heated Tube Former 256 may include the active ingredient(s) 34 positioned within the solid film(s) 66 and/or on at least one of the major surface(s) 73 of the solid film(s) 66 before the solid film(s) 66 enter the pinch point 258. The shaft outer surface 78 and pinch roller outer surface 261 are maintained at a separation distance, or pinch point 258, that compresses the film thicknesses 67 against the shaft outer surface 78 and/or the previously wrapped film thicknesses 67 that surround the shaft outer surface 78 when the film(s) 66 pass between the shaft 74 and the pinch roller 257. The pinch roller 257 and/or the shaft 74 may be attached to a spring loaded mount (not depicted) or other mechanism that allows the gap between the pinch roller 257 and the shaft 74 to adjust in size so that the pinch roller 257 accommodates the larger un-oriented tube 42 thickness 45 as additional film thicknesses 67 are added to the un-oriented tube 42 wall thickness 45 or a mechanism that keeps a substantially constant pressure on the compressed film thicknesses 67 as they are passing through the pinch point 258 during formation of the un-oriented tube 42. The shaft 74 spins in the clockwise direction 259 and the pinch roll 257 spins in the counterclockwise direction 260, or the opposite, so that the film(s) 66 wrap around the shaft 74 during un-oriented tube 42 formation. To interconnect the film thicknesses 67, the outer surface 261 of the pinch roller 257 and/or the outer surface 78 of the shaft 74 are maintained at a temperature between 0 and about 250.degree. C. In other embodiments the temperature of the outer surface 260 of the pinch roller 257 and/or the outer surface 78 of the shaft 74 are maintained at a temperature selected from the group of: (1) between 0 and 240.degree. C, (2) between 0 and 230.degree. C, (3) between 0 and 220.degree. C, (4) between 0 and 210.degree. C; (5) between 0 and 200.degree. C, (6) between 0 and 190.degree. C, (7) between 0 and 180.degree. C, (8) between 0 and 170.degree. C, (9) between 0 and 160.degree. C, (10) between 0 and 150.degree. C, (11) between 0 and 140.degree. C, (12) between 0 and 130.degree. C, (13) between 0 and 120.degree. C, (14) between 0 and 110.degree. C, (15) between 0 and 100.degree. C, (16) between 0 and 90.degree. C., (17) between 0 and 80.degree. C or (18) between 0 and 70.degree. C. When the Over-Film Thickness 93 passes over the Under-Film Thickness 94 that is supported by the shaft 74 in a cylindrical configuration, the heated pinch roller 257 presses the film thicknesses 67 together and quickly thermally fuses the Over-Film Thickness 93 to the Under-Film Thickness 94 by imparting heat on the film thicknesses 67 for the short duration that the film thicknesses 67 are compressed between the pinch roller 257 and the shaft 74, which interconnects the film thicknesses 67 when the compressed film thicknesses 67 leave the pinch point 258 and cool. The heated Over-Film Thickness 93 and Under-Film Thickness 94 may be cooled when they pass through the gaseous environment 90 as the shaft 74 rotates the joined surfaces away from the pinch point 258. The cooling process may be accelerated by blowing at least one cool gas or liquid, which is at a temperature below about 70.degree. C, on the Under-Film Thickness 94 and the Over-Film Thickness 93 as they exit the pinch point 258 or at any position outside of the pinch point 258. The cooling process may be very rapid if, for example, liquid nitrogen or another cool substance that is at a temperature below 70.degree. C is sprayed on the heated Under-Film Thickness 94 and the heated Over-Film Thickness 93 after they exit the pinch point 258 or the cooling may be very slow by producing the un-oriented tube 42 on a warmed shaft 74 or within a warm gaseous environment 90, wherein the warmed shaft 74 and/or the warmed gases are maintained at a temperature within the range of about 50 to 150.degree. C.

The Heated Tube Former 256 is operated within the gaseous environment 90. It is preferred that the gaseous environment 90 comprises a Protective Environment. The Protective Environment minimizes or prevents the reduction of the degree of polymerization within the stent material(s) 85 and/or minimizes or prevents the reduction in efficacy of the active ingredient(s) 34 when the film thicknesses 67 are heated during the Heated Tube Former 256 process. In the preferred embodiment, the gaseous environment 90 is held at a temperature within the range of negative 100.degree. C to positive 100.degree. C. In other embodiments, the gaseous environment 90 is at higher or lower temperatures. The gases within the gaseous environment 90 may be circulated or exchanged with fresh gases. Alternatively, or additionally, interconnecting the Over-Film Thickness 93 to the Under-Film Thickness 94 may be achieved by employing ultrasonic welding, hot gas welding, hot plate welding, induction welding, dielectric welding, vibration welding as the film(s) 66 pass through the pinch point 258 or when at least part or the complete wall thickness 45 is held together under pressure in the shape of the un-oriented tube 42. In an embodiment, the ultrasonic welding is achieved at a frequency within the range of 10 to 100 kHz for duration between greater than 0 to 25 seconds. In other embodiments, the ultrasonic welding is achieved at higher or lower frequencies.

FIG. 69 depicts a Solvent Process Tube Former 262. As depicted in FIG. 69, another method for interconnecting the film thicknesses 67 in the shape of a cylindrical-shaped tube comprises spraying a mist 153 comprising at least one solvent 86 and/or at least one glue comprising the liquid solution 83 onto at least one film major surface 73 at the interface between the Under-Film 94 and the Over-Film 93 just before the Over-Film 93 enters the pinch point 258 so that at least two film 81 thicknesses 67 are solvent bonded together, wherein the solution 83 comprises at least one stent material(s) 85 and at least one solvent 86. In an embodiment, the mist 153 includes at least one active ingredient 34. In another embodiment, the mist 153 excludes the active ingredient(s) 34. The solid film(s) 66 may include the active ingredient(s) 34 positioned at least in one of the following positions: (1) within the solid film(s) 66; (2) on at least one of the major surface(s) 73 of the solid film(s) 66; (3) within the solvent(s) 86; (4) within the liquid solution 83 that is being sprayed on at least one of the major surface(s) 73 of the solid film(s); (5) between at least two film thicknesses 67; (6) on at least one major surface 73 facing the un-oriented tube 42; or (7) on at least one major surface 73 facing the pinch roller 257. A strong solvent 86 may be used at full strength or diluted with a weak solvent 86 to prevent dissolving the solid film(s) 66 or causing the solid film(s) 66 to tear while being fed into the Solvent Process Tube Former 262.

Alternatively, or additionally, at least one of the solid films 66 are fed between the shaft 74 and the pinch roller 257 of the Solvent Process Tube Former 262 when at least one or all of the solid(s) film(s) 66 are swollen, wherein the swollen, solid film 66 comprises between greater than 0 wt. % and 80 wt. % solvent(s) 86 and the remainder of the swollen, solid film 66 comprises the stent material(s) 85 or stent material(s) 85 and the active ingredient(s) 34. In other embodiments, the swollen, solid film 66 includes greater or lesser solvent(s) 86. At least one of the swollen, solid film(s) 66 may include the active ingredients 34 positioned within the swollen, solid films 66 and/or on at least one of the major surface(s) 73 of the swollen, solid films 66. In other embodiments, the swollen, solid film(s) 66 do not include the active ingredient(s) 34. When the swollen, solid film(s) 66 are wrapped around the spinning shaft 74 the Over-Film Thickness 93 is interconnected to the Under-Film Thickness 94 because there is sufficient mobility of the molecules within the stent material(s) 85 within each film thickness 67 to allow at least one of the molecules or all of the molecules on the film major surfaces 73 to cross the knit line 65 so that when the solvent(s) 86 are removed from the swollen, solid film(s) 66 a bond is formed between the Over-Film thicknesses 93 and the Under-Film thicknesses 94. The viscosity of the stent material(s) 82 that are within the swollen, solid film(s) 66 are very high so that there is very little mixing of the stent material(s) 85 that are located within the bulk of the Over-Film Thickness 93 and the Under-Film Thickness 94. This means that if the Under-Film Thickness 94 comprises 94 different stent material(s) 85 or a different mixture of stent material(s) 85 and active ingredient(s) 34 than the over layer 93, that discrete layer(s) 51 are formed within the wall thickness 45 of un-oriented tube 42, which is converted into the oriented tube 38 and/or the stent 10. Conversely, if the Under-Film Thickness 94 comprises 94 the same stent material(s) 85 or the same mixture of stent material(s) 85 and active ingredient(s) 34 as the over layer 93, that one layer 51 comprising homogenous stent material(s) 85 or a homogeneous mixture of the stent material(s) 85 and the active ingredient(s) 34 is formed within the wall thickness 45 of un-oriented tube 42. Since the layer(s) 51 are configured in the shape of the roll 52 that includes the transition 95 an a pattern where each film thickness 67 gets gradually farther from the central axis 4 of the un-oriented tube 42, the layers 52 within the un-oriented tube 42 and/or the layers 52 within the stent 10 have a tendency to be non-concentric or slightly un-concentric when viewed from the end of the un-oriented tube 42 and or the stent 10.

In one more embodiment of the Solvent Process Tube Former 262, at least one swollen, solid film 66 and at least one dry, solid film 66 are fed between the shaft 74 and the pinch roller 257 of the Solvent Un-Oriented Tube Former 262, wherein the swollen, solid film(s) 66 comprise between greater than 0 wt. % and 80 wt. % solvent(s) 86 and the remainder of the swollen, solid film(s) 66 comprise the stent material(s) 85 or the stent material(s) 85 and the active ingredient(s) 34 and the dry, solid film(s) 66 comprises between 0 wt. % and 10 wt. % solvent(s) 86 and the remainder of the dry, solid film(s) 66 comprise the stent material(s) 85 or stent material(s) 85 and the active ingredient(s) 34. In other embodiments, the swollen, solid film(s) 66 and/or the dry, solid film(s) 66 include higher and/or lower weight percentage of the solvent(s) 86. At least one of the swollen, solid film(s) 66 and/or the dry, solid film(s) 66 may include the active ingredient(s) 34 positioned within the solid film(s) 66 and/or on at least one of the major surface(s) 73 of the solid film(s) 66. When there are multiple dry solid film(s) fed into the Solvent Process Tube Former 262, it is preferred to have at least one swollen, solid film 66 adjacent to each dry, solid film 66. In other embodiments, the swollen, solid film(s) 66 and/or the dry, solid film(s) 66 do not include the active ingredient(s) 34. When the swollen, solid film(s) 66 and the dry, solid film(s) 66 are wrapped around the spinning shaft 74 the Over-Film Thickness 93 is interconnected to the Under-Film Thickness 94 because there is sufficient mobility of the molecules within the stent material(s) 85 in the swollen, solid film thickness 67 to allow at least one molecule or all of the molecules on the films' major surfaces 73 to cross the knit line(s) 65 so that when the solvent(s) 86 are removed from the swollen, solid film(s) 66 a bond is formed between the Over-Film thicknesses 93 and the Under-Film thicknesses 94. Passing the swollen, solid film 66 and the dry, solid film through the pinch point 258 applies pressure on at least the two adjacent solid films 66 as the solid films 66 are wrapped around the shaft 74, which facilitates interconnecting the Under-Film thicknesses 94 and the Over-Film thicknesses 93. In another embodiment of the Solvent Process Tube Former 69, there may be sufficient tension within the solid film(s) 66 being wrapped around the shaft 74 that it is unnecessary to use the pinch roller 257. In one more embodiment, the shaft 74 may be stationary and the solid film(s) 66 may be wrapped around the shaft 74 by the solid film(s) 66 articulating around the shaft 73 in a motion that forms the roll 52 or the Roll Including Active Ingredient(s) 143 on the shaft outer surface 78.

Alternatively, or additionally, in another embodiment, at least one swollen, solid film 66 and/or at least one dry, solid film 66 are fed between the shaft 74 and the pinch roller 257 of the Solvent Tube Former 262, wherein the swollen, solid film 66 and/or the dry, solid film 66 are elongated in the machine direction 79 and/or widened in the transverse direction 80 or elongated and widened in the biaxial direction 81 prior to being wrapped around the shaft 74. At least one of the swollen, solid films 66 and/or the dry, solid films 66 may include the active ingredient(s) 34 positioned within the swollen, solid films 66 and/or within the dry, solid films 66 and/or on at least one of the major surface(s) 73 of the swollen, solid films 66 and/or the dry, solid films 66. In other embodiments, the swollen, solid film(s) 66 and/or the dry, solid film(s) 66 do not include the active ingredient(s) 34. Elongating and/or widening the swollen, solid film(s) 66 and/or the dry, solid film(s) 66 strains the solid films 66 in the direction of strain just before wrapping the swollen, solid film(s) 66 and/or the dry, solid film(s) around the shaft 74, which converts the solid film(s) 66 into the oriented solid films 66 that include molecular orientation in the direction of strain. Orientation of the stent material's 85 molecules that are positioned within the solid films 66 strengthens the solid film(s) 66 in the direction of strain.

When the oriented, solid film(s) 66 are wrapped around the spinning shaft 74 the Over-Film Thickness 93 is interconnected to the Under-Film Thickness 94 because there is sufficient mobility of the molecules within the stent material(s) 85 within the swollen, solid film thickness 67 to allow at least one molecule or all of the molecules on the film major surfaces 73 of the swollen, solid film(s) 66 to cross the knit line(s) 65 so that when the solvent(s) 86 are removed from the swollen, solid film(s) 66 a bond is formed between the Over-Film thicknesses 93 and the Under-Film thicknesses 94, which results in the formation of the oriented tube 38. In an embodiment, the solid film(s) 66 are elongated and widened the same amount; in an embodiment, the solid film(s) 66 are elongated more than widened; and in an embodiment the solid film(s) 66 are widened more than elongated. If the solid film(s) 66 are aligned within the wall thickness of the roll 52 or the Roll Including Active Ingredient(s) 143 so that the central axis of the solid film(s) 70 is perpendicular to the central axis 77 of the shaft 74, elongating the solid film(s) 66 increases the radial strength of the stent 10 and widening the solid film(s) 66 increase the longitudinal strength of the stent 10. In this embodiment of the Solvent Process Tube Former 262, the oriented tube 38 is formed because the molecular orientation imparted in the solid film(s) 66 is at least partially or completely retained within the wall thickness 27 of the oriented tube 38 being formed on the shaft 74. It is believed that the more quickly that the residual solvent(s) 86 are removed from the oriented tube 38 the more molecular orientation that is retained within the oriented tube wall thickness 27, which means that the more quickly the solvent(s) are removed from the oriented tube wall thickness 27 the stronger the oriented tube 38 becomes. Warming the oriented tube 38 and/or placing the oriented tube 38 under a vacuum to dry the oriented tube 38 may increase the rate removal of the solvent(s) 86 from the oriented tube 38. To avoid excessive loss of molecular orientation of the stent material(s) 85 within the oriented tube 38, it is believed that the oriented tube 38 should not be heated above the glass transition temperature (Tg) of at least one of the stent material(s) 85 comprising the oriented tube 38 after the film(s) 85 have been wrapped around shaft 74, more narrowly not above 120.degree. C. It is preferred to heat the oriented tube 38 on the shaft 74 within the Protective Environment during solvent(s) 86 removal. The oriented tube 38 may be dried, for example, in a vacuum dryer or desiccant dryer for greater than 15 seconds to 90 days, more narrowly between 5 minutes to 24 hours at between greater than 0 to 120.degree. C at a low vacuum less than 0.01 MPa. It is preferred to dry the oriented tube 38 on the shaft 74 until the solvent(s) 86 content within the oriented tube 38 is reduced to less than 500 ppm. In other embodiments, the oriented tube 74 is dried on the shaft 74 until it contains equal to or greater than 500 ppm solvent(s) 86. The swollen, solid film 66 tends to dry quickly when elongated and/or widened, which can result in a low concentration of the solvent(s) 86 within the solid films 66 prior to wrapping. To avoid lowering the amount of solvent(s) 86 within the solid film(s) 66 to a point that is lower than what is required to interconnect the adjacent wrapped film(s) 66, the gaseous environment 90 may be maintained at a cool temperature that slows the evaporation of the solvent(s) 86 and/or the solvent 86 concentration within the gaseous environment 90 or the relative humidity of the gaseous environment 90 may be kept at a high level to slow down the evaporation of the solvent(s) 86 while the solid films 66 are being conveyed to the pinch point 258 and while the solid film(s) 86 are being wrapped around the shaft 74. The solvent 86 concentration within the gaseous environment 90 may be maintained to comprise between greater than 0% to 60% solvent and the remainder of the gaseous environment 90 comprise gas and/or the relative humidity of the gaseous environment 90 may be maintained to comprise greater than 0% to 90% moisture and the remainder of the gaseous environment 90 comprise gas. In other embodiments, the solvent 86 concentration within the gaseous environment 90 and/or the relative humidity within the gaseous environment 90 are higher. Increasing the pressure of the gaseous environment 90 may also slow down the evaporation of the solvent(s) 86 that are within the solid film(s) 86. The pressure of the gaseous environment 90 may be held between 0.1 MPa to 100 MPa during conveyance of the solid films 66 to the pinch point 258 and/or while the solid film(s) 66 are being wrapped around the shaft 74. In other embodiments the gaseous environment 90 is held at lower or higher pressures during conveyance of the solid films 66 to the pinch point 258 and/or while the solid film(s) 66 are being wrapped around the shaft 74.

The Solvent Process Tube Former 262 is operated within the gaseous environment 90. It is preferred that the gaseous environment 90 comprises a Protective Environment. In the preferred embodiment, the gaseous environment 90 is held at a temperature within the range of negative 100.degree. C to positive 100.degree. C, more narrowly room temperature. The gases within the gaseous environment 90 may be circulated or exchanged with fresh gases to facilitate removal of the solvent(s) 86 from the oriented tube wall thickness 27 or the un-oriented tube wall thickness 45. Fresh gases comprise virgin gases or recycled gases, wherein at least part of the volatile solvent(s) 86 that are removed from the solid film(s) 66 are removed from the gases. The removed solvent(s) 86 may be reused within the Solvent Process Tube Former 262.

The swollen, solid film(s) 66 and/or the dry, solid film(s) 66 may be under tension in the machine direction 79, transverse direction 80 or the biaxial direction 81 by applying a load within the range of greater than 0 MPa to 40 MPa on the swollen, solid film(s) 66, the dry, solid film(s) 66 and/or the softened, solid film(s) 66 prior to passing the solid film(s) 66 through the pinch point 258 and/or when wrapping the solid film(s) 66 around the shaft 74. In other embodiments, the tension within the solid film(s) 66 may be achieved by applying a load to the solid film(s) 66 that is equal to or greater than 40 MPa.

In an embodiment, passing the Under-Film Thickness 94 and the Over-Film Thickness 93 through the pinch point 258 applies pressure on the film thicknesses 67, which facilitates creation of a bond between the Over-Film Thickness 93 and the Under-Film thicknesses 94. The shaft 67 may rotate at greater than 0 to 10,000 revolutions per minute ("RPM") so that the film thicknesses 93 are heated just long enough to thermally weld the film thicknesses 93 together as they pass between the two cylinders or pinch point 258, which results in forming the un-oriented tube 42 around the shaft 74 when there have been sufficient wraps interconnected to produce a wall thickness 45 of sufficient thickness 13 to produce the stent 40. Depending on the thickness of the film(s) 67, there could be between 2 to about 1000 wraps of the film(s) 66 required to produce the un-oriented tube 42 using the Heated Tube Former 256 method or the Solvent Tube Former 262 method. In an embodiment, at least one of the film major surfaces 73 is at least partially or completely covered with the active ingredient(s) 34 within the Active Ingredient Storage Area 141 prior to feeding the solid film(s) 66 between the shaft 74 and the pinch roller 257 and/or wrapping the solid film(s) 66 around the shaft 74 so that the active ingredient(s) 34 are positioned between at least two wraps of film 66, which results the active ingredient(s) 34 being positioned between two film thicknesses 67 excluding the active ingredient(s) 34 that are welded together like the example depicted in FIG. 49 or other embodiments described herein. Alternatively, or additionally the active ingredient(s) 34 are positioned within the film thickness 67 of at least one of the solid films 66 so that the active ingredient(s) 34 are positioned within the Roll Including Active Ingredient(s) 143. The short duration of the contact of the heated pinch roller 257 on the solid film thicknesses 67 and the active ingredient(s) 34 maintains at least part of or the entire efficacy of the active ingredient(s) 82. Welding the solid film(s) 66 under the Protective Environment, for example within an inert gas, also at least partially or completely preserves the efficacy of the active ingredient(s) 34 and the stent material's 85 degree of polymerization. The Heated Tube Former 256 method or the Solvent Tube Former 262 methods of forming the un-oriented tube 42 or the oriented tube 38 from the solid film(s) 66 interconnects the film thicknesses 67 without exposing the active ingredient(s) 34 to a long heating cycle, which at least partially or completely preserves the efficacy of the active ingredient(s) 272 that are incorporated into the stent 10.

Alternatively, heating the roll 52 or the Roll Including Active Ingredient (s) 143 in an oven forms the un-oriented tube 42. The un-oriented tube 42 may be formed by following these steps: (1) preparing at least one solid film 66 that includes or excludes the active ingredient(s) 34; (2) wrapping at least one solid film 66 that includes or excludes the active ingredient(s) 34 around the shaft 74 to produce the roll 52 or the Roll Including Active Ingredient(s) 143; (3) placing the roll 52 or the Roll Including Active Ingredient(s) 143 while conforming to the shaft 74 outer surface 78 in an oven or in a pre-heated oven that is at least partially or fully comprises the gaseous environment 90 that preferably comprises the Protective Environment; (4) heating the roll 52 or the Roll Including Active Ingredient(s) 143 while still positioned on the shaft 74 within the oven that is maintained at a temperature within the range of greater than 0.degree. C to 250.degree. C for between greater than 0 seconds to 30 minutes; (5) removing the roll 52 and/or the Roll Including Active Ingredient(s) 143 while positioned on the shaft 74 from the oven; (6) cooling the roll 52 or the Roll Including Active Ingredient(s) 143 on the shaft 74 to a temperature below 65.degree. C or to normal room temperature (about 23-23.degree C.) within greater than 0 seconds to 60 minutes; and (7) removing the un-oriented tube 74 from the shaft 74. The un-oriented tube 42 that was formed in the oven and cooled on the shaft 74 is converted into the oriented tube 38 and/or the stent 10. In an embodiment, heating the roll 52 or the Roll Including Active Ingredient(s) 143 while positioned on the shaft 74 interconnects the various film thicknesses 67 by bonding the film thicknesses 67 together or sintering the film thicknesses 67 together forming the un-oriented tube 42.

The Heated Tube Former 256, the Solvent Process Tube Former 262 and the heating the roll 52 or Roll Including Active Ingredient(s) 143 on the shaft 52 in the oven methods of producing the un-oriented tube 42 and/or the oriented tube 38 form discrete layers 51 within the wall thickness 45 or wall thickness 27 when the adjacent film thicknesses 67 comprises different stent material(s) 85 or when one film thickness 67 includes the active ingredient(s) 34 and the adjacent film thickness 67 does not include the active ingredient(s) 34 or when the adjacent film thicknesses 67 include a different quantity of the active ingredient(s) 34 or when the adjacent film thicknesses 67 include different active ingredient(s) 34 or when the adjacent film thicknesses 67 include a different combination of the active ingredient(s) 34. The discrete layers 51 are formed because the viscosity of the solid films 66 when in dry form, swollen form, softened form or melted form only permit minor mixing of the stent material(s) 85 at the molecule level within the bond(s) 65. In these embodiments, most of the stent material(s) 85 (the "bulk") within the film thicknesses 67 do not intermix, which results in formation of discrete layer(s) 51 in the stent 10 wall thickness 13. In an embodiment, mixing of the stent material(s) 85 is minor because there is virtually no shear between the adjacent film thicknesses 67 when they are interconnected. In these embodiments, the adjacent film thicknesses 67 are arranged in a roll configuration and statically joined by a mechanism wherein at least some of the molecules within the stent material(s) 85 in each film thickness 67 are mobilized by softening the adjacent film thicknesses 67 by heating the film thicknesses 67 or including at least one solvent 86 within at least one of the solid films 66 so that at least some the molecules within each of the film thicknesses 67 at least partially move or migrate across the bond(s) 65 in a way that ties the two separate film thicknesses 67 together when the assembly is cooled and/or the solvent(s) 86 are at least partially or completely removed from the wall thickness 45 or the wall thickness 27. In an embodiment, to prevent shearing of the assembled film thicknesses 67, the pinch roller 257 applies less than 500 Newton's on the solid film(s) 66 being wrapped around the shaft 74.

FIG. 70 through FIG. 75 depict two embodiments of portions of the wall thickness 13 of the linear ring struts 20 and the link struts 21. Referring to FIG. 70, which depicts a cross sectional view of the stent 10 wall thickness 13, in an embodiment the wall thickness 13 may be divided into four discrete layers 51, wherein the layer 51-A is positioned closest to the outer surface 16, the layer 51-B is positioned underneath layer 51-A, the layer 51-C is positioned underneath layer 51-B, and the layer 51-D is positioned closest to the inner surface 17 or underneath layer 51-C. As depicted in FIG. 71, which depicts a cross sectional view of the stent 10 wall thickness 13, in another embodiment the wall thickness 13 may be divided into four discrete layers 51, wherein the layer 51-A is positioned closest to the inner surface 17, the layer 51-B is positioned on top of layer 51-A, the layer 51-C is positioned on top of layer 51-B, and the layer 51-D is positioned closest to the outer surface 16 or on top of layer 51-C. In embodiments wherein the layers 51 are arranged as depicted in FIG. 70 and FIG. 71, the stent material(s) 85 comprising layer 51-A may degrade and/or resorb faster than the stent material(s) 85 comprising layer 51-B, the stent material(s) 85 comprising layer 51-B may degrade and/or resorb faster than the stent material(s) 85 comprising layer 51-C, and the stent material(s) 85 comprising layer 51-C may degrade and/or resorb faster than the stent material(s) 85 comprising layer 51-D. Alternatively, or additionally, in embodiments wherein the layers 51 are arranged as depicted in FIG. 70 and FIG. 71, the stent material(s) 85 comprising layer 51-A may comprise a lower weight average molecular weight than the stent material(s) 85 comprising layer 51-B, the stent material(s) 85 comprising layer 51-B may comprise a lower weight average molecular weight than the stent material(s) 85 comprising layer 51-C, and the stent material(s) 85 comprising layer 51-C may comprise a lower weight average molecular weight than the stent material(s) 85 comprising layer 51-D. The layer 51-A, the layer 51-B, the layer 51-C and the layer 51-D depicted in FIG. 70 and FIG. 71 are formed from at least one or multiple film thicknesses 67. Although FIG. 70 and FIG. 71 depict the layer 51-A, the layer 51-B, the layer 51-C and the layer 51-D as having the same layer thickness 91, in other embodiments at least one or all the layer 51 thicknesses 91 are a different layer thickness 91 than at least one or all the other layer thicknesses 91 within the wall thickness 13. Although, FIG. 70 and FIG. 71 depict four layers 51, in other embodiments there may be greater than or less than four layers 51 within the wall thickness 13, wherein the degradation rate and/or the weight average molecular weight of the stent material(s) 85 decrease layer-by-layer starting with the layer 51 that is positioned on the outer surface 16 having the fastest degradation rate and/or the lowest weight average molecular weight and ending with the layer 51 that is positioned on the inner surface 17 having the slowest degradation rate and/or the highest weight average molecular weight, or the opposite. It should be appreciated that the embodiments depicted in FIG. 70 and FIG. 71 may include the active ingredient(s) 34 having at least one or all the positions selected from the group of: (1) between at least two or all the layer thicknesses 91; (2) between at least two or all the film thicknesses 67; (3) within at least one or all the layer thicknesses 91; or (4) within at least one or all of the film thicknesses 67. The active ingredient(s) 34 within each of the layers 51 may comprise the same or different chemical composition and/or the same or different active ingredient(s)' 34 dosage.

In an embodiment, the layer 51-A and the layer 51-D are barrier layers 51 that exclude the active ingredient(s) 34 and the layer 51-B and the layer 51-C are therapeutic layers 51 that include the active ingredient(s) 34. Additionally, the wall thickness 13 may optionally include the coating 30 that includes additional active ingredient(s) 34 positioned on at least the outer surface 16. The barrier layers 51 are useful for enabling the stent 10 to provide radial support to the anatomical lumen 36 until the anatomical lumen 36 is self-supporting and the barrier layers 51 also delay or slow down the delivery of the active ingredient(s) 34 stored within and/or between the therapeutic layers 51 or between the therapeutic layer(s) 51 and the barrier layers 51 by at least temporarily protecting the therapeutic layers 51 from erosion and placing an additional thickness of the stent material(s) 85 between the therapeutic layer(s) 51 and the anatomical lumen 36 that the active ingredient(s) 36 must pass through to reach the anatomical lumen 36. Alternatively, the layer 51-A and the layer 51-C may be therapeutic layers 51 and the layer 51-B and the layer 51-C may be the barrier layers 51. In yet one more embodiment, layer 51-A and the layer 51-D may be therapeutic layers 51 and the layer 51B and the layer 51-C may be the barrier layers 51. It should be appreciated that the wall thicknesses 13 depicted in FIG. 70 and FIG. 71 that include barrier layer(s) 51 and therapeutic layer(s) 51 are not limited to an embodiment having four layers 51 and that other embodiments having the same configurations may be made having less than four or greater than four layers 51.

As depicted in FIG. 72 through FIG. 75, which depict cross sectional views of the stent 10 wall thickness 13, the wall thickness 13 may be divided into three discrete layers 51. As depicted in FIG. 72 and FIG. 73, in an embodiment the layer 51-A and the layer 51-C may be thicker than the layer 51-B. In other embodiments, as depicted in FIG. 74 in FIG. 75, the layer 51-B may be thicker than layer 51-A and layer 51-C. Although not depicted, in other embodiments the layer 51-C may be thicker than layer 51-B and the layer 51-B may be thicker than layer 51-A, or the opposite. In one more embodiment, the layer 51-A, the layer 51-B and the layer 51-C comprise substantially the same thickness 91. The layer thicknesses 91 may be arranged within the stent 10 wall thickness 13 in any possible combination or permutation. For example, using the pattern format (closest to outer surface 16, middle of wall thickness 13, closet to inner surface 17) the layers 91 may be arranged in at least one configuration selected from the group: (1) thinnest layer 51, thicker layer 51, thickest layer 51; (2) thinnest layer 51, thickest layer 51, thicker layer 51, (3) thicker layer 51, thinnest layer 51, thickest layer 51; (4) thicker layer 51, thickest layer 51, thinnest layer 51; (5) thickest layer 51, thicker layer 51, thinnest layer 51; or (6) thickest layer 51, thinnest layer 51, thicker layer 51, wherein the thickest layer 51 is greater than the thicker layer 91 and the thicker layer 51 is greater than the thinnest layer 51. Although, FIG. 72 through FIG. 75 depict three layers 51, in other embodiments there may be greater than or less than three layers 51, wherein the layer thickness 91 is different in at least one of the layers 51 than the other layers 51. It should be appreciated that the embodiments depicted in FIG. 72 through FIG. 75 may include the active ingredient(s) 34 having at least one position or all of the positions selected from the group of: (1) between at least two layer thicknesses 91; (2) between at least two film thicknesses 67; (3) within at least one or all of the layer thicknesses 91; (4) within at least one or all of the film thicknesses 67; (5) on the outer surface 16 or (6) on the inner surface 17. The therapeutic layer(s) 51 and/or the therapeutic film thicknesses 67 may be separated by at least one of the barrier layers 51 or the barrier film thicknesses 67. The active ingredient(s) 34 within each of the layers 51 may comprise the same or different chemical composition and/or the same or different active ingredient(s) 34 dosage. In an embodiment, the dosage of the active ingredient(s) 34 within each discrete layer 51 is the same so that as each layer 51 is resorbed the same amount of the active ingredient(s) 34 are delivered to the anatomical lumen 36 during resorption of all the layers 51 and in another embodiment, at least one or all of the layers 51 contain a different dosage of the active ingredient(s) 34 within each discrete layer 51 so that as each layer 51 is resorbed a different amount of the active ingredient(s) 34 is delivered to the anatomical lumen 36 during the resorption of each layer 51. In one more embodiment, the dosage of the active ingredient(s) 34 within each layer 51 is proportional to the mass of the stent material(s) 85 within each layer 51. For example, if the wall thickness 13 configuration depicted in FIG. 72 has 40% of the stent material'(s) 85 mass located with the layer 51-A, 20% of the stent material'(s) 85 mass located with the layer 51-B and 40% of the stent material'(s) 85 mass located with the layer 51-C, the stent wall thickness 13 would have 40% of the active ingredient'(s) 34 mass located within the layer 51-A, 20% of the active ingredient'(s) 34 mass located with the layer 51-B and 40% of the active ingredient'(s) 34 mass located with the layer 51-C. In another embodiment, the dosage of the active ingredient(s) 34 within each layer 51 is disproportionate to the mass of the stent material(s) 85 within each layer 51. For example, the layer 51 comprising at least one part faster degrading stent material(s) 85 may include a higher dosage than the layer 51 comprising at least one part slower degrading stent material(s) 85 or the layer 51 comprising at least one part the stent material(s) 85 that comprising glycolide may include a higher dosage of the active ingredient(s) 34 than the stent material(s) 85 comprising homopolymers of L-lactide. The release of the active ingredient(s) 34 that are positioned within the layers 51 at least partially or completely reduce the risk of side effects of the stent material(s) 85 resorbing during the duration of the resorption process. For example, the active ingredient(s) 34 prevent restenosis and/or device thrombosis at least during the duration that the stent 10 is implanted within the anatomical lumen 36 and/or during the resorption time.

In an embodiment of the wall thickness 13 depicted in FIG. 72 through FIG. 75, the layer 51-A and the layer 51-C (outer layers 51) may comprise the stent material(s) 85 that degrade and/or resorb slower than the stent material(s) 85 comprising layer 51-B (middle layer 51). When at least two layers 51 comprised of slower degrading and/or resorbing stent material(s) 85 are separated by at least one layer 51 of faster degrading stent material(s) 85, the wall thickness 13 of the implanted stent 10 may delaminate within the anatomical lumen 36, which results in the entire implanted stent 10 resorbing faster than if the implanted stent 10 that does not delaminate within the anatomical lumen 36 because the delaminated wall thickness 13 has more surface area exposed to the contents 6, cells and/or tissue surrounding the implanted wall thickness 13 that degrade the stent material(s) 85 within the stent 10. In an embodiment that results in a delaminated implanted wall thickness 13, the implanted stent's 10 wall thickness 13 delaminates because the faster degrading and/or resorbing layer 51 weakens, erodes and/or losses mass in a way that the two adjacent layers 51 comprising the slower degrading and/or resorbing stent material(s) 85 become at least partially or completely disconnected within the anatomical lumen 36, which results in at least partial or complete separation of the two slower degrading and/or resorbing layers 51. Additionally, the tissue and cells surrounding the implanted stent 10 may grow within the delaminated wall thickness 13, which may result in reinforcement of the stent 10 and/or acceleration of the resorption of the remaining mass of the stent material(s) that are within the anatomical lumen 36. When the faster degrading and/or resorbing layer 51 includes the active ingredient(s) 34, the active ingredient(s) 34 within the faster degrading and/or resorbing layer 51 may be partially or completely released before the active ingredient(s) 34 located within the slower degrading and/or resorbing layers 51. The slower degrading and/or resorbing layer 51-A and layer 51-C may at least partially protect the faster degrading and/or resorbing layer 51-B against the content(s) 6, cell and tissue surrounding the implanted stent 10 that cause degradation and/or resorption of the stent 10 so that the stent 10 can provide support to the anatomical lumen 36 until the anatomical lumen 36 is substantially self-supporting. The stent's 10 capability supporting the anatomical lumen 36 can be determined by measuring lumen loss after implantation of the stent 10 within the anatomical lumen 36. The slower degrading and/or resorbing layer 51-A and layer 51-C may, for example, at least temporarily protects the faster degrading and/or resorbing layer 51 against hydrolysis by slowing the entry of water into the faster degrading and/or resorbing layer 51. Slowing the penetration of water into the faster degrading and/or resorbing layer 51 delays the loss of mechanical strength of the stent 10, which enables the stent 10 to mechanically support the anatomical lumen 36 until the anatomical lumen 36 has healed from the injury it experiences during implantation of the stent 10 within the anatomical lumen 36 and/or until the anatomical lumen 36 become self-supporting. In an embodiment, after the anatomical lumen no longer needs support from the stent 10, the stent 10 may be rapidly resorbed.

The stent 10 may retain sufficient strength to support and/or substantially hold open the anatomical lumen 36 for a duration starting from the time of the stent 10 implantation within the anatomical lumen 36 selected from the group of: (1) greater than 0 to 30 days, (2) greater than 0 to 60 days, (3) greater than 0 to 90 days, (4) greater than 0 to 120 days, (5) greater 0 to 150 days or (6) greater than 0 to 180 days, (7) greater than 0 to 210 days, (8) greater than 0 to 240 days, (9) greater than 0 to 270 days, (10) greater than 0 to 300 days, (11) greater than 0 to 330 days or (12) greater than 0 to 360 days. In other embodiments, the stent 10 may retain sufficient strength to support and/or hold open the anatomical lumen 35 for a longer time. For a vascular stent 10, it is preferred that the stent 10 be capable of providing support to the anatomical lumen 36 for between about 5 days to about 180 days after the stent 10 is implanted within the anatomical lumen 36.

The mass of the stent 10 may resorbed within a duration starting from the time of the stent 10 implantation within the anatomical lumen 36 selected from the group of: (1) greater than 0 to 30 days, (2) greater than 0 to 60 days, (3) greater than 0 to 90 days, (4) greater than 0 to 120 days, (5) greater 0 to 150 days or (6) greater than 0 to 180 days, (7) greater than 0 to 210 days, (8) greater than 0 to 240 days, (9) greater than 0 to 270 days, (10) greater than 0 to 300 days, (11) greater than 0 to 330 days, (12) greater than 0 to 360 days, (13) greater than 0 to 390 days, (14) greater than 0 to 420 days, (15) greater than 0 to 450 days, (16) greater than 0 to 480 days, (17) greater to 0 to 510 days, (18) greater than 0 to 540 days, (19) greater than 0 to 570 days, (20) greater than 0 to 600 days, (21) greater than 0 to 630 days, (22) greater than 0 to 660 days, (23) greater than 0 to 690 days, (24) greater than 0 to 720 days, (25) greater than 0 to 750 days, (26) greater than 0 to 780 days, (27) greater than 0 to 810 days, (28) greater than 0 to 840 days, (29) greater than 0 to 870 days), (30) greater than 0 to 900 days, (31) greater than 0 to 930 days, (32) greater than 0 to 960 days, (33) greater than 0 to 990 days, (34) greater than 0 to 1,020 days, greater than 0 to 1,050 days, or (35) greater than 0 to 1,080 days or greater than 0 to 1,110 days. In other embodiments, the mass of the stent 10 may resorbed within a longer duration than 1,110 days to no longer than 5 years.

In an embodiment, the stent 10 includes a Stent-To-Anatomical Lumen Coverage Area ("STALCA") within the range of greater than 0.0% to about less than 99.0%, more preferably in the range of about 0.5% to 45.0%, and most preferably in the range of 0.5% to equal to or less than about 25.0% or whatever is experimentally determined to be the optimum STALCA for the end-use application determined by those skilled in the art. In other embodiments, the stent 10 includes a STALCA equal to or greater than ninety percent. The STALCA equals the surface area of the stent's 40 outer surface 16 area divided by the surface area of the anatomical lumen 36 within the treatment site 35. In an embodiment, for example, the stent 10 has a STALCA less than 25%, which means that at least 75% of the mass of the un-oriented tube 42 or the oriented tube 38 is removed when the strut pattern 171 is cut into the un-oriented tube 42 or the oriented tube 38. In an embodiment, the stent 10 has a volume within the range of greater than 0 cubic millimeters to 2463 cubic millimeters or 2.463 cubic centimeters ("cm3"). Therefore, in an embodiment the stent 10 comprising the stent material(s) 85 having a nominal density of 1.3 g/cm3, the maximum stent 10 mass equals about 3.2 g. In other embodiments, comprising less dense or more dense stent 10 material(s) 85 the mass of the stent 10 may be higher or lower. For, example, if the stent 10 including reinforcements 240 comprising metal elements, the maximum mass of the stent 10 is greater than 3.2 g. The mass of a typical stent 10 used in a coronary artery, however, is much lower. For example, if the stent 10 is produced within the portion of the oriented tube 38 depicted on row 15 of the table in FIG. 110, which has the inner diameter equal to 3 mm, the wall thickness equal to 0.080 mm and the length equal to 18 mm, the stent 10 comprised of the stent 10 material(s) 85 having density of 1.3 g/cm3, the stent 10 has a mass equal to or about 0.0045 g when the stent 10 has the STALCA equal to 25%. The mass of this embodiment of the stent 10 is calculated by 0.013934 cm3.times.1.3 g/cm3.times.0.25=0.0045 g. In other embodiments, the stent 10 used in a coronary artery may have higher or lower stent 10 mass. For example, stents 10 having a smaller inner diameter 12, smaller wall thickness 13, shorter length and/or lower STALCA would have a lower stent mass than 0.0045 g or stents 10 having a larger inner diameter 12, larger wall thickness 13, longer length 15 and/or higher STALC would have a higher stent mass than 0.0045 g. Other factors may also affect the mass of the stent 10. For example, a stent 10 comprising stent material(s) 85 having a higher degree of crystallinity will have a higher stent mass than a stent 10 comprising stent material(s) having a lower degree of crystallinity. For example, the density of poly (L-lactide) can vary between 1.1 g/cm3 to 1.5 g/cm3 depending on the degree of crystallinity, wherein 1.1 g/cm3 is for more amorphous poly (L-lactide) and 1.5 g/cm3 is for more crystalline poly (L-lactide). Moreover, the mass of the stent 10 may be affected by blending of multiple stent material(s) 85 during formation of the stent 10. For example, blending of poly (L-lactide) having a nominal density of 1.3 with poly (glycolide) having a nominal density of 1.53 g/cm3 may increase the mass of the stent 10 or blending of poly (L-lactide) having a nominal density of 1.3 g/cm3 with poly (caprolactone) having a nominal density of 1.145 g/cm3 may decrease the mass of the stent 10. Likewise, inclusion of reinforcements 240 comprising a magnesium alloy having a nominal density between 1.7 g/cm3 to 2.3 g/cm3 within poly (L-lactide) having a nominal density within the range of 1.2 g/cm3 to 1.5 g/cm3 or other stent material(s) 85 will increase the density of the stent 10. Alternatively or additionally, adding at least one active ingredient 34 to the stent material(s) 85 may increase or decrease the mass of the stent 10. For example, including the active ingredient 34 Sirolimus, which has a density of about 1.2 g/cm3, would have a negligible impact on the mass of the stent 10 comprised of poly (L-lactide) having a low degree of crystallinity.

The implanted stent 10 wall thickness 13 may be configured to distribute at least one of the active ingredients 34 between the implanted linear ring struts 20, link struts 21 and/or adjacent to the rings 19 located on the proximal end 25 and distal end 26 of the stent 10. At least one active ingredient 34 may migrate away from the deployed location of the stent 10 in an embodiment of the implanted stent 10 that delaminates within the anatomical lumen 36, wherein the deployed location of the stent 10 is the location of the stent 10 immediately after the catheter 37 completes compressing the stent 10 against the interior of the anatomical lumen 36. In an embodiment, at least one of the released active ingredient(s) 34 is distributed and at least partially retained within region of the implanted linear ring struts 20 and/or link struts 21 until at least the mass of the stent 10 is partially or completely resorbed. The stent 10 may be configured to release the active ingredient(s) 34 from the stent 10 so that the active ingredient(s) 34 spread to a distance of about between 0.0 mm to 1 mm away from the implanted linear ring strut 20 and/or link strut 21. In other embodiments, the stent 10 may be configured to release at least one of the active ingredient(s) 34 so that the active ingredient(s) 34 are distributed and at least partially retained within at least part of the region between greater than 0 mm to about 5 mm surrounding the implanted linear ring struts 20 and/or link struts 21 until the mass of the stent 10 is partially or completely resorbed. In an embodiment, the stent 10 is configured to release at least one of the active ingredient(s) 34 so that the active ingredient(s) 34 are distributed and/or at least partially retained within the tissue and/or cells positioned on the abluminal side of the implanted stent 10 at least until the stent 10 is partially or completely resorbed. In another embodiment, the stent 10 is configured to release the active ingredient(s) 34 so that the active ingredient(s) 34 are distributed and at least partially retained within the tissue and/or cells positioned on the luminal side of the implanted stent 10 at least until the stent 10 is partially or completely resorbed. In one more embodiment, the stent 10 is configured to release the active ingredient(s) 34 so that the active ingredient(s) 34 are distributed and at least partially retained within the tissue and/or cells positioned on the luminal side and the abluminal side of the implanted stent 10 at least until the stent 10 is partially or completely resorbed. In an embodiment, the wall thickness 13 is capable of releasing at least one part of the active ingredient(s) 34 located within the faster degrading and/or resorbing layer 51 after the endothelial cells at least partially or completely cover the linear ring struts 20 and/or the link struts 21, which prevents part or all of the active ingredient(s) 34 that are released from the stent 10 from being washed away by the content(s) 6 so that there is at least one active ingredient 34 at least temporarily retained within the area surrounding the linear ring strut(s) 20 and/or link strut(s) 21 until the mass of the stent 10 is resorbed.

In another embodiment of the wall thickness 13 depicted in FIG. 72 through FIG. 75, the stent material(s) 85 that comprise the layer 51-A degrade and/or resorb faster than the stent material(s) 85 that comprise the layer 51-B and the stent material(s) 85 that comprise layer 51-B degrade and/or resorb faster than the stent material(s) 85 that comprise the layer 51-C, or the opposite. In one more embodiment of the wall thickness 13 depicted in FIG. 72 through FIG. 75, the layer 51-A may comprise the stent material(s) 85 that have a lower weight average molecular weight than the stent material(s) 85 that comprise the layer 51-B and the stent material(s) 85 that comprise the layer 51-B may comprise the stent material(s) 85 that have a lower weight average molecular weight than the stent material(s) 85 that comprise the layer 51-C, or the opposite. Therefore, the layers 51 within the wall thickness 13 of the stent 10 may resorb and/or erode sequentially, wherein the abluminal layer 51 is substantially resorbed and/or eroded first, the middle layer 51 is substantially resorbed and/or eroded second and the luminal layer 51 is substantially resorbed and/or eroded last, or the opposite. In another embodiment, the luminal layer 51 has a higher crystallinity that the abluminal layer(s) 51. Even though FIG. 72 through FIG. 75 depict the stent 10 wall thickness 13 having three layers 51, in other embodiments the stent 10 wall thickness 13 comprises greater than or less than three layers 51, wherein the layers 51 within the wall thickness 13 of the stent 10 may resorb or erode sequentially in a way that the abluminal layer 51 is substantially resorbed or eroded first, the middle layers 51 (if present) are sequentially resorbed or eroded next and the luminal layer 51 is resorbed or eroded last, or the opposite. In the embodiments of the stent 10 comprising sequentially resorbing or eroding layers 51, at least one or all the layer(s) 51 include at least one active ingredient 34 that is sequentially delivered to the anatomical lumen 36 as the layers 51 resorb and/or erode. In another embodiment, the luminal layer 51 within the stent 10 degrades slower than the abluminal layer(s) 51 because the stent material(s) 85 within the luminal layer 51 have a higher degree of crystallinity than the stent material(s) 85 within the abluminal layer(s) 51. The quantity of the stent material(s) 85 resorbed over time may be controlled by the thickness 91 of the layers 51. To produce the stent 10 wherein the mass of the layer(s) 51 resorb at approximately the same time, the layer(s) 51 comprising slower degrading rate stent material(s) 85 should be thinner than the layer(s) 51 comprising the fast-degrading rate stent material(s) 85.

In an embodiment, the stent 10 wall thickness 13 comprises at least one therapeutic layer 51 and one barrier layer 51, wherein the therapeutic layer 51 comprises a mixture of at least one stent material 85 and at least one active ingredient 34 and the barrier layer 51 comprises at least one stent material 85. In an embodiment, the therapeutic layer 51 is positioned between two barrier layers 51. In an embodiment, at least one barrier layer 51 is positioned between the inner surface 17 and the therapeutic layer 51 so that the barrier layer 51 at least partially or completely inhibits the delivery of the active ingredient(s) 34 to the anatomical lumen 36 that are within the therapeutic layer 51 of the implanted stent 10 until the barrier layer 51 is at least partially or completely resorbed. Alternatively, or additionally, in an embodiment, at least one barrier layer 51 is positioned between the outer surface 16 and the therapeutic layer 51 so that the barrier layer 51 at least partially or completely inhibits the delivery of the active ingredient(s) 34 to the anatomical lumen 36 that are within the therapeutic layer 51 of the implanted stent 10 until the barrier layer 51 is at least partially or completely resorbed. The inhibition of the delivery of the active ingredient(s) 34 facilitates delivering the optimum dosage of the active ingredient(s) 34 during the duration that the mass of the stent 10 is within the anatomical lumen 36. In other embodiments, there may be two barrier layers 51, three barrier layers 51, four barrier layers 51, five barrier layers 51 and so on between and/or surrounding each therapeutic layer 51. Alternatively, or additionally, in other embodiments there may be two therapeutic layers 51, three therapeutic layers 51, four therapeutic layers 51, five therapeutic layers 51, or so on between and/or surrounding each barrier layer 51. The therapeutic layer(s) 51 and the barrier layer(s) 51 may comprise the same or different stent material(s) 85. In other embodiments, (1) the therapeutic layer(s) 51 may be the same thickness 91 as the barrier layer(s) 51, (2) at least one of therapeutic layer(s) 51 may be thicker than at least one of the barrier layer(s) 51, (3) at least one barrier layers 51 may be thicker than at least one of the therapeutic layer(s) 51, (4) at least one barrier layer 51 may be thicker than at least one other barrier layer 51, and/or (5) at least one therapeutic layer 51 may be thicker than at least one other therapeutic layer 51.

FIG. 76 through FIG. 93 depict various cross-sectional views of embodiments of the wall thickness 13 of the linear ring struts 20 and/or the link struts 21, wherein the wall thickness 13 comprises multiple interconnected film thicknesses 67. FIG. 76, depicts the wall thickness 13 of the linear ring struts 20 and/or the link struts 21, wherein the wall thickness 13 comprises two interconnected film thicknesses 67 comprising the same stent material(s) 85. The two film thicknesses 67 are interconnected with one bond 65. FIG. 77, depicts the wall thickness 13 of the linear ring struts 20 and/or the link struts 21, wherein the wall thickness 13 comprises three interconnected film thicknesses 67 comprising the same stent material(s) 85. The three film thicknesses 67 are interconnected with two bonds 65. FIG. 78, depicts the wall thickness 13 of the linear ring struts 20 and/or the link struts 21, wherein the wall thickness 13 comprises four interconnected film thicknesses 67 comprising the same stent material(s) 85. The four film thicknesses 67 are interconnected with three bonds 65. The wall thicknesses 13 depicted in FIG. 76 through FIG. 78 may be formed with one solid film 66-A or two separate solid films 66 that comprise the same stent material(s) 85. In other embodiments, the wall thickness 13 may comprise greater than four interconnected film thicknesses 67 comprising the same stent material(s) 85. The wall thickness 13 of the stent 10 may include up to 2,000 film thicknesses 67.

FIG. 79, depicts the wall thickness 13 of the linear ring struts 20 and the link struts 21, wherein the wall thickness 13 comprises two film thicknesses 67 that comprise two different solid films 66 (solid film 66-A and solid film 66-B) that are made from two different stent material(s) 85. Alternatively, the wall thickness 13 depicted in FIG. 79 may comprise two interconnected film thicknesses 67 formed from two solid films 66, wherein the solid films 66 are selected from any combination or permutation of solid film 66-A, solid film 66-B, solid film 66-C or solid film 66-D. Likewise, the arrangement of the solid films 66 may be reversed so that the solid film 66-A is near located near the inner surface 17 and the solid film 66-B is located near the outer surface 16. The two different film thicknesses 67 are interconnected with one bond 65.

FIG. 80, depicts the wall thickness 13 of the linear ring struts 20 and the link struts 21, wherein the wall thickness 13 comprises three different film thicknesses 67 that comprise three different solid films 66 (solid film 66-A, solid film 66-B, solid film 66-C) that are made from three different stent material(s) 85. Alternatively, the solid films 66 may be chosen from any three of the following solid films 66, wherein at least two or all the solid films 66 are different: solid film 66-A, solid film 66-B, solid film 66-C, solid film 66-D, solid film 66-D and so on. The three different solid films 66 may also be arranged in a different order than what is depicted in FIG. 80. For example, wherein the solid film 66 order within the wall thickness 66 is inner surface 17, middle, outer surface 16, the solid films 66 may be arranged: F-A, F-B, F-C; F-B, F-A, F-C; F-B, F-C, F-A; F-C, FA, F-B; F-C, F-B, F-A; or F-A, F-C, F-B, wherein "F-A" refers to solid film 66-A, "F-B" refers to solid film 66-B, and "F-C" refers to solid film 66-C. The three film thicknesses 67 are interconnected with two bonds 65. FIG. 81, depicts the wall thickness 13 of the linear ring struts 20 and the link struts 21, wherein the wall thickness 13 comprises four different film thicknesses 67 that comprise four different solid films 66 (solid film 66-A, solid film 66-B, solid film 66-C, solid film 66-D) that are made from four different stent material(s) 85. The four film thicknesses 67 are interconnected with three bonds 65. Although, FIG. 79 through FIG. 81 depict the different solid films 66 arranged so that solid film 66-A is positioned closest to the outer surface 16, solid film 66-B is positioned adjacent to solid film 66-A on the side facing the inner surface 17, solid film 66-C is positioned adjacent to solid film 66-B on the side facing the inner surface 17 and solid film 66-D is positioned adjacent to solid film 66-C on the side facing the inner surface 17, in other embodiments the solid films 66-A, 66-B, 66-C, and 66-D may be arranged in any combination or permutation of these positions. In other embodiments the group of film thickness 67 depicted in FIG. 79 thru FIG. 81 may repeat within the stent 10 thickness 13 at least one additional time, wherein the word "group" refers to the combination or permutation of solid film 66-A and solid film 66-B, combination or permutation of solid film 66-A, solid film 66-B and solid film 66-C, or combination or permutation of solid film 66-A, solid film 66-B, solid film 66-C and solid film 66-D. For example, in other embodiments, the wall thickness 13 depicted in FIG. 80 could have six film thicknesses 67, twelve film thicknesses 67, fifteen film thicknesses 67, eighteen film thicknesses 67, twenty-one film thicknesses 67, twenty-four film thicknesses 67, twenty-seven film thicknesses 67, thirty film thicknesses 67, thirty-three film thicknesses 67 and so on, wherein the group or pattern of three film thicknesses 67 comprising the same or different stent material(s) 85 is repeated in the group of film thicknesses 67 that are added to underlying group of film thicknesses 67 within the stent 10 wall thickness 13. The group or pattern of the film thicknesses 67 can be repeated as many times as necessary until the desired un-oriented 42 tube wall thickness 45 or oriented tube 38 wall thickness 27 is achieved so that the stent 10 can be formed having the wall thickness 13 within the specifications disclosed herein.

As previously disclosed, the number of different film thicknesses 67 within the wall thickness 13 is not limited to four different film thicknesses 67. Therefore, in other embodiments there may be solid film 66-E, solid film 66-F, solid film 66-G, solid film 66-H, solid film 66-I, solid film 66-J and so on added to the group of film thicknesses 67 depicted in FIGS. 76-81. In other embodiments, there may be other patterns of film thicknesses 67 within the wall thickness 13 that are not depicted in the figures. For example, in an embodiment having a group comprising six film thicknesses 67, there may be two solid films 66-A, two solid films 66-B and two solid film 66-C to form at least three different layers 51 within the wall thickness 13, wherein each layer 51 comprises two film thicknesses 67 or in another example embodiment there may be three solid films 66-A and three solid film 66-B to form at least two different layers 51 within the wall thickness 13. In yet a few other example embodiments, there may be a group of four film thickness 67 wherein one solid film 66 comprises solid film 66-A and three solid films comprise solid film 66-B or wherein two solid films 66 comprise solid film 66-A and two solid films comprise solid film 66-B.

Although it is not depicted in FIG. 76 thru FIG. 81, the stent wall thicknesses 13 formed of interconnected film thicknesses 67 may include the active ingredient(s) 34 located within at least one of the following positions: (1) within the film thickness 67; (2) on at least one of the film major surface(s) 73; (3) between at least two film thicknesses 67; (4) on the stent 10 outer surface 16; and/or (5) on the stent 10 inner surface 17. Positioning the active ingredient(s) 34 on or between the inner surface 17 and the outer surface 16 of the wall thickness 13 of the stent 10 enables the stent 10 to have a sustained delivery of the active ingredient(s) 34 until at least the mass of the stent material(s) 85 within the implanted stent 10 are resorbed. Forming the wall thickness 13 from solid films 66 allows the time of the release of the active ingredient(s) 34 to be controlled and the delivered dosage of the active ingredient(s) 34 to be controlled in a way that minimizes or prevents restenosis and/or stent thrombosis at least until the mass of the stent 10 is resorbed. The timing of the release of the active ingredient(s) 34 from the implanted stent 10 may be controlled during the treatment provided by the implanted stent 10 by at least one of the following: (1) the selection of the stent material(s) 85 comprising each film thickness 67, wherein the stent material(s) 85 having a faster degradation rate release the active ingredient(s) 34 in less time after deployment of the stent 10 than the stent material(s) 85 having a slower degradation rate; (2) the thickness of each film thickness 67; wherein the thicker the solid film 66 the slower the release of all the active ingredient(s) 34 that are positioned within that film thickness 67 if the film thicknesses 67 comprise the same stent material(s) 85; (3) the position of the active ingredient(s) 34 behind at least one barrier film thickness 67; wherein the barrier film thickness 67 at least temporarily prevents the degradable elements within the contents 6, local tissue and/or local cells that surround the implanted stent 10 from penetrating the therapeutic film thickness 67 that contains the active ingredient(s) 34; (4) the selection of the morphology of the active ingredient(s) 34 and/or the stent material(s) 85; wherein the more crystalline the active ingredient(s) 34 and/or the more crystalline the stent material(s) 85 the longer the duration of the drug therapy and the more amorphous the active ingredient(s) 34 and/or the more amorphous the stent material(s) 85 the shorter the duration of the drug therapy (5) the selection of the weight average molecular weight of the active ingredient(s) 34 and/or the stent material(s) 85; wherein the higher the weight average molecular weight of the active ingredient(s) 34 and/or the higher the weight average molecular weight of the stent material(s) 85 the slower the release of the active ingredient(s) 34 from the stent 10 and the longer the duration of the drug therapy and the lower the weight average molecular weight of the active ingredient(s) 34 and/or the lower the weight average molecular weight the stent material(s) 85 the faster the release of the active ingredient(s) 34 from the stent 10 and the shorter the duration of the therapy.

The resorption rate of the stent material(s) 85 is a major factor that controls the rate at which the stent material(s) 85 are resorbed. The following resorption rates provide guidance on how the chemical composition of the solid film 66 will affect the time that the implanted stent 10 can provide radial support to the anatomical lumen 36, the time that it takes to release the active ingredient(s) 34 and the time for the stent material(s) 85 within the stent 10 to be resorbed. The resorption rates provided in this guidance may be increased or decreased by at least one of the following: (1) co-polymerization of monomers; (2) blending of the stent material(s); (3) the stent 10 formation processes, which may increase or decrease the crystallinity of the stent material(s) and/or decrease the weight average molecular weight of the stent material(s); (4) inclusion of additives and/or active ingredient(s) 34 within the stent material(s) 85; (5) the stent 10 geometry, (6) implantation site and/or position of the film thickness 67 within the stent wall thickness 13. The following stent material(s) 85 have the approximate resorption times, wherein the "resorption time" means the time to complete the loss of stent material 85 mass after implantation of the stent 10 within the anatomical lumen 36: (1) poly (L-lactide) has a resorption time of greater than 24 months; (2) poly (DL-lactide) has a resorption time of 12 to 16 months; (3) poly (glycolide) has a resorption time of 6 to 12 months; (4) poly (epsilon.caprolactone) has a resorption time of greater than 24 months; (5) copolymer of DL-lactide and glycolide having a 50/50 molar ratio has resorption time of 1 to 2 months; (6) copolymer of L-lactide and glycolide having an 85/15 molar ratio has a resorption time of 12 to 18 months; and (7) copolymer of L-lactide and epsilon.caprolactone having 70/30 molar ratio has a resorption time of 12 to 24 months. In other embodiments, the stent material(s) 85 may have approximate resorption times selected from the group: (1) copolymer of DL-lactide and glycolide having a 50/50 molar ratio and having an IV equal to about 0.2 dl/g or weight average molecular weight equal to about 17 kg/mol has resorption time of about 0.5 to 1 month or 0.75 to 1.5 months; (2) copolymer of DL-lactide and glycolide having a 50/50 molar ratio having an IV equal to about 0.4 dl/g and/or weight average molecular weight equal to 44 kg/mol has resorption time of about 0.75 to 1 month or about 1 to 2 months; (3) copolymer of DL-lactide and glycolide having a 50/50 molar ratio having an IV equal to about 1.0 dl/g and/or weight average molecular weight equal to 153 kg/mol has resorption time of about 3 to 4 months; (4) copolymer of DL-lactide and glycolide having a 75/25 molar ratio having an IV equal to about 0.2 dl/g and/or weight average molecular weight equal to 17 kg/mol has resorption time of about 2 to 3 months or about 3 to 4 months; (5) copolymer of DL-lactide and glycolide having a 75/25 molar ratio having an IV equal to about 0.7 dl/g and/or weight average molecular weight equal to 95 kg/mol has resorption time of about 4 to 5 months; (6) poly (DL-lactide) having an IV equal to about 0.2 dl/g and/or weight average molecular weight equal to 17 kg/mol has resorption time of about 6 to 9 months or 9-12 months; (7) poly (DL-lactide) having an IV equal to about 0.4 dl/g and/or weight average molecular weight equal to 45 kg/mol has resorption time of about 10 to 14 months; and/or (8) poly (DL-lactide) having an IV equal to about 0.5 dl/g and/or weight average molecular weight equal to 61 kg/mol has resorption time of about 12 to 16 months. It should be appreciated that stent material(s) 85 having resorption times between the examples provided herein may be formulated by varying the chemical composition (e.g. molar ratio of the monomers), blending the stent material(s) 85 to form a mixture and/or the varying the weight average molecular weight (Mw) of the stent material(s) 85 so that the resorption time of these variants fall within the ranges provided herein and that these variants are within the scope of the present invention.

Forming the wall thickness 13 from the solid films 66 creates a new mechanism for releasing the active ingredient(s) 34 into the area surrounding the stent's 10 implanted linear ring struts 20 and/or links struts 21 because as each active ingredient (34)-containing film thickness 67 erodes the stent 10 replenishes the anatomical lumen 36 with the active ingredient(s) 34, which at least partially or completely mitigate the adverse reaction that may be the result of the stent material(s) 85 being resorbed. The new mechanism is superior to the drug delivery mechanism of the prior art that comprises a coating that is less than 0.005 mm thick comprising a mixture of a polymer and a drug that is adhered to the outer surface of the solid metallic or solid polymeric backbone of the stent because in the prior art mechanism the drug delivery starts immediately after implantation of the stent within the anatomical lumen, wherein 75% to 85% of the drug within the coating is released with 30 days of when the prior art stent is implanted within the anatomical lumen. This results in most of the prior art drug being vulnerable to being quickly washed away by the contents flowing through the prior art stent. The prior art bioresorbable stent provides virtually no drug delivery once the coating is removed from the prior art bioresorbable stent, which results in a long period of time wherein the material comprising the prior art stent is resorbing without any drug delivery to prevent late stent thrombosis. The prior art bioresorbable stent can be at least partially resorb within the anatomical lumen for 35 months without drug delivery. In contrast, in an embodiment of the stent 10, the active ingredient(s) 34 are gradually released from the mass of the stent material(s) 85 that are positioned between the inner surface 17 and the outer surface 16 ("the backbone") from the time the stent 10 is implanted within the anatomical lumen 36, which results in the active ingredient(s) 34 being at least partially or completely retained within the proximity of the treatment site 35 so that they can prevent restenosis and/or late stent thrombosis from occurring until the mass of the stent material(s) 85 within the stent 10 backbone are resorbed.

In an embodiment, the amount of the active ingredient(s) 34 that are included within the stent 10 coating 30 may be within the range of: (1) greater than 0 to 25.mu.g/cm.sup.2 of treatment site 35 area; (2) greater than 0 to 50.mu.g/cm.sup.2 of treatment site 35 area; (3) greater than 0 to 75.mu.g/cm.sup.2 of treatment site 35 area; (4) greater than 0 to 100 .mu.g/cm.sup.2 of treatment site 35 area; (5) greater than 0 to 150.mu.g/cm.sup.2 of treatment site 35 area; (6) greater than 0 to 175.mu.g/cm.sup.2 of treatment site 35 area; (7) greater than 0 to 200.mu.g/cm.sup.2 of treatment site 35 area; (8) greater than 0 to 225 .mu.g/cm.sup.2 of treatment site 35 area; (9) greater than 0 to 250.mu.g/cm.sup.2 of treatment site 35 area; (10) greater than 0 to 275.mu.g/cm.sup.2 of treatment site 35 area; (11) greater than 0 to 300.mu.g/cm.sup.2 of treatment site 35 area; (12) greater than 0 to 325 .mu.g/cm.sup.2 of treatment site 35 area; (13) greater than 0 to 325.mu.g/cm.sup.2 of treatment site 35 area; (14) greater than 0 to 350.mu.g/cm.sup.2 of treatment site 35 area; or (15) greater than 0 to 400.mu.g/cm.sup.2 of treatment site 35 area, wherein the treatment site 35 area is calculated by the formula: Area equals 2.pi.rh, where r=the stent outer diameter 11 divided by two and h equals the stent length 15. In other embodiments, the amount of the active ingredient(s) 34 that are included within the stent 10 coating 30 may be within the range of greater than 400.mu.g/cm.sup.2 to 5 g/cm.sup.2. The dosage of active ingredient(s) 34 depends on the application.

In an embodiment, the amount of the active ingredient(s) 34 that are included within the stent 10 may be within the range of: (1) greater than 0 to 25.mu.g/cm.sup.2 of treatment site 35 area; (2) greater than 0 to 50.mu.g/cm.sup.2 of treatment site 35 area; (3) greater than 0 to 75.mu.g/cm.sup.2 of treatment site 35 area; (4) greater than 0 to 100.mu.g/cm.sup.2 of treatment site 35 area; (5) greater than 0 to 150.mu.g/cm.sup.2 of treatment site 35 area; (6) greater than 0 to 175.mu.g/cm.sup.2 of treatment site 35 area; (7) greater than 0 to 200 .mu.g/cm.sup.2 of treatment site 35 area; (8) greater than 0 to 225.mu.g/cm.sup.2 of treatment site 35 area; (9) greater than 0 to 250.mu.g/cm.sup.2 of treatment site 35 area; (10) greater than 0 to 275.mu.g/cm.sup.2 of treatment site 35 area; (11) greater than 0 to 300 .mu.g/cm.sup.2 of treatment site 35 area; (12) greater than 0 to 325.mu.gAcm.sup.2 of treatment site 35 area; (13) greater than 0 to 325.mu.g/cm.sup.2 of treatment site 35 area; (14) greater than 0 to 350.mu.g/cm.sup.2 of treatment site 35 area; or (15) greater than 0 to 400.mu.g/cm.sup.2 of treatment site 35 area, wherein the treatment site 35 area is calculated by the formula: Area equals 2.pi.rh, where r=the stent outer diameter 11 divided by two and h equals the stent length 15. In other embodiments, the amount of the active ingredient(s) 34 that are included within the stent 10 to the stent 10 may be within the range of greater than 400 .mu.g/cm.sup.2. The dosage of active ingredient(s) 34 depends on the application.

The inclusion of the active ingredient(s) 34 within the stent wall thickness 13 may result in lowering the ductility of the wall thickness 13. Reducing the ductility of the stent 10 wall thickness 13 can result in the stent 10 having low dilatation limits, which means that the stent 10 may become brittle and not be capable of having dilatation limits above 0.5 mm. The dilatation limits of the stent 10 including the active ingredient(s) 34 may be increased above 0.5 mm by including at least 0.01 wt. % of poly (epsilon.caprolactone) or a copolymer of epsilon.caprolactone in at least one of the solid films 66 containing the active ingredient(s) 34 that are used to form the stent 10. The dilatation limits of the stent 10 including the active ingredient(s) 34 may be increased above 0.5 mm by including between greater than 0.0 wt. % to 25 wt. % of poly (epsilon.caprolactone) or a copolymer of epsilon.caprolactone and at least one other stent material(s) 85 in at least one of the solid films 66 used to form the stent 10. Copolymers of (epsilon.caprolactone) and L-lactide, copolymers of (epsilon.caprolactone) and DL-lactide, blends of poly (epsilon.caprolactone) and poly (L-lactide) or blends of poly (epsilon.caprolactone) and poly (DL-lactide) are a few examples of useful stent material(s) 85 for increasing the stent's 10 ductility. In an embodiment, the poly (epsilon.caprolactone) may be included in at least one or all of therapeutic layers 51. In another embodiment, the poly (epsilon.caprolactone) and/or copolymer of epsilon.caprolactone may be included in at least one or all of the barrier layers 51. In yet one more embodiment, the poly (epsilon.caprolactone) and/or the copolymer of epsilon.caprolactone may be included in at least one or all of the barrier layers and at least one or all of the therapeutic layers 51. In an embodiment, every other layer 51, every third layer 51 every forth layer 51 or every fifth layer 51 may include at least one part poly (epsilon.caprolactone) or the copolymer of epsilon.caprolactone to increase the ductility of the stent 10 so that it does not fracture while being implanted in the anatomical lumen 36.

The wall thickness 13 of the linear ring struts 20 and the link struts 21 depicted FIG. 82 comprise two film thicknesses 67 that are interconnected by one bond 65, wherein the active ingredient(s) 34 are positioned between the two film thicknesses 67 in the proximity of the bond 65. The wall thickness 13 of the linear ring struts 20 and the link struts 21 depicted FIG. 83 comprise three film thicknesses 67 that are interconnected by two bonds 65, wherein the active ingredient(s) 34 are positioned between the three film thicknesses 67 in the proximity of the bonds 65. The wall thickness 13 of the linear ring struts 20 and the link struts 21 depicted in FIG. 84 comprise four film thicknesses 67 that are interconnected by three bonds 65, wherein the active ingredient(s) 34 are positioned between the four film thicknesses 67 in the proximity of the bonds 65.

The wall thickness 13 of the linear ring struts 20 and the link struts 21 depicted FIG. 85 comprise two film thicknesses 67 that are interconnected by one bond 65, wherein the active ingredient(s) 34 are positioned within the two film thicknesses 67 in the proximity of the middle of the film thicknesses 67. The wall thickness 13 of the linear ring struts 20 and the link struts 21 depicted FIG. 86 comprise three film thicknesses 67 that are interconnected by two bonds 65, wherein the active ingredient(s) 34 are positioned within the three film thicknesses 67 in the proximity of the middle of the film thicknesses 67. The wall thickness 13 of the linear ring struts 20 and the link struts 21 depicted FIG. 87 comprise four film thicknesses 67 that are interconnected by three bonds 65, wherein the active ingredient(s) 34 are positioned within the four film thicknesses 67 in the proximity of the middle of the film thicknesses 67.

The wall thickness 13 of the linear ring struts 20 and the link struts 21 depicted FIG. 88 comprises two film thicknesses 67 that are interconnected by one bond 65, wherein the active ingredient(s) 34 are positioned within the two film thicknesses 67 in the proximity of the middle of the film thicknesses 67 and between the two film thicknesses 67 in the proximity of the bond 65. The wall thickness 13 of the linear ring struts 20 and the link struts 21 depicted FIG. 89 comprise three film thicknesses 67 that are interconnected by two bonds 65, wherein the active ingredient(s) 34 are positioned within the three film thicknesses 67 in the proximity of the middle of the film thicknesses 67 and between the three film thicknesses 67 in the proximity of the bond 65. The wall thickness 13 of the linear ring struts 20 and the link struts 21 depicted FIG. 90 comprise four film thicknesses 67 that are interconnected by three bonds 65, wherein the active ingredient(s) 34 are positioned within the four film thicknesses 67 in the proximity of the middle of the film thicknesses 67 and between the four film thicknesses 67 in the proximity of the bonds 65.

The wall thickness 13 of the linear ring struts 20 and the link struts 21 depicted FIG. 91 comprise two different film thicknesses 67 comprising two different solid films 66 (solid film 66-A, solid film 66-B) that are made from two different stent material(s) 85 that are interconnected by one bond 65, wherein the active ingredient(s) 34 are positioned between the two film thicknesses 67 in the proximity of the bond 65. The wall thickness 13 of the linear ring struts 20 and the link struts 21 depicted FIG. 92 comprise three film thicknesses 67 comprising three different solid films 66 (solid film 66-A, solid film 66-B, solid film 66-C) that are made from three different stent materials 85 that are interconnected by two bonds 65, wherein the active ingredient(s) 34 are positioned within the three film thicknesses 67. The wall thickness 13 of the linear ring struts 20 and the link struts 21 depicted FIG. 93 comprise four film thicknesses 67 comprising four different solid films 66 (solid film 66-A, solid film 66-B, solid film 66-C, solid film 66-D) that are interconnected by three bonds 65, wherein the active ingredient(s) 34 are positioned within the four film thicknesses 67 and between the four film thicknesses 67 in the proximity of the bonds 65. Although FIG. 78, FIG. 81, FIG. 84, FIG. 87, FIG. 90 and FIG. 93 depict four film thicknesses 67 within the linear strut 20 and link strut wall thicknesses 13, in other embodiments, there may be greater than four film thicknesses within the wall thickness 13. In other embodiments, the wall thickness 13 may include up to 2,000 interconnected film thicknesses 67 in the depicted configurations. Although FIG. 82 through 93 depict the active ingredient(s) 34 arranged in an orderly way, in other embodiments the active ingredient(s) 34 may be dispersed within the solid film 66 and/or between the solid films 66 in a disorderly way. In an embodiment, for example, when multiple, different solid films 66 are wrapped around the shaft 74 during formation of the un-oriented tube 42 and/or the oriented tube 38, the group of multiple solid films 66 repeats within the wall thickness 13 as many times as the multiple, different solid films 66 were wrapped around the shaft 74. Although FIG. 92 depicts that both solid film 66-A and solid film 66-B include the active ingredient(s) 34, in other embodiments either solid film 66-A or solid film 66-B may be a barrier film 66 that excludes the active ingredient(s) 34 and the other solid film 66 may be the therapeutic solid film 66 that includes the active ingredient(s) 34. Likewise, although FIG. 92 and FIG. 93 depict that solid film 66-A, solid film 66-B, solid film 66-C and/or solid film 66-D include the active ingredient(s) 34 positioned within all the solid films 66 and/or positioned between all the film thicknesses 67, in other embodiments there may be at least one solid film 66 that is a barrier film 66 that excludes the active ingredient(s) 34 and at least one solid film 66 that is a therapeutic film 66 that includes the active ingredient(s) 34. Although FIG. 91 through FIG. 93 always depict that solid film 66-A is near the outer surface 16, in other embodiment the solid film 66-A and the other solid films 66 are arranged within the wall thickness 13 in any possible combination or permutation of the multiple solid films 66.

FIG. 94, depicts the wall thickness 13 of the linear ring struts 20 and the link struts 21 in cross sectional view, wherein the wall thickness 13 comprises two layers 51 that are made from two different stent material(s) 85. Layer 51-A and layer 51-B each comprise at least one film thickness 67. At least one of the two-layers 51 may comprise up to 999 film thicknesses 67 that are interconnected by the bonds 65. The two different layers 51 are interconnected with one bond 65. FIG. 95, depicts the wall thickness 13 of the linear ring struts 20 and the link struts 21 in cross sectional view, wherein the wall thickness 13 comprises three different layers 51 that are made from three different stent material(s) 85. Layer 51-A, layer 51-B and layer 51-C each comprise at least one film thickness 67. At least one of the three-layers 51 may comprise up to 998 film thicknesses 67 that are interconnected by the bonds 65. The three layers 51 are interconnected with two bonds 65. FIG. 96, depicts the wall thickness 13 of the linear ring struts 20 and the link struts 21 in cross sectional view, wherein the wall thickness 13 comprises four layers 51 that are made from four different stent material(s) 85. Layer 51-A, layer 51-B, layer 51-C and layer 51-D each comprise at least one film thickness 67. The layers 51 are interconnected with three bonds 65. Although FIG. 96 depicts that the four layers 51 comprise four different stent material(s) 85, the four-layer 51 embodiments may comprise only two different stent material(s) 85 because a layer 51 is formed when two immediately adjacent film thicknesses 67 comprising different stent material(s) 85 abut one another within the wall thickness 13. Therefore, for example, layer 51-A could be the same stent material 85 as layer 51-C in FIG. C so long as layer 51-B comprises a different stent material 85 than layer 51-A and layer 51-C or layer 51-B could be the same stent material 85 as layer 51-D so long as layer 51-C comprises a different stent material 85 than layer 51-B and layer 51-D.

FIG. 97, depicts the wall thickness 13 of the linear ring struts 20 and the link struts 21 in cross sectional view, wherein the wall thickness 13 comprises the active ingredient(s) 34 positioned between two layers 51 that are made from two different stent material(s) 85. FIG. 98, depicts the wall thickness 13 of the linear ring struts 20 and the link struts 21 in cross sectional view, wherein the wall thickness 13 comprises the active ingredient(s) 34 positioned within three layers 51 that are made from three different stent material(s) 85. FIG. 99, depicts the wall thickness 13 of the linear ring struts 20 and the link struts 21 in cross sectional view, wherein the wall thickness 13 comprises the active ingredient(s) 34 positioned between the four layers 51 and within the four layers 51 that are made from four different stent material(s) 85. Although FIG. 97 through FIG. 99 depict one row of the active ingredient(s) 34 within each layer 51, it should be appreciated that each layer 51 may be comprised of multiple film thicknesses 67, wherein the active ingredient(s) 34 are positioned within the film thicknesses 67 or between the film thicknesses 67. Therefore, in another embodiment there may be multiple rows of the active ingredient(s) 34 within one or multiple layers 51. Furthermore, in an embodiment of the wall thickness 13 at least one of the film thicknesses 67 within the layer(s) 51 is a therapeutic film thickness 67 that includes the active ingredient(s) 34 and at least one of the film thicknesses 67 within the layer(s) 51 is a barrier film thickness 67 that excludes the active ingredient(s) 34. In yet one more embodiment, at least one of the layers 51 within the wall thickness 13 is a therapeutic layer 51 that includes the active ingredient(s) 34 and at least one of the layers 51 within the wall thickness 13 is a barrier layer 51 that excludes the active ingredient(s) 34.

The layer(s) 51 comprises at least one and typically multiple film thicknesses 67, which when the film thicknesses 67 are interconnected forms the layer thickness 91. FIG. 100 depicts a portion of the wall thickness 13 within the linear ring strut 20 or the link strut 21. The portion of the wall thickness 13 depicted in FIG. 100 depicts three discrete layers 51-A, 51-B and 51-C, wherein the abluminal layer 51 (51-A) that is located near the outer surface 16 comprises five film thicknesses 67, the luminal layer 51 (51-C) that is located near the inner surface 17 comprises seven film thicknesses 67 and the middle layer 51 (51-B) comprises six film thicknesses 67. Although FIG. 100 depicts the wall thickness 13 comprising three layers 106, there can be virtually any number of layers 51 within the wall thickness 13, but generally not greater than 2,000 discrete layers 51. Moreover, even though FIG. 100 depicts there being five to 7 film thicknesses 67 within each layer 51, the layer(s) 51 may comprise virtually any number of film thicknesses 67 within each discrete layer 51, but generally not greater than 2,000 film thicknesses 67 within each discrete layer 51. The luminal layer 51 located near the inner surface 17 may comprise more film thicknesses 67 than the middle layer(s) 51 and the middle layer(s) 51 may comprise more film thicknesses 67 than the abluminal layer 51 located near the outer surface 16 as depicted in FIG. 100, or the opposite. It is also possible that the middle layer(s) 51 comprise greater or lesser film thicknesses 67 than the abluminal layer 51 that is located near the outer surface 16 and/or the luminal layer 51 that is located near the inner surface 17. It will be appreciated that even though FIG. 100 depicts that the solid films 66 have the same thicknesses 67 within each of the layer(s) 51, that the film thicknesses 67 may be different within each discrete layer 51. The film thicknesses 67 and the layer thicknesses 91 may be the same or varied to control the delivery rate of the active ingredient(s) 34 after the stent 10 is implanted within the anatomical lumen 36. The stent 10 wall thickness 13 comprising one solid film 66 that is formed into the roll 52 having multiple, immediately adjacent film thicknesses 67 comprising the same stent material 85 or the same blends of different stent material(s) 85 forms the stent 10 wall thickness 13 comprising one layer 51 having one layer thickness 91 like the embodiment depicted in FIG. 34. The stent 10 wall thickness 13 comprising at least two solid films 66 that are formed into the roll 52 having multiple, immediately adjacent film thicknesses 67, wherein each of the solid films 66 comprise different stent materials 85 or different blends of stent materials 85, forms the stent 10 wall thickness 13 comprising multiple layers 51 like the embodiments depicted in FIG. 36, FIG. 38, FIG. 40, FIG. 42 and FIG. 44. For example, in an embodiment the solid film 66-B comprising poly (L-lactide) is superimposed on top the solid film 66-A comprising a copolymer of glycolide and L-lactide (at any molar ratio) as depicted in FIG. 35 and arranged in the wall thickness 57 to form the roll 52 like depicted in FIG. 36 comprising alternating layers 51 wherein the inner surface 62 comprises poly (L-lactide) and every other layer 51 is poly (L-lactide) separated by the copolymer of glycolide and L-lactide, and the outer surface 61 comprises the copolymer of glycolide and L-lactide, or the opposite. In yet one more embodiment of the two-solid film 66 roll 52, the first solid film 66-B comprises poly (L-lactide) having any weight average molecular weight described herein and the second solid film 66-A comprises poly (DL-lactide) having any weight average molecular weight described herein, a copolymer of DL-lactide and L-lactide having any molar ratio described herein, a copolymer of caprolactone and L-lactide having any molar ratio described herein, a copolymer of DL-lactide and glycolide having any molar ratio described herein, poly (DL-lactide) having any weight average molecular weight described herein, poly (glycolide) having any weight average molecular weight described herein, poly (caprolactone) having any weight average molecular weight described here, copolymers L-lactide and DL-lactide having any molar ratio described herein, copolymers of L-lactide and glycolide at any molar ratio described herein, copolymers of L-lactide and caprolactone at any molar ratio described herein, or the opposite. In yet one more embodiment, the first solid film 66-B comprises poly (L-lactide) having a weight average molecular weight between 1,014,000 g/mol and about 3,000,000 g/mol and the second solid film 66-A comprises poly (L-lactide) having a weight average molecular weight between greater than 0 g/mol to 1,013,999 g/mol, or the opposite. The wall thickness 13 is formed of multiple layers 51 to control the degradation rate and/or resorption rate of the stent 10 or to control the delivery rate of the active ingredient(s) 34.

FIG. 111 depicts a table that includes example Stent Material Formulas 275 and FIG. 112 depict a table that includes example Blend Formulas 276. In FIG. 111 the names of the stent material(s) 85 are abbreviated, wherein poly (L-lactide) is abbreviated a "PL," poly (DL-lactide) is abbreviated as "PDL," poly (glycolide) is abbreviated as "PG," poly (D-lactide) is abbreviated "PD," poly (.epsilon.caprolactone) is abbreviated as "PC," the co-polymer of L-lactide and DL-lactide is abbreviated as "PLDL," the copolymer of L-lactide and glycolide is abbreviated as "PLG," the copolymer of L-lactide and .epsilon.caprolactone is abbreviated as "PLC," the copolymer of DL-lactide and glycolide is abbreviated "PDLG," and the copolymer of L-lactide and D-lactide is abbreviated "PLD." In the tables depicted in FIG. 111 and FIG. 112 the terms "greater than" are abbreviated as ">" and the terms "less than" are abbreviated as "<."

In an embodiment, the stent 10 comprises at least one "formula number" 275 and/or at least one "blend formula" 276. For brevity "formula number 1" may be abbreviated "F-1," "formula number 2" may be abbreviated "F-2," "formula number 3" may be abbreviated "F-3" and the remaining formula numbers may also be abbreviated using "F- and the next sequential number" until the last formula number 80, which is abbreviated "F-80." Likewise, "blend number" 81 may be abbreviated "B-81," "blend number 82" may be abbreviated "B-82," "blend number 83" may be abbreviated "B-83" and the remaining blend numbers may also be abbreviated using "B- and the next sequential number" until the last blend number 180, which is abbreviated "B-180." In an embodiment, the stent 10 is formed from the solid film 66 comprising at least one of the eighty "formula numbers" shown in FIG. 111 (referred to as F-1 to F-80) and/or at least one of the one hundred "blend numbers" shown in FIG. 112 (referred to as B-81 to B-180). In other embodiments, the stent 10 is formed from the other stent material(s) 85 or blends of the stent material(s) 85 provided within this specification.

FIG. 111 depicts a table entitled "Example Stent Material 85 Formulations For Use In Producing The Film 66" having nine columns, wherein: (1) column one is the formula number, (2) column two is the stent material 85 name, (3) column three provides the molar ratio of L-lactide in the polymer or copolymer, (4) column four provides the molar ratio of DL-lactide in the polymer or copolymer, (5) column five provides the molar ratio of D-lactide in the polymer or copolymer, (6) column six provides the molar ratio of glycolide in the polymer or copolymer, (7) column seven provides the molar ratio of caprolactone in the polymer or copolymer, (8) column eight provides the weight average molecular weight of the polymer or copolymer and (9) column nine provides the Inherent Viscosity of the polymer or copolymer. For example, Formula number 1 ("F-1") comprises Poly (L-Lactide), which is a homopolymer of L-lactide that has a weight average molecular weight ranging from 55,000 g/mol to 3,000,000 g/mol and an Inherent Viscosity ("IV") ranging from 0.7 to 11.0 dl/g. In another embodiment, Formula number 41 ("F-41") comprises a copolymer of L-lactide and glycolide, wherein the molar ratio is 90 to less than 100 L-lactide and greater than 0 to 10 glycolide that has a molecular weight within the range of 55,000 g/mol to 3,000,000 g/mol and an IV within the range of 0.7 to 11.0 dl/g. The data provided for the other formula numbers shown in the other rows shown in FIG. 111 may be interpreted the same way.

FIG. 112 depicts a table entitled "Example Blend Formulations For Use In Producing Film 66" that has four columns, wherein: (1) column one is the "blend number" ("B-81 to B-180), (2) column two is the blend formulation that comprises blending or mixing at least two of the stent material 85 that are referred to by their formula number (e.g. F-1 may be blended with F-19), (3) column three provides the weight percentage (wt. %) of the first stent material(s) 85 constituent within the blend ("Part A"), and (4) column four provides the weight percentage (wt. %) of the second stent material 85 constituent within the blend ("Part 2"). For example, blend number 81 ("B-81") comprises a mixture of formula number 6 ("F-6") and at least one of the formulas numbers 2, 3, 4 and/or 5 ("F-2, F-3, F-4, F-5"), which means that blend 81 ("B-81") may comprise at least one of fourteen combinations of stent material formulations 275 that are depicted in FIG. 111. In an embodiment, at least one of the solid films 66 is produced from a blend of at least one of the formulas 275 identified as F-1 to F-80 and at least one of the blends 276 identified as B-81 to B-180.

For illustration purposes, the blend 81 ("B-81") may be one of the following combinations: (1) F-6 and F-2, wherein F-6 comprises 90 wt. % to less than 100 wt. % and F-2 comprises greater than 0 wt. % to 10 wt. % of the blend; (2) F-6 and F-3, wherein F-6 comprises 90 wt. % to less than 100 wt. % and F-3 comprises greater than 0 wt. % to 10 wt. % of the blend; (3) F-6 and F-4, wherein F-6 comprises 90 wt. % to less than 100 wt. % and F-4 comprises greater than 0 wt. % to 10 wt. % of the blend; (4) F-6 and F-5, wherein F-6 comprises 90 wt. % to less than 100 wt. % and F5 comprises greater than 0 wt. % to 10 wt. % of the blend; (5) F-6 and F-2 and F-3, wherein F-6 comprises 90 wt. % to less than 100 wt. % and F-2 and F-3 comprise greater than 0 wt. % to 10 wt. % of the blend; (6) F-6 and F-2 and F-4, wherein F-6 comprises 90 wt. % to less than 100 wt. % and F-2 and F-4 comprise greater than 0 wt. % to 10 wt. % of the blend; (7) F-6 and F-2 and F-5, wherein F-6 comprises 90 wt. % to less than 100 wt. % and F-2 and F-5 comprise greater than 0 wt. % to 10 wt. % of the blend; (8) F-6 and F-3 and F-4, wherein F-6 comprises 90 wt. % to less than 100 wt. % and F-3 and F-4 comprise greater than 0 wt. % to 10 wt. % of the blend; (9) F-6 and F-3 and F-5, wherein F-6 comprises 90 wt. % to less than 100 wt. % and F-3 and F-5 comprise greater than 0 wt. % to 10 wt. % of the blend; (10) F-6 and F-4 and F-5, wherein F-6 comprises 90 wt. % to less than 100 wt. % and F-4 and F-5 comprise greater than 0 wt. % to 10 wt. % of the blend; (11) F-6 and F-2 and F-3 and F-4, wherein F-6 comprises 90 wt. % to less than 100 wt. % and F-2 and F-3 and F-4 comprise greater than 0 wt. % to 10 wt. % of the blend; (12) F-6 and F-2 and F-3 and F-5, wherein F-6 comprises 90 wt. % to less than 100 wt. % and F-2 and F-3 and F-5 comprise greater than 0 wt. % to 10 wt. % of the blend; (13) F-6 and F-2 and F-4 and F-5, wherein F-6 comprises 90 wt. % to less than 100 wt. % and F-2 and F-4 and F-5 comprises greater than 0 wt. % to 10 wt. % of the blend; or (14) F-6 and F-2 and F-3 and F-4 and F-5, wherein F-6 comprises 90 wt. % to less than 100 wt. % and F-2 and F-3 and F-4 and F-5 comprise greater than 0 wt. % to 10 wt. % of the blend. For example, in one embodiment of B-81, wherein B-81 comprises 95 wt. % F-6 and 5 wt. % F-3, the F-6 comprises Poly (L-lactide) having a weight average molecular weight (Mw) within the range of 2,044,000 to 3,000,000 g/mol or an IV within the range of greater than 8.0 to 11.5 dl/g and F-3 comprises Poly (L-lactide) having a weight average molecular weight (Mw) within the range of 298,000 to 621,000 g/mol or an IV within the range of greater than 2.2 to 3.6 dl/g. In other embodiment(s) of the B-81, the blend ratio of the stent material 85 constituents may be higher or lower so long as the B-81 comprises Formula Number 6 within the range of greater than 90 wt. % to less than 100 wt. % and Formula Number 3 within the range of greater than 0 to 10 wt. %. For example, the B-81 may comprise a mixture comprising 99.9 wt. % F-6 and 0.1 wt. % F-3 or the B-81 may comprise 90.1 wt. % F-6 and 9.9 wt. % F-3. Alternatively, the B-81 may comprise: (1) a mixture of F-6 and F-2, wherein the mixture comprises 90 wt. % to less than 100 wt. % F-6 and greater than 0 to 10 wt. % F-2; (2) a mixture of F-6 and F-4, wherein the mixture comprises 90 wt. % to less than 100 wt. % F-6 and greater than 0 to 10 wt. % F-4; (3) a mixture of F-6 and F-5, wherein the mixture comprises 90 wt. % to less than 100 wt. % F-6 and greater than 0 to 10 wt. % F-5; (4) a mixture of F-6 and F-2 and F-3, wherein the mixture comprises 90 wt. % to less than 100 wt. % F-6 and greater than 0 to 10 wt. % F-2 and F-3; (5) a mixture of F-6 and F-2 and F-4, wherein the mixture comprises 90 wt. % to less than 100 wt. % F-6 and greater than 0 to 10 wt. % F-2 and F-4; (6) a mixture of F-6 and F-2 and F-5, wherein the mixture comprises 90 wt. % to less than 100 wt. % F-6 and greater than 0 to 10 wt. % F-2 and F-5; (7) a mixture of F-6 and F-3 and F-4, wherein the mixture comprises 90 wt. % to less than 100 wt. % F-6 and greater than 0 to 10 wt. % F-3 and F-4; (8) a mixture of F-6 and F-3 and F-5, wherein the mixture comprises 90 wt. % to less than 100 wt. % F-6 and greater than 0 to 10 wt. % F-3 and F-5; (9) a mixture of F-6 and F-4 and F-5, wherein the mixture comprises 90 wt. % to less than 100 wt. % F-6 and greater than 0 to 10 wt. % F-4 and F-5; (10) a mixture of F-6 and F-2 and F-3 and F-4, wherein the mixture comprises 90 wt. % to less than 100 wt. % F-6 and greater than 0 to 10 wt. % F-2 and F-3 and F-4; (11) a mixture of F-6 and F-2 and F-3 and F-5, wherein the mixture comprises 90 wt. % to less than 100 wt. % F-6 and greater than 0 to 10 wt. % F-2 and F-3 and F-5; (12) a mixture of F-6 and F-2 and F-4 and F-5, wherein the mixture comprises 90 wt. % to less than 100 wt. % F-6 and greater than 0 to 10 wt. % F-2 and F-3 and F-4; or (13) a mixture of F-6 and F-2 and F-3 and F-4 and F-5, wherein the mixture comprises 90 wt. % to less than 100 wt. % F-6 and greater than 0 to 10 wt. % F-2 and F-3 and F-4 and F-5. The Blend Formulations 276 for Blend Numbers 82 through 180 ("B-82 to B-180") may be interpreted using the same approach as described for Blend Number 81. Those persons skilled in the art of statistics are capable determining the applicable combinations and permutations of the blend formulations comprising the blend numbers 276 provided in FIG. 112 for blend numbers 82 through 180 ("B-82 to B-180") using the methodology described for blend number 81 ("B-81").

Converting the stent material 85 constituents of the formulations 275 into the solution 83 makes the blends or mixtures. The solution 83 including the stent material formulations 275 and/or the blend formulations 276 is converted into the film 66, the film(s) 66 are converted into the roll 52 or the Roll Including Active Ingredients 143, the roll 52 or the Roll Including Active Ingredients 143 are converted into the un-oriented tube 42 or the oriented tube 38 and the un-oriented tube 42 or the oriented tube 38 are converted into the stent 10 as describe herein.

Industry sometimes describes the weight average molecular weight of a material in terms of "Inherent Viscosity." One method of converting the weight average molecular weight into Inherent Viscosity or Inherent Viscosity into the weight average molecular weight is to use the Mark-Houwink equation as known by those skilled in the art. The Inherent Viscosity ("IV") is determined by viscometry of diluted solutions. Measurements are performed in chloroform at a concentration of 0.1 g/dl. For low IV values higher concentrations are used: 2.0 g/dl for IV less than 0.2 dl/g; 1.0 g/dl for 0.2 dl/g less than or equal to IV less than 0.3 dl/g; 0.5 g/dl for 0.3 dl/g less than or equal to IV less than 1.0 dl/g. Gel Permeation Chromatography (GPC) determines the weight average molecular weight (Mw) in chloroform at 35.degrees. C relative to polystyrene (PS) standards. The Mark-Houwink equation gives the relation between the intrinsic viscosity ([n]) and viscosity average molecular weight (Mv), where [n]=K.(Mv)a. The constant "K" and "a" are the Mark-Houwink parameters. These are constant for fixed temperature, polymer type and solvent. Based on IV and GPC measurements the relationship between IV and Mw is determined. The data are fitted with the linearized form of the Mark-Houwink equation: $\ln(IV)=\ln(K^*)+a^*.\ln(Mw)$. The Mark-Houwink parameters are marked with an asterisk to emphasize the use of the inherent viscosity (IV) instead of the intrinsic viscosity ([n]), and the weight average molecular weight (Mw) instead of the viscosity average molecular weight (Mv). Examples of Mark-Houwink parameters are: for homopolymers of L-lactide are about $K^*=4.710\text{-}4$ dl/g and $a^*=0.67$, homopolymer of DL-lactide are about $K^*=1.810\text{-}4$ dl/g and $a^*=0.72$, copolymer of L-lactide and glycolide at a 85/15 molar ratio are about $K^*=3.3^*10\text{-}4$ dl/g and $a^*=0.67$ and a copolymer of L-lactide and caprolactone at a 70/30 molar ratio are about $K^*=2.710\text{-}4$ dl/g and $a^*=0.71$. The present invention is not limited to material(s) having the Mark-Houwink parameters (K*, a*) or Inherent Viscosity (IV) and weight average molecular weight (Mw) correlations shown herein. Other parameters (K*, a*) for other Polymer(s) that are suitable for use in the present invention may be obtained by those skilled in the art of viscometry, GPC and the use of the Mark-Houwink equation.

In an embodiment, the stent 10 is formed from the roll 52 that is depicted in FIG. 36, FIG. 40, FIG. 42 or the Roll Including The Active Ingredient(s) 143 that is depicted in FIG. 54, FIG. 60, FIG. 61 wherein the solid film 66-A and solid film 66-B within the roll 52 comprise at least one of the eighty "formula numbers" shown in FIG. 111 that are identified as F-1 through F-80 and/or comprise at least one of the one-hundred "blend formulas" shown in FIG. 112 that are identified as B-81 through B-180. In an embodiment, the solid film 66-A comprises the same stent material formulation 275 or the same blend formulation 276 as solid film 66-B. In another embodiment, the solid film 66-A comprises a different stent material formulation 275 or a different blend formulation 276 than solid film 66-B. In other embodiment(s) the stent 10 is formed from the roll 52 that is depicted in FIG. 36, FIG. 40, FIG. 42 or the Roll Including The Active Ingredient(s) 143 that is depicted in FIG. 54, FIG. 60, FIG. 61 wherein the solid film 66-A and solid film 66-B within the roll 52 at least partially or completely comprise at least one of the other stent material(s) 85 disclosed herein. The other stent material(s) 85 may also be used independently or when mixed together to form other blends or when mixed with the stent material formulations 275 and/or the blend materials 276 to form other blends. The stent 10 may also be formed from these other blends.

In an embodiment, the stent 10 is formed from the roll 52 that is depicted in FIG. 38 or FIG. 44, and/or the Roll Including The Active Ingredient(s) 143 that is depicted in FIG. 56 or FIG. 58 wherein the solid film 66-A, solid film 66-B and solid film 66-C within the roll 52 comprise at least one of the eighty "formula numbers" shown in FIG. 111 that are identified as F-1 through F-80 and/or comprise at least one of the one-hundred "blend formulas" shown in FIG. 112 that are identified as B-81 through B-180. In an embodiment, the solid film 66-A comprises the same stent material formulation 275 or the same blend formulation 276 as solid film 66-B and solid film 66-C. In another embodiment, at least one of the solid film(s) 66 comprises a different material formulation 275 or different blend formulation 276 as at least one or all of the additional solid films 66 within the roll 52. In other embodiment(s) the stent 10 is formed from the roll 52 that is depicted in FIG. 38 or FIG. 44 or the Roll Including The Active Ingredient(s) 143 that is depicted in FIG. 56 or FIG. 58, wherein the solid film 66-A, solid film 66-B and solid film 66-C within the roll 52 at least partially or completely comprise at least one of the other stent material(s) 85 disclosed herein. The other stent material(s) 85 may also be used independently or when mixed together to form other blends or when mixed with the stent material formulations 275 and/or the blend materials 276 to form other blends. The stent 10 may also be formed from these other blends.

For simplicity, in the examples depicted in FIG. 33 through FIG. 67, the solid film 66-A may be abbreviated "F-A," solid film 66-B may be abbreviated as "F-B," solid film 66-C may be abbreviated as "F-C" and so on. Likewise, the layer 51-A may be abbreviated "L-A," the layer 51-B may be abbreviated "L-B," the layer 51-C may be abbreviated "L-C," and so on. There may be greater than three solid films 66 included in the roll 52 and the Roll Including Active Ingredients 143. These additional solid films 66 are not depicted in the figures because the features of the roll 52 and the feature of the Roll Including Active Ingredients 143 would not be clearly visible when additional solid films 66 are added to the figures. Therefore, it should be appreciated that in other embodiments, that there may be solid film 66-D, solid film 66-E, solid film 66-F and so on sequentially until there are five hundred solid films 66 within the roll 52 or the Roll Including Active Ingredients 143. When using the bijective base 26 numbering system, the five hundredth solid film 66 would be labeled solid film 66-SF (abbreviated "F-SF").

In an embodiment, the solid film 66, the solid film 66-A, the solid film 66-B, the solid film 66-C, the solid film 66-D through solid film 66-SF that are depicted FIG. 33, FIG. 34, FIG. 35, FIG. 36, FIG. 37, FIG. 38, FIG. 39, FIG. 40, FIG. 41, FIG. 42, FIG. 43, FIG. 44, FIG. 45, FIG. 46, FIG. 47, FIG. 48, FIG. 49, FIG. 50, FIG. 51, FIG. 52, FIG. 53, FIG. 54, FIG. 55, FIG. 56, FIG. 57, FIG. 58, FIG. 59, FIG. 60, FIG. 61, FIG. 62, FIG. 63, FIG. 64, FIG. 65, FIG. 66, FIG. 67, FIG. 68, FIG. 69, FIG. 70, FIG. 71, FIG. 72, FIG. 73, FIG. 74, FIG. 75, FIG. 76, FIG. 77, FIG. 78, FIG. 79, FIG. 80, FIG. 81, FIG. 82, FIG. 83, FIG. 84, FIG. 85, FIG. 86, FIG. 87, FIG. 88, FIG. 89, FIG. 90, FIG. 91, FIG. 92, FIG. 93, and/or FIG. 100, as well as variants thereof that are described herein, and/or the layer 51-A, the layer 51-B, the layer 51-C through layer 51-SF, that are depicted in FIG. 8, FIG. 70, FIG. 71, FIG. 72, FIG. 73, FIG. 74, FIG. 75, FIG. 94, FIG. 95, FIG. 96, FIG. 97, FIG. 98, FIG. 99 as well as variants thereof that are described herein, that are formed into the un-oriented tube 42, which is converted into the oriented tube 38 and/or the stent 10 as described herein, comprises at least one of the formula numbers 275 depicted in FIG. 111 and/or the bend numbers 276 depicted in FIG. 112 selected from the group of: F-1, F-2, F-3, F-4, F-5, F-6, F-7, F-8, F-9, F-10, F-11, F-12, F-13, F-14, F-15, F-16, F-17, F-18, F-19, F-20, F-21, F-22, F-23, F-24, F-25, F-26, F-27, F-28, F-29, F-30, F-31, F-32, F-33, F-34, F-35, F-36, F-37, F-38, F-39, F-40, F-41, F-42, F-43, F-44, F-45, F-46, F-47, F-48, F-49, F-50, F-51, F-52, F-53, F-54, F-55, F-56, F-57, F-58, F-59, F-60, F-61, F-62, F-63, F-64, F-65, F-66, F-67, F-68, F-69, F-70, F-71, F-72, F-73, F-74, F-75, F-76, F-77, F-78, F-79, F-80, B-81, B-82, B-83, B-84, B-85, B-86, B-87, B-88, B-89, B-90, B-91, B92, B-93, B-94, B-95, B-96, B-97, B-98, B-99, B-100, B-101, B-102, B-103, B-104, B-105, B-106, B-107, B-108, B-109, B-110, B-111, B-112, B-113, B-114, B-115, B-116, B-117, B-118, B-119, B-120, B-121, B-122, B-123, B-124, B-125, B-126, B-127, B-128, B-129, B-130, B-131, B-132, B-133, B-134, B-135, B-136, B-137, B-138, B-139, B-140, B-141, B-142, B-143, B-144, B-145, B-146, B-147, B-148, B-149, B-150, B-151, B-152, B-153, B-154, B-155, B-156, B-157, B-158, B-159, B-160, B-161, B-162, B-163, B-164, B-165, B-166, B-167, B-168, B-169, B-170, B-171, B-172, B-173, B-174, B-175, B-176, B-177, B-178, B-179 and/or B-180. In an embodiment comprising multiple solid films 66, each of the individual solid films 66 comprise the same stent material formulation 275 or the same blend formulation 276. For example, in a three-film 66 embodiment, the film 66-A, the solid film 66-B and the solid film 66-C all comprise the same stent material formulation 275 or the same blend formulation 276. In an embodiment, at least two or all the solid films 66 in a multi-film 66 embodiment comprise different stent material formulations 275 and/or blend formulations 276.

For example, in a three-film 66 embodiment, the roll 52 or the roll including active ingredients 143 may be configured in one of the following ways: (1) F-A, F-B and F-C all comprise the same stent material formulations 275 and/or blend formulations 276; (2) F-B and F-C comprise the same stent material formulations 275 and/or blend formulations 276 and F-A comprises a different stent material formulation 275 and/or blend formulation 276; (3) F-A and F-B comprise the same stent material formulations 275 and/or blend formulations 276 and F-C comprises a different stent material formulation 275 and/or blend formulation 276; or (4) F-A and F-C comprise the same stent material formulations 275 and/or blend formulas 276 and solid F-B comprises a different stent material formulation 275 and/or blend formulation 276. In a multi-film 66 embodiment wherein at least two of the solid films 66 comprise a different stent material formulation 275 and/or blend formulation 276, the composition of the each of the different solid films 66 may be selected from any of the possible combinations or permutations of the stent material formulations 275 and/or the blend formulations 276 provided in FIG. 111 and FIG. 112. In embodiments including greater than two different solid films, a person skilled in the art of statistics can calculate how many permutations and combinations are possible when selecting the composition of each of the solid films 66 within the roll 52 or the roll including active ingredients 143, that are converted into the un-oriented tube 42, which is converted into the oriented tube 38 and/or the stent 10.

In a multi-layer embodiment, the stent 10 is formed from the roll 52 depicted in FIG. 36, FIG. 40 or FIG. 42 or the Roll Including Active ingredient(s) 143 depicted in FIG. 54, FIG. 60 or FIG. 61 and their variants described herein, wherein the solid film 66-A ("F-A") and the solid film 66-B ("F-B") composition is arranged in one of the following configurations: (1) F-B comprises F-6 and F-A comprises F-5; (2) F-B comprises F-6 and F-A comprises F-4; (3) F-B comprises F-6 and F-A comprises F-3; (4) F-B comprises F-6 and F-A comprises F-2; (5) F-B comprises F-5 and FA comprises F-4; (6) F-B comprises F-5 and F-A comprises F-3; (7) F-B comprises F-5 and F-A comprises F-2; (8) F-B comprises F-4 and F-A comprises F-3; (9) F-B comprises F-4 and F-A comprises F-2; (10) F-B comprises F-4 and F-A comprises F-5; (11) F-B comprises F-4 and F-A comprises F-6; (12) F-B comprises F-3 and F-A comprises F-2; (13) F-B comprises F-3 and F-A comprises F-4; (14) F-B comprises F-3 and F-A comprises F-5; (15) F-B comprises F-3 and F-A comprises F-6; (16) F-B comprises F-2 and F-A comprises F-6; (17) F-B comprises F-2 and F-A comprises F-5; (18) F-B comprises F-2 and F-A comprises F-4; (19) F-B comprises F-2 and F-A comprises F-3; (20) F-B comprises F-1 and F-A comprises F-7; (21) F-B comprises F-1 and F-A comprises F-8; (22) F-B comprises F-1 and F-A comprises F-9; (23) F-B comprises F-1 and F-A comprises F-10; (24) F-B comprises F-1 and F-A comprises F-11; (25) F-B comprises F-1 and F-A comprises F-12; (26) F-B comprises F-1 and F-A comprises F-31; (27) F-B comprises F-1 and F-A comprises F-32; (28) F-B comprises F-1 and F-A comprises F-33; (29) F-B comprises F-1 and F-A comprises F-34; (30) F-B comprises F-1 and F-A comprises F-35; (31) F-B comprises F-1 and F-A comprises F-36; (32) F-B comprises F-1 and F-A comprises F-37; (33) F-B comprises F-1 and F-A comprises F-38; (34) F-B comprises F-1 and F-A comprises F-39; (35) F-B comprises F-1 and F-A comprises F-40; (36) F-B comprises F-1 and F-A comprises F-41; (37) F-B comprises F-1 and F-A comprises F-42; (38) F-B comprises F-1 and F-A comprises F-43; (39) F-B comprises F-1 and F-A comprises F-44; (40) F-B comprises F-1 and F-A comprises F-45; (41) F-B comprises F-1 and F-A comprises F-46; (42) F-B comprises F-1 and F-A comprises F-47; (43) F-B comprises F-1 and F-A comprises F-51; (44) F-B comprises F-1 and F-A comprises F-52; (45) F-B comprises F-1 and F-A comprises F-53; (46) F-B comprises F-1 and F-A comprises F-54; (47) F-B comprises F-1 and F-A comprises F-71; (48) F-B comprises F-1 and F-A comprises F-72; (49) F-B comprises F-1 and F-A comprises F-73; (50) F-B comprises F-1 and F-A comprises F-74; (51) F-B comprises F-1 and F-A comprises F-75; or (52) F-B comprises F-1 and F-A comprises F-76. It should be appreciated in other embodiments, the material formulations 275 comprising F-B and F-A may be reversed in the preceding fifty-two configurations so that the material formulations 275 provided for solid film 66-A ("F-A") are used to produce solid film 66-B and the material formulations 275 provided for solid film 66-B ("F-B") are used to produce solid film 66-A so that the roll 52 or the roll including the active ingredient(s) 143 is in the opposite configuration as what is provided in the preceding fifty-two configurations. Alternatively, in other embodiments, the F-6 may be replaced with B-81, B-86, B-91, B-96, B-101, B-106, B-111, B-116, B-121, or B-126 in the preceding fifty-two configurations; F-5 may be replaced by B-82, B-87, B-92, B-97, B-102, B-107, B-112, B-117, B-122, or B-127; F-4 may be replaced by B-83, B-88, B-93, B-98, B-103, B-108, B-113, B-118, B-123, or B-128; F-3 may be replaced by B-84, B-89, B-94, B-99, B-104, B-109, B-114, B-119, B-124, or B-129; F-2 may be replaced by B-85, B-90, B-95, B-100, B105, B-110, B-115, B-120, B-125, or B-130, F-1 may be replaced by at least one of the blends B-81 through B-180 in the preceding fifty-two configurations. Alternatively, or additionally, in other embodiments, F-7, F-8, F-9, F-10, F-11, F-12 may be replaced by B-131, B-132, B-133, B-134, B-135, B-136, B-137, B-138, B-139 or B-140 in the preceding fifty-two configurations. Alternatively, or additionally, in other embodiments, F-41, F42, F-43, F-44, F-45, F-46 may be replaced by B-151, B-152, B-153, B-154, B-155, B-156, B-157, B-158, B-159 or B-160 in the preceding fifty-two configurations. Alternatively, or additionally, in other embodiments, F-51, F-52, F-53, F-54, may be replaced by B-161, B-162, B-163, B-164, B-165, B-166, B-167, B-168, B-169 or B-170 in the preceding fifty-two configurations. It should be appreciated that the present invention is not limited to the preceding fifty-two configurations and that other configurations are possible within the scope of the present invention.

In other multi-layer embodiments, the stent 10 is formed from the roll 52 depicted in FIG. 38 or FIG. 44 or the Roll Including Active ingredient(s) 143 depicted in FIG. 56 or FIG. 58 and their variants described herein, wherein the solid film 66-A ("F-A"), the solid film 66-B ("F-B") and the solid film 66-C ("F-C") compositions are arranged in one of the following configurations: (1) F-A comprises F-6, F-B comprises F-5 and F-C comprises F-6; (2) F-A comprises F-6, F-B comprises F-4 and F-C comprises F-6; (3) F-A comprises F-6, F-B comprises F-3 and F-C comprises F6; (4) F-A comprises F-6, F-B comprises F-2 and F-C comprises F-6; (5) F-A comprises F-5, F-B comprises F-6 and F-C comprises F-5; (6) F-A comprises F-5, F-B comprises F-4 and F-C comprises F-5; (7) F-A comprises F-5, F-B comprises F-3 and F-C comprises F-5; (8) F-A comprises F5, F-B comprises F-2 and F-C comprises F-5; (9) F-A comprises F-4, F-B comprises F-3 and F-C comprises F-4; (10) F-A comprises F-4, F-B comprises F-2 and F-C comprises F-4; (11) F-A comprises F-3, F-B comprises F-2 and F-C comprises F-3; (12) F-A comprises F-6, F-B comprises F-7 and F-C comprises F-6; (13) F-A comprises F-1, F-B comprises F-8 and F-C comprises F-1; (14) F-A comprises F-1, F-B comprises F-9 and FC comprises F-1; (15) F-A comprises F-1, F-B comprises F-10 and F-C comprises F-1; (16) F-A comprises F-1, F-B comprises F-11 and F-C comprises F-1; (17) F-A comprises F-1, F-B comprises F-12 and F-C comprises F-1; (18) F-A comprises F-1, F-B comprises F-31 and F-C comprises F-1; (19) F-A comprises F-1, F-B comprises F-32 and F-C comprises F-1; (20) F-A comprises F-1, F-B comprises F-33 and F-C comprises F-1; (21) F-A comprises F-1, F-B comprises F-34 and F-C comprises F-1; (22) F-A comprises F-1, F-B comprises F-35 and F-C comprises F-1; (23) F-A comprises F-1, F-B comprises F-36 and F-C comprises F-1; (24) F-A comprises F-1, F-B comprises F-37 and F-C comprises F-1; (25) F-A comprises F-1, F-B comprises F-38 and F-C comprises F-1; (26) F-A comprises F-1, F-B comprises F-39 and F-C comprises F-1; (27) F-A comprises F-1, F-B comprises F-40 and F-C comprises F-1; (28) F-A comprises F-1, F-B comprises F-41 and F-C comprises F-1; (29) F-A comprises F-1, F-B comprises F-42 and F-C comprises F-1; (30) F-A comprises F-1, F-B comprises F-43 and F-C comprises F-1; (31) F-A comprises F-1, F-B comprises F-44 and F-C comprises F-1; (32) F-A comprises F-1, F-B comprises F-45 and F-C comprises F-1; (33) F-A comprises F-1, F-B comprises F-46 and F-C comprises F-1; (34) F-A comprises F-1, F-B comprises F-47 and F-C comprises F-1; (35) F-A comprises F-1, F-B comprises F-48 and F-C comprises F-1; (36) F-A comprises F-1, F-B comprises F-49 and F-C comprises F-1; (37) F-A comprises F-1, F-B comprises F-50 and F-C comprises F-1; (38) F-A comprises F-1, F-B comprises F-51 and F-C comprises F-1; (39) F-A comprises F-1, F-B comprises F-52 and F-C comprises F-1; (40) F-A comprises F-1, F-B comprises F-53 and F-C comprises F-1; (41) F-A comprises F-1, F-B comprises F-54 and F-C comprises F-1; (42) F-A comprises F-1, F-B comprises F-55 and F-C comprises F-1; (43) F-A comprises F-1, F-B comprises F-56 and F-C comprises F-1; (44) F-A comprises F-1, F-B comprises F-57 and F-C comprises F-1; (45) F-A comprises F-1, F-B comprises F-58 and F-C comprises F-1; (46) F-A comprises F-1, F-B comprises F-59 and F-C comprises F-1; (47) F-A comprises F-1, F-B comprises F-60 and F-C comprises F-1; (48) F-A comprises F-1, F-B comprises F-70 and F-C comprises F-1; (49) F-A comprises F-1, F-B comprises F-71 and F-C comprises F-1; (50) F-A comprises F-1, F-B comprises F-72 and F-C comprises F-1; (51) F-A comprises F-1, F-B comprises F-73 and F-C comprises F-1; (52) F-A comprises F-1, F-B comprises F-74 and F-C comprises F-1; (53) F-A comprises F-1, F-B comprises F-75 and F-C comprises F-1; (54) F-A comprises F-1, F-B comprises F-76 and F-C comprises F-1; (55) F-A comprises F-1, F-B comprises F-77 and F-C comprises F-1; (56) F-A comprises F-1, F-B comprises F-78 and F-C comprises F-1; (57) F-A comprises F-1, F-B comprises F-79 and F-C comprises F-1; (58) F-A comprises F-1, F-B comprises F-80 and F-C comprises F-1; (59) F-A comprises F-6, F-B comprises F-5 and F-C comprises F-75; (60) F-A comprises F-5, F-B comprises F-4 and F-C comprises F-75; (61) F-A comprises F-4, F-B comprises F-3 and F-C comprises F-75; (62) F-A comprises F-3, F-B comprises F-2 and F-C comprises F-75; (63) F-A comprises F-6, F-B comprises F-5 and F-C comprises F-76; (64) F-A comprises F-5, F-B comprises F-4 and F-C comprises F-76; (65) F-A comprises F-4, F-B comprises F-3 and F-C comprises F-76; (66) F-A comprises F-3, F-B comprises F-2 and F-C comprises F-76; (67) F-A comprises F-74, F-B comprises F-1 and F-C comprises F-74; (68) F-A comprises F-75, F-B comprises F-1 and F-C comprises F-75; (69) F-A comprises F-76, F-B comprises F-1 and F-C comprises F-76; (70) F-A comprises F-74, F-B comprises F-1 and F-C comprises F-75; (71) F-A comprises F-74, F-B comprises F-1 and F-C comprises F-76; (72) F-A comprises F-76, F-B comprises F-1 and F-C comprises F-75; (73) F-A comprises F-75, F-B comprises F-1 and F-C comprises F-76; (74) F-A comprises F-76, F-B comprises F-1 and F-C comprises F-74; (75) F-A comprises F-76, F-B comprises F-1 and F-C comprises F-75; (76) F-A comprises F-1, F-B comprises F-7 and F-C comprises F-42; (77) F-A comprises F-1, F-B comprises F-7 and F-C comprises F-42; (78) F-A comprises F-1, F-B comprises F-7 and F-C comprises F-43; (79) F-A comprises F-1, F-B comprises F-51 and F-C comprises F-7; (80) F-A comprises F-1, F-B comprises F-52 and F-C comprises F-7; (81) F-A comprises F-1, F-B comprises F-53 and F-C comprises F-7; (82) F-A comprises F-1, F-B comprises F-51 and F-C comprises F-41; (83) F-A comprises F-1, F-B comprises F-52 and F-C comprises F-41; (84) F-A comprises F-1, F-B comprises F-53 and F-C comprises F-41; (85) F-A comprises F-1, F-B comprises F-51 and F-C comprises F-42; (86) F-A comprises F-1, F-B comprises F-52 and F-C comprises F-42; (87) F-A comprises F-1, F-B comprises F-53 and F-C comprises F-43; (88) F-A comprises F-1, F-B comprises F-51 and F-C comprises F-43; (89) F-A comprises F-1, F-B comprises F-52 and F-C comprises F-43; (90) F-A comprises F-1, F-B comprises F-53 and F-C comprises F-43; (91) F-A comprises F-1, F-B comprises F-71 and F-C comprises F-7; (92) F-A comprises F-1, F-B comprises F-72 and F-C comprises F-7; (93) F-A comprises F-1, F-B comprises F-73 and F-C comprises F-7: (94) F-A comprises F-1, F-B comprises F-74 and F-C comprises F-7; (95) F-A comprises F-1, F-B comprises F-75 and F-C comprises F-7; (96) F-A comprises F-1, F-B comprises F-76 and F-C comprises F-7; (97) F-A comprises F-1, F-B comprises F-77 and F-C comprises F-7; (98) F-A comprises F-1, F-B comprises F-78 and F-C comprises F-7; (99) F-A comprises F-1, F-B comprises F-79 and F-C comprises F-7 or (100) F-A comprises F-1, F-B comprises F-80 and F-C comprises F-7. It should be appreciated in other embodiments, the material formulations 275 comprising F-A and F-C may be reversed in the preceding one hundred configurations so that the material formulations 275 provided for solid film 66-A ("F-A") are used to produce solid film 66-C ("F-C") and the material formulations 275 provided for solid film 66-C are used to produce solid film 66-A so that the roll 52 or the roll including the active ingredient(s) 143 is in the opposite configuration as what is provided in the preceding one hundred configurations. It is also possible in other configurations for solid film 66-B to be in the position of solid film 66-A and/or solid film 66-C. Alternatively, in other embodiments, the F-6 may be replaced with B-81, B-86, B-91, B-96, B-101, B-106, B-111, B-116, B-121, or B-126 in the preceding fifty-two configurations; F-5 may be replaced by B-82, B-87, B-92, B-97, B-102, B-107, B-112, B-117, B-122, or B-127; F-4 may be replaced by B-83, B-88, B-93, B-98, B-103, B-108, B-113, B118, B-123, or B-128; F-3 may be replaced by B-84, B-89, B-94, B-99, B-104, B-109, B-114, B-119, B-124, or B-129; F-2 may be replaced by B-85, B-90, B-95, B-100, B-105, B-110, B-115, B-120, B-125, or B-130, F-1 may be replaced by at least one of the blends B-81 through B-130 in the preceding one hundred configurations. Alternatively, or additionally, in other embodiments, F-7, F-8, F-9, F-10, F-11, F-12 may be replaced by B131, B-132, B-133, B-134, B-135, B-136, B-137, B-138, B-139 or B-140 in the preceding one hundred configurations. Alternatively, or additionally, in other embodiments, F-41, F-42, F-43, F-44, F-45, F-46 may be replaced by B-151, B-152, B-153, B-154, B-155, B-156, B-157, B-158, B-159 or B160 in the preceding one hundred configurations. Alternatively, or additionally, in other embodiments, F-51, F-52, F-53, F-54, may be replaced by B-161, B-162, B-163, B-164, B-165, B-166, B-167, B-168, B-169 or B-170 in the preceding one hundred configurations. It should be appreciated that the present invention is not limited to the preceding one hundred configurations and that other configurations are possible within the scope of the present invention.

In the multi-film 66 embodiments, the films 66 are arranged in any order that provides the desired stent 10 degradation and/or resorption sequence while the stent 10 is implanted within the anatomical lumen 36 within the treatment site 35. In an embodiment, the film thicknesses 67 and/or the layer thicknesses 51 are arranged within the stent wall thickness 13 so that the stent material(s) 85 comprising the stent wall thickness 13 erode starting from the outer surface 16 and ending at the inner surface 16. In another embodiment, the film thicknesses 67 and/or the layer thicknesses 51 are arranged within the stent wall thickness 13 so that the stent material(s) 85 comprising the stent wall thickness 13 erode starting from the inner surface 17 and ending at the outer surface 16. In one more embodiment, the film thicknesses 67 and/or the layer thicknesses 51 are arranged within the stent wall thickness 13 so that the stent material(s) 85 comprising the stent wall thickness 13 erode starting from between the inner surface 17 and the outer surface 16 (i.e. the middle of the stent wall thickness 13) and ending at the outer surface 16 and/or the inner surface 17, which results in the stent wall thickness 13 delaminating while the stent 10 is implanted within the anatomical lumen 36. In another embodiment, the film thicknesses 67 and/or the layer thicknesses 51 are arranged within the stent wall thickness 13 so that the stent material(s) 85 comprising the stent wall thickness 13 erode first at the outer surface 16, second at between the inner surface 17 and the outer surface 16 (i.e., the middle of the stent wall thickness 13) and third at the inner surface 17. In another embodiment, the film thicknesses 67 and/or the layer thicknesses 51 are arranged within the stent wall thickness 13 so that the stent material(s) 85 comprising the stent wall thickness 13 erode first at the inner surface 17, second at between the inner surface 17 and the outer surface 16 (i.e., the middle of the stent wall thickness 13) and third at the outer surface 16. In another embodiment, the film thicknesses 67 and/or the layer thicknesses 51 are arranged within the stent wall thickness 13 so that the stent material(s) 85 erode layer-by-layer and/or film-by-film in any of the sequences described herein.

The capability of the stent 10 to erode layer-by-layer 51 and/or film-by-film 66 when it is implanted within the anatomical lumen 36, provides the stent 10 with the capability to provide a sustained drug delivery (i.e. delivery of the active ingredient(s) 34) during at least part or all of the duration that is takes for the mass of the stent material(s) 85 within the implanted stent 10 to be resorbed so that there is substantially no stent 10 mass left in the treatment area 35. Moreover, the capability of the stent 10 to delaminate when it is implanted within the anatomical lumen 36, provides the stent 10 with the capability to deliver the active ingredient(s) 34 to locations where the implanted ring struts 20 and link struts 21 contact the anatomical lumen 36 as well as to areas that are adjacent to where the cutting surfaces 191 of the linear ring struts 20 and link struts 21 contact the anatomical lumen 36. In an embodiment, the stent 10 delivers the active ingredient(s) 34 to the portion of the anatomical lumen 36 that is in direct contact with the linear ring struts 20 and link struts 21 and/or to the region of the anatomical lumen 36 that is within 1 mm of all sides of where the liner ring struts 20 and the link struts 21 contact the anatomical lumen 36, wherein the sides include at least one or all of: the outer surface 16, inner surface 17 or the cutting surfaces 191.

In an embodiment, after the stent 10 is implanted within the anatomical lumen 36, at least one or all of the linear ring struts 20 and/or at least one or all of the link struts 21 are at least partially or completely covered with endothelial cells and/or partly or completely embedded within the thickness of the anatomical lumen 36, so that the active ingredient(s) 34 that are positioned within the wall thickness 13 of the stent 10 are released in the area surrounding at least one or all of the linear ring struts 20 and/or at least one or all of the link struts 21 by at least one or all of the following mechanisms: (1) erosion of at least one film thickness 67, wherein the active ingredient(s) 34 are located within at least one or all the film thicknesses 67; (2) erosion of at least one of the film thicknesses 67, wherein the active ingredient(s) 34 are located between at least two film thicknesses 67 wherein all the film thicknesses 67 do not contain any active ingredient(s) 34 within the film thicknesses 67; (3) erosion of at least one of the film thicknesses 67, wherein the active ingredient(s) 34 are located between at least two film thicknesses 67 wherein the outer film thickness 67 (closest to the abluminal surface) contains at least one active ingredient 34 and the inner film thickness 67 (closest to the luminal surface) does not contain any active ingredient(s) 34; (4) erosion of at least one of the film thicknesses 67, wherein the active ingredient(s) 34 are located between at least two film thicknesses 67 wherein the outer film thickness 67 (closest to the abluminal surface) does not contain any active ingredient(s) 34 and the inner film thickness 67 (closest to the luminal surface) contains at least one active ingredient 34; (5) erosion of at least one of the film thicknesses 67, wherein the active ingredient(s) 34 are located between at least two film thicknesses 67 wherein the outer film thickness 67 (closest to the abluminal surface) contains at least one active ingredient 34 and the inner film thickness 67 (closest to the luminal surface) contains at least one active ingredient 34; (6) delamination of at least one of the film thicknesses 67, wherein the active ingredient(s) 34 are located between at least two film thicknesses 67 wherein all the film thicknesses do not contain any active ingredient(s) 34 within the film thicknesses 67; (7) delamination of at least one of the film thicknesses 67, wherein the active ingredient(s) 34 are located between at least two film thicknesses 67 wherein the outer film thickness 67 (closest to the abluminal surface) contains at least one active ingredient 34 and the inner film thickness 67 (closest to the luminal surface) does not contain any active ingredient(s) 34; (8) delamination of at least one of the film thicknesses 67, wherein the active ingredient(s) 34 are located between at least two film thicknesses 67 wherein the outer film thickness 67 (closest to the abluminal surface) does not contain any active ingredient(s) 34 and the inner film thickness 67 (closest to the luminal surface) contains at least one active ingredient 34; (9) delamination of at least one of the film thicknesses 67, wherein the active ingredient(s) 34 are located between at least two film thicknesses 67 wherein the outer film thickness 67 (closest to the abluminal surface) contains at least one active ingredient 34 and the inner film thickness 67 (closest to the luminal surface) contains at least one active ingredient 34; (10) diffusion of at least one active ingredient 34, wherein the active ingredient(s) 34 are located between at least two film thicknesses 67 wherein all the film thicknesses do not contain any active ingredient(s) 34 within the film thicknesses 67; (11) diffusion of at least one active ingredient 34, wherein the active ingredient(s) 34 are located between at least two film thicknesses 67 wherein the outer film thickness 67 (closest to the abluminal surface) contains at least one active ingredient 34 and the inner film thickness 67 (closest to the luminal surface) does not contain any active ingredient(s) 34; (12) diffusion of at least one active ingredient 34, wherein the active ingredient(s) 34 are located between at least two film thicknesses 67 wherein the outer film thickness 67 (closest to the abluminal surface) does not contain any active ingredient(s) 34 and the inner film thickness 67 (closest to the luminal surface) contains at least one active ingredient 34; (13) diffusion of at least one active ingredient 34, wherein the active ingredient(s) 34 are located between at least two film thicknesses 67 wherein the outer film thickness 67 (closest to the abluminal surface) contains at least one active ingredient 34 and the inner film thickness 67 (closest to the luminal surface) contains at least one active ingredient 34; and/or (14) diffusion of at least one active ingredient(s) 34, wherein the active ingredient(s) 34 are located within at least one or all the film thicknesses 67.

In an embodiment, after the stent 10 is implanted within the anatomical lumen 36, at least one or all of the linear ring struts 20 and/or at least one or all of the link struts 21 are at least partially covered with endothelial cells and/or partly or completely embedded within the thickness of the anatomical lumen 36, so that the active ingredient(s) 34 that are positioned within the wall thickness 13 of the stent 10 are released in part or the complete area surrounding at least one or all of the linear ring struts 20 and/or at least one or all of the link struts 21 as the film thicknesses 67 erode. In an embodiment, after the stent 10 is implanted within the anatomical lumen 36, at least one or all of the linear ring struts 20 and/or at least one or all of the link struts 21 are at least partially or completely covered with endothelial cells and/or partially or completely embedded within the thickness of the anatomical lumen 36, so that the active ingredient(s) 34 that are positioned within the wall thickness 13 of the stent 10 are released in the area surrounding at least one or all of the linear ring struts 20 and/or at least one or all of the link struts 21 as the wall thickness 13 of the stent 10 delaminates. In an embodiment, after the stent 10 is implanted within the anatomical lumen 36, at least one or all of the linear ring struts 20 and/or at least one or all of the link struts 21 are at least partially or completely covered with endothelial cells and/or partially or completely embedded within the thickness of the anatomical lumen 36, so that the active ingredient(s) 34 that are positioned within the wall thickness 13 of the stent 10 are released in the area surrounding at least one or all of the linear ring struts 20 and/or at least one or all of the link struts 21 by diffusion, wherein diffusion is the result of the contents 6 or body fluids migrating into the wall thickness 13 of the stent 10, partially or completely solubilizing and/or relocating at least part or all of the active ingredient(s) 34 so that at least part or all of the active ingredient(s) 34 that are within the stent 10 wall thickness 13 are released into the area surrounding the implanted linear ring struts 20 and link struts 21.

In an embodiment, stent 10 is formed from the roll 52 or Roll Including Active Ingredient(s) 143 that includes the solid film 66-A comprising at least one stent material 85 that is faster degrading and/or resorbing than the solid film 66-B when the stent 10 is implanted in the anatomical lumen 36, or the opposite. In an embodiment wherein the solid film 66-A degrades and/or resorbs faster than the solid film 66-B, the solid film 66-A comprises at least of the following thirty-six fast rate degrading and/or resorbing stent material(s) 85: F-19, F-20, F-21, F-22, F-23, F24, F-41, F-42, F-43, F-44, F-45, F-46, F-47, F-48, F-49, F-50, F-71, F-72, F-73, F-74, F-75, F-76, F-77, F-78, F-79, F-80, B-151, B-151, B-152, B153, B-154, B-155, B-156, B-157, B-158, B-159, B-160, B-171, B-172, B-173, B-174, B-175, B-176, B-177, B-178, B-179 or B-180. Alternatively, in an embodiment wherein the solid film 66-A degrades and/or resorbs faster than the solid film 66-B, the solid film 66-A comprises at least of the following twenty-six medium rate degrading and/or resorbing stent material(s) 85: F-7, F-8, F-9, F-10, F-11, F-12, F-31, F-32, F-33, F-34, F-35, F36, F-37, F-38, F-39, F-40, B-131, B-132, B-133, B-134, B-135, B-136, B-137, B-138, B-139 or B-140. In an embodiment wherein the solid film 66-A degrades and/or resorbs faster than the solid film 66-B, the solid film 66-B comprises at least of the following one hundred eighteen slow rate degrading and/or resorbing stent material(s) 85: F-1, F-2, F-3, F-4, F-5, F-6, F-13, F-14, F-15, F-16, F-17, F-18, F-25, F-26, F-27, F-28, F-29, F-30, F-51, F-52, F-53, F-54, F-55, F-56, F-57, F-58, F-59, F-60, F-61, F-62, F-63, F-64, F-65, F-66, F-67, F-68, F-69, F-70, B-71, B-72, B-73, B-74, B75, B-76, B-77, B-78, B-79, B-80, B-81, B-82, B-83, B-84, B-85, B-86, B-87, B-88, B-89, B-90, B-91, B-92, B-93, B-94, B-95, B-96, B-97, B-98, B-99, B-100, B-101, B-102, B-103, B-104, B-105, B-106, B-107, B-108, B-109, B-110, B-111, B-112, B-113, B-114, B-115, B-116, B-117, B-118, B-119, B-120, B-121, B-122, B-123, B-124, B-125, B-126, B-127, B-128, B-129, B-130, B-141, B-142, B-143, B-144, B-145, B-146, B-147, B-148, B149, B-150, B-161, B-162, B-163, B-164, B-165, B-166, B-167, B-168, B-169 or B-170. The two solid films 66-A and solid film 66-B may be arranged within the roll 52 or the Roll Including Active Ingredient(s) 143 in any of the possible combinations or permutations that are the result of selecting two different Stent Material Formulas 275 and/or Blend Formulas 276 from the eighty Stent Material Formulas 275 and one hundred Blends Formulas 276 shown in FIGS. 111 and 112.

In an embodiment the solid film 66-A and solid film 66-B are arranged in at least one of the following configurations: (1) solid film 66-A ("F-A") comprises slow rate degrading and/or resorbing stent material(s) 85 and solid film 66-B ("F-B") comprises medium rate degrading and/or resorbing stent material(s) 85, (2) F-A comprises slow rate degrading and/or resorbing stent material(s) 85 and solid film 66-B comprises fast rate degrading and/or resorbing stent material(s) 85 or (3) solid film 66-A comprises medium rate degrading and/or resorbing stent material(s) 85 and solid film 66-B comprises fast rate degrading and/or resorbing stent material(s) 85, wherein the terms "slow rate" mean that the mass of the slow rate stent material(s) 85 are resorbed when the stent 10 is implanted in the anatomical lumen 36 in a longer time than "medium rate" and "fast rate" stent material(s) 85, the terms "medium rate" mean the mass of the medium rate stent material(s) 85 are resorbed when the stent 10 is implanted in the anatomical lumen 36 in a longer time than the "fast rate" stent material(s) 85 and the terms "fast rate" mean that the mass of the fast rate stent material(s) 85 are resorbed when the stent 10 is implanted in the anatomical lumen 36 in a shorter time than the "medium rate" and "slow rate" stent material(s) 85. In another embodiment the F-A and solid film F-B are arranged in at least one of the following configurations: (1) F-B comprises slow rate degrading and/or resorbing stent material(s) 85 and F-A comprises medium rate degrading and/or resorbing stent material(s) 85, (2) F-B comprises slow rate degrading and/or resorbing stent material(s) 85 and F-A comprises fast rate degrading and/or resorbing stent material(s) 85 or (3) F-B comprises medium rate degrading and/or resorbing stent material(s) 85 and F-A comprises fast rate degrading and/or resorbing stent material(s) 85. Without intent on limiting, for example, the mass of the "fast rate" stent material(s) 85 may disappear from the treatment site 35 in less than 6 months after implantation of the stent 10 within the anatomical lumen 36, the mass of the "medium rate" stent material(s) 85 may disappear from the treatment site 35 in less than 9 months after implantation of the stent 10 within the anatomical lumen 36 and the mass of the "slow rate" stent material(s) 85 may disappear from the treatment site 35 in less than 12 to 24 months after implantation of the stent 10 within the anatomical lumen 36. In other embodiments, the "fast rate," "medium rate" and "slow rate" stent material(s) 85 may disappear from the treatment site 35 in longer or shorter periods of time after implantation of the stent 10 within the anatomical lumen 36.

Modifying the composition of the stent material formula 275 or the blend formula 276 influences the speed of degradation and/or resorption of the stent material(s) 85 when the stent 10 is implanted within the anatomical lumen 36. For example, when the same stent material 85 has a lower weight average molecular weight it will degrade and/or resorb faster than when the stent material 85 has a higher weight average molecular weight. For example, F-6 will degrade and/or resorb slower than F-5, F-5 will degrade and/or resorb slower than F-4, F-4 will degrade and/or resorb slower than F-3 and F-3 will degrade and/or resorb slower than F-2, when all other properties of the stent material 85 are the same. Alternatively, or additionally, modifying the chemical composition of the stent material formula 275 or the blend formula 276, will influence the speed of degradation of the stent material(s) 85. For example, polymers or copolymers that partially or completely comprise L-lactide, D-lactide or caprolactone will degrade and/or resorb slower than polymers or copolymers that partially or completely comprise DL-lactide and polymers or copolymers that partially or completely comprise DL-lactide will degrade and/or resorb slower than polymers or copolymers that partly or completely comprise glycolide.

Modifying, the crystallinity of the stent material(s) 85 will also influence the speed of degradation and/or resorption of the stent material(s) 85 when the stent 10 is implanted within the anatomical lumen 36. For example, the same stent material 85 having a degree of crystallinity of 60% will degrade and/or resorb slower than the same stent material 85 having a degree of crystallinity of 50%, the same stent material 85 having a degree of crystallinity of 50% will degrade and/or resorb slower than the same stent material 85 having a degree of crystallinity of 40%, the same stent material 85 having a degree of crystallinity of 40% will degrade and/or resorb slower than the same stent material 85 having a degree of crystallinity of 30%, the same stent material 85 having a degree of crystallinity of 30% will degrade and/or resorb slower than the same stent material 85 having a degree of crystallinity of 20% and the same stent material 85 having a degree of crystallinity of 20% will degrade and/or resorb slower than the same stent material 85 having a degree of crystallinity of 10% because the molecules within the crystalline regions of the semicrystalline stent materials 85 are cleaved 98 slower than the amorphous regions. The more crystalline regions of the stent material(s) 85 are also slower to release the active ingredient(s) 34 than the more amorphous regions of the stent material(s) 85 within the implanted stent 10 by, for example, diffusion and/or erosion, because the crystalline regions are more ordered and the molecules within the crystalline region are more closely packed together, which makes it more difficult for body fluids within the treatment area 35 to penetrate the crystalline regions and initiate the degradation and/or resorption processes. By modifying these parameters as described herein, the degradation rate and/or the resorption rate of the stent 10 may be modified to achieve the optimum length of time that the stent 10 mechanically supports the anatomical lumen 36 for each treatment, the optimum drug delivery rate and duration of drug delivery during for each treatment, the optimum stent 10 decomposition mechanism for each treatment and the optimum time that the mass of the stent 10 is resorbed so that there is substantially no remaining stent material(s) 85 remaining within the treatment site 35 when there is no clinical need for the stent 10 to be implanted in the anatomical lumen 36. Stent Material Formulas 275 and Blend Formulas 276 that are generally classified as fast rate degrading include at least one of the following: F-19, F-20, F-21, F-22, F-23, F-24, F-41, F-42, F-43, F-44, F-45, F-46, F-47, F-48, F-49, F-50, F-71, F-72, F-73, F-74, F-75, F-76, F-77, F-78, F-79, F-80, B-151, B-152, B-153, B-154, B-155, B-156, B-157, B-158, B-159, B-160, B-171, B-172, B-173, B-174, B-175, B-176, B-177, B178, B-179 or B-180. Stent Material Formulas 275 and Blend Formulas 276 that are generally classified as medium rate degrading include at least one of the following: F-7, F-8, F-9, F-10, F-11, F-12, F-31, F-32, F-33, F-34, F-35, F-36, F-37, F-38, F-39, F-40, B-131, B-132, B-133, B-134, B-135, B-136, B-137, B-138, B-139 or B-140. Stent Material Formulas 275 and Blend Formulas 276 that are generally classified as slow rate degrading include at least one of the following: F-1, F-2, F-3, F-4, F-5, F-6, F-13, F-14, F-15, F-16, F-17, F-18, F-25, F-26, F-27, F-28, F-29, F-30, F-51, F-52, F-53, F-54 F-55, F-56, F-57, F-58, F-59, F-60, F-61, F-62, F-63, F-64, F-65, F-66, F-67, F-68, F-69, F-70, B-81, B-82, B-83, B-84, B-85, B-86, B-87, B-88, B-89, B-90, B-91, B-92, B-93, B-94, B-95, B-96, B-97, B-98, B-99, B-100, B-101, B-102, B-103, B-104, B-105, B-106, B-107, B-108, B-109, B110, B-111, B-112, B-113, B-114, B-115, B-116, B-117, B-118, B-119, B-120, B-121, B-122, B-123, B-124, B-125, B-126, B-127, B-128, B-129, B130, B-141, B-142, B-143, B-144, B-145, B-146, B-147, B-148, B-149, B-150, B-161, B-162, B-163, B-164, B-165, B-166, B-167, B-168 or B-170.

Notwithstanding the last paragraph, the rolls 52 depicted in FIG. 36, FIG. 40, FIG. 42 and their variants and the Rolls Including Active Ingredient(s) 143 depicted in FIG. 54, FIG. 60, FIG. 61 and their variants may comprise the faster rate degrading and/or resorbing stent material(s) 85 and/or the slower rate degrading and/or resorbing stent material(s) 85 when both solid films 66 have the same composition but different weight average molecular weights. For example, the roll 52 depicted in FIG. 36, FIG. 40 or FIG. 42 and the Roll Including Active Ingredient(s) 143 depicted in FIG. 54, FIG. 60 or FIG. 61 and their variants described herein may have one of the following configurations: (1) F-A comprises F-2 and F-B comprises F-6 or the opposite, (2) F-A comprises F-2 and F-B comprises F-5 or the opposite, (3) F-A comprises F-2 and F-B comprises F-4 or the opposite, (4) F-A comprises F-2 and F-B comprise F-3 or the opposite, (5) F-A comprises F-3 and F-B comprises F-6 or the opposite, (6) F-A comprise F-3 and F-B comprises F-5 or the opposite, (7) F-A comprise F-3 and F-B comprises F-4 or the opposite, (8) F-A comprises F-4 and F-B comprises F-6 or the opposite, (9) F-A comprises F-4 and F-B comprises F-5 or the opposite, or (10) F-A comprises F-5 and F-B comprises F-6, or the opposite. The same concept applies to other embodiments of the roll 52 and/or the Roll Including Active Ingredient(s) 143 comprising multiple solid films 66.

In embodiments, the rolls 52 depicted in FIG. 38 and FIG. 44 and their variants, and the Rolls Including Active Ingredient(s) 143 depicted in FIG. 56, FIG. 58 and their variants, are configured so that the solid films 66 have one of the following compositions: (1) F-A comprises slow rate degrading and/or resorbing stent material(s) 85, F-B comprises fast rate degrading and/or resorbing stent material(s) 85 and F-C comprises slow rate degrading and/or resorbing stent material(s) 85; (2) F-A comprises slow rate degrading and/or resorbing stent material(s) 85, F-B comprises medium rate degrading and/or resorbing stent material(s) 85 and F-C comprises slow rate degrading and/or resorbing stent material(s) 85; (3) F-A comprises fast rate degrading and/or resorbing stent material(s) 85, F-B comprises slow rate degrading and/or resorbing stent material(s) 85 and F-C comprises fast rate degrading and/or resorbing stent material(s) 85; (4) F-A comprises fast rate degrading and/or resorbing stent material(s) 85, F-B comprises medium rate degrading and/or resorbing stent material(s) 85 and F-C comprises fast rate degrading and/or resorbing stent material(s) 85; (5) F-A comprises medium rate degrading and/or resorbing stent material(s) 85, F-B comprises fast rate degrading and/or resorbing stent material(s) 85 and F-C comprises medium rate degrading and/or resorbing stent material(s) 85; (6) F-A comprises medium rate degrading and/or resorbing stent material(s) 85, F-B comprises slow rate degrading and/or resorbing stent material(s) 85 and F-C comprises medium rate degrading and/or resorbing stent material(s) 85; (7) F-A comprises fast rate degrading and/or resorbing stent material(s) 85, F-B comprises medium rate degrading and/or resorbing stent material(s) 85 and F-C comprises slow rate degrading and/or resorbing stent material(s) 85; or (8) F-A comprises slow rate degrading and/or resorbing stent material(s) 85, F-B comprises medium rate degrading and/or resorbing stent material(s) 85 and F-C comprises fast rate degrading and/or resorbing stent material(s) 85.

Alternatively or additionally, inn an embodiment, the rolls 52 depicted in FIG. 38, FIG. 44 and their variants, and the Rolls Including Active Ingredient(s) 143 depicted in FIG. 56, FIG. 58 and their variants, are configured so that the solid films 66 have one of the following compositions: (1) F-A comprises a brittle stent material 85, F-B comprises a ductile stent material 85 and F-C comprises a brittle stent material 85; (2) F-A comprises a ductile stent material 85, F-B comprises a brittle stent material 85 and F-C comprises a ductile stent material 85; (3) F-A comprises a brittle stent material 85, F-B comprises a brittle stent material 85 and F-C comprises a ductile stent material 85; (4) F-A comprises a ductile stent material 85, F-B comprises a brittle stent material 85 and F-C comprises a brittle stent material 85; (5) F-A comprises a ductile stent material 85, F-B comprises a ductile stent material 85 and F-C comprises a brittle stent material 85; or (6) F-A comprises a brittle stent material 85, F-B comprises a ductile stent material 85 and F-C comprises a ductile stent material 85, wherein at brittle stent material 85 has an elongation-to-break equal to greater than 0% to 15% and the ductile stent material 85 has an elongation-to-break equal to equal to 15% to 100%.

FIG. 101 depicts a Direct Roll Formation Process 149. The Direct Roll Formation Process 149 is another method of producing the roll 52, which is converted into the un-oriented tube 42. As depicted in FIG. 101, the Direct Roll Formation Process 149 fundamentally comprises the shaft 74 that serves as the release media 84, a head 150, the liquid solution 83, a Distance Between The Head And Shaft 151, a Shaft Rotation Direction 152, the liquid film 87, the solid film 66, a gaseous medium 90, the Shaft Central Axis 77, a Beginning Of The Application Area 158, an End Of The Application Area 159 and a Drying Area 160. The roll 52 and/or the Roll Including Active Ingredient(s) 143, which are converted into the unoriented tube 42, are formed directly on the shaft 74 by forming a plurality of liquid film thicknesses 88 that are converted into the solid film thicknesses 67 arranged in the configuration of the roll 52 on the shaft 74. The shaft 74 is located adjacent to the head 150. The shaft 74 rotates in the shaft rotation direction 152. A Distance Between The Head And Shaft 151 separates the head 150 from the shaft 74. In an embodiment, when the shaft 74 rotates in the opposite direction, the Beginning Of The Application Area 158 and End Of The Application Area 159 also have reversed positions. The head 150 applies the liquid solution 83 to the shaft 74 as the shaft 74 slowly rotates. Upon deposition the liquid solution 83 it coalesces on the shaft 74 forming the liquid film 87 on the shaft 74 outside of the drying area 160. The shaft 74 rotates slowly so that the liquid film 78 is converted into the sufficiently dry solid film 66 within the gaseous environment 90 prior to application of another liquid film thickness 88 comprising. The gaseous environment 90 is located outside the shaft 74 during deposition. In an embodiment, there is at least one head 150 depositing liquid film thickness 88 so that the shaft 74 is covered for at least the length equal to the un-oriented tube length 46. The deposited liquid film thickness 88 on the shaft 74 has at least one of the liquid film thicknesses 88 provided in FIG. 113. As the shaft 74 rotates around the shaft central axis 77, the liquid film 87 is created between the Beginning Of Application Area 158 and the End Of Application Area 159. As the shaft 74 rotates the liquid film 87 into the drying area 160, the liquid film 87 is converted into a substantially dry solid film 66 by removing at least part of the solvent(s) 86 from the liquid film thickness 88 so that the solid film 66 includes substantially zero or insignificant bubbles and/or blisters. The solid film thicknesses 67 forms the un-oriented tube wall thickness 45 on the shaft 74. When the liquid film 87 passes through the drying area 160 the liquid film thickness 88 is converted into the solid film thickness 67 that is much smaller than the liquid film thickness 88. Once the shaft 74 completes a rotation around the shaft central axis 77 another liquid film thickness 88 is deposited over the previously deposited, substantially dry solid film 66, which results in the second deposited film thickness 67 ("Over-Film Thickness 93") being adhered to first deposited film 66 ("Under-Film Thickness 94"). The Direct Roll Formation Process 149 is repeated until the desired un-oriented wall thickness 45 that is capable of being formed into the oriented tube 38 and/or the stent 10 is achieved. Once the desired unoriented wall thickness 45 is achieved the un-oriented tube 42 that was formed on the shaft 74 is removed from the shaft 74 and converted into the oriented tube 38 and/or stent 10.

The un-oriented tube 42 formed from the liquid solution 83 comprising the stent material 85 by the Indirect Roll Formation Process 138 or the Direct Roll Formation Process 149 may result in the formation of the un-oriented tube 42 that shrinks during heating and/or cooling. The unoriented tube 42 may shrink in length 46 by between 0% to 30% and until it snuggly fits the shaft outer diameter 75 when the un-oriented tube 42 is heated above the glass transition temperature of at least one or all the stent material(s) 85 comprising the un-oriented tube 42 and cooled below the glass transition temperature of at least one or all the stent material(s) 85 comprising the un-oriented tube 42. It is believed that the unoriented tube 42 shrinks when heated and cooled because it undergoes a transition from a more amorphous to a more crystalline morphology. The un-oriented tube 42 is formed into the oriented tube 38 and/or the stent 10.

In an embodiment, radially expanding and/or axially elongating the un-oriented tube 42 produces the oriented tube 38. Orienting the molecular chains within the stent material(s) 85 that are within the un-oriented tube 42 by deforming the un-oriented tube 42 is believed to strengthen the un-oriented tube 42. As depicted in FIG. 13, the oriented tube 38 has a larger nominal diameter and/or longer nominal length 39 than the un-oriented tube 42, which is depicted in FIG. 12, as a result of the deformation process. Radially expanding and/or axially elongating the un-oriented tube 42 deforms the un-oriented tube 42, which results in the oriented tube 38 becoming larger than the pre-cursor un-oriented tube 42. In other embodiments, the un-oriented tube 42 is not deformed prior to converting the un-oriented tube 42 into the stent 10 and the stent 10 is formed from the un-oriented tube 42.

A Mechanical Tube Orientation Process may be used to orient the stent material(s) 85 within the un-oriented tube 42 through deformation of the un-oriented tube 42. The un-oriented tube 42 may be deformed by radially expanding and/or axially elongating the un-oriented tube 42 by passing the un-oriented tube 42 over a cylindrical-shaped shaft having a conical-shaped end. The cylindrical-shaped shaft having a conical-shaped end comprises a cylindrical-shaped shaft 74 and a cone on at least one end of the cylindrical-shaped haft having a conical-shaped end, wherein the small end of the cone is facing outward and the large end of the cone is facing toward and connected to the cylindrical-shaped shaft. The cone includes a taper so that the inner diameter 43 of the un-oriented tube 42 at least partially slides onto the cone and can transition to a larger outer diameter of the cylindrical-shaped shaft having conical-shaped end. In an embodiment the cone and/or the cylindrical-shaped shaft having a conical-shaped end are lubricated, covered with a lubricious coating, is polished or has a smooth surface to reduce drag as the unoriented tube 42 passes over the cylindrical-shaped shaft having a conical-shaped end. Alternatively, the cylindrical-shaped shaft having a conical-shaped end is not lubricated, coated, or smoothed. In an embodiment, drag exists when the un-oriented tube 42 passes over the cylindrical-shaped shaft having a conical-shaped end so that the un-oriented tube 42 is at least partially axially elongated as the un-oriented tube 42 passes over the cylindrical-shaped shaft having a conical-shaped End. The un-oriented tube 42 slides over the cylindrical-shaped shaft having a conical-shaped end in the direction of distal end 26 passing over the cone first and the proximal end 25 passing over the end of the cone second.

The outer diameter of the cylindrical-shaped shaft having a conical-shaped end is substantially the same size as the outer diameter of the large end of the cone. The unoriented tube 42 has a starting inner diameter 43 that is smaller than the outer diameter of the cylindrical-shaped shaft having a conical-shaped end but large enough to slide over the small end of the cone. To achieve this the small end of the cone may be a sharp point or blunted point. In an embodiment, the un-oriented tube 43 is softened by heating the stent material(s) 85 within the un-oriented tube 42 to a temperature equal to or above the glass transition temperature of at least one or all the stent material(s) 85 comprising the un-oriented tube 42. Alternatively, or additionally, the stent material(s) 85 comprising the un-oriented tube 42 are heated to a temperature below the glass transition temperature of at least one or all the stent material(s) 85 comprising the un-oriented tube 42. The shaft 74 may be positioned within the Un-oriented Tube Passageway 5 during the softening process up until the time the un-oriented tube 42 passes from the shaft 74 onto the cone to prevent the unoriented tube 42 from becoming distorted or sagging during its softened state. The temperature of the cylindrical-shaped shaft having a conical shaped end and/or the gaseous environment 90 may be heated to a temperature greater than negative 100.degree. C to about the melting temperature of at least one of the stent material(s) 85 comprising the un-oriented tube 42 during the process; more narrowly within +/−50% of the glass transition temperature of at least one of the stent material(s) 85 comprising the un-oriented tube 42 during the mechanical tube orientation process. In other embodiments, the gaseous environment 90 is held at a higher or lower temperature. In the preferred embodiment, the gaseous environment 90 is a Protective Environment. Alternatively, the gaseous environment 90 is a liquid or protective liquid. In an embodiment, the entrance to the unoriented tube's 42 inner diameter 43 is positioned adjacent to the cone so that when the un-oriented tube 42 is pulled and/or pushed over the cone the un-oriented tube 42 slides over the cone in such a way that the inner diameter 43 of the un-oriented tube 42 increases in size as it is stretched over the cone. The cylindrical-shaped shaft having a conical-shaped end may be stationary or moving as the un-oriented tube 42 passes onto the cylindrical-shaped shaft having a conical-shaped end. Once the un-oriented tube 42 completely slides over the cone it slides onto a cylindrical portion of the cylindrical-shaped shaft having a conical end so that the inner diameter 41 of the oriented tube 38 substantially matches the size and shape of the cylindrical portion of the cylindrical-shaped shaft having a conical end. The inner diameter of the tube continues to increase until it reaches a fully expanded state wherein the oriented tube inner diameter 41 equals about the outer diameter of the cylindrical-shaped shaft having a conical end. The wall thickness 45 of the un-oriented 42 is drawn-down until it reaches the wall thickness 27 of the oriented tube 38 as depicted in the example provided in FIG. 100. As the un-oriented inner diameter 43 increases in size to the size of the oriented inner diameter 41 radial expansion of the un-oriented tube 42 occurs, which orients at least part or all the molecular chains within the stent material(s) 85 in the radial direction, which results in the oriented tube 38 having higher radial strength than the un-oriented tube 42. Higher radial strength improves the capability of the stent 10 to hold open the anatomical lumen 36 after implantation. Alternatively, or additionally, the un-oriented tube 42 may be elongated as it is pulled and/or pushed over the cone and/or the cylindrical portion pf the cylindrical-shaped shaft having a conical end so that axial elongation occurs, which orients the at least part of the molecular chains within the stent material(s) 85 in the longitudinal direction, which results in the oriented tube 38 having higher tensile strength than the un-oriented tube 42. Higher tensile strength prevents the stent 10 from fracturing when bending during deployment. As the un-oriented tube 42 passes over the cone, at least part of the molecular chains within the stent material(s) 85 within the oriented tube 38 orient in the direction of strain. After the unoriented tube 42 has passed over the cone and the oriented tube 38 is positioned so that it is in good fit and alignment with the cylindrical portion of the cylindrical-shaped shaft having a conical end, the oriented tube 38 and/or the cylindrical-shaped shaft having a conical shaped End are cooled to lock-in the molecular orientation and new dimensions of the oriented tube 38. When the un-oriented tube 42 is converted into the oriented tube 38, the volume of stent material(s) 85 flow into a new configuration, which results not only in an increase in diameter and/or length but also generally results in the wall thickness 27 of the oriented tube 38 being smaller than the wall thickness 45 of the unoriented tube 42. The oriented tube 38 is removed from the cylindrical-shaped shaft having a conical-shaped end to be converted into the stent 10 as describe herein.

The rate of radial expansion and/or axial elongation can be influenced by the angle of the cone. A gradually increasing cone diameter will more slowly deform the diameter and/or length of the un-oriented tube 42 and a steep or abruptly increasing cone diameter will more quickly deform the diameter and/or length of the un-oriented tube 42 as the un-oriented tube 42 passes over the cone. In the preferred embodiment, the angle between the cylindrical-shaped shaft having conical end central axis and the cone outer surface ranges from greater than 0 degrees to about 80 degrees. In other embodiments, the angle is larger but up to no more than 90 degrees from the central axis of the shaft 77. The speed at which the un-oriented tube 42 passes over the cone can range from greater than 0 mm/sec to about 10,000 cm/sec. In other embodiments, the speed is faster than 10,000 cm/sec but not faster than 900,000,000 m/sec.

Another method of converting the un-oriented tube 42 into the oriented tube 38 is a Stretch Blow Molding Process. The Stretch-Blow Molding Process may be used convert the roll 52 and/or the un-oriented tube 42 into the oriented tube 38. The Stretch-Blow Molding Process fundamentally includes a parison, a parison closed end, a parison open end, a heater, a blow pin, a mold, a mold cavity, a gas and an elongation pin The parison is the un-oriented tube 42 including one closed end. The parison is softened by inserting the within the heater. The heater preferably softens the parison by heating the parison to a temperature that is above the glass transition temperature of at least one of the stent material(s) 85 comprising the parison, but no higher than 250 degrees Celsius. The softened parison is placed within the cavity of the mold and the two mold halves close. The cavity has the shape of a bottle. The elongation pin is inserted through the open end of the softened parison so that the elongation pin stretches the softened parison so that the length of the parison is increased. The elongation pin is withdrawn and the gas is forced through the open end of the parison through the blow pin so that the parison is inflated until the outer surface of the parison conforms to the mold cavity at which time the softened parison is cooled to a temperature that is at least below of the glass transition temperature of at least one of the stent material(s) 85 comprising the parison so that the parison retains the shape of the cavity and forms the bottle within the cavity. Cooling the expanded parison below the glass transition temperature is preferably performed within the range of greater than 0 degrees Celsius/minute to 500 degrees Celsius/nanosecond ("quenching"). Quenching may occur by, for example, by dipping the bottle in a cold liquid (below 40 degrees Celsius) or by exposing the part with liquid nitrogen. Typically cooling the parison occurs within the mold so that the bottle retains the shape of the cavity. Inflating the parison increases the smaller outer diameter 44 to the larger outer diameter 40. The Stretch-Blow Molding Process produces the bottle. The bottle is removed from the mold by re-opening the mold halves. The bottle is removed from the mold and is converted into the oriented tube 38 by cutting a bottle top and a bottle bottom off the bottle. Alternatively, the stent 10 is formed from the bottle by cutting the strut pattern 171 directly into the bottle. The oriented tube 38 is the remaining portion of the bottle.

In embodiment, the stent materials(s) 85 are held at a temperature greater than the glass transition temperature of at least one of the stent material(s) 85 comprising the oriented tube 38 or bottle for a time within the range of greater than 0.0 seconds to about 30.0 minutes prior to cooling the oriented tube 38 or bottle to obtain the optimum crystallization of the oriented tube 38. In other embodiments, the oriented tube 38 or the bottle is held at a temperature greater than the glass transition temperature of at least one of the stent material(s) 85 within the oriented tube 38 or bottle prior to cooling the oriented tube 38 or bottle on the cylindrical-shaped shaft having a conical end 166 or within the mold. The optimum residence time of the oriented tube 38 on the cylindrical-shaped shaft having conical end or bottle within the mold may be experimentally determined by conducting ladder experiments where the residence time and temperature are varied to determine the optimum conditions that produce the oriented tube 38 having the mechanical properties and degree of crystallinity required for the treatment to be provided by the stent 10. In the preferred embodiment, the degree of crystallinity of the stent material(s) 85 within the stent 10 are within the range of greater than 0.0 percent to about 50 percent. In other embodiments, the degree of crystallinity of the stent material (s) 85 within the stent 10 are equal to or greater than 50 percent.

In an embodiment, the average degree of crystallinity of the stent material(s) 85 within the stent 10 is within the range of one of the following: (1) between 0% to 10% crystalline; (2) between greater than 0% to 10% crystalline; (3) between greater than 0% to 15% crystalline; (4) between greater than 0% to 20% crystalline; (5) between greater than 0% to 25% crystalline; (6) between greater than 0% to 30% crystalline; (7) between greater than 0% to 35% crystalline; (8) between greater than 0% to 40% crystalline; (9) between greater than 0% to 45% crystalline; (10) between greater than 0% to 50% crystalline; (11) between 5% to 10% crystalline; (12) between 10% to 15% crystalline; (13) between 15% to 20% crystalline; (14) between 20% to 25% crystalline or (15) between 25% to 30% crystalline. Differential Scanning calorimetry ("DSC") may be used to determine the degree of crystallinity of the stent material(s) 85 within the Sent 10.

The roll 52, the Roll Including the Active Ingredient(s) 143 and/or the un-oriented tube 42 may be radially expanded so that the Radial Expansion Ratio ("RER") is within the range of greater than 0.0 to about 10.0. In other embodiments the RER is equal to or higher than 10.0. The RER means the nominal diameter of the oriented tube 38 (after expansion) divided by the smaller nominal diameter of the roll 52 or the un-oriented tube 42 (before expansion). Without intent on limiting, an un-oriented tube 42 having a starting nominal diameter equaling 0.5 millimeters, which is increased to be an oriented tube 38 having nominal diameter equaling 3.0 millimeters, would have an RER equal to 3.0 divided by 0.5, which means the RER equals 6.0.

Alternatively, or additionally, the roll 52, the Roll Including Active Ingredient(s) 143 and/or the un-oriented tube 42 may be axially elongated so that the Axial Elongation Ratio ("AER") is within the range of 0.0 to about 10.0. In other embodiments, the AER is equal to or greater than 10.0. The AER means the larger length 39 of the oriented tube 38 (after axial elongation) divided by the smaller length 46 of the un-oriented tube 42 (before axial elongation) or the larger length 39 of the oriented tube 38 (after axial elongation) divided by the smaller length 58 of the roll 52 (before axial elongation). Without intent on limiting, an un-oriented tube 42 having a starting length 46 equaling 14.4 millimeters, which is increased to be an oriented tube 38 having length 39 equaling 18.0 millimeters, would have a AER equal to 18.0 divided by 14.4, which means the RER equals 1.25.

Since the stent 10 experiences both radial and axial loads during use, in an embodiment, the oriented tube 38 comprising the stent 10 may be formed from the roll 52, the Roll Including Active Ingredient(s) 143 and/or un-oriented tube 42 including both radial expansion and axial elongation. The Radial Expansion To Axial Elongation Ratio ("RETAER") of the oriented tube 38 equals the RER divided by the AER. The RETAER quantifies the relative amount of radial deformation to axial deformation imparted on the roll 52, Roll Including Active Ingredient(s) 143 and/or oriented tube 38 used to fabricate the stent 10, where a RETAER equaling 1.0 means that the oriented tube 38 used to produce the stent 10 includes an equal amount of radial expansion and axial elongation. It is believed it is better to have greater molecular orientation in the radial direction than in the axial direction of the oriented tube 38, so in the preferred embodiment the RETAER is within the range of greater than 1.0 to about 10.0. In other embodiments, the RETAER is equal to or greater than 10.0 or if there is no axial elongation imparted on the roll 52 and/or the un-oriented tube 42 the RETAER does not exist. Without intent on limiting, in the previous examples, RETAER is calculated by dividing 4.0 by 1.25, which means the RETAER is 3.2.

In an embodiment, the starting roll wall thickness 54 or the starting un-oriented tube 42 wall thickness 45 (before radial expansion/axial elongation) is thicker than the oriented tube's 38 ending wall thickness 13 (after radial expansion/axial elongation). In the preferred embodiment, the roll's 51 starting wall thickness 57 and/or the un-oriented tube's 42 starting wall thickness 45 may be larger than the oriented tube's 38 ending wall thickness 27 so that the wall thickness 57, 45 may be drawn down from the larger wall thickness 57, 45 to the smaller wall thickness 27 to increase the strength of the oriented tube 38, which results in the stronger stent 10. In other embodiments, the roll's 52 wall thickness 57 and/or the un-oriented tube's 42 starting wall thickness 45 is not made substantially larger than the oriented tube's 38 ending wall thickness 13 because the wall thickness may not need to be drawn down from a larger wall thickness 57, 45 to a smaller wall thickness 13 to increase the strength of the stent 10. It is believed that some Polymer(s) do not neck down when strained so that when these Polymer(s) are used, the roll wall thickness 57 and/or the unoriented tube wall thickness 45 may not need to be thicker than the oriented wall thickness 13 to achieve a strengthened oriented tube wall thickness 27. The benefits of drawing down the wall thickness can be experimentally determined by drawing the stent material(s) 85 to ascertain if drawing down improves the mechanical properties of the stent material(s) 85. The Wall Thickness Draw Down Ratio ("WTDDR") means the roll 52 starting wall thickness 57 divided by the oriented tube 38 wall thickness 27 or the un-oriented tube 42 starting wall thickness 45 divided by the oriented tube 38 ending wall thickness 27. In the preferred embodiment, the WTDDR is within the range of greater than 0.0 and less than 10.0. In other embodiments, the WTDDR is equal to or greater than 10.0.

In the preferred embodiment, the stent material(s) 85 are fully comprised of one or more bioresorbable polymers, copolymers or combinations thereof. The stent material(s) 85 may have one chemical composition ("one material") or multiple chemical compositions ("multiple materials"). The polymer(s) are either natural or synthetic. In other embodiments the stent material(s) 85 include other substances. In an embodiment, the bioresorbable polymer(s) are comprised of one or more molecule(s). The molecule(s) may be linear, branched or combination thereof. In the most preferred embodiment, the stent material(s) 85 within the stent 10 include at least one-part ultra-high weight average molecular weight (Mw) polymer(s) or copolymer(s), wherein the ultra-high weight average molecular weight (Mw) polymers have a weight-average molecular weight between greater than 621,000 g/mol to 3,000,000 g/mol, more narrowly greater than 1,014,000 g/mol to 3,000,000 g/mol.

In an embodiment, the stent 10 is partially or fully comprised of at least one of the following stent material(s) 85: 3-polyhydroxyalkanoate, acrylamide, aliphatic polyesters, aromatic copolyesters, caprolactones, carboxymethyl cellulose, carboxy methyl cellulose (CAS registry 9000-11-7), cellulose gum, chitin, chitosan, ethyl hydroxyethyl cellulose, ethylene glycol, ethylene glycol methacrylates, glucosyl ethyl methacrylate, hydroxybutyrate, hydroxyethyl cellulose, hydroxyethyl cellulose (CAS Registry 9004-62-0), hydroxyethyl methacrylate, hydroxypropyl cellulose (CAS registry 9004-64-2), hydroxypropyl cellulose (HPC), hydroxypropyl methacrylam ides, hydroxypropyl methylcellulose (CAS registry 9004-65-3), hydroxypropyl methylcellulose (HPMC), hypromellose, homopolymers, copolymers, terpolymers of lactic acid, lactic-co-glycolic acid, methyl cellulose, methyl cellulose (CAS registry 9004-67-5), n-isopropylacrylamide, poly (trimethylene carbonate), polypropylene adipate (PPA), poly (butylene adipate-co-terephthalate), poly(amino acids), poly(D-lactide), poly(D, L-lactide-co-glycolide), poly(D,L-lactide-co-trimethylene carbonate), poly(D,L-lactide-glycolide-caprolactone) (PDLLAGACL), poly(DL-lactide), poly(D,L-lactide), poly(N-vinyl-pyrrolidone)-block-poly (DL-lactode) poly(ester amide), poly[(R,S)-3-hydroxybutyrate] (a-PHB), poly (4-hydroxy butyrate), fully amorphous poly[(R,S)-3-hydroxybutyrate], poly(glycolic acid-co-trimethylene carbonate), poly(glycolide-co-caprolactone), poly(L-lactide-co-D, L-lactide), poly(L-lactide-co-glycolide), poly(L-lactide), polylactic acid (PLA), poly(lactide-co-caprolactone), poly (lactide-co-glycolide), poly(ortho esters), poly(tyrosine ester), poliglecaprone 25, polyanhydrides, poly(butylene succinate); poly(c-caprolactone), polydioxanones, polyester amides, polyesteram ides, polyethers, polyethers, polyethylene glycol (CAS registry 25322-68-3), polyethylene glycol (PEG), polyethylene glycol 400, polyethylene glycol 400 (CAS registry 2532268-3), polyethylene oxide (PEO), polyglycolide, polyglycolic acid, polyhydroxyalkanoate, polyhydroxyvalerate, polylactide (PLA), polyhydroxy acides, polymandelide, polyorthocarbonates, polyorthoesters, polyoxyethylene (POE), polyphosphazenes, propylene glycol, vinylacetate caprolactone, vinylalcohol, vinylpyrrolidone, vinylacetate, poly(L-lactide), poly(D-lactide), poly(L-lactide-co-DL-lactide), polymandelide, polyglycolide, poly(lactide-co-glycolide), poly(D,L-lactide-co glycolide), poly(L-lactide-co-glycolide), poly(ester amide), poly(ortho esters), poly(glycolic acid-cotrimethylene carbonate), poly (L-lactide-co-trimethylene carbonate), poly (trimethylene carbonate), poly(lactide-co-caprolactone), poly(glycolide-cocaprolactone), poly(tyrosine ester), poly anhydrides, and copolymers thereof, terpolymers thereof, derivatives thereof, mixtures thereof. In other embodiments, the stent 10 is comprised of other materials or polymers. There are virtually an infinite amount of materials that can be used to form the stent 10 using the processes described herein and the stent material(s) 85 should not be limited to those materials mentioned herein.

In an embodiment, the post-processed stent material(s) 85 within the stent 10 include less than 0.01 percent residual solvent(s) 86. In other embodiments, the post-processed material(s) 85 within the stent 10 include equal to or greater than 0.01 percent residual solvent as determined by gas chromatography ("GC"). In an embodiment, the post-processed stent material(s) 85 within the stent 10 include less than 0.01 percent residual monomer as determined by GC. In other embodiments, the post-processed material(s) 85 within the stent 10 include equal to or greater than 0.01 percent residual monomer as determined by GC. In an embodiment, the post-processed stent material(s) 85 within the stent 10 include less than 0.5 percent water as determined by coulometric titration. In other embodiments, the postprocessed material(s) 85 within the stent 10 include equal to or greater than 0.5 percent residual water as determined by coulometric titration. In the preferred embodiment, the post-processed stent material(s) 85 within the stent 10 include less than 50 ppm residual tin content as determined by atomic absorption spectroscopy. In other embodiments, the post-processed material(s) 85 within the stent 10 include equal to or greater than 50 ppm tin content.

In an embodiment, the stent 10 comprises at least one part or completely comprises post-processed, ultra-high weight average molecular weight (Mw) poly (L-lactide), which has a post-processed weight average molecular weight (Mw) equal to or greater than 110,000 grams per mole (g/mol), more preferably equal to or greater than 130,000 grams per mol (g/mol), even more preferably equal to or greater than 300,000 grams per mole (g/mol), yet more preferably equal to or greater than 725,000 grams per mole (g/mol), still even more preferably equal to or greater than 1,000,000 grams per mole (g/mol) and most preferably equal to or greater than 1,300,000 grams per mole (g/mol) using Gel Permeation Chromatography (GPC) performed in chloroform at 35.degree. C relative to polystyrene (PS) as standards. In other embodiments, the stent 10 comprises at least one part or completely comprises post-processed poly (L-lactide), which has a weight average molecular weight (Mw) after processing that is less than 100,000 grams per mole (g/mol) or above 1,300,000 grams per mole (g/mol). It should be appreciated that the weight average molecular weight (Mw) of the Polymer(s) can be determined by other methods know by those skilled in the art and that the molecular weight measurements are not limited to measuring using Gel Permeation Chromatography (GPC) performed in chloroform at 35.degree. C relative to polystyrene (PS) as standards.

In an embodiment, at least one film thickness 67 comprising the ultra-high weight average molecular weight material(s) 85 is positioned on the inner surface 17 of the stent 10. In an embodiment, at least one film thickness 67 comprising the ultra-high weight average molecular weight material(s) 85 is positioned on the outer surface 16 of the stent 10. In an embodiment, at least one film thickness 67 comprising the ultra-high weight average molecular weight material(s) 85 is positioned on the inner surface 17 and the outer surface of the stent 10. It is believed that the ultra-high weight average molecular weight (Mw) material(s) 85 degrade more slowly than medium or low weight average molecular weight stent material(s) 85, which helps maintain the stent's 10 radial strength during the initial part of the time that the stent 10 is implanted within the anatomical lumen 36. In an embodiment, the stent 10 maintains at least 85% to 100% of its initial radial strength for a duration selected from the group of: (1) greater than 0 minutes to 1 day; (2) greater than 1 day to 1 week, (3) greater than 1 week to 1 month, (4) greater than 1 month to 45 days, (5) greater than 45 days to 2 months, (6) greater than 2 months to 3 months, (7) greater than 3 months to 4 months, (8) greater than 4 months to 5 months, (9) greater than 5 months to 6 months, (10) greater than 6 months to 7 months, (11) greater than 7 months to 8 months, (12) greater than 8 months to 9 months, (13) greater than 9 months to 10 months, (14) greater than 10 months to 11 months or greater than 11 months to 12 months, wherein the duration starts when the stent 10 is implanted within the anatomical lumen 36. In an embodiment, the stent 10 maintains at least 60% to 100% of its initial radial strength for a duration selected from the group of: (1) greater than 0 minutes to 1 day; (2) greater than 1 day to 1 week, (3) greater than 1 week to 1 month, (4) greater than 1 month to 45 days, (5) greater than 45 days to 2 months, (6) greater than 2 months to 3 months, (7) greater than 3 months to 4 months, (8) greater than 4 months to 5 months, (9) greater than 5 months to 6 months, (10) greater than 6 months to 7 months, (11) greater than 7 months to 8 months, (12) greater than 8 months to 9 months, (13) greater than 9 months to 10 months, (14) greater than 10 months to 11 months or greater than 11 months to 48 months, wherein the duration starts when the stent 10 is implanted within the anatomical lumen 36. In other embodiments, the stent 10 maintains equal to or less than 60 percent of its initial radial strength for the same durations. In an embodiment, the stent 10 has an initial radial strength equal to 100 mmHg (0.013 MPa) to 2000 mmHg (0.27 MPa), wherein the initial radial strength is the radial strength at the time the stent 10 is implanted within the anatomical lumen 36. In other embodiments, the stent 10 has an initial radial strength equal to or lower than 100 mmHg or higher than 2000 mmHg.

A polydispersity index ("PDI" or "Dispersity"), which is calculated by dividing the weight-average molecular weight (Mw) by the number-average molecular weight (Mn), is a suitable method for determining the molecular weight distribution of the post-processed stent material(s) 85. A monodisperse stent material 85 has a PDI equal to 1.0. A PDI that is in the range of greater than 1.0 to about 1.1 is generally considered to be a narrow molecular weight distribution. A PDI that is in the range of equal to or greater than 1.1 to about 2.0 is a moderate molecular weight distribution. A PDI that is in the range of equal to or greater than 2.0 is a broad molecular weight distribution. The stent 10 may be comprised of raw stent material(s) 85 or post-processed stent material(s) 85 having a narrow, moderate or broad molecular weight distribution. Therefore, in an embodiment the stent 10 is comprised of polydisperse raw stent material(s) 85 or post-processed stent material(s) 85 having a PDI that is greater than 1. In an embodiment, the stent 10 comprises post-processed stent material(s) 85 comprising a broad molecular weight distribution having a PDI within the range of about 2.5 to 5.0, which is believed to produce a stronger stent 10.

The stent 10 may be comprised of an amorphous polymer. The stent 10 may be comprised of a crystalline polymer. The stent 10 is preferably comprised of a semi-crystalline polymer. The wall thickness 13 of the stent 10 may include at least one layer 51 of semi-crystalline stent material(s) 85 and at least one layer of amorphous stent material(s) 85, wherein the semi-crystalline layer 51 provides temporary support to the anatomical lumen 36 or a temporary barrier to the release of the active ingredient(s) 34 and the amorphous layer 51 provides storage for the active ingredient(s) 34 and release of the active ingredient(s) 34. It is also possible that the layer 51 closest to the inner surface 17 (luminal surface) has a higher degree of crystallinity than the layer 51 or layers 51 that are near the outer surface 16 (abluminal surface) so that the luminal layer 51 maintains radial strength longer and/or resorbs slower than the abluminal layer(s) 51. The more crystalline luminal layer 51 may be formed by forming the first roll 52 of interconnected film thicknesses 67 on the shaft 74 and heating and cooling the luminal layer 51 until the crystallinity of the luminal layer 51 increased and then attaching additional film thicknesses 67 to the more crystalline layer 51 that are more amorphous or less crystalline. The semi-crystalline polymer includes a lamellae. The stent 10 may include at least one spherulite. The spherulites include a nuclei, the lamellae and a tie chain molecules, which interconnect the lamella. It is preferred that the spherulites be smaller than 0.010 mm, more narrowly less than 0.005 mm, in size.

In an embodiment, the stent 10 can be radially expanded during deployment so that the stent's deployed diameter is greater than 0.5 millimeters (mm) larger than the stent's 10 nominal diameter, more preferably more than twenty (20) percent (%) larger than the stent's 10 nominal diameter, more preferably greater than forty-five (45) percent (%) larger than the stent's 10 nominal diameter, without fracturing and still being able to support the anatomical lumen 36 during the treatment time. In other words, the stent's 10 maximum post-dilatation diameter is preferably greater than 0.5 millimeters larger than the stent's 10 nominal diameter, more preferably greater than 20% larger than the stent's 10 nominal diameter, and most preferably greater than 45% larger than the stent's 10 nominal diameter, wherein the nominal diameter equals the nominal diameter of the un-oriented tube 42 or oriented tube 38 at the time the strut pattern 171 is cut into the un-oriented tube 42 or oriented tube 38 plus the thickness of the coating 30 (if present).

The stent material(s) 85 comprising the stent 10 may be adapted to include at least one reinforcement to form a composite material. The reinforcement(s) may have any shape. For example, the reinforcement may have a substantially spherical shape, an ovoid or egg shape, a rod shape, a flake shape or other structural shapes. The reinforcement includes a reinforcement outer surface. The reinforcement may include at least one undercut that may manifest itself as a texture, protrusion, indentation or fissure within the reinforcement's outer surface. The configuration of the reinforcement's outer surface(s) or a coating on the outer surface(s) may improve the strength of the bond between the stent material(s) 85 and the reinforcements.

In an embodiment, the stent 10 may be comprised of the composite material, wherein the composite matrix is formed of the reinforcements(s) that are at least partially or completely separated by the stent material(s) 85. The composite matrix within the composite material separates the reinforcement(s) by a Y-axis separation distance, a Z-axis separation distance and an X-axis separation distance. In an embodiment, the reinforcement(s) may comprise at least one active ingredient(s) 34. In an embodiment, the reinforcement(s) comprise at least one chemical metal element or alloy comprising multiple chemical metal elements. The alloy may include HRE and/or RE. The reinforcement may include a passivation layer. In an embodiment, the Y-axis separation distance ranges from 0.000 mm to 0.085 mm and the Z-axis separation distance and the X-axis separation distance range in size from about 0.00 mm to 0.150 mm, wherein the Y-axis separation distance is the position of the reinforcement within the wall thickness 13, Z-axis separation distance is the position of the reinforcement within the diameter and X-axis separation distance is the position of the reinforcement within the length 15.

FIG. 102 depicts an ultra-high molecular weight stent material 96 and FIG. 105 depicts a low molecular weight stent material 97. In an embodiment, the stent material 85 comprises at least one part made from an ultra-high molecular weight material 96. As depicted in FIG. 131, a long molecular chain characterizes the ultra-high molecular weight material 96. Forming the stent 10 from at least one ultra-high molecular weight stent material 96 increases the radial strength of the stent 10, increases the elongation-to-break of the stent 10 so that the stent 10 may have larger dilatation limits, makes at least one part of the stent 10 degrade and/or resorb more slowly, releases the active ingredient(s) 34 more slowly, and/or makes a longer lasting barrier layer 51 that delays or slows down the release of the active ingredient(s) 34 positioned within a therapeutic layer 51 and/or film thickness 67. Forming one part of the stent 10 from at least ultra-high molecular weight stent material 96 and another part with at least one part with a lower molecular weight stent material 134 is a critical element of making the controlled drug delivery stent 10 having sustained drug delivery when using the stent material formulations 275 and blend formulations 276 provided in FIG. 111 and FIG. 112.

During formation of the ultra-high molecular weight stent material 96 into the stent 10, the long chain is cleaved 98 at random locations along the chain as depicted in FIG. 103. The term "cleaved" may also be referred to as scission. The cleaving of the chain results in dividing the long chain into shorter chains of varying lengths as depicted in FIG. 104, which results in the stent 10 comprising post-processed stent materials 99 that have shorter chains. Cleaving of the ultra-high molecular weight stent material 96 may also reduce the mechanical properties of the stent 10, wherein, for example, the radial strength and/or elongation-to-break properties are reduced. Converting the ultra-high molecular weight stent material 96 into at least part of the stent 10 using the stent 10 formation methods described herein reduces the negative impact of converting the ultra-high molecular weight stent material 96 into the stent 10 because the ultra-high molecular weight stent material 96 is not exposed to high shear stresses, high temperatures and the formation methods preferably occurs within a Protective Environment. Converting the ultra-high molecular weight stent material 96 into at least part of the stent 10 using the methods described herein may reduce the reduction in the weight average molecular weight of the stent material(s) 85 within the stent 10. However, using the methods of producing the stent 10 described herein may reduce the weight average molecular weight of the stent material(s) 85 within the stent 10 during formation of the stent 10 so that the pre-processed ("raw") stent material(s) 85 have a weight average molecular weight (Mw) that is reduced to a post-processed stent material(s) 85 weight average molecular weight (Mw).

In the prior art, bioresorbable stents are comprised of the low molecular weight material 97 as depicted in FIG. 105. Like the ultra-high molecular weight material 96, during the conversion of the low molecular weight material 97 into a prior art stent the low molecular weight material 97 is also cleaved 98 into shorter chains at random locations along the chain a depicted in FIG. 106. However, after cleavage, the low molecular weight material 97 results in very low post-processed molecular weight polymers 99 having significantly shorter chains as depicted in FIG. 107. In an embodiment, the present invention forms the stent 10 from stent materials 85 at least partially comprising the ultra-high molecular weight material 96 because starting the formation of the stent 10 from the longer ultra-high molecular weight material chains 96 results in a much stronger stent 10 having superior crack resistance than when the stent 10 is formed of the low molecular weight material 97, which is prone to cracking.

The un-oriented tube 42 may not be concentric or it may include irregularities on the outer surface 47. The Plate Rounding Fixture 266, depicted in FIG. 110, and/or the Roller Rounding Fixture 267, depicted in FIG. 109, may be used to improve the concentricity and/or surface 47 of the un-oriented tube 43 prior to converting the un-oriented tube 42 into the stent 10 or the oriented tube 38. It is desirable for the un-oriented tube 42 to be concentric when cutting a high precision strut pattern into the tube wall thickness. As depicted in FIG. 110, the Plate Rounding Fixture 266 method comprises a flat surface 264, a spacer 265, the shaft 74 and the un-oriented tube 42. The concentricity and surface of the un-oriented tube 42 may be improved by the following method: (1) placing the spacers 265 having a thickness equal to the final un-oriented tube 42 wall thickness 45 on the flat surface 264; (2) positioning the un-oriented tube 74 on the shaft 74 outer surface 78; (3) softening the stent material(s) 85 comprising the un-oriented tube 42 by heating the un-oriented tube 42 on the shaft 74; (4) rolling the heated un-oriented tube 74 over the flat surface 264 while keeping the shaft 74 outer surface 78 in contact with the spacers 265 and (5) cooling the un-oriented tube 42 after the softened un-oriented tube 42 has rolled over the flat surface 264 at least on complete revolution.

As depicted in FIG. 109, the Roller Rounding Fixture 267 method comprises a cylindrical-shaped roller 268, the shaft 74 and the unoriented tube 42. The concentricity and surface of the un-oriented tube 42 may be improved by the following the method: (1) positioning the unoriented tube 74 on the shaft 74 outer surface 78; (3) softening the stent material(s) 85 comprising the un-oriented tube 42 by heating the unoriented tube 42 on the shaft 74; (4) spinning the un-oriented tube 42 on the shaft 74 clockwise and spinning the shaping roller 268 counter clockwise (or the opposite directions) so that the un-oriented tube 42 wall thickness 45 is set by the distance between the shaft central axis 77 and the shaping roller central axis 269 and (5) cooling the un-oriented tube 42 after the complete outer circumference of softened un-oriented tube 42 has passed between the shaping roller 268 and the shaft 74 at least one time.

The stent 10 includes a strut pattern 171. The strut pattern 171, which is depicted in flat planar view in FIG. 114, is cut into the oriented tube's 38 wall thickness 27 or the un-oriented tube's 42 wall thickness 45. The strut pattern 171 forms a tubular shape surrounding the stent central axis 14 when a Strut Pattern Bottom Edge 187 and a Strut Pattern Top Edge 188 (19 shown) are connected in a tubular configuration. The strut pattern 171 fundamentally includes a crest 189 and a trough 190, which forms the approximately sinusoidal-shaped ring 19 that is connected to other rings 19 with the link struts 21. A cutting surface 191 forms the boundary around the rings 19 and the link struts 21 that forms the cell 22 within the un-oriented tube 42 or the oriented tube 38. The cell 22 is an empty space within the wall thickness 27 of the oriented tube 38 or wall thickness 45 of the un-oriented tube 42 the stent material(s) 85 have been removed during the strut pattern 171 cutting process. The linear ring struts 20 and the link struts 21 partially or completely surround the cell 22. FIG. 114 depicts eight linear ring struts 20 and two link struts 21 completely surrounding the cell 22. At the junction of each linear ring strut 21 and/or link strut 21 there is a curved hinge element 281. Five of the curved hinge elements 281 have been circled with a dashed line so that the curved hinge elements 281 can be identified. In other embodiments, there may be more or less ring struts 20 and link struts 21 surrounding the cell 22. One of the cells 22 is shown hatched and one of the cutting surfaces 191 is shown in a bold line in FIG. 114 for easy visualization. The strut pattern 171 may also include a at least one marker strut 192, which contains a radiopaque material to assist with visualization of the proximal end 25 and distal end 26 of the stent 10 during delivery and implantation of the stent 10 within the anatomical lumen 36. Alternatively, the linear ring strut 20 and the link strut 21 may at least partially comprise a mixture of a radiopaque material and the stent material(s) 85 that enable the entire stent 10 to be visualized during delivery of the stent 10 to the treatment site 35. The radiopaque material may be in the range of greater than 0.000 mm to 0.001 mm, preferably nano size. Platinum powder may, for example, provide visualization of the stent 10 during delivery and may be bioresorbable as the body of the implanted stent 10 loses mass. The linear ring strut 20 has a linear strut width 279 and the link strut has a link strut width 280.

A pattern of rings 19 and link struts 21 may be formed within the un-oriented tube 42 or the oriented tube 38 by removing portions of the un-oriented wall thickness 45 or the oriented wall thickness 13 by chemical etching, mechanical cutting, or laser cutting materials away from within the wall thickness 45 of the un-oriented tube 42 and/or the wall thickness 13 of the oriented tube 38. Without limitation, the strut pattern 192 may be cut into the un-oriented wall thickness 45 or oriented wall thickness 13 with an ultra-short-pulse laser having pulse with duration shorter than about a picosecond (=10-12), an ultra-short-pulse laser having a pulse duration shorter than about a femtosecond (=10-13 or in some cases 10-15), or a long pulse laser having a pulse duration of about a nanosecond (=10-9). Suitable lasers are available from Rofin-Baasel Laser GmbH, Petersbrunner Str., Starnberg, Germany (now called Coherent Munich GmbH & Co. KG, ZeppelinstraRe 10-12, 82205 Gilching, Germany).

FIG. 115 depicts an Exploded Tube 271 from the end view of an un-oriented tube 42 or oriented tube 38 that was formed from one solid film 66. As previously disclosed, in other embodiments there may be multiple solid films 66. The Exploded Tube 270 depicts the film thicknesses 67 separated within the un-oriented tube 42 wall thickness 45 or the oriented tube 38 wall thickness 27 so that the spiral configuration of the solid film 66 can be easily visualized. In an embodiment, the adjacent film thicknesses 67 are interconnected and there is no gas or empty space within the separation distance 60 between the film thicknesses 67.

However, in another embodiment there may be active ingredient(s) 34 positioned within the separation distance 60, wherein the areas surrounding the active ingredient(s) 34 are substantially filled with the stent material(s) 85. In yet one more embodiment, there may be at least one part void space 127 within the wall thickness 13. Generally, the void space 127 is less than 10 vol. % of the wall thickness 13. In other embodiments, the void space 127 may be equal to or greater than 10 vol. %.

FIG. 115 depicts a retained portion 272 that is adjacent to two removed portions 273 of the wall thickness, which are created when the strut pattern 171 is cut into the un-oriented tube wall thickness 45 or the oriented wall thickness 27. The cutting lines 278 show the approximate pathway of where at least one part of where the cutting device travels when cutting out the removed portions 273 from the un-oriented tube 42 or the oriented tube 38. The cutting lines 278 are shown as dashed lines in FIG. 115. The retained portion 272 becomes the linear ring strut 20 or the link strut 21. The removed portion 272 becomes waste that may be disposed of or recycled. FIG. 115 depicts fourteen cutting surfaces 191, which would result in the production of seven equally spaced struts surrounding the central axis 14 of the stent 10 if the tube is cut at each of the fourteen cutting surfaces 191. One of the linear ring struts 20 or link struts 21 is shown in the balloon 274 so that it is easy to visualize how the linear ring struts 20 and link struts 21 are formed of the interconnected film thicknesses 67 and/or layers 51. It should be appreciated that the cutting lines 278 and the balloon 274 are not part of the stent 10.

The stent 10, the un-oriented tube 42, the oriented tube 38, the film 66, the fiber 116, the multi-fiber 117, the fibrous sheet 108, the laminate 100, the infused fibrous sheet 126, the roll 52, the Roll Including Active Ingredient(s) 143, the infused fiber-reinforced laminate 130, the reinforcement(s), the active ingredient(s) 34 and/or combinations thereof may be formed or processed under a protective environment. To at least partially preserve the degree of polymerization of the stent material(s) 85, at least partially preserve the molecular weight of the stent material(s) 85 or the stability of the reinforcement(s) during processing, the stent 10 may be formed within a protective environment (herein referred to as "Protective Environment"). Without limitation, the mixing, dissolving, storing, film forming, fiber forming, roll forming, heating, liquefying, casting, cooling, infusing, assembling, laminating, solidifying, fusing, sintering, crystallizing, strut pattern cutting, surface modification, coating, transferring, crimping, packaging, sterilizing or combinations thereof processes may be performed within the Protective Environment. The Protective Environment, for example, minimizes or prevents degradation of the stent material(s) 85 or active ingredient(s) 34 efficacy due to thermal processing, hydrolysis, or shear stresses; minimizes or prevents oxidation of the reinforcement(s); minimizes or prevents fires; minimizes or prevents reactivity of the reinforcement(s) with ambient air or moisture; minimizes or prevents the degradation of the active ingredient(s) 34, or combinations thereof. The Protective Environment may be, for example, partially or fully comprise an inert atmosphere, noble gases (i.e., helium, neon, argon, krypton, xenon, and radon), nitrogen, dried air (e.g., air including humidity below 20%), moisture-free air, low oxygen containing or oxygen-free air, carbon dioxide, or combinations thereof. The Protective Environment may also include minimization or avoidance of high shear stresses imparted on the stent material(s) 85 during processing.

Without intent on limiting, the coating 30 may be comprised of at least one of the coating materials 31 selected from the group of: absorbable polymers; acrylate-based materials; acrylic; alkyds; alginates; amorphous polymers; 3-aminopropyltrimethoxylsilane (APS); 3aminopropyltriethoxysilane (C9H23NO3Si); biostable polymers; biodegradable polymers; C10 polymer; C19 polymer; C19 polymer with hydrophobic and hydrophilic polyvinylpyrrolidinone groups; collagen; copolymers of DL-Lactide and glycolide; copolymers of DL-Lactide and L-lactide; copolymers of L-lactide and D-lactide; copolymers of L-lactide and DL-lactide; copolymers of DL-lactide and .epsilon.-caprolactone; crystalline polymers; cross linked poly vinyl alcohol (PVA) and gelatin; crystalline materials; degradable polymers; dissolvable polymers; durable polymers; epoxy-based materials; erodible polymers; ethylene copolymers; fluoropolymers; gelatin; heparin; high molecular weight polymers; hydrophilic materials; hydrophobic materials; hydrocolloids; hydroxyapatite; hydrophilic polyvinyl-pyrrolidone; hydrophobic hexyl methacrylate; hydrogels; hydrolyzed collagen; hydrophobic hexyl methacrylate and hydrophilic vinyl pyrrolidinone and vinyl acetate monomers; hydrophobic butyl methacrylate; iodine; lactide-based materials; light curing materials; low molecular weight polymers; lubricious materials; parylene; stent materials 85 listed herein; materials having glass transition temperature less than 40 degrees centigrade; materials having a glass transition temperature at or above 40 degrees centigrade; mixtures of poly(DL-Lactide) and poly(glycolide); mixtures of poly(DL-lactide) and poly(L-lactide); mixtures of poly (DL-lactide) and poly (.epsilon.caprolactone); mixtures of poly (DL-Lactide), poly(glycolide), and/or poly(L-Lactide); mixtures of poly(L-lactide) and poly(D-lactide); mixtures of amorphous polymers and semi-crystalline polymers; mixtures of poly (DL-lactide), poly (L-lactide), poly(glycolide), and poly(.epsilon.caprolactone); mixtures comprised of greater than 0 wt. % to 75 wt. % poly(glycolide) and the remainder poly(DL-lactide); mixtures comprised of greater than 0 wt. % to 85 wt. % poly(L-lactide) and the remainder poly(DL-lactide); mixtures comprised of greater than 0 wt. % to 85 wt. % poly(.epsilon.caprolactone) and the remainder poly(DL-lactide); modified derivatives of .epsilon.-caprolactone polymers; moisture curing materials; olefins; oxides; photo-curable hydrogels; phosphorylcholine; phosphates; platinum; polyacrylates; polyalkylene esters; polyamides; polyamides esters; poly (n-butyl methacrylate); polycaprolactone; poly (.epsilon.-caprolactone); polyethylene glycol; poly-DL-Lactide; poly (L-lactide)/poly (butylene succinate-co-L-lactate) blends; poly trimethyl carbonate; polyesters; poly (ethylene succinate); polyhydroxyalkanoates; poly-L-lactide; poly (L-lactide); poly (D-lactide); poly (D,L-lactide); poly (DL-lactide); poly (D,L-lactide) or poly (DL-lactide) having a degradation time between 3 months to 24 months where the degradation time equals the time to substantially complete mass loss of the coating; poly (D,L-lactide) or poly (DL-lactide) having a degradation time equal to or less than 3 months where the degradation time equals the time to substantially complete mass loss of the coating; poly (DL-lactide) or poly (DL-lactide) having a degradation time equal to or greater than 24 months where the degradation time equals the time to substantially complete mass loss of the coating; DL-lactide and glycolide copolymer having a degradation time between greater than 0.0 months to 24.0 months where the degradation time equals the time to substantially complete mass loss of the coating; DL-lactide and glycolide copolymer having a degradation time equal to or greater than 24.0 months where the degradation time equals the time to substantially complete mass loss of the coating; DL-lactide/glycolide copolymer(s) of any monomer ratio; poly (DL-lactide-co-glycolide); poly (D,L-lactide-co-glycolide) glycolide; poly (D,L-lactide-co-glycolide) lactide; L-lactide/D-lactide copolymers of any monomer ratio; L-lactide/DL-lactide copolymer(s) of any monomer ratio; povidone-iodine (PVP-1); any chemical complex of polyvinylpyrrolidone and elemental iodine; any polymer and radiopaque materials; lactones; L-lactide copolymer(s); L-lactide/glycolide copolymer(s) of any monomer ratio; L-lactide/.epsilon.-caprolactone copolymer(s) of any monomer ratio; Polymer(s) having degradation time 0.5 months to 48 months; Polymer(s) having degradation time equal to or less than 0.5 months; Polymer(s) having degradation time equal to or greater than 48 months; biodegradable Polymer(s) having molecular weight (Mw) 10 kg/mol to 220 kg/mol; biodegradable Polymer(s) having molecular weight (Mw) equal to or less than 10 kg/mol; biodegradable Polymer(s) having molecular weight (Mw) equal to or greater than 220 kg/mol; any material that temporarily prevents the substantial penetration of water into the stent material(s) 85 comprising the stent's wall thickness 13; any material(s) that prevent the substantial penetration of water into the stent material(s) 85 comprising the stent's wall thickness 13 for a period of time within the range of greater than 0.0 minutes to less than about 6.0 months after the deployment of the stent 10; any material(s) that prevent the substantial penetration of water into the stent material(s) 85 comprising the stent's wall thickness 13 for equal to six months to less than about five years; any material(s) that temporarily controls the penetration of water into the stent material(s) 85 comprising the stent's wall thickness 13; any material(s) that control the substantial penetration of water into the stent material(s) 85 comprising the stent's 40 wall thickness 13 for a period of time within the range of greater than 0.0 seconds to less than about 3.0 months after the deployment of the stent 10 within the treatment site 35; any material(s) that control the substantial penetration of water into the stent material(s) 85 comprising the stent's 40 wall thickness 13 for a period of time of equal to about 3 months to about less than 5 years after the deployment of the stent 10 within the treatment site 35; any material(s) that increase the storage stability of wall thickness 13 of the stent 10 at ambient storage conditions; any material(s) that increase the storage stability of the wall thickness 13 of the stent 10 at temperatures above 23.degree. C; any material(s) that increase the storage stability of the wall thickness 13 of the stent 10 at a relative humidity above 30% relative humidity; any material(s) that affect the pH of the treatment site 35 after deployment of the stent 10 within the anatomical lumen 36 equal to or below about 7.4 pH; material(s) that affect the pH of the treatment site 35 after deployment of the stent 10 within the anatomical lumen 36 equal to or above about 7.4 pH; poly (butylene succinate) (PBS); polycaprolactone copolyglycolic acid; polycaprolactone glycerylmonostearate; polysaccharides; polytrimethylene carbonate; polyethylene co-vinyl acetate; polyolefins; polyvinyl pyrrolidinone (PVP); polyvinyl alcohols; polyethylene glycol; polyvinyl esters; proteins; resorbable polymers; resorbable excipients; styrene-based materials; starch acetate; styrene isoprene butadiene (SIBS) Block copolymers; terminal diols; urethane based materials; vinyl-based materials; wax; carnauba wax; beeswax; animal waxes; vegetable waxes; mineral waxes; synthetic waxes; petroleum waxes; homopolymer(s); copolymer(s) thereof; terpolymer(s) thereof; complexes thereof; combinations thereof; derivatives, analogs, and functional equivalents.

The stent 10 may be incorporated into a stent-graft 254 as depicted in FIG. 108. The stent-graft is comprised of the stent 10 and a graft 255. The graft 255 is comprised of tube-shaped material that covers all or part of the inner surface 17 and/or the outer surface 16 of the stent 10. The graft 255 may be attached or detached from the stent 10. The graft 255 may be comprised of the bioresorbable stent material(s) 87 or durable materials. The graft 255 may be comprised of solid or porous material(s).

The applications or treatments include: a vascular stent; a peripheral vascular stent; a carotid stent; a cerebral stent; a cell transportation device; a cell growth platform; an endovascular application; an endovascular application in the popliteal artery; a device for supporting an anatomical lumen; a device for reinforcing an anatomical lumen; a device for patching a defect, tear or hole in an anatomical lumen; a device for delivering a drug or drugs to or within an anatomical lumen; a device for the treatment of lesions; a device for the treatment of lesions less than 24 millimeters in length; a device for the treatment of lesions equal to or greater than 24 millimeters in length; a device for treatment of lesions located in in arterial or saphenous veins or grafts; a device for treatment of lesions located in unprotected left main; a device for the treatment of ostial lesions; a device for treatment of lesions located at a bifurcation; a device for the treatment of previously stented lesion; a device for the treatment of calcified lesions; a device for the treatment of three-vessel disease; a device for the treatment of coronary artery within the range of greater than 0.00 millimeters to 4.0 millimeters in diameter; a device for the treatment of coronary artery equal to or greater than 4.0 millimeters in diameter; a renal stent; a iliac stent; a superficial femoral artery stent; a urethral stent; a ureter stent; a urinary stent; a biliary stent; an implantable scaffold; a drug delivery scaffold; a drug eluting scaffold; a vascular scaffold, a drug eluting vascular scaffold; a tracheal stent; a large bronchi stent; a nasal stent; a gastrointestinal stent; an esophageal stent; a drug delivery stent; a drug delivery device; a self-expandable stent; a balloon-expandable stent; a ratcheting stent; a modular stent; a bifurcated stent; a stent-graft; an abdominal aorta stent-graft; a birth control device; a bone replacement device; a nerve guide; an orthopedic device; an intrauterine device (IUD); an embolic filter; an anatomical lumen repair or splicing device; a device for local delivery of active ingredient(s) 34 to tubular shaped lumen or organs for treatment of cancer; a device for treatment of colon or rectal cancer; a device for the treatment of cancer; an implant; a patch; a percutaneous coronary intervention (PCI) device; a plug; a mechanical support device; a reinforcement device; a repair device; an attachment device; an oncology treatment device; a device for treatment of cancer within or near an anatomical lumen; a device to assist in remodeling of diseased anatomical lumens; a device for the treatment of angina; a device for revascularization; a device for treatment of calcified lesions; a device for prevention of thrombosis; an endovascular aneurysm repair (EVAR) device; an abdominal aorta aneurysm repair device; an iliac artery repair treatment device; a superficial femoral artery treatment device; a tissue engineering application (bone, cartilage, blood vessels, bladder, skin, tissue, muscle, etc.); a bone fixation device; bone plates; a temporomandibular joint repair or replacement; a medical textile; a repair; a transparent thin film transistor; a transparent semiconductor; a suture anchor; a surgical mesh; a device for reconstruction, or replacement/repair of ligaments; a device for repair, reconstruction, or replacement of rotator cuffs; a device for repair, reconstruction, replacement of hollow organ tissue; a suppository; a sinus stent; a tissue reinforcement device; an implantable device; a patch; regenerative medicine; a valve; a heart valve; and a vena cava filter. In other embodiments, the present invention may be applied to other devices, end-use applications and/or treatments.

In an embodiment, the packaged stent 10 and/or unpackaged stent 10 including or excluding the catheter 37 are sterilized before delivery into the anatomical lumen 36. Sterilization results in the stent 10 being freed from viable microorganisms. The stent 10 may be freed from viable microorganisms by destroying the microorganisms. Without intent on limiting, the sterilized stent 10 must be free of viable microorganisms that include bacterial and fungi (yeast/mold) such as yeast (*Candida albicans*), mold (*Aspergillus Niger*), bacteria (*E. coli, Pseudomonas, Staphylococcus aureus*). Without limitation, the packaged or the unpackaged stent 10 including or excluding the catheter 37 and/or packaging may be sterilized with at least one of the following sterilization processes: (1) gamma irradiation (e.g., radioactive Cobalt 60); (2) electron beam irradiation (e.g., e-beam)/X-ray; (3) ethylene oxide (Eta); (4) low temperature plasma, (5) molding processes; (6) steam and (7) dry heat, (8) ultraviolet light, and (9) any other process capable of sterilizing the components described herein. The stent 10, catheter 37 and/or the packaging may be exposed to a dose of irradiation between about 10 to about 35 kGy. In other embodiments, the stent 10, the catheter 37 and/or the packaging may be exposed to a dose of irradiation equal to or greater than about 35 kGy or exposed to a dose of irradiation equal to or less than about 10 kGy. Aseptic production and packaging environments may also be used. Depending on the application, the minimum sterility requirements may be explained in SAL-6 and SAL-3. Those skilled in the art of sterilization of medical devices may perform sterilization according to industry standards. Care must be taken to minimize the impact of sterilization on the molecular weight of the stent material(s) 85, the crystallinity of the stent material(s) 85, the mechanical properties of the stent material(s) 85, and/or the efficacy of the active ingredient(s) 34 during sterilization.

The sterilized stent 10 may be further processed to stabilize the stent material(s) 85 within the stent 10. The sterilized stent 10 may be further processed to stabilize the stent material(s) 85 by heating the stent 10 in at least one cycle above about the ambient temperature but below the glass transition temperature of some or all the stent material(s) 85 comprising the stent 10 within the range of greater than 0.0 minutes to 24.0 hours to stabilize the physical and/or mechanical properties of the stent 10. In other embodiments, the sterilized stent 10 may be heated to above ambient temperature but below the glass transition temperature of some or all the stent material(s) 85 comprising the stent 10 for equal to or greater than 24 hours. In an embodiment the sterilized stent 10 is comprised of at least one part or completely comprised of post-processed stent material(s) 85 having a weight average molecular weight (Mw) greater than 110,000 g/mol after sterilization and/or having a weight average molecular weight (Mw) greater than 110 kilodaltons (kDa) and/or having an Inherent Viscosity (IV) greater than about 1.2 dl/g.

In an embodiment, the stent 10 is configured to partially or fully degrade by hydrolysis after deployment of the stent 10 within the treatment site 35 within the anatomical lumen 36, which results in a substantially complete loss of the mass of the stent 10 after the treatment time. The stent 10 may partially or fully degrade by the cleaving 98 of the molecular chains comprising the post-processed bioresorbable stent material(s) 85 within the stent 10 from a higher molecular weight to a lower molecular weight within the treatment site 35, which results in a substantially complete loss of the mass of the stent 10 after the treatment time. In other embodiments, the stent 10 may partially or fully degrade by corrosion or bio-corrosion within the treatment site 35, which results in a substantially complete loss of the mass of the stent 10 after the treatment time. The stent 10 may also partially or fully degrade by cleaving 98 the molecular chains comprising the stent material(s) 85 and corroding or bio-corroding the reinforcement(s), which results in a substantially complete loss of the mass of the stent 10 after the treatment time. The constituents of the stent 10 may be partially or fully configured to be solubilized in water and/or biological fluids and partially or fully transported away from the treatment site 35.

Part or all the stent 10 may degrade by hydrolysis. In another embodiment the stent 10 may configured to degrade by a bacterial attack. The bioresorbable stent 10, during the initial phases of degradation, may degrade by the long or high molecular weight chains hydrolyzing into lower molecular weight oligomers. The rate of hydrolysis may be accelerated or de-accelerated by acids or bases incorporated into the stent 10. The rate of hydrolysis is dependent on moisture content and temperature of the stent 10. The crystallinity of the stent material(s) 85 and blends of the stent material(s) 85 within the stent 10 affect the rate of degradation of the stent material(s) 85 comprising the stent 10, where crystalline stent material(s) 85 degrade slower than amorphous stent material(s) 85 and/or hydrophobic stent material(s) 85 degrade slower than hydrophilic stent material(s) 85.

While several particular forms of the invention have been depicted and described, it will also be apparent that various modifications can be made without departing from the scope of the invention. For example, and without limitation, the strut pattern 171 may have a lesser or greater number of rings 19 than what is depicted in FIG. 114. As a further non-limiting example, the strut pattern 171 may have any number of open or closed cells 22 circumferentially arranged to encircle the stent 10 central axis 14. In FIG. 114, there are three W-shape cells 22 that are circumferentially arranged, although a lesser or greater number of W-shape or other shapes may be implemented in a strut pattern 192 of other embodiments. Moreover, the strut pattern 171 can have any number of W-shape or other shape open or closed cells 22 arranged axially along the entire longitudinal length 15 of the stent 10 in other embodiments. In FIG. 114, there are eighteen W-shape closed cells axially arranged, although a lesser or greater number of W-shape or other shapes may be implemented in the strut pattern 171 of other embodiments.

In other embodiments, adjustments to the previously specified strut pattern 171 design may be made to compensate for unique characteristics of the stent material(s) 85 used to construct the stent 10, manufacturing processes used to produce the stent 10, end-use application, or equipment utilized to deploy the stent 10. Some or all the crests 189 may be connected to some or all the troughs 190 of adjacent rings 19 with the link struts 21, some or all the crests 189 may be connected to some or all the crests 189 of adjacent rings 19 with the link struts 21, some or all the troughs 190 may be connected to some or all the troughs 190 of adjacent rings 19 with the link struts 21, or combinations thereof. Some or all the linear ring struts 20 and/or link struts 21 may include curved or bent portions; some or all the linear ring struts 20 and/or link struts 21 may include a serpentine configuration; some or all the linear ring struts 20 and/or link struts 21 may include at least one feature such as and without limitation indentations, radii, grooves, cuts, thru holes and other features that enhance operability of the stent 10 during crimping, deployment and/or treatment. In other embodiments, the shape of the cells 22 may be a mixture of different shapes and configurations. There may be more or less than eight linear ring struts 20 and/or more or less than two link struts 21 to form the cells 22. The size and shape of the cells 22 may vary in different portions of the strut pattern 171. For example, the cells 22 may be different near the proximal 25 and distal 26 ends than near the central portion of the stent 10. The width 279 of the linear ring strut 20 and the width 280 of the link strut 21 and thickness 13 of the linear ring struts 20 and/or the link struts 21 may vary in one or more portions of the stent 10. The thickness 13 of the stent 10 may be thinner in one or more portions of the stent 10 such as thinner near the proximal 25 and distal 26 ends than near the center portion of the length 15 so that stress concentrations do not develop at the intersection of the stent 10 and the anatomical lumen 36. The exemplary strut pattern 171 depicted in FIG. 114 has nineteen rings 19. In other embodiments, there are more or less rings 19. There could be more rings 19 used within the same length 15, for example, to decrease the linear ring strut width 204 and/or thickness 13 while maintaining substantially the same amount of support to the anatomical lumen 36. In another variation, the link struts 21 may be on an angle and/or curved to facilitate longitudinal bending of the stent 10 rather than being straight and parallel to the central axis 14 as depicted in FIG. 114. Moreover, some or all the areas subjected to higher stress during crimping, delivery, deployment, and/or treatment time like, without limitation, at curved hinge element 281 may be reinforced by thickening or thinning the affected areas.

The cross-sectional profile of the linear ring struts 20 and/or link struts 21 may vary at least one time or not vary within the stent 10. The wall thickness 13 and/or cross-sectional shape of the of the linear ring struts 20 and/or link struts 21 may be the same in the crest(s) 189 and/or the trough(s) 190 as in the remaining portion of the ring(s) 19 or the wall thickness 13 and/or cross-sectional shape of the some or all of the linear ring strut(s) 20 and/or link strut(s) 21 at or near the crest(s) 195 and/or the trough(s) 196 may be different than the remaining portion of the ring(s) 19. The wall thickness 13 at or near some or all the crest(s) 189 and/or trough(s) 190 may be thicker than the wall thickness 13 in some or all of the remaining portions of the ring(s) 19 or the wall thickness 13 at or near some or all of the crest(s) 189 and/or trough(s) 190 is thinner than the wall thickness 13 in some or all of the remaining portions of the ring(s) 19. The linear ring strut width 279 and/or link strut width 280 at or near some or all of the crest(s) 189 and/or trough(s) 190 may be wider than the linear ring strut width 279 and/or link strut width 280 in some or all of the remaining portions of the ring(s) 19 or the linear ring strut width 279 and/or link strut width 280 at or near some or all of the crest(s) 189 and/or trough(s) 190 may be narrower than the linear ring strut width 279 and/or link strut width 280 in some or all of the remaining portions of the ring(s) 19.

Some or all the crest(s) 189 and/or trough(s) 190 may include at least one open loop to improve flexibility and/or reduce stress concentrations at some or all the crest(s) 189 and/or trough(s) 190. The strut pattern 171 may include at least one radius or fillet located at least at one intersection(s) of the linear ring strut(s) 20 and link strut(s) 21. Some or all the linear ring struts 20 and/or the link strut(s) 21 may include a serpentine configuration located between some or all the crest(s) 189 and trough(s) 190. Some or all the linear ring strut(s) 20 and/or the link strut(s) 21 may include a straight configuration located between some or all the crest(s) 189 and trough(s) 190. Some or all the linear ring strut(s) 20 and/or link strut(s) 21 may include a serpentine configuration located between some or all the curved hinge elements 281. Some or all the linear ring strut(s) 20 and/or the link strut(s) 21 include a straight configuration located between some or all the curved hinge elements 281. The need for including the aforementioned features within the strut pattern 171 depends on the requirements of the treatment and the need can be experimentally determined by those skilled in the art of stent strut design.

Although it is preferred to convert the stent material(s) 85 and/or composite material(s) into the stent 10 using processes described herein, it will be apparent that modifications to the processes or sequences of processes can be made without departing from the scope and intent of the invention. Moreover, the stent 10 of the present invention or the processes of forming the stent 10 may be any single embodiment or any combinations of at least two embodiments described herein in all possible variations unless otherwise indicated herein or otherwise clearly contradicted by context. The variations of features are virtually endless and therefore it is impossible to list all these herein.

The composition of the stent material(s) 85 and/or reinforcement(s) may be tuned to meet the specific mechanical properties, the physical dimensions, degradation rate, and/or resorption rate required by the specific end-use application or treatment. There is almost an endless number of variations of the ratios of bioresorbable monomer(s), polymer(s), and copolymer(s) specified herein that are useful in the blend(s) of polymer(s) and/or copolymer(s) specified herein that can produce the stent material(s) 85 meeting the requirements of the broad number of end-use applications. There is almost an endless number of variations of ratios chemical elements specified herein that can produce the reinforcement(s) or alloys comprising the reinforcement(s) meeting the requirements of the broad number of end-use applications. It should be appreciated that any possible ratios of the monomer(s), the polymer(s), the copolymer(s), and the chemical element(s) mentioned herein may be included within the stent 10. It should also be appreciated that the addition of trace amounts of chemical element(s) not mentioned herein, or combinations of chemical element(s) not specifically mentioned herein but produce a material having substantially the same mechanical properties, degradation properties, and other properties as those described herein are all within the scope of the present invention.

Polymer(s) are comprised of molecules having different chain lengths. The length of the chain can be determined by the molecular weight or molecular mass of the polymer(s). This specification describes ultra-high molecular weight polymer(s) in terms of weight average molecular weight (Mw) and Inherent Viscosity (IV). It should be appreciated that the same polymer(s) may be described in terms of number average molecular weight (Mn) or higher average molecular weights (Mz, Mz+1) and that these alternative measurements may be the same polymer(s) incorporated into the present invention and if these polymer(s) are the same that they fall within the scope of the present invention.

The operational steps for forming the stent material(s) 85 and/or composite material(s) into the stent 10 may be performed in a continuous process. The operational steps for forming the stent material(s) 85 and/or composite material(s) into the stent 10 may be performed in a discontinuous or batch processes. In an embodiment, some or all the processing steps described herein may be combined into one or more processing steps or some or all the operations or the processing steps described herein may be disaggregated into multiple steps to form the stent 10. Moreover, some or all the processing steps described herein may be performed in a different order or sequence when forming the stent 10 from the stent material(s) 85 and/or the composite material(s). It should be appreciated that the stent 10 may include some or all the features described herein.

Definitions

"Active ingredient" means any substance that is biologically active, therapeutically active, or an active pharmaceutical ingredient (API).

"Alloy" means a material composed of at least two metals or a metal and a nonmetal. An alloy may be a solid solution of the elements (a single phase), a mixture of metallic phases (two or more solutions), or an intermetallic compound with no distinct boundary between the phases.

"Anatomical lumen" means a cavity, duct, or a tubular organ.

"Axial" and "longitudinal" mean a direction, line, or alignment that is parallel or substantially parallel to the central axis of a cylindrical structure or the long length of a film, sheet or tube.

"Bioresorbable" means the breakdown of a compound into a simpler substance, materials or their degradative byproducts that are absorbed and/or eliminated by the body, or substances that do not require mechanical removal. The term "bioresorbable" can also generally refer to any material that is: absorbable; bioabsorbable; biodegradable; bio-adsorbable; bioremovable; bio-corrodible; bio-erodible; dissolvable; degradable; soluble; metabolizable; erodible in physiological conditions; degradable via hydrolytic mechanism; able to disappear via phagocytosis; able to disappear via chemical breakdown by physiological environment; broken down by a living body and does not require mechanical removal; corrodible; eliminated by a living body; eliminated by the a living body without mechanical removal; eliminated by cellular activity; eventually dispersed throughout the living body; a macromolecule that experiences cleavage of the main chain and is broken down into by-products and can be eliminated by biological pathways such as through the kidneys or lungs; soluble in blood or broken down to materials that are soluble in blood; or any substance that partially or fully disappears or losses mass within the living body after deployment.

"Chemical element" or "element" means a pure chemical substance consisting of a single type of atom distinguished by its atomic number, which is the number of protons in its atomic nucleus.

"Circumferential" and "circumferentially" mean a direction along a circumference of a stent or circular structure.

"Copolymer" means a chemical compound formed by uniting the molecules of at least two different compounds or monomers.

"Cleaved" or "Scission" means that a molecule is split, by breaking a chemical bond.

"Degradation rate" means the speed at which loss of mass of the material within the implanted stent occurs.

"Degradation time" means the time to complete mass loss of the material within the stent and/or the coating.

"Degree of polymerization" means the number of monomeric units within a molecule of a macromolecule, polymer or oligomer.

"Delivery" means introducing and transporting the stent through an anatomical lumen to a desired treatment site and/or active ingredient to the treatment site.

"Deploy," "Deployed," and "Deployment" means positioning or implantation of the stent within the anatomical lumen so that it can perform the treatment.

"Dry," "dries," or "dried" mean including no or very little liquid or volatile substances.

"Drug" (also known as medicine) means a substance intended for use in the diagnosis, cure, mitigation, treatment, or prevention of disease.

"Ductile" means the capability of the material(s) to be changed in shape and/or size under stress and/or strain.

"Durable" means the material can withstand wear, environmental conditions, and pressure, and generally remains substantially in original implanted location, shape, and/or form greater than about five years or regularly for the life a patient.

"Erodes" or "Erosion" means that the material(s) within the stent are gradually reduced and/or relatively slowly destroyed after deployment of the stent within the anatomical lumen.

"Expand" or "Expanding" means become or make larger.

"Fiber" means any nano filament, microfilament, filaments, belts, monofilaments, multi-filaments, strands, strips, strands, straps, tapes, threads, twine, wires, yarns, or any objects having a length that is greater than its thickness.

"Film" means a thin layer of the material(s).

"Fracture" means when the specimen breaks into multiple pieces, cracks, ruptures or is disrupted.

"Graft" means an implantable member comprised of a living or artificial material that can replace or repair a diseased or injured cells, tissue, organ or combinations thereof.

"Homopolymer" means a chemical compound formed by uniting the molecules of one compound or monomer.

"HRE" means heavy rare earth chemical elements including Sm, Eu, Gd, Tb, Dy, Ho, Er, Tm, Yb, Lu or chemical elements having atomic number between 62 and 71).

"Inherent Viscosity" means the natural logarithm of relative viscosity divided by polymer concentration in dilute solutions.

"Bond" (aka "weld line" or "knit line") means when two polymers join to form an object.

"Layer" means a single thickness of material laid or lying over or under another.

"Luminal" means the innermost surface having the shortest radial distance from the central axis of the stent.

"Shaft" means a rod, shaft, bar or other object around which material may be shaped.

"Mechanical property" means strength, tensile strength, yield strength, ultimate tensile strength, elastic modulus, modulus of elasticity, Young's modulus, flexural modulus, bending modulus, modulus of rupture, flexural strength, fracture strength, ductility, stiffness, impact strength, Charpy impact strength, compressive strength, fatigue strength, elongation-to-break, elasticity, plasticity, fatigue limit, endurance limit, Poisson's ratio or combination thereof.

"Melt" or "Melting" mean the process of a substance undergoing a phase transition from a solid into a liquid.

"Metal Chemical Element" means the chemical elements having the symbols Ag, Al, Au, Ba, Be, Bi, Ca, Cd, Ce, Co, Cr, Cu, Dy, Er, Fe, Ga, Gd, Ge, Hf, Ho, In, Ir, K, La, Li, Lu, Mg, Mn, Mo, Na, Nb, Nd, Ni, Pd, Pr, Pt, Re, Rh, Ru, Sb, Sc, Si, Sm, Sn, Sr, Ta, Tb, Tc, Ti, Tm, V, W, Y, Yb, Zn, and Zr.

"Monomer" means a molecule that can combine with others to form a polymer.

"Molecular chain" means at least two like or different atoms linked together by forces.

"Nominal diameter" means the sum of the inner diameter and the outer diameter of the stent prior to crimping or deployment divided by two.

"Oligomer" means a molecule containing a few monomer units (up to about five monomer units).

"Passivation layer" means a shielding outer-layer so that base material is less affected by environmental factors.

"Physical properties" or "mechanical properties" mean the modulus of elasticity, shear modulus, bulk modulus, Young's modulus, yield strength, elongation-to-break, degradation rate, molecular weight, solubility, viscosity, melt index, density, and resorption rate. All physical properties and mechanical properties data provided herein are at room temperature (about 23-24.degree. C) unless otherwise noted.

"Physiological conditions" mean conditions within the human body including or conditions simulating the conditions within the human body.

"Polymer" means natural or synthetic compounds consisting of repeating units linked by chemical bonds.

"Post-processed" means after completion of all processes that form the material(s) into the stent, including crimping and sterilization.

"Radiopaque" means the relative inability of electromagnetic radiation, particularly X-rays, to pass through a particular material.

"Radial strength" means the ability of a stent or tube to resist radial compressive forces.

"Radial Expansion Ratio" means the tube larger ending diameter (after being deformed) divided by the tube smaller starting diameter (before being deformed).

"Restenosis" means the reoccurrence of stenosis in a blood vessel or heart valve after it has been treated by, for example, balloon angioplasty, stenting, or valvuloplasty.

"Resorb" means a loss of the stent materials from the implantation site by destruction and/or physiological means.

"Resorption rate" means the speed in which the material substantially loses all its mass during the time the stent is implanted within the anatomical lumen.

"Resorption time" means the time that is necessary for the complete mass of the stent to disappear or be removed from the anatomical lumen, wherein the time is measured starting from the time the stent is implanted in the anatomical lumen and ending with the time there is no stent mass remaining within the anatomical lumen.

"RE" means rare earth chemical elements including La, Ce, Pr, Nd, Pm, Sm, Eu, Gd, Tb, Dy, Ho, Er, Tm, Yb, La, Lu, Sc, and Y.

"Scaffold" means a mechanical structure or framework that provides support, holds tissue or cells together, or maintains tissue contour; a scaffold is often used when providing temporary functionality.

"Sheet" means a relatively thin, normally rectangular or square form, piece, plate or slab comprised of at least one fiber.

"Shrink" means to become or make smaller in size or amount; to contract or cause to contract; to become smaller or more compacted.

"Solvent" means "a substance in the form of a liquid, solid, or gas that dissolves a solute (a chemically different liquid, solid, or gas) resulting in a solution.

"Solid" means firm and stable in shape; substantially free of liquid or fluid.

"Sintering" means the process of partially or fully interconnecting and/or coalescing the particles, layers, fibers, sheets, films, layers, or combinations thereof into a solid or porous mass by heating and/or compressing them without liquefaction of the material(s) comprising the particles, layers, fibers, sheets, films, or layers.

"Solution" means a homogeneous mixture of at least two substances that can be a solid, liquid, or gas, where such mixture is comprised of a solute, which is a substance dissolved in another substance, known as a solvent.

"Soluble" means the ability of one compound to dissolve in another compound.

"Spiral" means winding in a continuous curve around a central point usually getting farther away from it.

"Stent" means a short narrow tube often in the form of a mesh that is inserted into the lumen of an anatomical vessel (as an artery or bile duct).

"Sterilized" means a state of being free from viable microorganisms.

"Stress" means the applied load divided by the original cross-sectional area of the specimen.

"Strain" means the change in the specimen's length divided by its original length.

"Stiffness" means the rigidity of the wall thickness or to the extent the wall thickness resists deformation in response to an applied force.

"Swollen" means object become larger in size, typically because of accumulation of liquid. A swollen material may also be a gel.

"Treatment" means administration or application of remedies to a patient for a disease or an injury; medicinal or surgical management; therapy or the action or manner of treating a patient medically or surgically.

"Treatment time" means the duration of the treatment.

"Treatment site" means the location or position of deployment of the stent.

"Tube" means a hollow elongated cylinder such as a channel, conduit, duct, or pipe.

"Therapeutic agent" means any substance that when administered in a therapeutically effective amount to a patient has a therapeutic beneficial effect on the health and well-being of the patient such as without limitation curing a disease, slowing the progress of a disease, causing the disease to retrogress, or alleviating a symptom of a disease.

"Tissue" means any group of cells that in the aggregate perform the same function.

"Un-oriented tube" means that the tube has not been deformed.

"Volatile" means a substance that vaporizes readily at normal temperatures.

"Vaporize" means conversion of a solid or liquid into a gas.

"Void" means an empty space.

"Weight Percent" or "wt. %" means the weight percent of the component within the material or formulation wherein all components add up to 100 weight percent unless otherwise noted.

"about" and "approximately" mean numerical values or ranges that those skilled in the are would consider a value different from the exact number or outside the actual range to be close enough to be with the aegis of that number or range. At the very least, the terms "about" and "approximately" are understood to mean plus or minus.25 percent of a given numerical value or range starting and ending point.

"Substantial" or "substantially" mean that the object of the adjective or adverb is not a perfect example of such object but would be immediately known by those skilled in the art to warrant the general designation.

The terms "stent" and "scaffold" are used interchangeably herein and mean the same except where specifically noted to be different.

The terms "a," "an," and "the" are to be construed as referring to one or more of whatever the word modifies.
It is understood that use of singular throughout this application including the claims includes the plural and vice versa. It is understood that use of plural throughout this application including the claims includes the singular.
The term "may" is to be construed as referring to whatever the word refers to as being optional unless whatever the word refers to is mentioned in the claims herein, which would mean whatever the word refers to is included.

EXAMPLES

The following examples are presented to more particularly illustrate our invention and are not to be construed as limitations thereon.

Example 1: Bioresorbable, Implantable Film

Solid granules of raw stent material 85 comprised of two homopolymers of L-lactide (available from Corbion Purac, the Netherlands) were combined with the solvent 86 comprised of methylene chloride (aka, Dichloromethane-CH2Cl2) (herein after referred to as "DCM") in a container and stirred until the homopolymer of L-lactide was liquefied by dissolving the homopolymers of L-lactide within the liquid solvent 86 to form the liquid solution 83. The first homopolymer of L-lactide had a weight average molecular weight (Mw) of 2,000,000 grams per mole (g/mol) and Inherent Viscosity of 8.0 dl/g (hereinafter referred to as "PLLA") (i.e. "F-5") and the second homopolymer of L-lactide had a weight average molecular weight (Mw) of 221,000 grams per mole (g/mol) and Inherent Viscosity of 1.8 dl/g (hereinafter referred to as "PL-18") (i.e. "F-2") to make a blend ("B-87"). The weight average molecular weight (Mw) was determined by Gel Permeation Chromatography (GPC) in chloroform at 35.degree. C relative to polystyrene (PS) standards. The Inherent Viscosity (IV) was determined by viscometry of diluted polymer solutions. Measurements were performed in chloroform at 25.degree. C at a concentration of 0.1 g/dl.

The liquid solution 83 was a more viscous liquid than the liquid solvent 86 (e.g., greater than about 0.41 cP at 25.degree. C). The liquid solution 83 included 0.55 grams PL-80, 0.1 grams PL-18 and 21.5 grams DCM, which resulted in about a 2.9 weight percent (wt. %) Polymer Concentration that produced a solid film 66 comprised of about 84.6 weight percent (wt. %) PL-80 and 15.4 weight percent (wt. %) PL-18. The manual workstation suitable for making the solid film 66 consisted of a release media 84, two stainless steel flat metal shims, a syringe, and a scraper. The release media 84 was comprised of a high-density polyethylene sheet; the stainless steel flat shims were about 0.13 millimeters thick and 200 millimeters long; and the scraper had a blade that was about 100 millimeters wide. The two flat stainless steel shims were taped onto the release media 84 so that the shims had a separation distance of about 75 millimeters so that the solid film 66 could be formed on the release media 84 within the space between the two shims.

The liquid solution 83 was drawn into the barrel of the syringe by inserting the open end of the syringe into the container so that the tip of the syringe was partially submerged within the liquid solution 83 and pulling on the plunger of the syringe to transfer at least enough of the liquid solution 83 to make one solid film 66 from the container into the barrel of the syringe. The liquid solution 83 within the syringe was then dispensed on the release media 84 between the two shims at the spreading start position. The scraper blade was positioned so that the left side of the blade rested on the left shim and the right side of the blade rested on the right shim near the spreading start position and behind the dispensed liquid solution 83 so that there was approximately equal overlap of the scraper blade on each of the shims. With the scraper blade resting on the shims and tilted so that it was oriented approximately sixty degrees from the release media 84, the scraper blade was pulled toward the spreading end position at a relatively uniform rate of speed in a way that spread the liquid solution 83 in the form of the liquid film 78 on the surface of the release media 84 at a substantially uniform liquid film thickness 88 approximately equal to the height and length of the shims. The liquid film 88 was about 75 mm wide (about 3 inches wide). The liquid film 78 was allowed to dry on the release media 84 within an exhaust hood filled with air so that the volatile solvent 86 could substantially leave the liquid film 78 by evaporating or vaporizing to produce the thin solid film 66 comprised of the blend of PL-80 and PL-18 on the surface of the release media 84. After the solid film 66 was substantially dry, the thin, adhered solid film 66 was removed from the release media 84. Removal of the DCM from the liquid film 78 forms a solid film 66 that is temporarily attached (i.e., bonded) to the polyethylene sheet 84. The solid film 66 was removed from the release media 84 by lifting one corner of the solid film 66 from the polyethylene sheet (the release media 84) so that at least one part of the temporary bond between the solid film 66 and the polyethylene sheet 84 was broken so that the rest of the solid film 66 could be peeled off the polyethylene sheet 84. Removing the solid film 66 from the polyethylene sheet 84 was like peeling wallpaper off a wall except there was no adhesive between the solid film 66 and the polyethylene sheet 84. The solid film 66 thickness 67 was approximately 0.0039 mm when removed from the release media 84. It is believed that treating the solid film 66 with an antistatic gun like the Zero Stat 3 Milty as the solid film 66 was peeled off the release media 84 made handing the solid film 66 easier. The liquid solution 83 having a 2.9 weight percent (wt. %) polymer concentration produced a liquid film thickness 88 that was approximately 33.3 times the solid film thickness 67.

Example 2: Drug-eluting Bioresorbable, Implantable Film

A first drug-eluting bioresorbable, implantable film 66 was made by mixing an active ingredient 34 comprising Everolimus with a liquid solution 83 comprising a pre-processed stent material 85 comprising poly (L-lactide) (aka "PLLA") and a liquid solvent 86 comprising DCM. Alternatively, the active ingredient 34, the stent material 85 and the solvent 86 were mixed at the same time. The liquid solution 83 including the Everolimus, PLLA and DCM was formed into a liquid film 87 having a rectangular cross-section on a release media 84 comprising polyethylene sheet 84 within a gaseous environment 90 comprising ambient air at normal room temperature (about 24 degrees Celsius). The liquid film 87 had a starting size of 4 inches wide by 6 inches long and 20 mils (0.508 mm) thick. The DCM 86 was removed from the liquid film 87 by vaporizing the solvent 86 into the ambient air. Removal of the solvent 86 from the liquid film 87 formed a solid PLLA film 66 that was temporarily attached (i.e., bonded) to the polyethylene release media 84. The solid film 66 had ending dimensions that were about 4 inches wide by 6 inches long by 0.8 mils (0.020 mm) thick.

A second drug eluting bioresorbable, implantable film 66 was made from two different liquid solutions 83. The first liquid solution 83-A comprised an active ingredient 34 comprising Everolimus, a stent material 85 comprising PLLA and a solvent 86 comprising DCM and the second liquid solution 83-B comprised a stent material 85 comprising PLLA and a solvent comprising 86 comprising DCM. The first liquid solution 83-A was formed into a liquid film 87-A having a liquid film width 89 of 4 inches and a length of 3 inches and a liquid film thickness 88 of 0.8 mils (0.020 mm) on a release media 84 comprising polyethylene sheet 84. The second liquid solution 83-B was formed into a liquid film 87-B having a liquid film width 89 of 4 inches and a length of 3 inches and a liquid film thickness 88 of 0.8 mils (0.020 mm) on the same release media 84 so that the beginning of the second liquid film 87-B was adjacent to the end of the first liquid film 87-A. The liquid solution 83-A and liquid solution 83-B located at the adjacent ends of liquid film 87-A and liquid film 87-B merged to form on continuous liquid film 87 having a continuous length of 6 inches, wherein 3 inches of the length of the liquid film 87 forms an active ingredient free area 142 and a different 3 inches of the merged liquid film 87 forms an active ingredient storage area 141. The solvents 86 was removed from the liquid film 87-A and liquid film 87-B to form one continuous solid film 66 having a total length of 6 inches, wherein 3 inches of the solid film 66 comprises an active ingredient free area 142 and another different 3 inches of the solid film 66 comprises an active ingredient storage area 141.

The solid films were removed from the release media 84 by lifting one corner of the solid films 66 from the polyethylene sheet 84 and gradually peeling the solid films 66 that were adhered to the polyethylene sheet off the polyethylene sheet 84. The solid films were submerged in water, which simulated physiological conditions, and the mass of the solid film 66 was lost as the solid film 66 dissolved by hydrolysis in the water with time. The Everolimus was released from the solid films 66 as the solid films 66 absorbed the water and as the solid films 66 lost mass.

Example 3: Drug-Eluting Coated Bioresorable, Implantable Film

About 10 percent of the top major surface 73 of the Bioresorbable, Implantable Film 66 described in Example 1 was covered with a drug-polymer coating 30 comprising the active ingredient 34 Everolimus and the coating material 31 Poly (DL-lactide) to form an active ingredient storage area 141 and an active ingredient free area 143. About 25 percent of the top major surface 73 of the Drug-eluting Bioresorbable, Implantable Film 66 described in Example 2 was covered with a drug-polymer coating 30 comprising the active ingredient 34 Sirolimus and the coating material 31 a copolymer of L-lactide and glycolide to form an active ingredient storage area 141 and an active ingredient free area 143.

Example 4—Drug-Eluting Bioresorable, Implantable Roll

The Bioresorbable, Implantable Film 66 of Example 1 and the Drug-eluting Bioresorbable, Implantable Film of Example 2, and the Drug-eluting Coated Bioresorbable, Implantable Film 66 of Example 3 were transformed into a roll 52 configuration comprising a beginning of the roll 58, an end of the roll 59, a roll inner diameter 55, a roll outer diameter 54, a roll length 56, a roll passageway 64, a roll central axis 63 and a roll thickness 57 comprising multiple said film thicknesses 67 in spiral cross section perpendicular to the roll central axis 63, wherein said beginning of the roll 58 was disposed inside the roll passageway 64 and the end of the roll 59 was disposed outside the roll 52. The rolls 52 were formed by wrapping the Bioresorbable, Implantable Film 66, the Drug-eluting Bioresorbable, Implantable Film, and t Drug-eluting Coated Bioresorbable, Implantable Films 66 around a cylindrical-shaped shaft 74.

Example 5—Drug-Eluting Bioresorbable, Implantable Tube

The rolls 52 of Example 4 were transformed into an un-oriented tube 42 by forming a bond between the multiple, adjacent film thicknesses 67 within the roll thickness 57. The film thicknesses 67 were bonded together by thermal welding and solvent bonding the film thicknesses 67 on a cylindrical-shaped shaft 74. The un-oriented tubes 42 were removed from the shaft 74. Some of the un-oriented tubes 42 were converted into oriented tubes 38 by radially expanding and/or axially elongating the un-oriented tube 42.

Example 6—Drug-Eluting Bioresorbable Stent (Aka Scaffold)

The un-oriented tubes 42 and the oriented tubes 38 of Example 5 were transformed into stents 10 (aka Scaffolds) by laser cutting a strut pattern 171 in the un-oriented tubes 42 and the oriented tubes 38. The stents 10 were crimped onto balloon catheters 37 and the stents 10 and catheters 37 were placed in a sealed packaging containing a Protective Environment. The package was e-beam sterilized at a dose below 40 kGy.

Example 7—Drug-Eluting Bioresorbable Coated Stent (Aka Coated Scaffold)

The stents 10 of Example 6 were transformed into coated stents 10 (aka coated Scaffolds) by covering the outer surface 16 of the ring struts 20 and link struts 21 with a coating 30 comprising 50% Everolimus and 50% poly (DL-lactide). The coated stents 10 were crimped onto balloon catheters 37 and the stents 10 and catheters 37 were placed in a sealed packaging containing a Protective Environment. The package was e-beam sterilized at a dose below 40 kGy.

Example 8: Bioresorbable Film Stent Having Controlled Delivery of Multiple Drugs One solid film 66 including a first drug-polymer coating 30 covering approximately 10 percent of the film's bottom major surface 73 to make an active ingredient storage area 141 on one part of the one solid film's major surface 73 near the end of the roll 59 and a first active ingredient free area 143 on the remainder of the film's bottom major surface 73, and a second drug-polymer coating covering approximately 10 percent of the film's top major surface 73 near the beginning of the roll 58 and a second active ingredient free area 143 on the remainder of the film's top major surface 73, configured as a roll 52 having a roll thickness 57, the film thicknesses 67 within the roll thickness 57 inter-connected with a bond 65 forms a tube 38, wherein the one solid film 66 has a film length 68 of approximately 165 mm, a film width 69 of 100 mm and a film thickness 67 of approximately 0.005 mm and the coatings 30 have a coating thickness 33 of approximately 0.005 mm. The one solid film 66 comprises a stent material 85 comprising poly (L-lactide), the first coating 30 comprises an active ingredient 34 comprising approximately 25 vol. % paclitaxel and the remainder of the coating 30 comprises a stent material 85 comprising poly (D-lactide) and the second coating comprises an active ingredient 34 comprising fifty percent heparin and the remainder of the second coating comprises poly (L-lactide). The tube 42 comprises approximately 17 wraps of the one solid film 66 and has an inner diameter of 3 mm, an outer diameter of about 3.2 mm and a thickness of about 0.105 mm. There are approximately two wraps of the one film 66 covered with the coating 30 comprising the active ingredient 34 comprising paclitaxel and 13 of the uncoated solid film 66 wraps and approximately two wraps of the one film 66 covered with the coating 30 comprising the active ingredient 34 comprising paclitaxel. The tube thickness 45 has seven layers 51, wherein the first layer 51 that is positioned near the inner diameter 43 of the tube 42 comprises one second coating thickness 33, the second layer 51 comprises one film thickness 67 bonded to the underneath layer 51, the third layer comprises one second coating thickness 33 bonded to the underneath layer 51, the fourth layer comprises thirteen bonded solid film thicknesses 67 bonded to the underneath layer, the fifth layer 51 comprises one first coating thickness 33 bonded to the underneath layer 51, the sixth layer 51 comprises one solid film thickness 67 bonded to the underneath layer 51, and the seventh layer 51 positioned near the outer diameter 44 of the tube 42 comprises one first coating thickness 33 bonded to the underneath layer 51. The tube 42 includes a strut pattern 171 that makes the tube 42 a stent 10 having a stent inner diameter 12 of 30 mm, a stent outer diameter 11 of 3.2 mm and a stent thickness 13 of 0.105 mm. The stent 10 is crimped onto a balloon catheter 37 and the stent 10 and catheter 37 are placed in a sealed packaging containing a Protective Environment. The package is Eto sterilized. Another stent 10 comprising the first active ingredient storage area 141 positioned on the top major surface 73, the first active ingredient free area 143 positioned on the top major surface 73 of the solid film 66, the second active ingredient storage area 141 on the bottom major surface 73 and the second active ingredient free area 143 positioned on the bottom major surface 73. The stents 10 are configured for implantation in a segment of the peripheral artery below the knee for the treatment of arthrosclerosis (i.e., critical limb ischemia).

Example 9: Bioresorbable Film Stent Having Controlled Delivery of One Drug

One solid, film 66 (configured the opposite of what is depicted in FIG. 62) comprising a film width 69, a film length 68, two major surfaces 73, four minor surfaces 71 and a film thickness 67, wherein about eighteen and a half percent of the volume of the film thickness 67 (about 37.9 mm of the film length 68 starting at the end of the roll 59) comprises a stent material 85 comprising poly (DL-lactide) having a pre-sterilized weight average molecular weight below 300,000 g/mol and at least 150 micrograms of an active ingredient 34 comprising sirolimus and the remaining approximately eighty-one and a half percent of the volume of the film thickness 67 (about 167 mm of the film length 68 ending at the end of the roll 59) comprises a stent material 85 comprising poly (L-lactide) having a pre-sterilized weight average molecular weight of about 1,000,000 g/mol excluding the active ingredient 34 sirolimus. The film 66 conformable into a roll 52 having a beginning of the roll 58 disposed inside the roll's passageway 64 and an end of the roll 59 disposed outside the roll 52, the roll 52 including a roll inner diameter 55, a roll outer diameter 54, a roll length 56, a roll passageway 64, a roll central axis 63 and a roll thickness 57 comprising 21 wraps of the film thicknesses 67 in spiral cross section perpendicular to the roll central axis 63, the roll 52 converted into a tube 38 by interconnecting the film's 66 major surfaces with a bond 65. The un-oriented tube 42 wall thickness 45 comprises two layers 51, wherein one layer 51 comprising seventeen bonded film thicknesses 67 comprised of poly (L-lactide) is positioned on the inner diameter 43 of the un-oriented tube 42 and the second layer 51 comprising four bonded film thicknesses 67 comprising poly (DL-lactide) and the active ingredient 34 comprising sirolimus is positioned on the outer diameter 44 of the un-oriented tube 42. The un-oriented tube 42 includes a strut pattern 171 that makes the un-oriented tube 42 a stent 10, where the thickness 13 of the stent's 10 linear ring struts 20 and link struts 21 comprise one layer 51 comprising seventeen bonded film thicknesses 67 comprising poly (L-lactide) is positioned on the inner diameter 12 of the stent 10 and the layer 51 comprising four bonded film thicknesses 67 comprising poly (DL-lactide) and the active ingredient 34 comprising sirolimus is positioned on the outer diameter 11 of the stent 10. Two additional stents 10 comprise the same construct as previously described, but the un-oriented tube 42 is in one stent 10 is radially enlarged so that the stent 10 includes molecular orientation of the stent materials 85 in the circumferential direction to increase the stent's 10 radial strength and in another stent 10 the un-oriented tube 42 is radially enlarged and elongated so that the stent 10 includes molecular orientation of the stent materials 85 in the circumferential and longitudinal direction to increase the stent's 10 radial and longitudinal strength. The self-expanding stents 10 are crimped onto a catheter 37 and the stent 10 and catheter 37 are placed in a sealed packaging containing a Protective Environment. The package is e-beam sterilized at a dose below 40 kGy. The stent's 10 are configured to be implanted in a segment of the peripheral artery.

Two solid films 66 (configured as depicted in FIG. 59), wherein a first solid, film 66-A comprising stent materials 85 comprising a blend of poly (L-lactide) and poly (D-lactide), a film width 69-A, a film length 68-A, two major surfaces 73-A, four minor surfaces 71-A/72-A and a film thickness 67-A and at least one additional solid, film 66-B comprising poly (L-lactide) and iodine within at least one part of the additional solid, film 66-B, an additional film width 69-B having a size up to the size of the first solid, film, an additional film length 68-B having an additional length up to the size of the first solid, film, two additional major surfaces 73-B, four additional minor surfaces and an additional film thickness 67-B, the film 66-A and the additional film 66-B having a cylindrical roll 52 configuration comprising a roll outer diameter 54, a roll inner diameter 55, a roll length 56, a roll passageway 64, a roll central axis 63, wherein the roll 52 comprises multiple said film thicknesses in spiral cross section perpendicular to the roll central axis 63.

The invention claimed is:

1. A preform of a medical implant, comprising:
    (a) a release media; and
    (b) a film layer having a surface peelably bonded to a surface of the release media without an adhesive layer disposed between the surfaces of the release media and the film layer, such that the film layer is removable from the release media by lifting an edge of the film layer and peeling the film layer off the release media, wherein the film layer as presented on the surface of the release media comprises an amorphous bioresorbable polymer with a degree of crystallinity of less than 25% and having a weight average molecular weight of 16 kg/mol to 3,000 kg/mol as measured by Gel Permeation Chromatography (GPC) in chloroform at 35 degrees Celsius relative to polystyrene standards, and wherein the film layer is configured to be formable into shapes of a variety of different medical implants for different medical applications, after removal of the film layer from the release media, by manipulation of the film layer.

2. The preform of claim 1, wherein the film layer additionally comprises at least one additional polymer blended with the bioresorbable polymer.

3. The preform of claim 1, wherein the film layer is a solvent free or essentially solvent free form of a composition derived from the bioresorbable polymer dissolved within at least one liquid solvent at a polymer concentration in the at least one liquid solvent greater than 0 wt. % to 35 wt. % polymer, wherein the remainder of the composition is the at least one liquid solvent and optionally one or more additives.

4. The preform of claim 1, wherein the film layer has an inherent viscosity of in the range of 0.2 dl/g to 11.5 dl/g.

5. The preform of claim 1, wherein the crystallinity is not greater than 15%.

6. The preform of claim 1, wherein the bioresorbable polymer is a L-lactide homopolymer; a copolymer including L-lactide; a glycolide homopolymer; a copolymer including glycolide; a epsilon caprolactone homopolymer; a copolymer including epsilon caprolactone; a DL-lactide homopolymer; a copolymer including DL-lactide; a D-lactide homopolymer; a copolymer including D-lactide; dioxanone homopolymer; a trimethylene carbonate homopolymer; a copolymer including trimethylene carbonate; or a blend of any of the forgoing.

7. The preform of claim 1, wherein the film layer comprises a multilayer structure comprising:
(a) a first sublayer having the surface peelably bonded to the surface of the release media; and (b) a second sublayer bonded to a surface of the first sublayer which opposes the surface to which the release media is bonded.

8. The preform of claim 7, wherein the first sublayer and the second sublayer each comprise one of:
(i) a L-lactide homopolymer,
(ii) a copolymer including L-lactide,
(iii) a blend of a L-lactide homopolymer and an epsilon caprolactone homopolymer,
(iv) a blend of a L-lactide homopolymer and a copolymer including L-lactide and epsilon caprolactone,
(v) a blend of a L-lactide homopolymer, a DL-lactide homopolymer, and an epsilon caprolactone homopolymer,
(vi) a blend of a L-lactide homopolymer, a DL-lactide homopolymer, and a copolymer including L-lactide and epsilon caprolactone,
(vii) a blend of a copolymer including L-lactide and DL-lactide and an epsilon caprolactone homopolymer,
(viii) a blend of a copolymer including L-lactide and DL-lactide and a copolymer including L-lactide and epsilon caprolactone,
(ix)) a DL-lactide homopolymer,
(x) a copolymer including DL-lactide,
(xi) a copolymer including glycolide,
(xii) a dioxanone homopolymer, or
(xiii) a copolymer including dioxanone.

9. The preform of claim 1, additionally comprising at least one active agent embedded in the film layer, or coated on the film layer, or a combination of being embedded in and coated on the film layer.

10. The preform of claim 9, wherein the film layer comprises a multilayered structure and wherein (i) the film layer includes two active agent layers separated by an active agent free layer; or (i) the film layer includes an active agent layer between two active agent free layers; or (iii) all the film layers are active agent layers.

11. A bioresorbable implantable medical device configured from the film layer of claim 1.

12. The bioresorbable implantable medical device of claim 11,
wherein the implantable device has a tubular shape formed by rolling of the film layer into a tubular configuration.

13. The bioresorbable implantable medical device of claim 11, wherein the bioresorbable implantable medical device is selected from a group consisting of an abdomen implant, a vascular implant, a bile duct implant, a bladder implant, a bone or cartilage implant, a bronchi implant, a cerebrum implant, a colon implant, an esophagus implant, an intestinal implant, a kidney implant, a muscle implant, a sinus implant, a rectal implant, a stomach implant, a tracheal implant, an ureteral implant, a urethral implant, and a uterus implant.

14. The bioresorbable implantable medical device of claim 11, wherein the film layer is configured into an anchor, an attachment, or a fixation device; a birth control device; a cell growth platform; a cell transportation device; a drug delivery implant; a filter; a flow restoration device; an intrauterine device; an implantable mesh; an oncology implant; a patch; a plug; a reconstruction device; a regeneration device; a reinforcement device; a revascularization device; a roll or a tube; a vascular scaffold or stent; a splicing device; a suppository; a tissue engineering device; or a heart valve.

15. The bioresorbable implantable medical device of claim 11, wherein
(i) the film layer comprises an active agent, and further comprising a coating layer having the same or a different active agent over at least a part or the entire surface of the implantable medical device; or
(ii) the film layer is active agent free, and further comprising a coating layer having an active agent over at least a part or the entire surface of the implantable medical device.

* * * * *